(12) United States Patent
Larsen et al.

(10) Patent No.: US 9,533,069 B2
(45) Date of Patent: Jan. 3, 2017

(54) DEVICE FOR PROMOTION OF HEMOSTASIS AND/OR WOUND HEALING

(71) Applicant: Ferrosan Medical Devices A/S, Soeborg (DK)

(72) Inventors: Kristian Larsen, Vaerlose (DK); Mads Sabra, Copenhagen N (DK)

(73) Assignee: Ferrosan Medical Devices A/S, Søborg (DK)

( * ) Notice: Subject to any disclaimer, the term of this patent is extended or adjusted under 35 U.S.C. 154(b) by 117 days.

(21) Appl. No.: 14/136,578

(22) Filed: Dec. 20, 2013

(65) Prior Publication Data

US 2014/0220130 A1    Aug. 7, 2014

Related U.S. Application Data

(63) Continuation of application No. 12/919,643, filed as application No. PCT/DK2009/050048 on Feb. 27, 2009, now Pat. No. 8,642,831.
(Continued)

(30) Foreign Application Priority Data

Feb. 29, 2008  (DK) ................................ 2008 00309
Apr. 16, 2008  (DK) ................................ 2008 00556
Jan. 6, 2009   (DK) ................................ 2009 00029

(51) Int. Cl.
*A61F 13/00*    (2006.01)
*A61L 24/00*    (2006.01)
(Continued)

(52) U.S. Cl.
CPC ........ *A61L 24/0036* (2013.01); *A61L 24/0015* (2013.01); *A61L 24/102* (2013.01);
(Continued)

(58) Field of Classification Search
CPC .. A61L 24/0036; A61L 24/104; A61L 24/102; A61L 24/0015; A61L 26/0066; A61L 2300/254; A61L 2300/418
(Continued)

(56) References Cited

U.S. PATENT DOCUMENTS 2,465,357 A    3/1949    Correll et al.
2,465,860 A    3/1949    Fleischmann
(Continued)

FOREIGN PATENT DOCUMENTS

BG    0051589    7/1993
BG    0099900    3/1997
(Continued)

OTHER PUBLICATIONS

Andrew Raftery; "Absorbable haemostatic materials and intraperitoneal adhesion formation."; Br. J. Surg. 67; 1980; pp. 57-58.
(Continued)

*Primary Examiner* — Kim M Lewis
(74) *Attorney, Agent, or Firm* — Hamilton, Brook, Smith & Reynolds, P.C.

(57) ABSTRACT

Disclosed is a matrix material comprising a pharmaceutical composition such as a matrix material with a pharmaceutical composition printed on the surface. In one embodiment the pharmaceutical composition comprises thrombin. Further disclosed is a method for making the matrix material with a pharmaceutical composition printed on the surface and use of said matrix material for promotion of hemostasis and/or wound healing. Also disclosed is a kit-of-parts comprising a matrix with a pharmaceutical composition and a container with a peelable lid.

19 Claims, 9 Drawing Sheets

3 Mark on sidewall
4 Inner tray notch
5 base
6 handle
7 Sealing surface for lid
8 lid

Related U.S. Application Data

(60) Provisional application No. 61/032,495, filed on Feb. 29, 2008, provisional application No. 61/045,416, filed on Apr. 16, 2008, provisional application No. 61/142,678, filed on Jan. 6, 2009.

(51) Int. Cl.
*A61L 26/00* (2006.01)
*A61L 24/10* (2006.01)

(52) U.S. Cl.
CPC ......... *A61L 24/104* (2013.01); *A61L 26/0066* (2013.01); *A61L 26/0085* (2013.01); *A61L 2300/254* (2013.01); *A61L 2300/418* (2013.01)

(58) Field of Classification Search
USPC .................................. 602/41–43, 46, 48–50
See application file for complete search history.

(56) References Cited

U.S. PATENT DOCUMENTS

| | | |
|---|---|---|
| 2,507,244 A | 5/1950 | Correll |
| 2,558,395 A | 6/1951 | Studer |
| 2,899,362 A | 8/1959 | Sieger et al. |
| 3,089,815 A | 5/1963 | Kupelwieser et al. |
| 3,224,434 A | 12/1965 | Molomut et al. |
| 3,514,518 A | 5/1970 | Charier-Vadrot |
| 3,608,593 A | 9/1971 | McCormick et al. |
| 3,678,933 A | 7/1972 | Moore et al. |
| 3,815,580 A | 6/1974 | Oster |
| 3,869,539 A | 3/1975 | Kring et al. |
| 3,892,876 A | 7/1975 | Hobday et al. |
| 3,930,052 A | 12/1975 | De Brou et al. |
| 4,002,173 A | 1/1977 | Manning et al. |
| 4,006,220 A | 2/1977 | Gottlieb |
| 4,013,078 A | 3/1977 | Feild |
| 4,098,728 A | 7/1978 | Rosenblatt et al. |
| 4,107,288 A | 8/1978 | Oppenheim et al. |
| 4,124,705 A | 11/1978 | Rothman et al. |
| 4,150,744 A | 4/1979 | Fennimore |
| 4,164,559 A | 8/1979 | Miyata et al. |
| 4,179,400 A | 12/1979 | Tsao et al. |
| 4,194,392 A | 3/1980 | Lombard et al. |
| 4,256,877 A | 3/1981 | Karlsson et al. |
| 4,265,233 A | 5/1981 | Sugitachi et al. |
| 4,280,954 A | 7/1981 | Yannas et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,320,201 A | 3/1982 | Berg et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,416,813 A | 11/1983 | Ikeda et al. |
| 4,424,208 A | 1/1984 | Wallace et al. |
| 4,453,939 A | 6/1984 | Zimmerman |
| 4,482,386 A | 11/1984 | Wittwer et al. |
| 4,492,305 A | 1/1985 | Avery |
| 4,515,637 A | 5/1985 | Cioca |
| 4,522,302 A | 6/1985 | Paikoff |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,557,377 A | 12/1985 | Maloney |
| 4,559,304 A | 12/1985 | Kasai et al. |
| 4,600,574 A | 7/1986 | Lindner et al. |
| 4,640,834 A | 2/1987 | Eibl et al. |
| 4,655,211 A | 4/1987 | Sakamoto et al. |
| 4,685,597 A | 8/1987 | Hirao et al. |
| 4,696,812 A | 9/1987 | Silbering |
| 4,735,616 A | 4/1988 | Eibl et al. |
| 4,743,229 A | 5/1988 | Chu |
| 4,746,514 A | 5/1988 | Warne |
| 4,749,689 A | 6/1988 | Miyata et al. |
| 4,752,466 A | 6/1988 | Saferstein et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,885,161 A | 12/1989 | Cornell |
| 4,891,359 A | 1/1990 | Saferstein et al. |
| 4,920,158 A | 4/1990 | Murray et al. |
| 4,925,677 A | 5/1990 | Feijen |
| 4,936,835 A | 6/1990 | Haaga et al. |
| 4,946,870 A | 8/1990 | Partain, III. et al. |
| 4,965,203 A | 10/1990 | Silbering et al. |
| 4,982,769 A | 1/1991 | Fournier et al. |
| 4,997,753 A | 3/1991 | Dean, Jr. et al. |
| 5,007,916 A | 4/1991 | Linsky et al. |
| 5,017,229 A | 5/1991 | Burns et al. |
| 5,023,082 A | 6/1991 | Friedman et al. |
| 5,024,841 A | 6/1991 | Chu et al. |
| 5,037,740 A | 8/1991 | Tanaka et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,112,750 A | 5/1992 | Tanaka et al. |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,180,583 A | 1/1993 | Hedner |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,281,528 A | 1/1994 | Boctor et al. |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,350,581 A | 9/1994 | Kochinke |
| 5,352,715 A | 10/1994 | Wallace et al. |
| 5,356,614 A | 10/1994 | Sharma |
| 5,356,883 A | 10/1994 | Kuo et al. |
| 5,384,333 A | 1/1995 | Davis et al. |
| 5,385,606 A | 1/1995 | Kowanko |
| 5,387,208 A | 2/1995 | Ashton et al. |
| 5,394,886 A | 3/1995 | Nabai et al. |
| 5,397,704 A | 3/1995 | Boctor et al. |
| 5,399,361 A | 3/1995 | Song et al. |
| 5,401,511 A | 3/1995 | Margalit |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Alleyne |
| 5,441,491 A | 8/1995 | Verschoor et al. |
| 5,443,481 A | 8/1995 | Lee |
| 5,447,966 A | 9/1995 | Hermes et al. |
| 5,456,693 A | 10/1995 | Conston et al. |
| 5,462,860 A | 10/1995 | Mach |
| 5,478,352 A | 12/1995 | Fowler |
| 5,503,848 A | 4/1996 | Perbellini et al. |
| 5,507,744 A | 4/1996 | Tay et al. |
| 5,510,418 A | 4/1996 | Rhee et al. |
| 5,512,301 A | 4/1996 | Song et al. |

(56) References Cited

U.S. PATENT DOCUMENTS

| | | |
|---|---|---|
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,599,735 A | 2/1997 | Moslehi |
| 5,614,587 A | 3/1997 | Rhee et al. |
| 5,618,551 A | 4/1997 | Tardy et al. |
| 5,643,596 A * | 7/1997 | Pruss et al. .................. 424/426 |
| 5,645,849 A | 7/1997 | Pruss et al. |
| 5,648,506 A | 7/1997 | Desai et al. |
| 5,658,592 A | 8/1997 | Tanihara et al. |
| 5,660,854 A | 8/1997 | Haynes et al. |
| 5,667,839 A | 9/1997 | Berg |
| 5,669,934 A | 9/1997 | Sawyer |
| 5,672,336 A | 9/1997 | Sharma |
| 5,674,275 A | 10/1997 | Tang et al. |
| 5,690,675 A | 11/1997 | Sawyer et al. |
| 5,690,954 A | 11/1997 | Illium |
| 5,698,213 A | 12/1997 | Jamiolkowski et al. |
| 5,700,476 A | 12/1997 | Rosenthal et al. |
| 5,712,161 A | 1/1998 | Koezuka et al. |
| 5,714,370 A | 2/1998 | Eibl et al. |
| 5,723,308 A | 3/1998 | Mach et al. |
| 5,743,312 A | 4/1998 | Pfeifer et al. |
| 5,749,895 A | 5/1998 | Sawyer et al. |
| 5,752,974 A | 5/1998 | Rhee et al. |
| 5,770,229 A | 6/1998 | Tanihara et al. |
| 5,791,352 A | 8/1998 | Reich et al. |
| 5,795,330 A | 8/1998 | Tofighi et al. |
| 5,798,091 A | 8/1998 | Trevino et al. |
| 5,804,203 A | 9/1998 | Hang et al. |
| 5,823,671 A | 10/1998 | Mitchell et al. |
| 5,824,015 A | 10/1998 | Sawyer |
| 5,853,749 A | 12/1998 | Hobbs |
| 5,856,356 A | 1/1999 | Tsouderos et al. |
| 5,861,043 A | 1/1999 | Carn |
| 5,863,496 A | 1/1999 | McElhany |
| 5,874,500 A | 2/1999 | Rhee et al. |
| 5,883,078 A | 3/1999 | Seelich et al. |
| 5,890,610 A | 4/1999 | Jansen et al. |
| 5,895,412 A | 4/1999 | Tucker |
| 5,902,832 A | 5/1999 | Van Bladel et al. |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,959,735 A | 9/1999 | Maris et al. |
| 5,986,168 A | 11/1999 | Noishiki et al. |
| 5,997,895 A | 12/1999 | Narotam et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,056,970 A | 5/2000 | Greenawalt et al. |
| 6,063,061 A | 5/2000 | Wallace et al. |
| 6,066,325 A | 5/2000 | Wallace et al. |
| 6,074,663 A | 6/2000 | Delmottet et al. |
| 6,096,309 A | 8/2000 | Prior et al. |
| 6,099,952 A | 8/2000 | Cercone |
| 6,110,484 A | 8/2000 | Sierra |
| 6,113,948 A | 9/2000 | Heath |
| 6,129,761 A | 10/2000 | Hubbell |
| 6,132,759 A | 10/2000 | Schacht et al. |
| 6,162,241 A | 12/2000 | Coury et al. |
| 6,166,130 A | 12/2000 | Rhee et al. |
| 6,168,788 B1 | 1/2001 | Wortham |
| 6,179,872 B1 | 1/2001 | Bell et al. |
| 6,218,176 B1 | 4/2001 | Berthold et al. |
| 6,261,596 B1 | 7/2001 | Li et al. |
| 6,277,394 B1 | 8/2001 | Sierra |
| 6,280,727 B1 | 8/2001 | Prior et al. |
| 6,283,933 B1 | 9/2001 | D'Alessio et al. |
| 6,300,128 B1 | 10/2001 | Morota et al. |
| 6,303,323 B1 | 10/2001 | Laskey et al. |
| 6,312,474 B1 | 11/2001 | Francis et al. |
| 6,312,725 B1 | 11/2001 | Wallace et al. |
| 6,328,229 B1 | 12/2001 | Duronio et al. |
| 6,334,865 B1 | 1/2002 | Redmond et al. |
| 6,361,551 B1 | 3/2002 | Torgerson et al. |
| 6,364,519 B1 | 4/2002 | Ali |
| 6,387,413 B1 | 5/2002 | Miyata et al. |
| 6,416,739 B1 | 7/2002 | Rogerson |
| 6,454,787 B1 * | 9/2002 | Maddalo et al. ............. 606/214 |
| 6,458,380 B1 | 10/2002 | Leaderman |
| 6,458,386 B1 | 10/2002 | Schacht et al. |
| 6,458,889 B1 | 10/2002 | Trollsas |
| 6,461,325 B1 | 10/2002 | Delmotte et al. |
| 6,472,162 B1 | 10/2002 | Coelho |
| 6,495,127 B1 | 12/2002 | Wallace et al. |
| 6,548,081 B2 | 4/2003 | Sadozai et al. |
| 6,584,858 B1 | 7/2003 | Miyazawa et al. |
| 6,620,436 B1 | 9/2003 | Hughes et al. |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 6,831,058 B1 | 12/2004 | Ikada et al. |
| 6,887,974 B2 | 5/2005 | Pathak |
| 7,052,713 B2 | 5/2006 | Stimmeder |
| 7,056,722 B1 | 6/2006 | Coelho |
| 7,109,163 B2 | 9/2006 | Pendharkar et al. |
| 7,125,860 B1 | 10/2006 | Renier et al. |
| 7,320,962 B2 | 1/2008 | Reich et al. |
| 7,427,607 B2 | 9/2008 | Suzuki |
| 7,435,425 B2 | 10/2008 | Qian et al. |
| 7,547,446 B2 | 6/2009 | Qian et al. |
| 7,833,965 B2 | 11/2010 | Pendharkar et al. |
| 7,871,637 B2 | 1/2011 | Qian et al. |
| 7,923,431 B2 | 4/2011 | Wolff |
| 7,927,626 B2 | 4/2011 | Pendharkar et al. |
| 7,935,371 B2 | 5/2011 | Williams |
| 8,119,160 B2 | 2/2012 | Looney et al. |
| 8,303,981 B2 | 11/2012 | Wallace et al. |
| 8,357,378 B2 | 1/2013 | Wallace et al. |
| 8,512,729 B2 | 8/2013 | Wallace et al. |
| 8,551,941 B2 | 10/2013 | Pendharkar et al. |
| 8,603,511 B2 | 12/2013 | Wallace et al. |
| 8,642,831 B2 | 2/2014 | Larsen et al. |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt et al. |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0027146 A1 | 3/2002 | De LaForcade et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0064109 A1 | 4/2003 | Qian et al. |

(56) References Cited

U.S. PATENT DOCUMENTS

| | | | |
|---|---|---|---|
| 2003/0095993 A1 | 5/2003 | Benz et al. | |
| 2003/0162708 A1 | 8/2003 | Rolf | |
| 2003/0175410 A1 | 9/2003 | Campbell | |
| 2003/0175419 A1 | 9/2003 | Sessa | |
| 2003/0181659 A1 | 9/2003 | Naranda et al. | |
| 2003/0232746 A1 | 12/2003 | Lamberti et al. | |
| 2004/0076647 A1 | 4/2004 | Biering | |
| 2004/0079763 A1 | 4/2004 | Beiring | |
| 2004/0101546 A1 | 5/2004 | Gorman et al. | |
| 2004/0120993 A1 | 6/2004 | Zhang et al. | |
| 2004/0197388 A1 | 10/2004 | Sceusa | |
| 2004/0214770 A1 | 10/2004 | Reich et al. | |
| 2004/0243043 A1 | 12/2004 | McCarthy et al. | |
| 2004/0267352 A1 | 12/2004 | Davidson et al. | |
| 2005/0008632 A1* | 1/2005 | Stimmeder | 424/94.64 |
| 2005/0031691 A1 | 2/2005 | McGurk et al. | |
| 2005/0137512 A1 | 6/2005 | Campbell et al. | |
| 2005/0171001 A1 | 8/2005 | Pendharkar et al. | |
| 2005/0186253 A1 | 8/2005 | Lee et al. | |
| 2005/0214277 A1 | 9/2005 | Schaufler | |
| 2005/0218541 A1 | 10/2005 | Peng et al. | |
| 2005/0245905 A1 | 11/2005 | Schmidt et al. | |
| 2005/0284809 A1 | 12/2005 | Looney et al. | |
| 2006/0002890 A1 | 1/2006 | Hersel et al. | |
| 2006/0067976 A1* | 3/2006 | Ferraro et al. | 424/426 |
| 2006/0068013 A1 | 3/2006 | DiTizio et al. | |
| 2006/0115805 A1 | 6/2006 | Hansen | |
| 2006/0121080 A1 | 6/2006 | Lye et al. | |
| 2006/0121104 A1 | 6/2006 | Stern | |
| 2006/0147492 A1 | 7/2006 | Hunter et al. | |
| 2006/0159733 A1 | 7/2006 | Pendharkar et al. | |
| 2006/0167561 A1 | 7/2006 | Odar et al. | |
| 2006/0189516 A1 | 8/2006 | Yang et al. | |
| 2006/0193846 A1 | 8/2006 | Stimmeder | |
| 2006/0204490 A1 | 9/2006 | Pendharkar et al. | |
| 2006/0255053 A1 | 11/2006 | Li | |
| 2006/0282138 A1 | 12/2006 | Ota | |
| 2007/0009578 A1 | 1/2007 | Moiler et al. | |
| 2007/0025955 A1 | 2/2007 | Lowinger et al. | |
| 2007/0086958 A1 | 4/2007 | Drake et al. | |
| 2007/0128343 A1 | 6/2007 | Chappa | |
| 2007/0160543 A1 | 7/2007 | Moiler | |
| 2007/0250007 A1 | 10/2007 | Shekalim | |
| 2007/0264130 A1 | 11/2007 | Mallett | |
| 2007/0264301 A1 | 11/2007 | Cleek et al. | |
| 2007/0264302 A1 | 11/2007 | Cleek et al. | |
| 2008/0085316 A1 | 4/2008 | Qian et al. | |
| 2008/0091277 A1 | 4/2008 | Deusch et al. | |
| 2008/0095830 A1* | 4/2008 | Van Holten | 424/445 |
| 2008/0199539 A1* | 8/2008 | Baker et al. | 424/684 |
| 2008/0286376 A1 | 11/2008 | Qian et al. | |
| 2008/0311172 A1 | 12/2008 | Schapira et al. | |
| 2009/0087569 A1 | 4/2009 | Fan et al. | |
| 2009/0142396 A1 | 6/2009 | Odar et al. | |
| 2010/0028309 A1 | 2/2010 | Odar et al. | |
| 2010/0048758 A1 | 2/2010 | Chen et al. | |
| 2010/0063459 A1 | 3/2010 | Preiss-Bloom et al. | |
| 2010/0143447 A1 | 6/2010 | Hansen | |
| 2010/0292717 A1 | 11/2010 | Petter-Puchner et al. | |
| 2010/0318048 A1 | 12/2010 | Hoefinghoff et al. | |
| 2011/0045034 A1 | 2/2011 | Nur et al. | |
| 2011/0059228 A1 | 3/2011 | Gillick et al. | |
| 2015/0037314 A1 | 2/2015 | Larsen | |
| 2015/0045830 A1 | 2/2015 | Jensen et al. | |

FOREIGN PATENT DOCUMENTS

| | | |
|---|---|---|
| CN | 1270240 | 10/2000 |
| DE | 3146841 | 6/1983 |
| DE | 4119140 | 12/1992 |
| DE | 4407875 | 9/1995 |
| EP | 0132983 A1 | 2/1985 |
| EP | 0156649 | 10/1985 |
| EP | 0282316 | 9/1988 |
| EP | 0341007 | 11/1989 |
| EP | 0341745 | 11/1989 |
| EP | 0365705 | 5/1990 |
| EP | 0372966 | 6/1990 |
| EP | 0385916 A2 | 9/1990 |
| EP | 0395758 | 11/1990 |
| EP | 0132983 B2 | 6/1991 |
| EP | 0172710 | 3/1992 |
| EP | 0478827 | 4/1992 |
| EP | 0493387 | 10/1993 |
| EP | 0376931 | 6/1994 |
| EP | 0702081 | 3/1996 |
| EP | 0737467 | 10/1996 |
| EP | 0612252 | 5/1999 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |
| EP | 1084720 | 3/2001 |
| EP | 1140235 | 10/2001 |
| EP | 1174463 | 1/2002 |
| EP | 1258256 | 11/2002 |
| EP | 1283063 | 2/2003 |
| EP | 0790823 | 7/2003 |
| EP | 0891193 | 8/2003 |
| EP | 1484070 | 12/2004 |
| EP | 1095064 | 6/2005 |
| EP | 1649867 | 4/2006 |
| EP | 1361906 | 4/2007 |
| EP | 1414370 | 4/2007 |
| EP | 1059957 | 8/2007 |
| EP | 1608230 | 7/2010 |
| FR | 2679772 | 5/1993 |
| FR | 2759980 | 8/1998 |
| GB | 697603 | 9/1949 |
| GB | 648619 | 1/1951 |
| GB | 1037937 | 8/1966 |
| GB | 1199887 | 7/1970 |
| GB | 1584080 | 2/1981 |
| GB | 1591654 | 6/1987 |
| GB | 2266239 | 10/1993 |
| GB | 2393120 | 3/2004 |
| GB | 2414021 | 11/2005 |
| JP | 51-125156 | 11/1976 |
| JP | 59-113889 | 6/1984 |
| JP | 60214728 | 10/1985 |
| JP | 62070318 | 3/1987 |
| JP | 62221357 | 9/1987 |
| JP | 01130519 | 5/1989 |
| JP | 05308969 | 11/1993 |
| JP | 06254148 | 9/1994 |
| JP | 08-024325 | 1/1996 |
| JP | 9-504719 | 5/1997 |
| JP | 2004002271 | 1/2004 |
| JP | 2006-296896 | 11/2006 |
| JP | 07090241 | 4/2007 |
| KR | 910007847 | 10/1991 |
| KR | 100751046 | 8/2007 |
| WO | WO 83/01244 | 4/1983 |
| WO | WO 86/00912 | 2/1986 |
| WO | WO 89/02730 | 4/1989 |
| WO | WO 90/13320 | 11/1990 |
| WO | WO 92/21354 | 12/1992 |
| WO | WO 92/22252 | 12/1992 |
| WO | WO 93/06802 | 4/1993 |
| WO | WO 93/06855 | 4/1993 |
| WO | WO 93/10768 | 6/1993 |
| WO | WO 93/21908 | 11/1993 |
| WO | WO 94/08552 | 4/1994 |
| WO | WO 94/17840 | 8/1994 |
| WO | WO 94/27630 | 12/1994 |
| WO | WO 95/12371 | 5/1995 |
| WO | WO 95/15747 | 6/1995 |
| WO | WO 95/25748 | 9/1995 |
| WO | WO 95/31955 | 11/1995 |
| WO | WO 96/04025 | 2/1996 |
| WO | WO 96/06883 | 3/1996 |
| WO | WO 96/07472 | 3/1996 |
| WO | WO 96/10374 | 4/1996 |

(56) References Cited

FOREIGN PATENT DOCUMENTS

| | | |
|---|---|---|
| WO | WO 96/10428 | 4/1996 |
| WO | WO 96/12447 | 5/1996 |
| WO | WO 96/14368 | 5/1996 |
| WO | WO 96/16643 | 6/1996 |
| WO | WO 96/39159 | 12/1996 |
| WO | WO 96/40033 | 12/1996 |
| WO | WO 97/17023 | 5/1997 |
| WO | WO 97/17024 | 5/1997 |
| WO | WO 97/17025 | 5/1997 |
| WO | WO 97/29792 | 8/1997 |
| WO | WO 97/37694 | 10/1997 |
| WO | WO 98/08550 | 3/1998 |
| WO | WO 98/31403 | 7/1998 |
| WO | WO 98/34546 | 8/1998 |
| WO | WO 98/36784 | 8/1998 |
| WO | WO 98/43092 | 10/1998 |
| WO | WO 98/44963 | 10/1998 |
| WO | WO 98/51282 | 11/1998 |
| WO | WO 99/04828 | 2/1999 |
| WO | WO 99/12032 | 3/1999 |
| WO | WO 99/13902 | 3/1999 |
| WO | WO 99/38606 | 8/1999 |
| WO | WO 99/44901 | 9/1999 |
| WO | WO 99/45938 | 9/1999 |
| WO | WO 99/51208 | 10/1999 |
| WO | WO 00/09018 | 2/2000 |
| WO | WO 00/18301 | 4/2000 |
| WO | WO 00/27327 | 5/2000 |
| WO | WO 00/61201 | 10/2000 |
| WO | WO 00/74742 | 12/2000 |
| WO | WO 00/76533 | 12/2000 |
| WO | WO 01/13956 | 3/2001 |
| WO | WO 01/28603 | 4/2001 |
| WO | WO 01/34206 | 5/2001 |
| WO | WO 01/54735 | 8/2001 |
| WO | WO 01/66161 | 9/2001 |
| WO | WO 01/97826 | 12/2001 |
| WO | WO 02/18450 | 3/2002 |
| WO | WO 02/22059 | 3/2002 |
| WO | WO 02/22184 | 3/2002 |
| WO | WO 02/40068 | 5/2002 |
| WO | WO 02/058749 | 8/2002 |
| WO | WO 02/064182 | 8/2002 |
| WO | WO 02/070594 | 9/2002 |
| WO | WO 03/004072 | 1/2003 |
| WO | WO 03/007845 | 1/2003 |
| WO | WO 03/024426 | 3/2003 |
| WO | WO 03/024429 | 3/2003 |
| WO | WO 03/055531 | 7/2003 |
| WO | WO 03/070110 | 8/2003 |
| WO | WO 03/094983 | 11/2003 |
| WO | WO 2004/028404 | 4/2004 |
| WO | WO 2004/028423 | 4/2004 |
| WO | WO 2004/028583 | 4/2004 |
| WO | WO 2004/029095 | 4/2004 |
| WO | WO 2004/030711 | 4/2004 |
| WO | WO 2004/035629 | 4/2004 |
| WO | WO 2004/053051 | 6/2004 |
| WO | WO 2004/075650 | 9/2004 |
| WO | WO 2004/084869 | 10/2004 |
| WO | WO 2004/108035 | 12/2004 |
| WO | WO 2004/108179 | 12/2004 |
| WO | WO 2004/108418 A1 | 12/2004 |
| WO | WO 2005/000265 | 1/2005 |
| WO | WO 2005/009225 | 2/2005 |
| WO | WO 2005/041811 | 5/2005 |
| WO | WO 2005/044285 | 5/2005 |
| WO | WO 2005/062889 | 7/2005 |
| WO | WO 2005/063217 A1 | 7/2005 |
| WO | WO 2005/072700 | 8/2005 |
| WO | WO 2005/084650 A1 | 9/2005 |
| WO | WO 2005/107713 | 11/2005 |
| WO | WO 2006/005340 | 1/2006 |
| WO | WO 2006/031358 | 3/2006 |
| WO | WO 2006/034568 | 4/2006 |
| WO | WO 2006/063758 | 6/2006 |
| WO | WO 2006/128471 | 12/2006 |
| WO | WO 2007/001926 | 1/2007 |
| WO | WO 2007/018887 A2 | 2/2007 |
| WO | WO 2007/092618 A2 | 8/2007 |
| WO | WO 2007/133699 | 11/2007 |
| WO | WO 2007/137839 | 12/2007 |
| WO | WO 2008/016983 | 2/2008 |
| WO | WO 2008/051758 | 5/2008 |
| WO | WO 2008/090555 | 7/2008 |
| WO | WO 2009/020612 A1 | 2/2009 |
| WO | WO 2009/109194 | 9/2009 |
| WO | WO 2009/109963 | 9/2009 |
| WO | WO 2009/131752 A2 | 10/2009 |
| WO | WO 2011/151384 | 12/2011 |
| WO | WO 2011/151386 | 12/2011 |
| WO | WO 2011/151400 | 12/2011 |
| WO | WO 2012/146655 | 11/2012 |
| WO | WO 2013/053753 | 4/2013 |
| WO | WO 2013/053755 | 4/2013 |
| WO | WO 2013/053759 | 4/2013 |
| WO | WO 2013/060770 | 5/2013 |
| WO | WO 2013/131520 A2 | 9/2013 |
| WO | WO 2014/086996 | 6/2014 |

OTHER PUBLICATIONS

Arai, K., et al., "Clinical Effect of Thrombin-Collagen Sponge Sheet in Surgical Field," Chiryo (Pharmacology and Treatment), 11(5):413-418 (1983). (English translation of Office Action for Japanese counterpart application 2010-547957, Title: Device for Promotion of Hemostasis and/or Wound Healing, being provided to satisfy "concise explanation" requirement under 37 C.F.R. 1.98(a)(3)).

Boland, T., et al., "Application of Inkjet Printing to Tissue Engineering," Biotechnol. J., 1:910-917 (2006).

Branski et al., "Mucosal Wound Healing in a Rabbit Model of Subglottic Stenosis"; Arch Otolaryngol Head Neck Surg, vol. 131, Feb 2005, p. 153-157.

Brunt and Klausner, "Growth factors speed wound healing", Nature Biotechnology vol. 6 No. 1 (1988); pp. 25-30.

Campbell, P.G., et al., "Engineered Spatial Patterns of FGF-2 Immobilized on Fibrin Direct Cell Organization," Biomaterials, 26:6762-6770 (2005).

Campbell, P.G., et al., "Tissue Engineering with the Aid of Inkjet Printers," Expert Opin. Biol. Ther., 7:1123-1127 (2007).

Cantor et al., "Gelfoam® and Thrombin in treatment of massive gastroduodenal hemorrhage—A preliminary report". American Journal of Surgery, Dec. 1950.

Changez et al., Abstract of "Efficacy of antibiotics-loaded interpenetrating network (IPNs) hydrogel based on poly (acrylic acid) and gelatin for treatment of experimental osteomyelitis: in vivo study.", Biomaterials; vol. 26, No. 14; 2005; pp. 2095-2104.

De Iaco et al., "Efficacy of a Hyaluronan Derivative gel in postsurgical adhesion prevention in the presence of inadequate hemostasis." Surgery 130 (1); 2001; pp. 60-64.

Dembo M.A. et al.; Abstract of "Antiseptic hemostatic preparations, their properties and study.", Lech.Prep. Krovi. Tkanei; 1974; pp. 139-140.

Dodd et al., "Minimally invasive treatment of malignant hepatic tumors. At the threshold of a major breakthrough", Radiographies 2000; 20:9-27.

Drognitz et al., Abstract of "Release of vancomycin and teicoplanin from a plasticized and resorbable gelatin sponge: in vitro investigation of a new antibiotic delivery system with glycopeptides."; Indection Germany (Minich); 34 (1 ); 2006; pp. 29-34.

Ellegala et al., "Use of FloSeal Hemostatic Sealant in Transsphenoidal Pituitary Surgery: Technical Note."; Neurosurgery; vol. 51; Aug. 2002; pp. 513-516.

Hae-Won et al., Abstract of "Porus scaffolds of gelatin-hydroxyapatite nanocomposites obtained by biometic approach: Characterization and antibiotic drug release."; J. of Biomedical Materials Research 74B(2); 2005; pp. 686-698.

(56) References Cited

OTHER PUBLICATIONS

Hill et al., "Use of microfibrillar collagen hemostat (avitenet) and thrombin to achieve hemostats after median sternotomy."; J. Thorac Cardiovasc Surg.; vol. 108; 1994; pp. 1151-1152.
Hill-West et al., "Efficacy of a resorbable hydrogel barrier, oxidized regenerated cellulose and hyaluronic acid in the prevention of ovarian adhesions in a rabbit model."; Fertility and Sterility 62 (3); 1994; pp. 630-634.
Hong et al., Abstract of "Study on gelatin-containing artificial skin IV: a comparative study on the effect of antibiotic and EGF on cell proliferation during epidermal healing."; Biomaterials 22(20); 2001; pp. 2777-2783.
International Preliminary Report on Patentability, PCT/DK2007/050196, "Wound or Tissue Dressing Comprising Lactic Acid Bacteria", May 29, 2009.
International Search Report & Written Opinion of the International Searching Authority, PCT/DK2007/050196, "Wound or Tissue Dressing Comprising Lactic Acid Bacteria", Apr. 23, 2008.
Kelly M.J. et al., "The value of an operative wound swab sent in transport medium in the prediction of later clinical wound infection: A controlled clinical and bacteriological evaluation.", Brit. J. Surgery vol. 65; 1978; pp. 81-88.
Kocak et al., "Reduction of adhesion formation with cross-linked hyaluronic acid after peritoneal surgery in rats.", Fertility and Sterility 72 (5); 1999; pp. 873-878.
Larsson et al., "Surgicel®—an absorbable hemostatic material—in prevention of peritoneal adhesion in rats."; Acta Chir Scand., vol. 26, No. 144; 1978; pp. 375-378.
Laurent et al., "Hyaluronic acid reduces connective tissue formation in middle ears filled with absorbable gelatin sponge: An experimental study.", Am. J.Otolaryngol 7; 1986; pp. 181-186.
Li et al., "Evaluation of esterified hyaluronic acid as middle ear-packing material.", Arch Otolaryngol Head Neck Surg 127; 2001; pp. 534-539.
Luengo et al., "Prevention of peritoneal adhesions by the combined use of Spongostan and 32% Dextran 70: An experimental study in pigs." Fertility and Sterility 29 (4); 1978; pp. 447-450.
M.G. Cascone et al., "Collagen and hyaluronic acid based polymeric blends as drug delivery systems for the release of physiological concentrations of growth hormone." Journal of Materials science: Materials in Medicine; No. 5, 1994; pp. 770-774.
Maxson et al., "Efficacy of a modified oxidized cellulose fabric in the prevention of adhesion formation." Gynccol. Obstet. Invest. 26; 1988; pp. 160-165.
Miller, E.D., et al., "Dose-Dependent Cell Growth in Response to Concentration Modulated Patterns of FGF-2 Printed on Fibrin," *Biomaterials*, 27:2213-2221 (2006).
Min et al., "Molecular Weight Changes of Sodium Hyaluronate Powder and Solution by Heat treatment," Matrix Biology Institute, Proceedings of Hyaluronan, Oct. 11-16, 2003.
Oz et al., "Controlled clinical trial of a novel hemostatic agent in cardiac surgery.", Ann Thorac Surg. 2000; vol. 69; 2000; pp. 1376-1382.
Product leaflet for FloSeal® Matrix Hemostatic Sealant dated Jul. 2001 (Jul. 2001).
Purdy et al., "Microfibrillar collagen model of canine cerebral infarction"; Strokes, vol. 20 No. 10, Oct. 1989, p. 1361-1367.
Quintavalla et al., "Fiuorescently labeled mesenchymal stem cells (MSCs) maintain mutlilineage potential and can be detected following implantation into Particular cartilage defects.", Biomaterials 23; 2002; pp. 109-119.
Reese, "Role of fibronectin in wound healing", Report date: Sep. 12, 1986; Annual rept. Oct. 1, 1985-Mar. 31, 1986, Final rept. Oct. 1, 1983-Mar. 31, 1986. Corporate Author: Medical Coli of Gerogia Augusta Research Institute. Brunt and Klausner, "Growth factors speed wound healing", Nature Biotechnology vol. 6 No. 1 (1988); pp. 25-30.
Reijnen et al., "Prevention of intra-abdominal abscesses and adhesions using a hyaluronic acid solution in a rat peritonitis model." Arch Surg. 134; 1999; pp. 997-1001.

Roda, et al., "Protein Microdeposition Using a Conventional Ink-Jet Printer," *BioTechniques*, 28(3):492-496 (2000).
Sakurabayashi et al., "Clinical evaluation of new hemostatic agent for hemostasis from biopsy wounds in the liver."; Gastroenterological Endoscopy 30 (10); Oct. 1988.
Sanfilippo et al., "Comparison of avitene, topical thrombin and Gelfoam as sole hemostatic agent in tuboplasties.", Fertility and Sterility 33 (3); 1980; pp. 311-316.
Santomaso et al., "Powder flowability and density rations: the impact of granules packing", Chemical Engineering Science 58 (2003) 2857-2874.
Shushan et al., "Hyaluronic acid for preventing experimental postoperative intraperitoneal adhesions.", Journal of Reproductive Medicine 39 (5); 1994; pp. 398-402.
Soules et al., "The prevention of postoperative pelvic adhesions: An animal study comparing barrier methods with Dextran 70.", Am. J. Obstet. Gynecol. 143 (7); 1982; pp. 829-834.
Spence et al., "Cerebellar capillary hcmangioblastoma: its histogenesis studied by organ culture and electron microscopy.", Cancer 35 (2); Feb. 1975; pp. 326-341.
Swann, "Studies on hyaluronic acid—I. The preparation and properties of rooster comb hyaluronic acid", Biochemica et biophysica acta, 156 (1968) p. 17-30.
Vander salm T.J. et al., Abstract of "Reduction of sternal infection by application of topical vancomycin.", J. of Thoracic and Cardiovascular Surgery; vol. 98, No. 4; 1989; pp. 618-622.
Wachoi-Drewek et al., "Comparative investigation of drug delivery of collagen implants saturated in antibiotic solutions and a sponge containing gentamicin.", Biomaterials 17; 1996; pp. 1733-1738.
West et al., "Efficacy of adhesion barriers: Resorbable hydrogel, oxidized regenerated cellulose and hyaluronic acid.", The Journal of Reproductive Medicine 41 (3); 1996; pp. 149-154.
Wiesenthal et al., Abstract of "New method for packing the external auditory canal, middle ear space, and mastoid cavities after otologic surgery.", The Journal of Otolaryngology; vol. 28, No. 5; 1999; pp. 260-265.
Xu et al., "Viability and electrophysiology of neural cell structures generated by the inkjet printing method", Biomaterials vol. 27 p. 3580-3588, 2006.
Xu, T., et al., "Inkjet Printing of Viable Mammalian Cells," *Biomaterials*, 26:93-99 (2005).
Y.S. Choi et al., "Studies on Gelatin-Based Sponges. Part Ill: A Comparative Study of Cross-linked Gelatin/ Alginate, Gelatin/ Hyaluronate and Chitosan/Hyaluronate Sponges and their Application as a wound dressing in fullthickness skin defect of rat.", J. of Mat. Sci.; Mat. in Med.; vol. 12; Jan. 2001; pp. 67-73.
Y.S. Choi et al., "Studies on gelatin-containing artificial skin: II. Preparation and characterization of cross-linked gelatin-hyaluronate sponge.", J. Biomed Mater Res.; 1999; 48.; pp. 631-639.
Yuesong et al., Abstract of "Design and experimental study of a slow-release antibiotic membrane implant in surgery wound.", Intern. Des Services de San. Des Forces Armees; vol. 72, No. 7-9; Sep. 1999; pp. 194-196.
26th Annual Symposium: Clinical Update in Anaesthesiology, Surgery and Perioperative Medicine, Jan. 20-25, 2008.
Ansell, J., et al., "Gelfoam and Autologous Clot Embolization: Effect on Coagulation," *Investigative Radiology*, 13: 115-120 (1978).
Barrow, D.L., et al., "The Use of Greater Omentum Vascularized Free Flaps for Neurosurgical Disorders Requiring Reconstruction", *Journal of Neurosurgery*, 60: 305-311 (1984).
Barton, B., et al., "Fibrin Glue as a Biologic Vascular Patch—A Comparative Study," *Journal of Surgical Research*, vol. 40, 1 page; abstract retrieved from http://www.ncbi.nlm.nih.gov on Jan. 3, 2001. (1986).
Baxter, "GentaFleece Collagen Fleece—Version 5: Instructions for Use—Collagen Sponge with Antibiotic Protection for Surgical Use," Retrieved from http://www.advancingbiosurgery.com/en_EU/downloads/ifu_gentafleece.pdf on Mar. 2002, 2 pages. English portion second column of first page.
Baxter, "Product Catalogue: Collagen," 4 pages, retrieved from http://www.baxter-ecommerce.com/ecatalog on Feb. 2, 2006 (2006).

(56) References Cited

OTHER PUBLICATIONS

Baxter, "TissuFleece E Package Leaflet," *Baxter International Inc.*, 4 pages, English portion of instructions for use (2003).
Baxter, "TissuFleece E, TissuCone E and TissuFoil E: Biomaterials," *Basic scientific Information*, 9 pages (2003).
Boyers, S., et al., "Reduction of Postoperative Pelvic Adhesions in the Rabbit with Gore-Tex Surgical Membrane", *Fertility and Sterility*, 49(6,): 1066-1070 (1988).
Brannon-Peppas, L., et al., "The Equilibrium Swelling Behavior of Porous and Non-Porous Hydrogels," *Absorbent Polymer Technology, Elsevier, Amsterdam*, pp. 67-102 (1990).
Canal, T., et al., "Correlation Between Mesh Size and Equilibrium Degree of Swelling of Polymeric Networks" *Biomedical Materials Research*, 23: 1183-1193 (1989).
Cantor, M.O., et al., "Gelfoam and Thrombin in Gastroduodenal Bleeding: An Experimental Study," *Journal of Laboratory and Clinical Medicine*, 35(6): 890-893 (1950).
Cantor, M.O., et al., "Gelfoam and Thrombin in Treatment of Massive Upper Gastrointestinal Hemorrhage," *American Journal of Surgery*, 82(2): 230-235 (Aug. 1951).
Chaplin, J .M., et al., "Use of an Acellular Dermal Allograft for Dural Replacement: An Experimental Study," *Neurosurgery*, 45(2): 320-327 (1999).
Cheung, D., et al., "Mechanism of Crosslinking of Proteins by Glutaraldehyde IV: In Vitro and In Vivo Stability of a Crosslinked Collagen Matrix," *Connective Tissue Research*, 25: 27-34 (1990).
Christensen, F, et al., "Qualitative Description of the Wurster-Based Fluid-Bed Coating Process," *Drug Dev and Industry Pharmacy*, 23(5): 451-463 (1977).
Chuang, V.P., et al., "Sheath Needle for Liver Biopsy in High-Risk Patients" *Radiology*, 166: 261-262 (1988).
Coenye, K.E., et al., "A Qualitative Morphological comparison of Two Heamostatic Agents in a Porcine Liver Trauma Model," *Surgical Science*, 4: 359-364 (2013).
Collins, D., et al., "Enemata of Gelfoam Milk Suspension Combined with Thrombin-Solution to Control Massive Hemorrhage Following Anorectal Surgery," *The American Journal of Proctology*, 2: 60-63 (1951).
Collins, R., et al., "Use of Collagen Film as a Dural Substitute: Preliminary Animal Studies," *Journal of Biomedical Materials Research*, 25: 267-276 (1991).
De la Torre, R.A., et al., "Hemostasis and Hemostatic agents in minimally invasive surgery", *Surgery*, 142(4S): S39-S45 (2007).
DeLustro, F., et al., "A Comparative Study of the Biologic and Immunologic Response to Medical Devices Derived From Dermal Collagen," *Journal of Biomedical Materials Research*, 20: 109-120 (1986).
Duchene, D., et al., "Pharmaceutical and Medical Aspects of Bioadhesive Systems for Drug Administration," *Drug Dev and Industr Pharmacy*, 14(2&3):283-318 (1988).
Edgerton, M., et al., "Vascular Hamatomas and Hemagiomas: Classification and Treatment," *Southern Medical Journal*, 75(12): 1541-1547 (1982).
Filippi, R., et al., "Bovine Pericardium for Duraplasty: Clinical Results in 32 Patients," *Neurological Review*, 20:103-107 (2001).
Flory, P., "Phase Equilibria in Polymer Systems," *Principles of Polymer Chemistry*, 13: 541-594 (1953).
"Formulation and Evaluation of Absorbable Gelatin Sponges," *Chapter 3A of Rupali Kale thesis: Design and Development of Surgical Dressings for Advanced Wound Management* (2010).
Fujii, Y., et al., "Safety of GT XIII (Report 2)—Japanese + English translation," *The Clinical Report*, 20(17) (Dec. 1986).
Gall, R.M., "Control of Bleeding in Endoscopic Sinus Surgery: Use of a Novel Gelatin-Based Hemostatic Agent", *Journal of Otolaryngology*, 31(5): (2002).
"Gelfoam absorbable powder", Retrieved from Internet URL: http://www.fda.gov/cdrh/pdf/N18286S012c.pdf, [retrieved on May 22, 2009].
"Gelfoam Prescribing Information", Pharmacia & Upjohn (Nov. 1996).
"Gelfoam® Product Brochure", Pharmacia & Upjohn (Jun. 2013).
Gibble, J.W., et al., "Fibrin glue: the perfect operative sealant?" *Reviews: Transfusion*, 30(8): 741-747 (1990).
Guinto, F., "Preparation of Gelfoam Particles Using an Orthopedic Rasp," *Radiology*, 153: 250 (1984).
Gurny, R., et al., "Bioadhesive Intraoral Release Systems: Design, Testing and Analysis," *Biomaterials*, 5: 336-340 (1984).
Harris, W.H., et al., "Topical Hemostatic Agents for Bone Bleeding in Humans," *The Journal of Bone and Joint Surgery*, 60-A(4): 454-456 (1978).
Heller, J., et al., "Release of Norethindrone from Poly(Ortho Esters)," *Polymer Engineering and Science*, 21: 727-731 (1981).
Herndon, J., et al., "Compression of the Brain and Spinal Cord Following Use of Gelfoam," *Arch. Surg*, 104: 107 (Jan. 1972).
Hieb, L., et al, "Spontaneous Postoperative Cerebrospinal Fluid Leaks Following Application of Anti-Adhesion Barrier Gel," *SPINE*, 26(7): 748-751 (2001).
Hong, Y.M., et al., "The Use of Hemostatic Agents and Sealants in Urology", *The Journal of Urology*, 176: 2367-2374 (2006).
Hood, D., et al., "Efficacy of Topical Hemostat Floseal Matrix in Vascular Surgery," *24th World Congress of the International Society for Cardiovascular Surgery*, Sep. 12-16, 1999, 2 pages.
Hotz, G., et al., "Collagen and Fibrin as Biologic Binders from Granular Hydroxyapatite," *Deutsche Zeitschrift fur Mund-Kieferund Gesichts-Chirurgie*, 13(4): 296-300 (1989). Abstract retrieved from http://www.ncbi.nlm.nih.gov on Jan. 3, 2001.
International Preliminary Examination Report for International Application No. PCT/DK03/00855, "Gelatine-Based Materials as Swabs", completed Jun. 2, 2005.
International Preliminary Report on Patentability (Corrected Version) for International Application No. PCT/DK2005/000063, "Haemostatic Sprays and Compositions", completed Nov. 6, 2006.
International Preliminary Report on Patentability for International Application No. PCT/DK2005/000475, "Haemostatic Composition Comprising Hyaluronic Acid", completed Aug. 16, 2006.
International Preliminary Report on Patentability for International Application No. PCT/DK2009/050048, "Device for Promotion of Hemostasis and/or Wound Healing", completed Sep. 6, 2010.
International Preliminary Report on Patentability for International Application No. PCT/DK2013/050054, "Pressurized Container Containing Haemostatic Paste", issued Sep. 9, 2014.
International Preliminary Report on Patentability from counterpart International Application No. PCT/DK2011/050082, "A Method for Promotion of Hemostasis and/or Wound Healing", mailed Jul. 6, 2012.
International Search Report and Written Opinion of the International Searching Authority from counterpart International Application No. PCT/DK2011/050082, "A Method for Promotion of Hemostasis and/or Wound Healing", mailed Jun. 21, 2011.
International Search Report for International Application No. PCT/DK2005/000475, "Haemostatic Composition Comprising Hyaluronic Acid", mailed Oct. 25, 2005.
International Search Report for International Application No. PCT/DK2013/050054, "Pressurized Container Containing Haemostatic Paste", mailed Sep. 10, 2013.
International Search Report for International Application No. PCT/DK2013/050191, "Dry Haemostatic Composition", mailed Aug. 21, 2013.
International Search Report for International Application No. PCT/DK2003/000855, "Gelatine-Based Materials as Swabs", mailed Oct. 8, 2004.
International Search Report for International Application No. PCT/DK2005/000063, "Haemostatic Sprays and Compositions", received Jul. 28, 2005.
International Search Report for International Application No. PCT/DK2009/050048, "Device for Promotion of Hemostasis and/or Wound Healing", mailed on Apr. 6, 2010.
Jeong, B., et al., "Biodegradable Block Copolymers as injectable Drug-Delivery Systems," *Nature*, 388: 860-862 (1997).
Jonas, R., et al., "A new sealant for knitted Dacron prostheses: Minimally cross-linked gelatin," *Journal of Vascular Surgery*, 7(3): 414-419 (1988).

(56) References Cited

OTHER PUBLICATIONS

Katayama, T., et al., "GT XIII safety (3$^{rd}$ report)—Japanese + English translation," *The Clinical Report*, vol. 20 (1986).

Kim, K., et al., "Reduction in Leg Pain and Lower-Extremity Weakness with Oxiplex/SP Gel for 1 Year after Laminevtomy, Laminotomy, and Disectomy," *Neurosurgical Focus*, vol. 17:1-6 (2004).

Kline, D., et al., "Dural Replacement with Resorbable Collagen," *Archives of Surgery*, 91:924-929 (1965).

Knopp, U., "A New Collagen Foil Versus a Cadaveric Dura Graft for Dural Defects—A Comparative Animal Experimental Study," *European Association of Neurosurgical Societies—Proceedings of the 12$^{th}$ European Congress of Neurosurgery*, Lisbon, 17 pages (2003).

Kofidis, T., et al., "Clinically Established Hemostatis Scaffold (Tissue Fleece) as Biomatrix in Tissue and Organ Engineering Research," *Tissue Engineering*, 9: 517-523 (2003).

Kost J., and Langer R., "Equilibrium Swollen Hydrogels in Controlled Release Applications," *Ch. 5: Hydrogels in Medicine and Pharmacy, vol. III: properties and Applications*, N. Peppas ed., pp. 95-108 (1987).

Krill, D., et al., "Topical Thrombin and Powdered Gelfoam: An Efficient Hemostatic Treatment for Surgery," *Journal of Tennessee Dental Association*, 66(2): 26-27 (1986).

Kuhn, J., et al., "Bilateral Subdural Heamatomata and Lumbar Pseudomeningocele Due to a Chronic Leakage of Liquor Cerebrospinalis after a Lumbar Disectomy with the Application of ADCON-L Gel," *Journal of Neurology, Neurosergery & Psychiatry*, 76: 1031-1033 (2005).

Langer, R., et al., "Chemical and Physical Structure of Polymers as Carriers for Controlled Release of Bioactive Agents: A Review," *Journal of Macromolecular Science-Reviews in Macromolecular Chemistry and Physics*, C23: 61-126 (1983).

Laquerriere, A., et al., "Experimental Evaluation of Bilayered Human Collagen as a Dural Substitute," *Journal of Neurosurgery*, 78: 487-491 (1993).

Larson, P., "Topical Hemostatic Agents for Dermatologic Surgery," *Journal of Dermatologic Surgery & Oncology*, 14: 623-632 (1988).

Le, A., et al., "Unrecognized Durotomy After Lumbar Discectomy: A Report of Four Cases Associated with the Use of ADCON-L," *Spine*, 26(1): 115-118 (2001).

Lee, J., et al., "Experimental Evaluation of Silicone-Coated Dacron and Collagen Fabric-Film Laminate as Dural Substitutes," *Journal of Neurosurgery*, 27: 558-564 (1967).

Lee, P., "Interpretation of Drug-Release Kinetics from Hydrogel Matrices in Terms of Time-Dependent Diffusion Coefficients," *Controlled-Release Technology—Pharmaceutical Applications, Ch. 5, ACS Symposium Series 348*, pp. 71-83 (1986).

Leong, K., et al., "Polyanhydrides for Controlled Release of Bioactive Agents," *Biomaterials*, 7: 364-371 (1986).

Leong, K., et al., "Polymeric Controlled Drug Delivery," *Advanced Drug Delivery Reviews*, 1: 199-233 (1987).

Lewis, K., et al., "Comparison of Two Gelatin and Thrombin Combination Hemostats in a Porcine Liver Abrasion Model," *Journal of Investigative Surgery*, 26: 141-148 (2013).

Loeb, J, "The Influence of Electrolytes Upon the Osmotic Pressure of Gelatin Solutions", *J. Biol. Chem.*, 35: 497-508 (1918).

Masar, E., et al., "Synthesis of Polyurethanes and Investigation of their Hydrolytic Stability," *Journal of Polymer Science: Polymer Symposium*, 66: 259-268 (1979).

Masuzawa, M., et al., "Experimental Study Related to the Hemostasis Action of GT XIII," *The Clinical Report*, 20(2):471-476 (Feb. 1986).

Matsumoto, K., et al., "A Gelatin Coated Collagen—Polyglycolic Acid Composite Membrane as a Dural Substitute," *American Society for Artificial Internal Organs Journal*, 47: 641-645 (2001).

Maurer, P, et al., "Vicryl (Polyglactin 910) Mesh as a Dural Substitute," *Journal of Neurosurgery*, 63:448-452 (1985).

McClure, J., et al., "Massive Gastroduodenal Hemorrhage: Treatment with Powdered Gelfoam and Buffered Thrombin Solution," *Surgery*, 32: 630-637 (1952).

McPherson, J., et al., "An Examination of the Biologic Response to Injectable, Glutaraldehyde Cross-linked Collagen Implants," *Journal of Biomedical Materials Research*, 20: 93-107 (1986).

McPherson, J., et al., "Development and Biochemical Characterization of Injectable Collagen," *J. Dermatol. Surg. Oncol.*, 12(1): 13-20 (Jul. 7, 1988).

McPherson, J., et al., "The Effects of Heparin on the Physiochemical Properties of Reconstituted Collagen," *Collagen and Related Research*, 1: 65-82 (1988).

McPherson, J., et al., "The Preparation and Physiochemical Characterization of an Injectable Form of Reconstituted, Glutaraldehyde Crosslinked, Bovine Corium Collagen," *Journal of Biomedical Materials Research*, 20: 79-92 (1986).

Meddings, N., et al., "Collagen Vicryl—A New Dural Prosthesis," *Acta Neurochirurgica*, 117: 53-58 (1992).

Mello, L., et al., "Duraplasty with Biosynthetic Cellulose: An Experimental Study," *Journal of Neurosurgery*, 86: 143-150 (1997).

Miller, D., and Peppas, N., "Diffusional Effects During Albumin Adsorption on Highly Swollen Poly(vinyl Alcohol) Hydrogels," *Eur. Polym. J.*, 24(7): 611-615 (1988).

Millikan, L., "Treatment of Depressed Cutaneous Scars with Gelatin Matrix Implant: A Multicenter Study," *J. Am. Acad. Dermatol.*, 16: 1155-1162 (1987).

Moak, E., "Hemostatic Agents: Adjuncts to Control Bleeding," *Today's O.R. Nurse*, pp. 6-10 (1991).

Mueller, K., "Release and Delayed Release of Water-Soluble Drugs from Polymer Beads with Low Water Swelling," *Controlled-Release Technology—Pharmaceutical Applications, Ch. 11, ACS Symposium Series*, 348: 139-157 (1986).

Narotam, P., et al., "A Clinicopathological Study of Collagen Sponge as a Dural Graft in Neurosurgery," *Journal of Neurosurgery*, 82: 406-412 (1995).

Narotam, P., et al., "Experimental Evaluation of Collagen Sponge as a Dural Graft," *British Journal of Neurosurgery*, 7: 635-641 (1993).

Nimni, M., et al., "Chemically Modified Collagen: A Natural Biomaterial for Tissue Replacement," *Journal of Biomedical Materials Research*, 21: 741-771 (1987).

Nimni, M., Ph.D., "The Cross-Linking and Structure Modification of the Collagen Matrix in the Design of Cardiovascular Prosthesis," *Journal of Cardiac Surgery*, 3: 523-533 (1988).

Nogueira, L., et al., Comparison of gelatine matrix-thrombin sealants used during laparoscopic partial nephrectomy, *BJU International*, 102: 1670-1674 (2008).

Novak, D., "Embolization Materials," *Interventional Radiology*, pp. 295-313 (1990).

O'Neill, P., et al., "Use of Porcine Dermis as a Dural Substitute in 72 Patients," *Journal of Neurosurgery*, 61: 351-354 (1984).

Ofner, C.M. and Bubnis, W.A., "Chemical and Swelling Evaluations of Amino Group Crosslinking in Gelatin and Modified Gelatin Matrices," *Pharma. Res.*, 13: 1821-1827 (1996).

Oz, M.C., et al., "Controlled clinical trial of a novel hemostatic agent in cardiac surgery.", *Ann Thorac Surg*, 69: 1376-1382 (2000).

Palm, S., et al., "Dural Closure with Nonpenetrating Clips Prevents Meningoneural Adhesions: An Experimental Study in Dogs," *Neurosurgery*, 45(4): 875-882 (1999).

Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochirurgica*, 139: 827-838 (1997).

Park, Y-K., et al., "Prevention of Arachnoiditis and Postoperative Tethering of the Spinal Cord with Gore-Tex Surgical Membrane: An Experimental Study with Rats," *Neurosurgery*, 42(4): 813-824 (1998).

Peppas, N. and Barr-Howell, B., "Characterization of the Cross-Linked Structure of Hydrogels," *Ch. 2: Hydrogels in Medicine and Pharmacy, vol. I: Fundamentals*, N. Peppas ed., pp. 27-56 (1986).

Peppas, N. And Brannon-Peppas, L, "Hydrogels at Critical Conditions. Part 1. Thermodynamics and Swelling Behavior," *Journal of Membrane Science*, 48: 281-290 (1990).

(56) References Cited

OTHER PUBLICATIONS

Peppas, N. and Khare, A., "Preparation, Structure and diffusional Behavior of Hydrogels in Controlled Release," *Adv. Drug Delivery Reviews*, 11: 1-35 (1993).
Peppas, N. and Korsmeyer, R, "Dynamically Swelling Hydrogels in Controlled Release Applications," *Ch. 6: Hydrogels in Medicine and Pharmacy, vol. III: Properties and Applications*, N. Peppas ed., pp. 109-135 (1987).
Peppas, N. and Lustig, S., "Solute Diffusion in Hydrophilic Network Structures," *Ch. 3: Hydrogels in Medicine and Pharmacy, vol. I: Fundamentals*, N. Peppas ed., pp. 57-83 (1986).
Peppas, N. and Mikos, A., "Preparation Methods and Structure of Hydrogels," *Ch. 1: Hydrogels in Medicine and Pharmacy, vol. I: Fundamentals*, N. Peppas ed., pp. 1-25 (1986).
Peppas, N. and Moynihan, H, "Structure and Physical Properties of Poly(2-Hydroxyethyl Methacrylate) Hydrogels," *Ch. 2: Hydrogels in Medicine and Pharmacy, vol. II: Polymers*, N. Peppas ed., pp. 49-64 (1987).
Peppas, N., "Hydrogels and Drug Delivery," *Current Opinion in Colloid & Interface Science*, 2: 531-537 (1997).
Peppas, N., "Hydrogels in Medicine and Pharmacy," *Hydrogels in Medicine and Pharmacy*, vol. 1. Fundamentals, CRC Press, Boca Raton, FL, 180 pages (1986).
Peppas, N., "Hydrogels in Medicine and Pharmacy," *Hydrogels in Medicine and Pharmacy*, vol. 2. Polymers, CRC Press, Boca Raton, FL, 172 pages (1987).
Peppas, N., "Hydrogels in Medicine and Pharmacy," *Hydrogels in Medicine and Pharmacy*, vol. 3. Properties and Applications, CRC Press, Boca Raton, FL, 196 pages (1987).
Peppas, N., "Hydrogels of Poly (Vinyl Alcohol) and its Copolymers," *Ch. 1: Hydrogels in Medicine and Pharmacy, vol. II: Polymers*, N. Peppas ed., pp. 57 pgs (1987).
Peppas, N., ed., "Other Biomedical Applications of Hydrogels," *Ch. 9: Hydrogels in Medicine and Pharmacy, vol. III: Properties and Applications*, pp. 177-186 (1987).
Pietrucha, K., "New Collagen Implant as Dural Substitute," *Biomaterials*, 12: 320-323 (1991).
Pitt, C., et al., "Biodegradable Drug Delivery Systems Based on Aliphatic Polyesters: Application to Contraceptives and Narcotic Antagonists," *Controlled Release of Bioactive Materials*, R. Baker, ed., (NY: Academic Press) pp. 19-43 (1980).
Porchet, F., et al., "Inhibition of Epidural Fibrosis with ADCON-L: Effect on Clinical Outcome One Year Following Reoperation for Recurrent Lumbar Radiculopathy," *Neurological Research*, 21: 551-560 (1999).
Ratner, B., "Hydrogel Surfaces," *Ch. 4: Hydrogels in Medicine and Pharmacy, vol. I. Fundamentals*, N. Peppas ed., pp. 85-94 (1986).
Raul, J.S., et al., "Utilisation du Polyester Urethane (NEUROPATCH) Comme Substitut Dural," *Neurochirugie*, 49: 83-89, English abstract only on p. 83 (2003).
Reddy, M., et al., "A Clinical Study of a Fibrinogen-Based Collagen Fleece for Dural repair in Neurosergery," *Acta Neurochirurgica*, 144: 265-269 (2002).
Renkens, K., et al, "A Multicenter, Prospective, Randomized Trial Evaluating a New Hemostatic Agent for Spinal Surgery," *Spine*, 26(15): 1645-1650 (2001).
Riley, S., et al. "Percutaneous Liver Biopsy with Plugging of Needle Track: A Safe Method for Use in Patients with Impaired Coagulation," *Lancet*, p. 436 (1984).
Rosenblatt, J., et al., "Effect of Electrostatic Forces on the Dynamic Rheological Properties of Injectable Collagen Biomaterials," *Biomaterials*, 13: 878-886 (1982).
Rosenblatt, J., et al., "Injectable Collagen as a pHSensitive Hydrogel," *Biomaterials*, 12: 985-995 (1984).
Ross, J., et al., "Association Between Peridural Scar and Recurrent Radicular Pain After Lumbar Discectomy: Magnetic Resonance Evaluation," *Neurosurgery*, pp. 855-863 (1996).
Rossler, B., et al., "Collagen Microparticies: Preparation and Properties," *Journal of Microencapsulation*, 12: 49-57 (1995).

San-Galli, F., et al., "Experimental Evaluation of a Collagen-Coated Vicryl Mesh as a Dural Substitute," *Neurosurgery*, 30: 396-401 (1992).
Schramm, V., et al., "Gelfoam Paste Injection for Vocal Cord Paralysis," *The Laryngoscope*, 88: 1268-73 (1978).
Shaffrey, C.I., et al., "Neurosurgical Applications of Fibrin Glue: Augmentation of Dural Closure in 134 Patients," *Neurosurgery*, 26: 207-210 (1990).
Shuxian, M. and Zhili, C., "Clinical Observation of the Treatment of Hemoptysis by Ultrasonic Atomizing Inhalation of Thrombin", *Chinese Journal of Critical Care Medicine*, 16(2): 30 (1996).
Sidman, K., et al., "Biodegradable, Implantable Sustained Release Systems Based on Glutamic Acid Copolymers," *Journal of Membrane Science*, 7: 227-291 (1979).
Simamora, P., et al., "Controlled delivery of pilocarpine. 2. In-vivo evaluation of Gelfoam® device," *International Journal of Pharmaceutics*, 170(2): 209-214 (1998).
Smith, A., "New and Nonofficial Remedies: Absorbable Gelatin Sponge—Gelfoam-Upjohn," *Council on Pharmacy and Chemistry*, 135(14): p. 921 (1947).
Smith, K., et al., "Delayed Postoperative Tethering of the Cervical Spinal Cord," *Journal of Neurosurgery*, 81: 196-201 (1994).
Springorum, H., "Die Verwendung von Kollagenfolien Zur Uberbruckung von Defekten des Gleitgewebes bei Achillotenotomien and Achillessehnenrupturen," *Akt. Traumatol.*, 15: 120-121, English abstract only on p. 120 (1985).
Sugitachi, A., et al., "A Newly Devised Chemo-Embolic Agent, G.T. XIIIADM," *Gan. To. Kagaku Ryoho*, 12: 1942-1943 (1985). English abstract retrieved from http://www.ncbi.nlm.nih.gov on Jan. 2, 2001.
Sugitachi, A., et al., "Locoregional Therapy in Patients with Malignant Pleural Effusion—Two Different Kinds of 'BAC Therapy'," *Gan. To. Kagaku Ryoho*, 19: 1640-1643 (1992). English abstract retrieved from http://www.ncbi.nlm.nih.gov on Jan. 3, 2001.
Sugitachi, A., et al., "Preoperative Transcatheter Arterial Chemo—Embolization for Locally Advanced Breast Cancer: Application for New Thrombotic Materials." *Japanese Journal of Surgery*, 13: 456-458 (1992).
Surgiflo® Essential Prescribing Information, Hemostatic Matrix (Made from Absorbable Gelatin Sponge, U.S.P.), 1 page (2005).
Surgiflo® haemostatic matrix FlexTip, MS0009, 84 pages (2007).
Surgiflo® Prescription Information, Hemostatic Matrix, (Made from SURGIFOAM* Absorbable Gelatin Sponge U.S.P.) plus FlexTip, 2 pages (2008).
Surgiflo® product leaflet, "Surgiflo® Hemostatic Matrix Kit," 5 pages (2012).
Taheri, Z., "The Use of Gelfoam Paste in Anterior Cervical Fusion," *Journal of Neurosurgery*, 34: 438 (1971).
Tobin, M., et al., "Plugged Liver Biopsy in Patients with Impaired Coagulation," *Digestive Diseases and Science*, 34: 13-15 (1989).
Tucker, H., "Absorbable Gelatin (Gelfoam) Sponge," Springfield, Illinois, Charles T. Thomas, pp. 3-125 (1965).
Van den Bosch, E., et al., "Gelatin degradation at elevated temperature", *International Journal of Biological Macromolecules*, 32: 129-138 (2003).
Vandelli, M.A., et al., "The effect of the crosslinking time period upon the drug release and the dynamic swelling of gelatin microspheres," *Pharmazie*, 46: 866-869 (1991).
Verhoeven, A.G., et al., "XV. The use of microporous polymeric powders for controlled release drug delivery systems," *Controlled Drug Delivery*. Ch. 15, International Symposium of the Association for Pharmaceutical Technology (APV), Bad Homburg, Nov. 12-14 1984, pp. 226-237.
Vinas, F., et al.. "Evaluation of Expanded Polytetrafluoroethylene (ePTFE) versus Polydioxanone (PDS) for the Repair of Dura Mater Defects," *Neurological Research*, 21: 262-268 (1999).
Wallace, D., "The Relative Contribution of Electrostatic Interactions to Stabilization of Collagen Fibrils," *Biopolymers*, 29: 1015-1026 (1990).
Wallace, D., et al., "Injectable Cross-Linked Collagen with Improved Flow Properties," *Journal of Biomedical Materials Research*, 23: 931-945 (1989).

(56) References Cited

OTHER PUBLICATIONS

Warren, W., et al., "Dural Repair Using Acellular Human Dermis: Experience with 200 Cases: Technique Assessment," *Neurosurgery*, 46: 1391-1396 (2000).
Wassersug, J.D., M.D., "Use of Human Thrombin in Some Cases of Pulmonary Hemorrhage" *Pulmonary Hemorrhage*, vol. XVII, pp. 354-356 (Mar. 1950).
Weeks, R., "Microscopy of Soft Materials," *Chapter 1 in Experimental and Computational Techniques in Soft Condensed Matter Physics*, Jeffrey Olafsen, Ed, 2010 (2010).
Wilkinson, H., et al., "Gelfoam Paste in Experimental Laminectomy and Cranial Trephination," *Journal of Neurosurgery*, 54: 664-667 (1981).
Written Opinion of the International Searching Authority (Corrected Version) for International Application No. PCT/DK2005/000063, "Haemostatic Sprays and Compositions", received Jul. 26, 2005.
Written Opinion of the International Searching Authority for International Application No. PCT/DK2005/000475, "Haemostatic Composition Comprising Hyaluronic Acid", received Oct. 24, 2005.
Written Opinion of the International Searching Authority for International Application No. PCT/DK2007/050196, "Wound or Tissue Dressing Comprising Lactic Acid Bacteria".
Written Opinion of the International Searching Authority for International Application No. PCT/DK2009/050048, "Device for Promotion of Hemostatis and/or Wound Healing", completed Aug. 31, 2010.
Xing, Q., et al., "Increasing Mechanical Strength of Gelatin Hydrogels by Divalent Metal Ion Removal", *Sci. Rep.*, 4: 4706: DOI:10.1038/srep04706(2014).
Yaping, G., "Observation and Nursing of the Treatment of Hemoptysis of Pulmonary Tuberculosis by Ultrasonic Atomizing Inhalation of Thrombin", *Journal of Qilu Nursing*, 10(2): 126 (Feb. 2004).
Youwen, W. et al., "Clinical Observation of the Therapeutic Efficacy of the Treatment of 15 Patients with Hemoptysis by Ultrasonic Atomizing Inhalation of Thrombin", *Chengdu Medical Journal*, 30(5): 262 (Oct. 2004).
Yuki, N., et al., "Effects of Endoscopic Variceal Sclerotherapy Using GT XIII on Blood Coagulation Tests and the Renal Kallikrein-Kinin System," *Gastroentral. Japan*, 25: 561-567 (1990). English abstract retrieved from http://www.ncbi.nlm.nih.gov Jan. 2, 2001.
Ziegelaar, B., et al., "The Characterisation of Human Respiratory Epithelial Cells Cultured on Resorbable Scaffords: First Steps Towards a Tissue Engineered Tracheal Replacement," *Biomaterials*, 23: 1425-1438 (2002).
Ziegelaar, B., et al., "Tissue Engineering of a Tracheal Equivalent, Doctoral Thesis," Munich, Germany, Ludwig Maximilians University, 2004, 25 pages (2004).
Zins, M., et al., "US-Guided Percutaneous Liver Biopsy with Plugging of the Needle Track: A Prospective Study in 72 High-Risk Patients," *Radiology*, 184: 841-843 (1992).
Fiss, I., et al., "Use of Gelatin-Thrombin Hemostatic Sealant in Cranial Neurosurgery," *Neurologia Medico-Chirurgica*, 47(10):462-467 (2007).
Mitsuhashi, J., "Invertabrate Tissue Culture Methods," *Springer Lab Manual*, p. 407 (2002).
Oyelese, Yinka, et al., "Postpartum Hemhorrage," *Obstetrics and Gynecology Clinics of North America* 34.3, 421-441 (2007).
Pschyrembel®—Klinisches Wörterbuch, 261st edition, de Gruyter (2007).
Sigma-Aldrich Datasheet for "Hank's Balanced Salts," revised Apr. 2007.
Spotnitz, W. D., et al., "Hemostatus, Sealants, and Adhesives: Components of the Surgical Toolbox," *Transfusion*, 48(7): 1502-1516 (2008).
Stief, T. W., "Kallikrein Activates Prothrombin," *Clinical and Applied Thrombosis/Hemostasis*, 14.1:97-98 (2008).
Non-Final Office Action for U.S. Appl. No. 14/516,728, "Dry Haemostatic Composition", Date of Mailing: Apr. 14, 2015.
Non-Final Office Action for U.S. Appl. No. 14/516,728 dated Nov. 25, 2014 "Dry Haemostatic Composition".
Romanelli, M., et al., "Exudate Management Made Easy", downloaded from http://www.woundsinternational.com, 6 pgs., (Jan. 29, 2010).
Chronic Wound Care Guidelines © 2007 http://woundheal.org. documents/final_pocket_guide_treatment.aspx.

\* cited by examiner

1 Bottom of inner tray
2 Sidewall
3 Mark on sidewall
4 Inner tray notch
5 base
6 handle
7 Sealing surface for lid 3 Mark on sidewall
4 Inner tray notch
5 base
6 handle
7 Sealing surface for lid
8 lid 1 Bottom of inner tray
2 Sidewall
3 Mark on sidewall
5 base
6 handle
7 Sealing surface for lid
8 lid

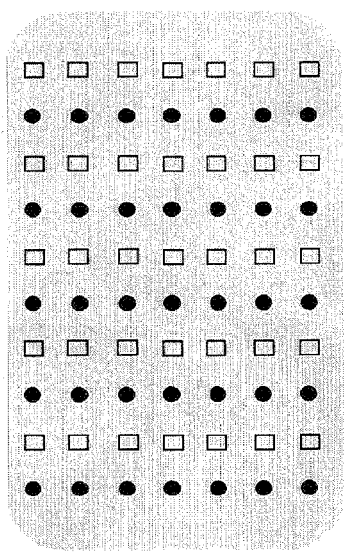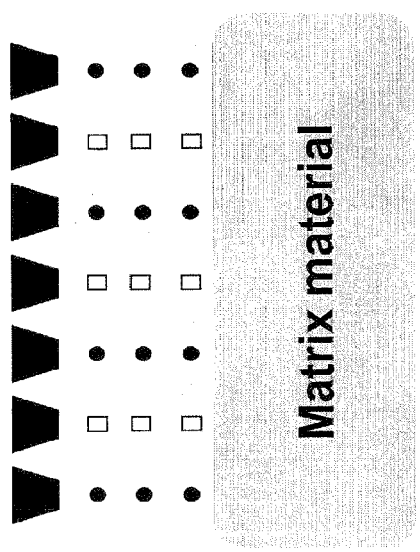
FIG. 7A
FIG. 7B
- Composition A
- Composition B
- Nozzle of print head

DEVICE FOR PROMOTION OF HEMOSTASIS AND/OR WOUND HEALING

This application is a continuation of U.S. application Ser. No. 12/919,643, filed Feb. 27, 2009, which is the U.S. National Stage of International Application No. PCT/DK2009/050048, filed on Feb. 27, 2009, published in English, which claims the benefit of U.S. Provisional Application No. 61/032,495, filed on Feb. 29, 2008, U.S. Provisional Application No. 61/045,416, filed on Apr. 16, 2008 and U.S. Provisional Application No. 61/142,678, filed on Jan. 6, 2009 and claims priority under 35 U.S.C. §119 or 365 to Denmark, Application No. PA 2008 00309 DK, filed on Feb. 29, 2008, PA 2008 00556 DK, filed on Apr. 16, 2008 and PA 2009 00029 DK, filed Jan. 6, 2009. The entire teachings of the above application(s) are incorporated herein by reference.

FIELD OF INVENTION

The present invention relates to a device for promoting hemostasis and/or wound healing as well as to methods for making or using such a device. The device comprises one or more bioactive compounds for promoting hemostasis and/or wound healing. Said bioactive compounds are preferably printed onto the surface of the device. The surface of the device can be the surface of a matrix of the device, such as the surface of a sponge. The invention further relates to a kit of parts comprising said device for promotion of hemostasis and/or wound healing and a container for storage and/or preparation of said device.

BACKGROUND OF INVENTION

The present invention relates to an improved device for promoting hemostasis and/or wound healing, and an improved method for making said device.

WO 2003/004072 discloses a method for coating a medical appliance, such as a stent, with a bubblejet printing head. The coating may comprise pharmaceutically active compounds and may e.g. be in the form of a polymer with a suspended drug or a non-thrombogenic agent.

Xu et al (Biomaterials Vol. 27, 2006, p. 3580-3588) discloses use of alternate inkjet printing of NT2 cells and fibrin gels (formed by the alternate printing of fibrinogen and thrombin), to create 3D cellular structures consisting of layers of neural cells.

U.S. Pat. Nos. 6,361,551 and 6,454,787 both relate to methods for depositing thrombin in solution or powder onto a hemostatic device, such as a sponge comprising collagen. The method of depositing thrombin comprises spraying thrombin in powder form onto the hemostatic device, or coating the device with a thrombin solution and subsequently drying the device of the invention by lyophilization or by conventional means.

U.S. Pat. No. 4,752,466 is directed to a thrombin aerosol. Thrombin is delivered in dry powdered form from a valve-actuated pressurized propellant-containing aerosol container. The thrombin has been lyophilized from an aqueous solution also comprising a thrombin-compatible synthetic polymer.

U.S. Pat. Nos. 6,472,162 and 7,056,722 both concern a thrombin-solution without particles. The particles have been removed by filtration so as to allow using the thrombin-solution as a spray.

U.S. Pat. No. 6,461,325 relates to a device for delivering fibrin and forming fibrin on a surface. The device delivers volumetric quantities of a first and a second biochemically reactive fluid comprising a spray unit for separately atomizing the first and second biochemically reactive fluids into an aerosol. The first or second biochemically reactive fluids may comprise thrombin.

U.S. Pat. No. 6,113,948 relates to soluble microparticles comprising thrombin or fibrinogen in free-flowing form. The microparticles can be mixed to give a dry powder to be used as a fibrin sealant that is activated only at a wound site. The microparticles are produced by spray-drying.

US 2003/0175419 relates to methods for preparing biomimetic scaffolds by using at least two bio-ink solutions. The bio-ink solutions can be deposited individually or simultaneously. One bio-ink, which is structural, can comprise thrombin, and inkjet technology can be employed to deposit the bio-inks of the biomimetic scaffold. Another form of a bio-ink can comprise gelatin.

U.S. Pat. No. 6,416,739 discloses microcapsules comprising thrombin for therapeutic use.

U.S. Pat. No. 6,649,162 is related to a hemostatic sponge based on collagen and thrombin and a method for producing such a sponge as well as a wound coverage containing said sponge. Thrombin is homogenously distributed in the sponge.

The prior art has not addressed sufficiently the issue of providing an improved matrix material, such as a sponge, comprising a pharmaceutical composition comprising one or more agents or bioactive agents, such as thrombin; wherein said composition is initially in fluid or liquid form and applied onto the surface of said matrix material by printing the fluid or liquid composition in individual and discrete locations onto the surface of the matrix material, thus obtaining an essentially uniform distribution of said fluid or liquid composition.

The printing technology according to the present invention allows for a more precise distribution of the composition onto the surface of the matrix material by applying an amount of the fluid or liquid composition which preferably prevents swelling of the matrix material. The invention avoids waste of fluid or liquid composition by exploiting the printing technology's more precise distribution of the fluid or liquid composition onto the matrix material. Compared to conventional techniques in the art, such as spraying, a more uniform distribution of the composition is also achieved.

SUMMARY OF THE INVENTION

In one aspect the present invention relates to a matrix material comprising a surface and a plurality of open and interconnected cells, wherein the surface of said matrix comprises a pharmaceutical composition comprising one or more bioactive agents, such as thrombin, printed onto said surface of the matrix material at individual and discrete locations.

The invention further relates to a matrix material comprising a pharmaceutical composition, such as thrombin, wherein said bioactive agent is printed onto the surface of said matrix material.

The present invention further relates to a device comprising the matrix material and a pharmaceutical composition as described above.

The present invention also relates to a kit of parts comprising the device described above and at least one additional component. In one embodiment the kit of parts comprises a container e.g. for sterile storage and/or preparation of said device. The container can be used to add liquid to the matrix material prior to use.

In another aspect the present invention relates to a method for making the device described above comprising the steps of 1) providing a matrix material and 2) printing a pharmaceutical composition in fluid or liquid form comprising one or more bioactive agents onto the surface of said matrix material e.g. at individual and discrete locations.

In yet another aspect the present invention relates to the use of the device or kit of parts described above to promote wound healing and/or hemostasis in an individual in need thereof.

The present invention is directed in another aspect to a method for manufacturing a matrix material comprising a pharmaceutical composition comprising one or more agents or bioactive agents deposited on the accessible, external surface of said matrix material in discrete locations thereof, said method comprising the steps of i. providing a matrix material,
ii. providing a printing device comprising a) one or more print heads each comprising one or more nozzles, and b) one or more reservoirs each comprising a pharmaceutical composition comprising the one or more agents or bioactive agents in solubilised form, or in the form of a suspension, wherein the pharmaceutical composition is in fluid or liquid form,
   said reservoir being connected to a degassing device and operably connected with said one or more print heads so that the fluid or liquid composition comprising the one or more agents or bioactive agents can be diverted from said reservoir to said one or more print heads,
   actuating the one or more print heads and diverting from each nozzle of each print head one or more droplets of the fluid or liquid composition comprising the one or more agents or bioactive agents to a predetermined and discrete location of the accessible, external surface of said matrix material,
   wherein, preferably, each droplet of the fluid or liquid composition contains a volume of liquid of less than about 100 nanoliters, such as less than about 80 nanoliters, for example less than about 60 nanoliters, such as less than about 40 nanoliters, for example less than about 20 nanoliters, such as less than about 10 nanoliters, for example less than about 1 nanoliter, such as less than about 0.8 nanoliters, for example less than about 0.6 nanoliters, such as less than about 0.4 nanoliters, for example less than about 0.2 nanoliters, such as less than about 0.1 nanoliters, for example less than about 0.08 nanoliters, such as less than about 0.06 nanoliters, for example less than about 0.04 nanoliters, such as less than about 0.02 nanoliters, for example less than about 0.015 nanoliters, such as less than about 0.010 nanoliters, for example less than about 0.005 nanoliters, such as less than about 0.004 nanoliters, for example less than about 0.002 nanoliters, such as less than about 0.001 nanoliters,
   wherein the distance covered by each droplet of fluid or liquid composition comprising the one or more agents or bioactive agents from the point of departure of each nozzle of each printing head to the point of impacting the accessible, external surface of the matrix material at a predetermined and discrete location thereof, is essentially the shortest possible distance, such as essentially the shortest distance defined by a diversion of droplet(s) from each nozzle head, which is the distance which is essentially perpendicular to the accessible, external surface of the matrix at the predetermined and discrete position of the surface where a given droplet impacts the matrix material,
   wherein, preferably, the distance from each nozzle head to the predetermined and discrete location to be impacted, at the time of actuating the nozzle head and initialising the diversion of said droplet(s) of liquid composition comprising the one or more solubilised, bioactive agents from the nozzle head to a given, predetermined and discrete location, is essentially similar for each droplet of the fluid or liquid composition and is less than about 4 millimeters, such as less than about 3.5 millimeters, for example less than about 3 millimeters, such as less than about 2.5 millimeters, for example less than about 2 millimeters, such as less than about 1.5 millimeters, for example less than about 1.2 millimeters, such as less than about 1.0 millimeters, for example less than about 0.8 millimeters, such as less than about 0.6 millimeters, for example less than about 0.4 millimeters, such as less than about 0.2 millimeters, for example less than about 0.1 millimeters,
   wherein, preferably, the liquid portion of each droplet of the composition comprising the one or more solubilised agents or bioactive agents evaporates essentially on impacting the accessible, external surface of the matrix material, wherein said evaporation is determined at least by the kinetic energy of the liquid of the droplet, including the temperature of the liquid of the droplet, the temperature of the matrix material and the temperature of the environment in which the impacting of the droplet and the matrix material takes place,
   wherein, preferably, said evaporation of said liquid part of said droplets of the composition comprising the one or more solubilised agents or bioactive agents results in essentially no swelling of the matrix material at the predetermined and discrete locations of the accessible, external surface of the matrix which are impacted by the droplets of the composition comprising the one or more solubilised, bioactive agents,
   wherein, preferably, said evaporation and/or said essentially no swelling of the matrix material results in the provision of a matrix material comprising a solid composition comprising one or more agents or bioactive agents deposited in solid form on the accessible, external surface of said matrix material in discrete locations thereof,
   wherein, preferably, the accessible and external surface of said matrix material has essentially the same physico-chemical properties before being impacted and after being impacted with the droplets of the composition comprising the one or more solubilised agents or bioactive agents.

The one or more bioactive agents can be thrombin or thrombin in combination with fibrinogen, or thrombin and fibrinogen in combination with Factor XIII, or thrombin and fibrinogen and Factor XIII in combination with tranexamic acid.

The one or more agents or bioactive agents may be comprised in the same fluid or liquid composition contained in the same reservoir and expelled from the same print head comprising one or more nozzles, or the one or more bioactive agents may be comprised in separate fluid or liquid compositions contained in separate reservoirs and expelled from separate print heads each comprising one or more nozzles or expelled from different channels of the same print head.

There is also provided a printing device comprising a) one or more print heads each comprising one or more nozzles, and b) one or more reservoirs each comprising a fluid or liquid composition comprising the one or more bioactive agents in solubilised form, such as the bioactive agents and combinations thereof cited herein immediately above, wherein said reservoir is connected to a degassing device and operably connected with said one or more print heads so that the liquid composition comprising the one or more solubilised, bioactive agents can be diverted from said reservoir to said one or more print heads and released from said print heads as droplets of a predetermined volume upon actuation of the nozzles of said print heads.

In one embodiment, two or more fluid or liquid compositions each comprising one or more agents or bioactive agents may be imprinted at the same or different discrete positions on the surface of said matrix material.

The two or more pharmaceutical compositions initially in fluid or liquid form may each comprise one or more bioactive agents which may be thrombin or thrombin in combination with fibrinogen, or thrombin and fibrinogen in combination with Factor XIII, or thrombin and fibrinogen and Factor XIII in combination with tranexamic acid.

It is understood, that printing onto a surface of a matrix material may comprise printing on the surface of any side of the matrix material. Thus, all or some of the planes of the matrix material may be imprinted. In one embodiment, the matrix material is a cube comprising six (6) planes, in which one or more planes are imprinted, such as 1 plane, for example 2 planes, such as 3 planes, for example 4 planes, such as 5 planes, for example 6 planes.

In a further aspect there is provided a composition comprising either thrombin, or thrombin in combination with fibrinogen, or thrombin and fibrinogen in combination with Factor XIII, or thrombin and fibrinogen and Factor XIII in combination with tranexamic acid, wherein said composition further comprises a viscosity modulating agent and optionally further a surfactant, wherein said composition preferably has a cps (centipoise) of at least 4 cps, such as at least 6 cps, for example at least 8 cps, such as at least 10 cps, for example at least 12 cps, and preferably less than 100 cps, such as less than 80 cps, for example less than 60 cps, for example less than 40 cps, such as less than 20 cps, for example less than 15 cps.

In a further embodiment there is provided a composition comprising either thrombin, or thrombin in combination with fibrinogen, or thrombin and fibrinogen in combination with Factor XIII, or thrombin and fibrinogen and Factor XIII in combination with tranexamic acid, wherein said composition preferably further comprises a viscosity modulating agent and optionally further a surfactant, wherein said composition preferably has a surface tension of between 0.020 to 0.050 N/m; for example 0.020-0.022 N/m, such as 0.022-0.024 N/m, for example 0.024-0.026 N/m, such as 0.026-0.028 N/m, for example 0.028-0.030 N/m, such as 0.030-0.032 N/m, for example 0.032-0.034 N/m, such as 0.034-0.036 N/m, for example 0.036-0.038 N/m, such as 0.038-0.040 N/m, for example 0.040-0.042 N/m, such as 0.042-0.044 N/m, for example 0.044-0.046 N/m, such as 0.046-0.048 N/m, for example 0.048-0.050 N/m.

In another aspect the present invention relates to a matrix material comprising a surface and a plurality of open and interconnected cells, wherein the surface of said matrix is printed with thrombin in individual and discrete locations. It has been found that the matrix printed with thrombin is surprisingly sticky when it e.g. is used for one or more dry applications. Traditionally, a hemostatic composition has comprised a mixture of thrombin and fibrinogen, which leads to generation of fibrin and a sticky effect. The present invention relates in one embodiment to a sticky pharmaceutical composition printed onto a matrix, where the pharmaceutical composition does not comprise fibrin and/or fibrinogen.

The sticky effect of the pharmaceutical composition on the matrix is observed by printing of thrombin in the range from 0.5 IU/cm$^2$ to 50 IU/cm$^2$, such as from 0.5 IU/cm$^2$ to 1 IU/cm$^2$, for example from 1 IU/cm$^2$ to 2 IU/cm$^2$, such as from 2 IU/cm$^2$ to 3 IU/cm$^2$, for example from 3 IU/cm$^2$ to 4 IU/cm$^2$, such as from 4 IU/cm$^2$ to 5 IU/cm$^2$, for example from 5 IU/cm$^2$ to 6 IU/cm$^2$, such as from 6 IU/cm$^2$ to 7 IU/cm$^2$, for example from 7 IU/cm$^2$ to 8 IU/cm$^2$, such as from 8 IU/cm$^2$ to 9 IU/cm$^2$, for example from 9 IU/cm$^2$ to 10 IU/cm$^2$, such as from 10 IU/cm$^2$ to 11 IU/cm$^2$, for example from 11 IU/cm$^2$ to 12 IU/cm$^2$, such as from 12 IU/cm$^2$ to 13 IU/cm$^2$, for example from 13 IU/cm$^2$ to 14 IU/cm$^2$, such as from 14 IU/cm$^2$ to 15 IU/cm$^2$, for example from 15 IU/cm$^2$ to 16 IU/cm$^2$, such as from 16 IU/cm$^2$ to 17 IU/cm$^2$, for example from 17 IU/cm$^2$ to 18 IU/cm$^2$, such as from 18 IU/cm$^2$ to 19 IU/cm$^2$, for example from 19 IU/cm$^2$ to 20 IU/cm$^2$, such as from 20 IU/cm$^2$ to 21 IU/cm$^2$, for example from 21 IU/cm$^2$ to 22 IU/cm$^2$, such as from 22 IU/cm$^2$ to 23 IU/cm$^2$, for example from 23 IU/cm$^2$ to 24 IU/cm$^2$, such as from 24 IU/cm$^2$ to 25 IU/cm$^2$, for example from 25 IU/cm$^2$ to 26 IU/cm$^2$, such as from 26 IU/cm$^2$ to 27 IU/cm$^2$, for example from 27 IU/cm$^2$ to 28 IU/cm$^2$, such as from 28 IU/cm$^2$ to 30 IU/cm$^2$, for example from 30 IU/cm$^2$ to 32 IU/cm$^2$, such as from 32 IU/cm$^2$ to 34 IU/cm$^2$, for example from 34 IU/cm$^2$ to 36 IU/cm$^2$, such as from 36 IU/cm$^2$ to 38 IU/cm$^2$, for example from 38 IU/cm$^2$ to 40 IU/cm$^2$, such as from 40 IU/cm$^2$ to 42 IU/cm$^2$, for example from 42 IU/cm$^2$ to 44 IU/cm$^2$, such as from 44 IU/cm$^2$ to 46 IU/cm$^2$, for example from 46 IU/cm$^2$ to 48 IU/cm$^2$, such as from 48 IU/cm$^2$ to 50 IU/cm$^2$.

In one preferred embodiment the amount of thrombin printed onto the matrix is in the range from 0.5 IU/cm$^2$ to 50 IU/cm$^2$, such as 1 IU/cm$^2$, for example 2 IU/cm$^2$, such as 3 IU/cm$^2$, for example 4 IU/cm$^2$, such as 5 IU/cm$^2$, for example 6 IU/cm$^2$, such as 7 IU/cm$^2$, for example 8 IU/cm$^2$, such as 9 IU/cm$^2$, for example 10 IU/cm$^2$, such as 12 IU/cm$^2$, for example 14 IU/cm$^2$, such as 16 IU/cm$^2$, for example 18 IU/cm$^2$, such as 20 IU/cm$^2$, for example 22 IU/cm$^2$, such as 24 IU/cm$^2$, for example 26 IU/cm$^2$, such as 28 IU/cm$^2$, for example 30 IU/cm$^2$, such as 32 IU/cm$^2$, for example 34 IU/cm$^2$, such as 36 IU/cm$^2$, for example 38 IU/cm$^2$, such as 40 IU/cm$^2$, for example 42 IU/cm$^2$, such as 44 IU/cm$^2$, for example 46 IU/cm$^2$, such as 48 IU/cm$^2$, for example 50 IU/cm$^2$ e.g. to obtain a sticky effect for one or more dry applications.

It has surprisingly been demonstrated that the sticky effect of thrombin on the matrix material is observed only when thrombin is printed onto said matrix material in accordance with the methods of the present invention. Spraying of thrombin onto the matrix material does not result in a sticky effect.

In one embodiment the printing of thrombin onto a matrix material results after dry application in a stickiness exemplified by requirement of an amount of tension force in Newtons (1 g mass exerts. 9.81 N) needed to pull a 2 cm$^2$ matrix from the skin is in the piconewton range, nanonewton range, micronewton range or in the millinewton range.

In another embodiment the printing of thrombin onto a matrix material results after dry application in a stickiness exemplified by requirement of an amount of tension force in Newtons (1 g mass exerts. 9.81 N) needed to pull a 2 cm² matrix from the skin of is more than 0.001 Newton, such as more than 0.01 Newton, for example 0.1 Newton, such as more than 0.5 Newton, for example 1 Newton, such as more than 10 Newton, for example 50 Newton, such as more than 100 Newton, for example 250 Newton, such as more than 500 Newton, for example 1,000 Newton.

A surprising hemostatic effect has been demonstrated for a matrix printed with a relatively low dose of thrombin for use in one or more dry applications.

In one further embodiment, any matrix material, such as a matrix material printed or otherwise coated with a pharmaceutical composition comprising one or more bioactive agents, for example thrombin, is provided in a container suitable for storing and preparing said matrix sealed from an external environment.

Storage of the matrix material in the container according to the present invention provides a sterile environment, and preparation of the matrix in the container may include the addition to the container of a suitable amount of any pharmaceutically acceptable liquid to moisten the matrix adequately.

Said container provides a means for easier addition of an appropriate and predetermined amount of liquid to the matrix, and it follows that the matrix will not be drained with excessive amounts of liquid to reduce the potential disadvantage of detachment of the pharmaceutical composition from the matrix into the excess liquid, and furthermore the moistened matrix material is easier to handle and apply to a wound or site of bleeding when not being excessively moistened. The container is very stable and hence simplifies storage of prepared product on uneven surfaces.

Definitions

IU: In pharmacology, the International Unit or IU is a unit of measurement for the amount of a substance, based on measured biological activity or effect. The precise definition of one IU differs from substance to substance and is established by international agreement for each substance. There is no equivalence among different substances; for instance, one IU of vitamin E does not contain the same number of milligrams as one IU of vitamin A. To define an IU of a substance, the Committee on Biological Standardization of the World Health Organization provides a reference preparation of the substance, arbitrarily sets the number of IUs contained in that preparation, and specifies a biological procedure to compare other preparations of that substance to the reference preparation. The goal in setting the standard is that different preparations with the same biological effect will contain the same number of IUs.

Human thrombin activity is expressed in international units (IU) obtained by comparison towards the current WHO International Standard, using fibrinogen as substrate. The current WHO International Standard is named WHO 2nd International Standard for Thrombin 01/580 (In US: US FDA/CBER Thrombin Standard Lot K), and contains 110 IU by definition.

A degassing device is any device or structure used for alleviation of gaseous build-up in a liquid comprised in a reservoir.

The term "Sticky" as used herein means that the substance has the property of adhering to or sticking to a surface. Stickiness can be measures as an adhesive force. Five mechanisms have been proposed to explain why one material sticks to another: 1) Mechanical adhesion: Adhesive materials fill the voids or pores of the surfaces and hold surfaces together by interlocking. Sewing forms a large scale mechanical bond, velcro forms one on a medium scale, and some textile adhesives form one at a small scale. This is similar to surface tension. 2) Chemical adhesion: Two materials may form a compound at the join. The strongest joins are where atoms of the two materials swap (ionic bonding) or share (covalent bonding) outer electrons. A weaker bond is formed if oxygen, nitrogen or fluorine atoms of the two materials share a hydrogen nucleus (hydrogen bonding). 3) Dispersive adhesion: In dispersive adhesion, also known as adsorption, two materials are held together by van der Waals forces: the attraction between two molecules, each of which has regions of positive and negative charge. In the simple case, such molecules are therefore polar with respect to average charge density, although in larger or more complex molecules, there may be multiple "poles" or regions of greater positive or negative charge. These positive and negative poles may be a permanent property of a molecule (Keesom forces) or a transient effect which can occur in any molecule, as the random movement of electrons within the molecules may result in a temporary concentration of electrons in one region (London forces). 4) Electrostatic adhesion: Some conducting materials may pass electrons to form a difference in electrical charge at the join. This results in a structure similar to a capacitor and creates an attractive electrostatic force between the materials. 5) Diffusive adhesion: Some materials may merge at the joint by diffusion. This may occur when the molecules of both materials are mobile and soluble in each other. This would be particularly effective with polymer chains where one end of the molecule diffuses into the other material. It is also the mechanism involved in sintering. When metal or ceramic powders are pressed together and heated, atoms diffuse from one particle to the next. This joins the particles into one. The strength of the adhesion between two materials depends on which of the above mechanisms occur between the two materials, and the surface area over which the two materials contact. Materials that wet against each other tend to have a larger contact area than those that do not. Wetting depends on the surface energy of the materials.

"Stickiness" or "Adhesive force" can be measured by by one of the methods described in U.S. Pat. No. 4,194,392, US 20060282138 or U.S. Pat. No. 6,584,858. Stickiness in scientific terms is called adhesion. Adhesion is measured in terms of adhesive force in Newtons (N). The higher the adhesive force, the higher will be the number of Newtons required to peel one object from the other.

"Hemostasis" is a term that refer to the physiologic process whereby bleeding is halted. It consists of multiple steps including 1) vasoconstriction to minimize vessel lumen diameter and slow bleeding, 2) platelet aggregation, 3) coagulation and 4) fibrinolysis whereby the blood clot is degraded.

Hemostatic agents are used herein interchangeably with the terms thrombogenic, thrombotic and pro-coagulant agents. Hemostatic agents are agents that induce blood clotting or hemostasis.

The term "blood clotting cascade" or "blood coagulation cascade" is part of secondary hemostasis and refers to the multi-step process whereby blood and vessel components react to stimuli by the enzymatic activation of coagulation factors sequentially, ultimately resulting in the formation of a solid blood clot comprising fibrin gel and platelets.

Vasoconstriction is a narrowing of the blood vessels resulting from contracting of the muscular wall of the vessels. When blood vessels constrict, the flow of blood is restricted or slowed. Factors causing vasoconstriction are called vasoconstrictor, also vasopressors or simply pressors. Vasoconstriction is mostly the result of increased intracellular concentration of calcium ($Ca^{2+}$). However, specific mechanisms for generating an increased intracellular concentration of calcium depend on the vasoconstrictor. In any case, this calcium results in contraction of smooth muscle resulting in a constriction of the vessel.

"Thrombosis" refers to thrombus formation, and a "thrombus" is a blood clot i.e. the final step in the blood coagulation cascade of hemostasis. A thrombus is physiologic in cases of injury, but pathologic in case of thrombosis thus occurring in an intact blood vessel.

An "embolism" occurs when an object (the embolus, plural emboli) migrates from one part of the body (through circulation) and cause(s) a blockage (occlusion) of a blood vessel in another part of the body.

A "Bioactive agent" is any agent, drug, compound, composition of matter or mixture which provides some pharmacologic, often beneficial, effect that can be demonstrated in-vivo or in vitro. As used herein, this term further includes any physiologically or pharmacologically active substance that produces a localized or systemic effect in an individual. Further examples of bioactive agents include, but are not limited to, agents comprising or consisting of an oligosaccharide, agents comprising or consisting of a polysaccharide, agents comprising or consisting of an optionally glycosylated peptide, agents comprising or consisting of an optionally glycosylated polypeptide, agents comprising or consisting of an oligonucleotide, agents comprising or consisting of a polynucleotide, agents comprising or consisting of a lipid, agents comprising or consisting of a fatty acid, agents comprising or consisting of a fatty acid ester and agents comprising or consisting of secondary metabolites. It may be used either prophylactically, therapeutically, in connection with treatment of an individual, such as a human or any other animal.

The terms "drug," "medicament," or "bioactive substance/agent" (i.e., biologically active substance/agent) as used herein include, biologically, physiologically, or pharmacologically active substances that act locally or systemically in the human or animal body.

The terms "treating", "treatment" and "therapy" as used herein refer equally to curative therapy, prophylactic or preventative therapy and ameliorating therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

A "treatment effect" or "therapeutic effect" is manifested if there is a change in the condition being treated, as measured by the criteria constituting the definition of the teams "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

"Pharmacologically effective amount", "pharmaceutically effective amount" or "physiologically effective amount" of a "bioactive agent" is the amount of an active agent present in a pharmaceutical composition as described herein that is needed to provide a desired level of active agent in the bloodstream or at the site of action in an individual (e.g., the lungs, the gastric system, the colorectal system, prostate, etc.) to be treated to give an anticipated physiological response when such composition is administered. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein. An "effective amount" of a bioactive agent can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The terms "enhancing" and "improving" a beneficial effect, and variations thereof, as used herein, refers to the therapeutic effect of the bioactive agent against placebo, or an increase in the therapeutic effect of a state-of-the-art medical treatment above that normally obtained when a pharmaceutical composition is administered without the bioactive agent of this invention. "An increase in the therapeutic effects" is manifested when there is an acceleration and/or increase in intensity and/or extent of the therapeutic effects obtained as a result of administering the bioactive agent(s). It also includes extension of the longevity of therapeutic benefits. It can also manifest where a lower amount of the pharmaceutical composition is required to obtain the same benefits and/or effects when it is co-administered with bioactive agent(s) provided by the present invention as compared to the administration in a higher amount of the pharmaceutical composition in the absence of bioactive agent. The enhancing effect preferably, but not necessarily, results in treatment of acute symptoms for which the pharmaceutical composition alone is not effective or is less effective therapeutically. Enhancement is achieved when there is at least a 5% increase in the therapeutic effects, such as at least 10% increase in the therapeutic effects when a bioactive agent of the present invention is co-administered with a pharmaceutical composition compared with administration of the pharmaceutical composition alone. Preferably the increase is at least 25%, more preferably at least 50%, even more preferably at least 75%, most preferably at least 100%.

"Co-administering" or "co-administration" of bioactive agent(s), or bioactive agents and state-of-the-art medicaments, as used herein, refers to the administration of one or more bioactive agents of the present invention, or administration of one or more bioactive agents of the present invention and a state-of-the-art pharmaceutical composition within a certain time period. The time period is preferably less than 72 hours, such as 48 hours, for example less than 24 hours, such as less than 12 hours, for example less than 6 hours, such as less than 3 hours. However, these terms also mean that the bioactive agent and a therapeutic composition can be administered together.

The term "Individual" refers to vertebrates, particular members of the mammalian species, and includes, but is not limited to domestic animals, such as cattle, horses, pigs, sheep, mink, dogs, cats, mice, guinea pigs, rabbits, rats; sports animals, such as horses, poly ponies, dogs, camels, and primates, including humans.

The term "Kit of parts" as used in the present invention provides the matrix material according to the present invention, such as a matrix material printed with thrombin, and at least one additional component. The additional component may in one embodiment be a container as specified herein. Accordingly, in one embodiment the kit comprises instructions for use of the matrix material.

'Wound': The term refers to cuts, incisions, abrasions, lacerations, amputations, burns induced by heat, ionizing radiation, ultraviolet radiation including sunlight, electricity, or chemical substances as well as to other forms of lesions such as ulcers, pressure sores and bedsores.

"Partial thickness wound" refers to wounds that encompass Grades I-III; examples of partial thickness wounds include burn wounds, pressure sores, venous stasis ulcers, and diabetic ulcers.

"Deep wound" is meant to include both Grade III and Grade IV wounds. The present invention contemplates treating all wound types, including deep wounds and chronic wounds.

"Chronic wound" refers to a wound that has not healed within 30 days. "Alginate" refers to a linear co-polymer with homopolymeric blocks of (1-4)-linked β-D-mannuronate (M) and its C-5 epimer α-L-guluronate (G) residues, respectively, covalently linked together in different sequences or blocks.

"Hydrocolloid" refers to a colloid system in which the colloid-forming components are dispersed in water, but not cross-linked. A colloid system is a system or mixture in which two substances are interspersed between each other. A hydrocolloid has colloid particles spread throughout water and depending on the quantity of water available can take on different states, e.g: gel-like consistency or a sol (liquid). Hydrocolloids can be either irreversible (single state) or reversible. Examples include carrageenan, gelatin and pectin.

"Wound healing-promoting agent" is any agent capable of accelerating the wound healing process.

"Promote wound healing" and "accelerate wound healing," and similar phrases, refer to either the induction of the formation of granulation tissue of wound contraction and/or the induction of epithelialization (i.e., the generation of new cells in the epithelium). Wound healing is conveniently measured by decreasing wound area.

A 'hydrogel' is a network of polymer chains that are water-insoluble, sometimes found as a colloidal gel in which water is the dispersion medium. Hydrogels are superabsorbent (they can contain over 99% water) natural or synthetic polymers. Hydrogels possess also a degree of flexibility very similar to natural tissue, due to their significant water content.

A 'polymer' is a substance composed of molecules with large molecular mass composed of repeating structural units, or monomers, connected by covalent chemical bonds. The word is derived from the Greek, polu, "many"; and meros, "part". Well known examples of polymers include plastics, DNA and proteins. A simple example is polypropylene. While the term "polymer" in popular usage suggests "plastic", polymers comprise a large class of natural and synthetic materials with a variety of properties and purposes. Natural polymer materials include shellac, amber and cellulose, which is the main constituent of wood and paper. There are three main classes of 'biopolymers': polysaccharides, polypeptides (proteins), and polynucleotides. A heteropolymer or copolymer is a polymer derived from two (or more) monomeric species, as opposed to a homopolymer where only one monomer is used.

'Polysaccharides' are relatively complex carbohydrates. They are polymers made up of many monosaccharides joined together by glycosidic bonds. They are therefore very large, often branched, macromolecules. They tend to be amorphous, insoluble in water, and have no sweet taste. When all the monosaccharides in a polysaccharide are the same type the polysaccharide is called a homopolysaccharide, but when more than one type of monosaccharide is present they are called heteropolysaccharides. Examples include storage polysaccharides such as starch and glycogen and structural polysaccharides such as cellulose and chitin. Polysaccharides have a general formula of $C_n(H_2O)_{n-1}$ where n is usually a large number between 200 and 2500. Considering that the repeating units in the polymer backbone are often six-carbon monosaccharides, the general formula can also be represented as $(C_6H_{10}O_5)_n$ where n={40 . . . 3000}.

'Peptides' are short polymers formed from the linking, in a defined order, of α-amino acids. The link between one amino acid residue and the next is known as an amide bond or a peptide bond. Proteins are 'polypeptide' molecules (or consist of multiple polypeptide subunits). The distinction is that peptides are short and polypeptides/proteins are long.

'Cross-links' are bonds that link one polymer chain to another. They can be covalent bonds or ionic bonds. "Polymer chains" can refer to synthetic polymers or natural polymers (such as proteins). When the term "cross-linking" is used in the synthetic polymer science field, it usually refers to the use of cross-links to promote a difference in the polymers' physical properties. When "crosslinking" is used in the biological milieu, it can be in reference to its use as a probe to link proteins together to check protein-protein interactions, as well as other creative cross-linking methodologies.

A 'drop' or 'droplet' is a small volume of liquid or fluid, bounded completely or almost completely by free surfaces. The volume of a drop is not well-defined: it depends on the device and technique used to produce the drop and on the physical properties of the fluid. A droplet according to the present invention has been defined regarding size elsewhere (pico to nano litre range).

A 'Surface' according to the present invention refers to the outer layer or outer part of a matrix material, which is the part that may be accessible for printing and thus do not comprise the inner and inaccessible part of the material. By accessible is meant accessible for a printing technique according to the present invention. The surface in such a setting may be the outer few millimeters of the material, and may be uneven or porous. The surface in one setting may be one-dimensional.

'Printing' according to the present invention refers to the deposition of a fluid or liquid composition onto the surface of a matrix material, in which the fluid or liquid composition in the form of droplet(s) makes contact with the surface of the matrix material of interest, and the solvent or liquid component of the droplet subsequently evaporates to leave a solid or dry composition on the surface of the printed matrix material. The small volume of fluid or liquid composition and the rapid evaporation of the solvent or liquid component means that essentially no swelling of the matrix material will occur. The printing technology should be distinguished from technologies such as 'spraying', 'dipping' or 'coating', as the printing method is more precise, more cost-effective, and results in a more uniform distribution of the composition (hence, the agent or bioactive agent of the composition) at discrete positions on the surface of a matrix. Printing furthermore occur perpendicular to the surface of the substrate, making the distance between nozzles of the print head and the surface of the substrate essentially identical for all droplets of the fluid or liquid composition. Further, the distance traversed by each droplet of the composition is in general shorter for printing than for spraying. Printing and jetting are used interchangeably herein. One means of printing involves the 'inkjet' printing technology.

'Perpendicular to the surface' is understood in that the droplet expelled from the nozzle will contact the surface of the matrix material essentially directly below the nozzle. Thus, the angle between the straight line of the distance that the droplet traverses from the nozzle and the nozzle of the print head will be essentially 90°. Deviations of up to about 5% from a 90° angle can be tolerated.

"Sterile storage" means that a compartment, container or box used for storage of the matrix material should facilitate a micro-environment made essentially free of infectious microorganisms at least to a degree which satisfies the intended use of the matrix material. To obtain sterility, a sterile matrix material could either be packed under sterile conditions, or a matrix material could be sealed within the packaging and subsequently be sterilised by methods known in the art, e.g. by radiation.

A pharmaceutical composition as used herein is a composition comprising one or more agents or bioactive agents, either in solid or dry form (after printing and evaporation) or in fluid or liquid form (prior to and during printing).

A fluid or liquid composition is a pharmaceutical composition in fluid or liquid form, used for printing onto the surface of a matrix material.

A solid composition is a pharmaceutical composition which was initially in fluid or liquid form, which has been printed onto the surface of a matrix material, and wherein the liquid portion or solvent component of each droplet of the fluid or liquid composition comprising the one or more solubilised agents or bioactive agents has evaporated essentially on impacting the surface of the matrix material.

DESCRIPTION OF DRAWINGS

In FIG. 1A, spraying occurs in an angled manner whereby the distance from nozzle to surface of the matrix material varies for the droplets from individual nozzles. Therefore, the composition will be deposited at higher density in the middle of the spray and a lower density at the edge of the spray, to make a concentration gradient. As shown in FIG. 1B, printing occur perpendicular to the surface of the matrix material, whereby the distance from nozzle to surface of the matrix material is identical for each droplet expelled form the nozzle. The deposited material will therefore be uniformly distributed. The distance from nozzle to surface of the matrix material is in general larger for spraying techniques than for printing techniques. The distance between the nozzle of the print head and surface of the matrix material is defined in the text. These features makes printing more precise and efficient than spraying, enabling printing in individual and discrete locations on the matrix material, and providing a uniform distribution of a smaller volume of the printer composition than that required by conventional techniques, such as spraying (please refer to text for more detail on this subject).

FIGS. 7A and 7B illustrate the printing of two different fluid or liquid compositions each comprising at least one agent or bioactive agent (composition A and composition B), wherein printing occurs at different and discrete positions for each composition onto the surface of a matrix material. The fluid or liquid compositions A and B may comprise agents or bioactive agents which are not compatible when comprised in the same fluid or liquid composition, and the printing technology allows for said incompatible agents or bioactive agents to be printed separately but in close proximity to each other, for example in alternating positions on the surface of a matrix material. FIG. 7A illustrates the printing of two different fluid or liquid compositions from a sideview; FIG. 7A is a topview of a matrix material which has been imprinted with compositions A and B in alternating discrete positions on the surface of the matrix material.

DETAILED DESCRIPTION OF THE INVENTION

Figure 1A:
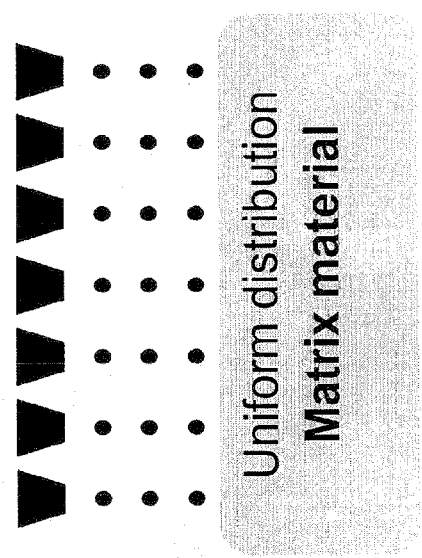
FIGS. 1A and 1B illustrates the modes of A) spraying and B) printing, to illustrate features of each method for depositing a fluid or liquid composition comprising one or more bioactive agents onto a surface of a matrix material. Differences between the two modes of application are thus illustrated.

Embodiments of the present invention are disclosed herein below with a view of disclosing both the present invention and equivalents thereof which are within reach of a skilled person having read the present application.

Deposition of a Pharmaceutical Composition onto a Surface by Printing

The present invention in one embodiment relates to a medical device comprising a composition, such as a pharmaceutical composition, which is deposited in discrete and individual positions onto the surface of the device, such as onto the surface of a matrix material of the device. The deposition of the composition is preferably achieved by printing the fluid or liquid composition onto the surface of the device, such as in a manner achieved by inkjet printing or any similar form of printing technology.

It follows that a fluid or liquid composition according to the present invention may be any liquid or gaseous composition, and covers any solution, suspension and emulsion. In one embodiment, the fluid or liquid composition is a particulate composition, which may be liquid, gaseous, solid or dry. A particulate composition may be employed if the size of the particles does not exceed the nozzle diameter which the composition exits from the print head (see below).

Printing the composition onto the surface of the device by using e.g. inkjet printing technologies does not involve a direct contact between a printing head and the surface of the device. To position a drop by printing is more precise and should be distinguished from e.g. spraying or coating the composition onto the device, or by otherwise contacting the device with the composition e.g. by contacting the device with the composition in any suitable fluid or liquid form, including dipping the device into a composition in liquid form.

Printing allows for a more uniform distribution of the composition. Further, the composition can be positioned at individual and discrete locations or positions on the surface of the matrix when using printing technology, thus dramatically increasing the precision of the deposited composition. Indeed, printing allows for a more uniform distribution of a small volume of a liquid composition, consequently reducing the swelling of the matrix material onto which the composition is printed, applying a smaller and more precise amount of the bioactive agent comprised in the composition, and reducing wastage of said liquid composition than conventional techniques such as spraying.

Further, with the printing technology, two or more separate compositions being contained in separate reservoirs and being printed from separate printing heads or expelled from different channels of the same print head may each be printed onto discrete and non-overlapping positions of the same matrix material. This allows for printing in discrete and/or alternating positions onto the same matrix material of two or more compositions each comprising one or more agents or bioactive agents which are incompatible when contained in the same liquid compositions.

Various suitable printing technologies are disclosed in more detail herein below.

Printing Technologies

Printing technologies may operate by propelling various size (mostly tiny) droplets of liquid, fluid or molten material onto a media. 'Inkjet printers' or 'bubblejet printers' are the most common type of computer printer for the general consumer due to their low cost, high quality of output, capability of printing in vivid color, and ease of use. Printing technologies may be used to deposit materials directly on substrates or matrixes. A piezoelectric printer is an example of a printing technology capable of depositing materials onto a substrate. An advantage of the material deposition technique or printing technique is the precision available with this technology, which may be required for some industrial applications. Further, reduced amounts of material may be used, thus reducing costs by using expensive materials more efficiently by placing material only where needed. This yields a more uniform distribution on the surface of the matrix of the pharmaceutical composition. The fluid or liquid composition to be printed (or 'jetted') must be compatible with the print head used and must have its viscosity as well as it surface tension within a specific range within operating temperature. The fluid to be printed may be e.g. a bio-ink, a fluid or liquid composition, such as a pharmaceutical composition, or a gaseous composition, and the fluid or liquid composition may contain one or more agents or bioactive agent(s).

In one embodiment of the present invention, a method for depositing material of a composition onto the surface of a substrate or matrix material is disclosed. The material to be deposited is in a preferred embodiment printed onto the surface of the matrix material. Printing may comprise 'inkjet' printing technologies or other printing technologies. The material to be printed may be a pharmaceutical composition, that in one embodiment comprises one or more or agents or bioactive agent(s). In one embodiment, the bioactive agent is thrombin. In yet an embodiment, the matrix material is a gelatin-based sponge.

Inkjet Printing

There are three main technologies in use in contemporary inkjet printers: thermal, piezoelectric, and continuous.

Thermal inkjets: Most consumer inkjet printers (Lexmark, Hewlett-Packard, Canon) use print cartridges with a series of tiny electrically heated chambers constructed by photolithography. To produce an image, the printer runs a pulse of current through the heating elements causing a steam explosion in the chamber to form a bubble, which propels a droplet of ink or fluid onto the substrate (hence Canon's tradename of Bubblejet for its inkjets). The ink's or fluid's surface tension as well as the condensation and thus contraction of the vapor bubble, pulls a further charge of ink or fluid into the chamber through a narrow channel attached to an ink or fluid reservoir. The bubblejet technology has been used for uniformly coating pharmaceutically active compounds onto medical appliances such as a stent, e.g. WO 2003/004072.

Piezoelectric inkjets: Most commercial and industrial inkjet printers use a piezoelectric material in a fluid-filled chamber behind each nozzle instead of a heating element. When a voltage is applied, the piezoelectric material changes shape or size, which generates a pressure pulse in the fluid forcing a droplet from the nozzle. This is essentially the same mechanism as the thermal inkjet but generates the pressure pulse using a different physical principle. Piezoelectric inkjet allows a wider variety of fluids than thermal or continuous inkjet printers.

Piezoelectricity is the ability of some materials (notably crystals and certain ceramics) to generate an electric potential in response to applied mechanical stress. This may take the form of a separation of electric charge across the crystal lattice. If the material is not short-circuited, the applied charge induces a voltage across the material. The word is derived from the Greek piezein, which means to squeeze or press. The piezoelectric effect is reversible in that materials exhibiting the direct piezoelectric effect (the production of electricity when stress is applied) also exhibit the converse piezoelectric effect (the production of stress and/or strain when an electric field is applied). For example, lead zirconate titanate crystals will exhibit a maximum shape change of about 0.1% of the original dimension. The effect finds useful applications such as the production and detection of sound, generation of high voltages, electronic frequency generation, microbalances, and ultra fine focusing of optical assemblies. It is also the basis of a number of scientific instrumental techniques with atomic resolution, the scanning probe microscopies.

Continuous inkjet: The continuous inkjet method is used commercially for marking and coding of products and packages. In continuous inkjet technology, a high-pressure pump directs liquid from a reservoir through a gunbody and a microscopic nozzle, creating a continuous stream of droplets. A piezoelectric crystal creates an acoustic wave as it vibrates within the gunbody and causes the stream of liquid to break into droplets at regular intervals—64,000 to 165,000 drops per second may be achieved. The droplets are subjected to an electrostatic field created by a charging electrode as they form, the field varied according to the degree of drop deflection desired. This results in a controlled, variable electrostatic charge on each droplet. Charged droplets are separated by one or more uncharged "guard droplets" to minimize electrostatic repulsion between neighboring droplets. The charged droplets pass through an electrostatic field and are directed (deflected) by electrostatic deflection plates to print on the receptor material (substrate), or allowed to continue on undeflected to a collection gutter for re-use. The more highly charged droplets are deflected to a greater degree. Only a few percent of the droplets are actually used to print, the majority being recycled. One of its advantages is the very high velocity (~50 m/s) of the droplets, which allows for a relatively long distance between print head and substrate. Another advantage is freedom from nozzle clogging as the jet is always in use, therefore allowing volatile solvents such as ketones and alcohols to be employed, giving the fluid the ability to "bite" into the substrate and dry quickly. The system requires active solvent regulation in order to accommodate for solvent evaporation during the time of flight (time between nozzle ejection and gutter recycling) and from the venting process whereby air that is drawn into the gutter along with the unused drops is vented from the reservoir.

Print Heads and Nozzles of the Printing Device

The printing technology according to the present invention in one embodiment employs one or more printing heads or print heads, wherein each printing head comprises one or more nozzles.

A nozzle is a mechanical device designed to control the characteristics of a fluid flow as it exits (or enters) an enclosed chamber or pipe via an orifice. A print head is the element of a printer that applies the fluid or liquid composition to the substrate or matrix material; thus being connected to one or more reservoirs comprising a fluid or liquid composition.

In one embodiment, one printing head with one nozzle is used. In another embodiment, one printing head with multiple individual printing nozzles is used. In another embodiment, two or more printing heads each with one nozzle are used. In yet another embodiment, two or more printing heads each with multiple individual printing nozzles are used.

Each print head may be connected to one or more reservoir(s) comprising a fluid or liquid composition. It follows, that the nozzles of any one print head may be connected via the same channels to the same reservoir thus ejecting the same fluid or liquid composition, or the nozzles of any one print head may be connected via separate channels to separate reservoirs thus ejecting separate fluid or liquid compositions. In one embodiment, a print head comprises 256 nozzles, composed of 4 times 64 addressable channels which may be connected to four separate reservoirs.

The fluid or liquid composition will be expelled from the nozzle(s) of the print head(s) in the form of droplets or particles.

The nozzle may be any type of nozzle, and the print head may be any type of print head. In one embodiment, the nozzle is a deformable hose that is forced to eject droplets by punching the hose with a piston. An example of a printing system comprising such a nozzle is the PipeJet™ dispensing technology of the BioSpot® systems (BioFluidix GmbH).

In one embodiment, the nozzles are actuated by a high-voltage fire pulse. In one embodiment, the print head ejects droplets at a velocity in the range of 0.1-100 m/sec; such as 0.1-1 m/sec, for example 1-2 m/sec, such as 2-3 m/sec, for example 3-4 m/sec, such as 4-5 m/sec, for example 5-6 m/sec, such as 6-7 m/sec, for example 7-8 m/sec, such as 8-9 m/sec, for example 9-10 m/sec, such as 10-15 m/sec, for example 15-20 m/sec, such as 20-30 m/sec, for example 30-40 m/sec, such as 40-50 m/sec, for example 50-60 m/sec, such as 60-70 m/sec, for example 70-80 m/sec, such as 80-90 m/sec, for example 90-100 m/sec.

The nozzle diameter may be in the range of 1-1000 microns; such as 1-5 microns, for example 5-10 microns, such as 10-20 microns, for example 20-30 microns, such as 30-40 microns, for example 40-50 microns, such as 50-60 microns, for example 60-70 microns, such as 70-80 microns, for example 80-90 microns, such as 90-100 microns, for example 100-200 microns, such as 200-300 microns, for example 300-400 microns, such as 400-500 microns, for example 500-600 microns, such as 600-700 microns, for example 700-800 microns, such as 800-900 microns, for example 900-1000 microns.

A print head may comprise any number of nozzles or addressable jets. In one embodiment, one print head comprises 4 times 64 nozzles making a total of 256 nozzles on one print head. Any number of nozzles per print head may be employed, such as 4, 16, 32, 64, 128, 256, 512, 1024, 2048; or any number in the range of 1-50, 50-100, 100-150, 150-200, 200-250, 250-300, 300-350, 350-400, 400-450, 450-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2500, 2500-3000, 3000-4000, 4000-5000, 5000-10, 000 nozzles per print head.

In one embodiment, one print head may comprise more than one independent piezoelectric slices each with a number of addressable channels. The nozzles may be arranged on the print head in any pattern, such as in a single line or in multiple lines.

In one embodiment, the print head contains means for selecting which nozzles to fire at which point in time, such as a serial-to-parallel converter.

The printing head(s) of the printing system may move with respect to the surface of the matrix material onto which a composition will be deposited.

Distance Between the Nozzle(s) and the Surface

In one preferred embodiment of the invention, the nozzle(s) of the printing head(s) and the surface of the substrate or matrix material are not in direct liquid contact, but the distance between surface and nozzle is kept at a minimum.

In particular, the distance between the nozzle and the surface is lower when using the printing technology than when spraying a composition onto a surface which results in a very precise location of each droplet.

A print head of a printing device used for depositing or printing a fluid or liquid composition deposits the fluid or liquid composition in a vertical manner onto a surface of a matrix material. The fluid or liquid composition in droplet form is thus transferred perpendicular to the surface of the matrix material or substrate. Each droplet of the fluid or liquid composition thus traverses an essentially identical distance with an essentially identical velocity from the nozzle of the print head to the surface of the matrix material. This greatly increases the precision of deposition, thus achieving a uniform distribution and reducing waste.

In one embodiment, the distance traversed by any droplet from the print head or nozzle(s) to the surface of the matrix material is less than 10 mm. The distance between the surface of the matrix material and the print head or nozzle may be less than 0.01 mm, such as less than 0.02 mm, for example less than 0.03 mm, such as less than 0.04 mm, for example less than 0.05 mm, such as less than 0.06 mm, for example less than 0.07 mm, such as less than 0.08 mm, for example less than 0.09 mm, such as less than 0.1 mm, for example less than 0.2 mm, such as less than 0.3 mm, for example less than 0.4 mm, such as less than 0.5 mm, for example less than 0.6 mm, such as less than 0.7 mm, for example less than 0.8 mm, such as less than 0.9 mm, for example less than 1.0 mm, such as less than 1.1 mm, for example less than 1.2 mm, such as less than 1.3 mm, for example less than 1.4 mm, such as less than 1.5 mm, for example less than 1.6 mm, such as less than 1.7 mm, for example less than 1.8 mm, such as less than 1.9 mm, for example less than 2.0 mm, such as less than 2.1 mm, for example less than 2.2 mm, such as less than 2.3 mm, for example less than 2.4 mm, such as less than 2.5 mm, for example less than 2.6 mm, such as less than 2.7 mm, for example less than 2.8 mm, such as less than 2.8 mm, for example less than 3.0 mm, such as less than 3.5 mm, for example less than 4.0 mm, such as less than 4.5 mm, for example less than 5.0 mm, such as less than 6.0 mm, for example less than 7.0 mm, such as less than 8.0 mm, for example less than 9.0 mm, such as less than 10.0 mm. This is illustrated in FIG. 1B.

In another embodiment of the invention, the distance between the surface of the matrix material and the print head or nozzle(s) is in the range 0.01 to 10.0 mm; for example 0.01-0.02 mm, such as 0.02-0.03, for example 0.03-0.04, such as 0.04-0.05, for example 0.05-0.06, such as 0.06-0.07, for example 0.07-0.08, such as 0.08-0.09, for example 0.1-0.2, such as 0.2-0.3, for example 0.3-0.4, such as 0.4-0.5, for example 0.5-0.6, such as 0.6-0.7, for example 0.7-0.8, such as 0.8-0.9, for example 0.9-1.0, such as 1.0-1.1, for example 1.1-1.2, such as 1.2-1.3, for example 1.3-1.4, such as 1.4-1.5, for example 1.5-1.6, such as 1.6-1.7, for example 1.7-1.8, such as 1.8-1.9, for example 1.9-2.0, such as 2.0-2.1, for example 2.1-2.2, such as 2.2-2.3, for example 2.3-2.4, such as 2.4-2.5, for example 2.5-2.6, such as 2.6-2.7, for example 2.7-2.8, such as 2.8-2.9, for example 2.9-3.0, such as 3.0-3.5, for example 3.5-4.0, such as 4.0-4.5, for example 4.5-5.0, such as 5.0-6.0, for example 6.0-7.0, such as 7.0-8.0, for example 8.0-9.0, such as 9.0-10.0 mm.

In another embodiment of the invention, the distance between the surface of the matrix material and the print head or nozzle(s) is in the range 0.01-10.0 mm, such as 0.02-10.0, for example 0.03-10.0, such as 0.04-10.0, for example 0.05-10.0, such as 0.06-10.0, for example 0.07-10.0, such as 0.08-10.0, for example 0.1-10.0, such as 0.2-10.0, for example 0.3-10.0, such as 0.4-10.0, for example 0.5-10.0, such as 0.6-10.0, for example 0.7-10.0, such as 0.8-10.0, for example 0.9-10.0, such as 1.0-10.0, for example 1.1-10.0, such as 1.2-10.0, for example 1.3-10.0, such as 1.4-10.0, for example 1.5-10.0, such as 1.6-10.0, for example 1.7-10.0, such as 1.8-10.0, for example 1.9-10.0, such as 2.0-10.0, for example 2.1-10.0, such as 2.2-10.0, for example 2.3-10.0, such as 2.4-10.0, for example 2.5-10.0, such as 2.6-10.0, for example 2.7-10.0, such as 2.8-10.0, for example 2.9-10.0, such as 3.0-10.0, for example 3.5-10.0, such as 4.0-10.0, for example 4.5-10.0, such as 5.0-10.0, for example 6.0-10.0, such as 7.0-10.0, for example 8.0-10.0, such as 9.0-10.0 mm.

In another embodiment of the invention, the distance between the surface of the matrix material and the print head or nozzle(s) is in the range 0.01-0.02 mm, such as 0.01-0.03, for example 0.01-0.04, such as 0.01-0.05, for example 0.01-0.06, such as 0.01-0.07, for example 0.01-0.08, such as 0.01-0.09, for example 0.01-0.2, such as 0.01-0.3, for example 0.01-0.4, such as 0.01-0.5, for example 0.01-0.6, such as 0.01-0.7, for example 0.01-0.8, such as 0.01-0.9, for example 0.01-1.0, such as 0.01-1.1, for example 0.01-1.2, such as 0.01-1.3, for example 0.01-1.4, such as 0.01-1.5, for example 0.01-1.6, such as 0.01-1.7, for example 0.01-1.8, such as 0.01-1.9, for example 0.01-2.0, such as 0.01-2.1, for example 0.01-2.2, such as 0.01-2.3, for example 0.01-2.4, such as 0.01-2.5, for example 0.01-2.6, such as 0.01-2.7, for example 0.01-2.8, such as 0.01-2.9, for example 0.01-3.0, such as 0.01-3.5, for example 0.01-4.0, such as 0.01-4.5, for example 0.01-5.0, such as 0.01-6.0, for example 0.01-7.0, such as 0.01-8.0, for example 0.01-9.0, such as 0.01-10.0 mm.

In one embodiment, each droplet of the printed fluid or liquid composition traverses a distance from nozzle the to surface of a substrate or matrix material that varies between each droplet within a range of 0.01% to a maximum of 10%; such as 0.01 to 0.1%, for example 0.1 to 1%, such as 1 to 2%, for example 2 to 3%, such as 3 to 4%, for example 4 to 5%, such as 5 to 6%, for example 6 to 7%, such as 7 to 8%, for example 8 to 9%, such as 9 to 10%.

In one embodiment, each droplet of the printed fluid or liquid composition traverses a distance from nozzle the to surface of a substrate or matrix material with a velocity that varies between each droplet within a range of 0.01% to a maximum of 10%; such as 0.01 to 0.1%, for example 0.1 to 1%, such as 1 to 2%, for example 2 to 3%, such as 3 to 4%, for example 4 to 5%, such as 5 to 6%, for example 6 to 7%, such as 7 to 8%, for example 8 to 9%, such as 9 to 10%.

The perpendicular mode of deposition of droplets and the shorter distance between nozzle and surface of the matrix material makes printing more efficient than spraying. With printing, one may print all the way to the edge of the surface of the matrix material, whereas a spraying technique will deposit a composition in an angled way, thereby 'over-spraying' to reach the edges of the surface. This has to do with both the angled spraying, the generation of aerosols and the greater distance from nozzle to surface when spraying. The angled deposition of a fluid or liquid composition with spraying causes the distance for each droplet to vary greatly. Thus, the composition will be deposited at higher density in the middle of the spray and a lower density at the edge of the spray, resulting in a less uniform distribution and promoting a concentration gradient. Thus, printing may occur essentially without generating aerosols.

Figure 1B:
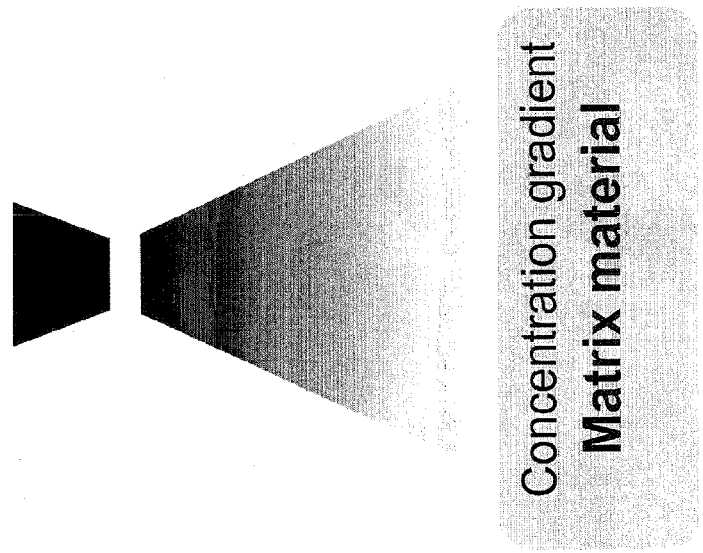
Figure 2A:
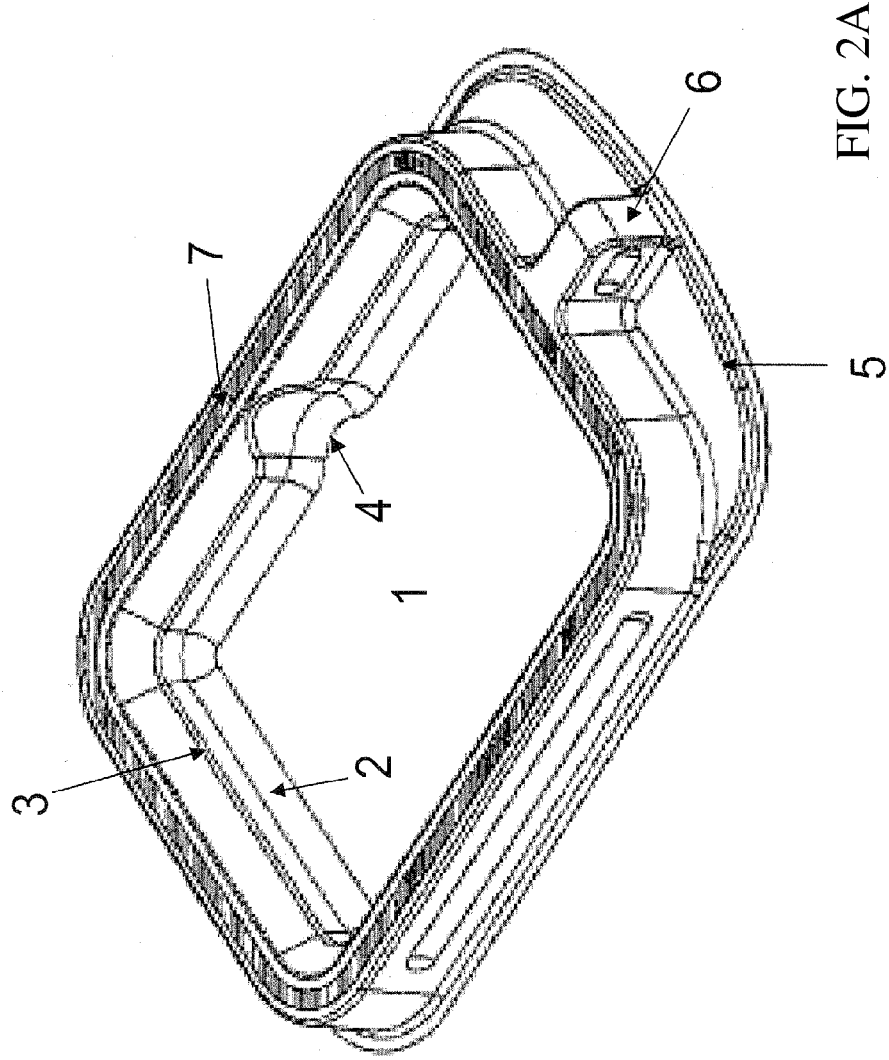
FIGS. 2A and 2B illustrate a container without and with a a matrix material, respectively. The bottom of the inner tray is marked (1), the sidewall is marked (2), the mark on the sidewall is marked (3), the inner tray notch is marked (4), the base is marked (5), the handle is marked (6), the sealing surface for the lid is marked (7) and the lid is marked (8).
Figure 2B:
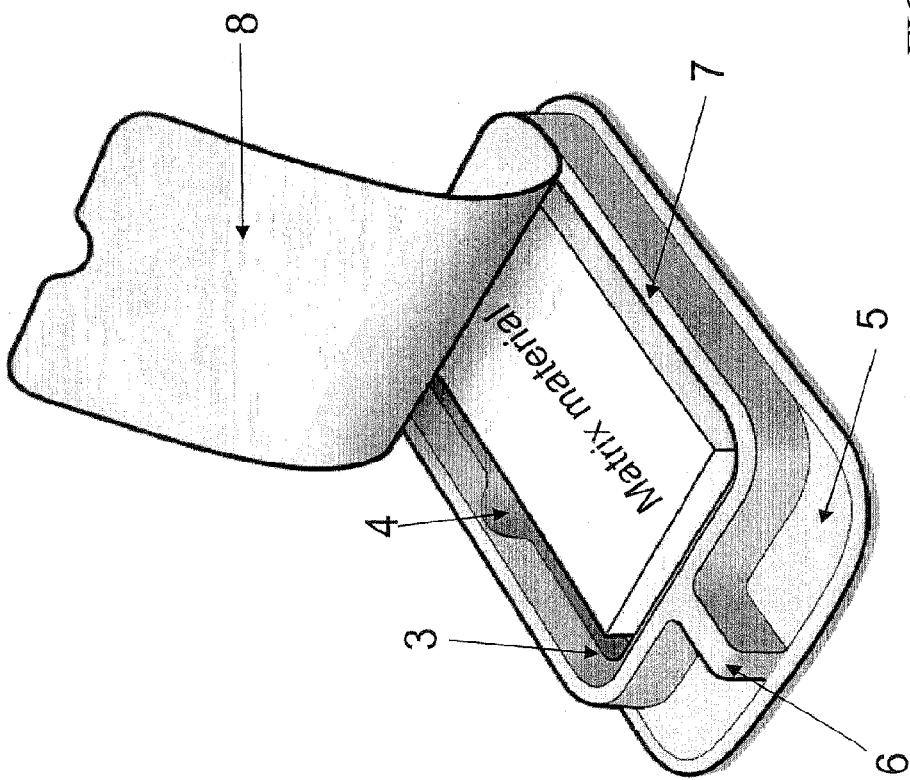
Figure 3A:
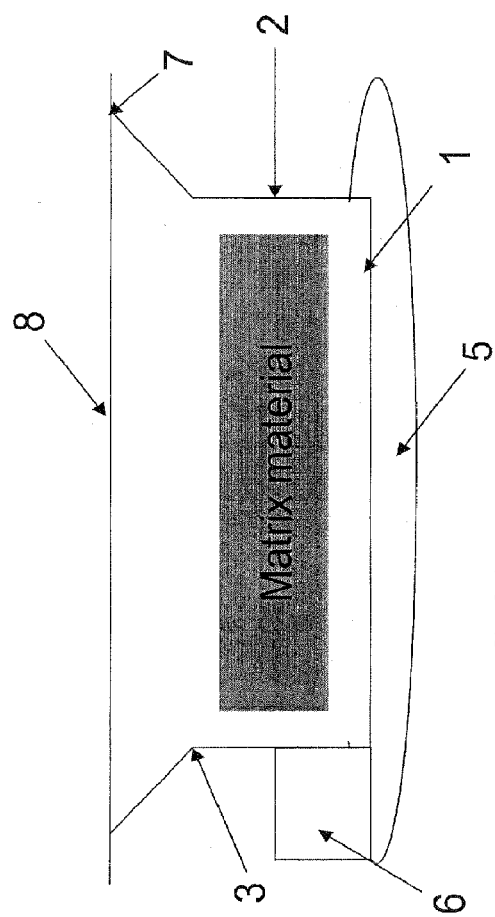
FIGS. 3A and 3B illustrate a container containing a matrix material. The bottom of the inner tray is marked (1), the sidewall is marked (2), the mark on the sidewall is marked (3), the base is marked (5), the handle is marked (6), the sealing surface for the lid is marked (7) and the lid is marked (8).
Figure 3B:
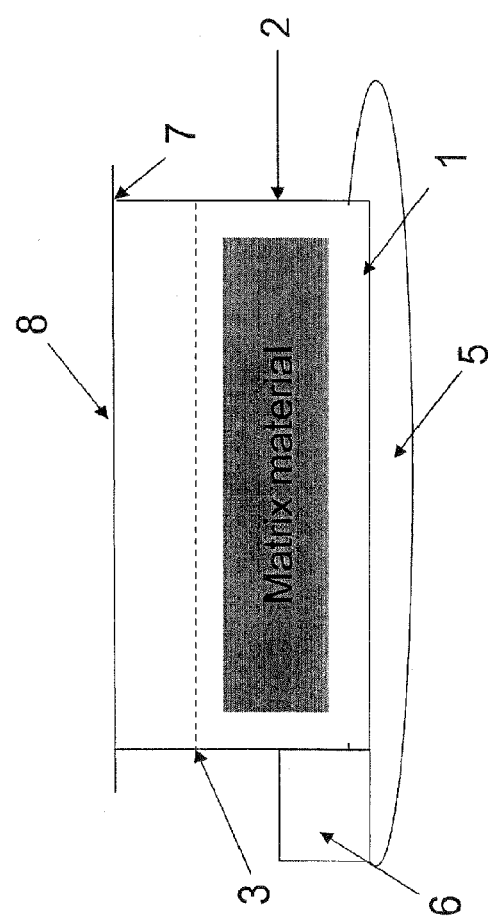

Differences between spraying and printing are illustrated in FIGS. 1A and 1B.

The material of the composition to be deposited on the surface of a matrix material is deposited in a discrete manner, that is, in discrete locations or positions on the surface of the matrix material.

In one embodiment, the invention relates to a device comprising a matrix material, comprising discretely deposited material. The discretely deposited material may be denoted 'islands'. These islands thus comprise discrete positions on the surface of the matrix material of the device. The islands may comprise a pharmaceutical composition.

Droplet Size of the Fluid or Liquid Composition

When printing a fluid or liquid composition onto a surface of a matrix material, the amount of liquid deposited per position on the matrix surface; i.e. the volume of each droplet, is in the pico liter (pL) to nano liter (nL) range. In one embodiment, the amount of liquid deposited per position on the matrix surface; i.e. the volume of each droplet is less than 100 nL, such as less than 90 nL, for example less than 80 nL, such as less than 70 nL, for example less than 60 nL, such as less than 50 nL, for example less than 40 nL, such as less than 30 nL, for example less than 20 nL, such as less than 10 nL, for example less than 1 nL or 1000 pL, such as less than 900 pL, for example less than 800 pL, such as less than 700 pL, for example less than 600 pL, such as less than 500 pL, for example less than 400 pL, such as less than 300 pL, for example less than 250 pL, such as less than 200 pL, for example less than 150 pL, such as less than 100 pL, for example less than 90 pL, such as less than 80 pL, for example less than 70 pL, such as less than 60 pL, for example less than 50 pL, such as less than 40 pL, for example less than 30 pL, such as less than 20 pL, for example less than 10 pL, such as less than 9 pL, for example less than 8 pL, such as less than 7 pL, for example less than 6 pL, such as less than 5 pL, for example less than 4 pL, such as less than 3 pL, for example less than 2 pL, such as less than 1 pL per position.

In another embodiment, the amount of liquid deposited per position on the surface of the matrix; i.e. the volume of each droplet, is in the range of 0.1 pL to 100 nL; such as 0.1-1 pL, for example 1-5 pL, such as 5-10 pL, for example 10-20 pL, such as 20-30 pL, for example 30-40 pL, such as 40-50 pL, for example 50-60 pL, such as 60-70 pL, for example 70-80 pL, such as 80-90 pL, for example 90-100 pL, such as 100-110 pL, for example 110-120 pL, such as 120-130 pL, for example 130-140 pL, such as 140-150 pL, for example 150-160 pL, such as 160-170 pL, for example 170-180 pL, such as 180-190 pL, for example 190-200 pL, such as 200-250 pL, for example 250-300 pL, such as 300-350 pL, for example 350-400 pL, such as 400-450 pL, for example 450-500 pL, such as 500-550 pL, for example 550-600 pL, such as 600-650 pL, for example 650-700 pL, such as 700-750 pL, for example 750-800 pL, such as 800-850 pL, for example 850-900 pL, such as 900-950 pL, for example 950-1000 pL or 1 nL, such as 1-2 nL, for example 2-3 nL, such as 3-4 nL, for example 4-5 nL, such as 5-6 nL, for example 6-7 nL, such as 7-8 nL, for example 8-9 nL, such as 9-10 nL, for example 10-15 nL, such as 15-20 nL, for example 20-25 nL, such as 25-30 nL, for example 30-35 nL, such as 35-40 nL, for example 40-45 nL, such as 45-50 nL, for example 50-60 nL, such as 60-70 nL, for example 70-80 nL, such as 80-90 nL, for example 90-100 nL.

In another embodiment, the amount of liquid deposited per position on the surface of the matrix; i.e. the volume of each droplet, is in the range of 0.1 pL-100 nL, for example 1 pL-100 nL, such as 5 pL-100 nL, for example 10 pL-100 nL, such as 20 pL-100 nL, for example 30 pL-100 nL, such as 40 pL-100 nL, for example 50 pL-100 nL, such as 60 pL-100 nL, for example 70 pL-100 nL, such as 80 pL-100 nL, for example 90 pL-100 nL, such as 100 pL-100 nL, for example 110 pL-100 nL, such as 120 pL-100 nL, for example 130 pL-100 nL, such as 140 pL-100 nL, for example 150 pL-100 nL, such as 160 pL-100 nL, for example 170 pL-100 nL, such as 180 pL-100 nL, for example 190 pL-100 nL, such as 200 pL-100 nL, for example 250 pL-100 nL, such as 300 pL-100 nL, for example 350 pL-100 nL, such as 400 pL-100 nL, for example 450 pL-100 nL, such as 500 pL-100 nL, for example 550 pL-100 nL, such as 600 pL-100 nL, for example 650 pL-100 nL, such as 700 pL-100 nL, for example 750 pL-100 nL, such as 800 pL-100 nL, for example 850 pL-100 nL, such as 900 pL-100 nL, for example 950 pL-100 nL, such as 1-100 nL, for example 2-100 nL, such as 3-100 nL, for example 4-100 nL, such as 5-100 nL, for example 6-100 nL, such as 7-100 nL, for example 8-100 nL, such as 9-100 nL, for example 10-100 nL, such as 15-100 nL, for example 20-100 nL, such as 25-100 nL, for example 30-100 nL, such as 35-100 nL, for example 40-100 nL, such as 45-100 nL, for example 50-100 nL, such as 60-100 nL, for example 70-100 nL, such as 80-100 nL, for example 90-100 nL.

In yet another embodiment, the amount of liquid deposited per position on the surface of the matrix; i.e. the volume of each droplet, is in the range of 0.1-1 pL, for example 0.1-5 pL, such as 0.1-10 pL, for example 0.1-20 pL, such as 0.1-30 pL, for example 0.1-40 pL, such as 0.1-50 pL, for example 0.1-60 pL, such as 0.1-70 pL, for example 0.1-80 pL, such as 0.1-90 pL, for example 0.1-100 pL, such as 0.1-110 pL, for example 0.1-120 pL, such as 0.1-130 pL, for example 0.1-140 pL, such as 0.1-150 pL, for example 0.1-160 pL, such as 0.1-170 pL, for example 0.1-180 pL, such as 0.1-190 pL, for example 0.1-200 pL, such as 0.1-250 pL, for example 0.1-300 pL, such as 0.1-350 pL, for example 0.1-400 pL, such as 0.1-450 pL, for example 0.1-500 pL, such as 0.1-550 pL, for example 0.1-600 pL, such as 0.1-650 pL, for example 0.1-700 pL, such as 0.1-750 pL, for example 0.1-800 pL, such as 0.1-850 pL, for example 0.1-900 pL, such as 0.1-950 pL, for example 0.1-1000 pL or 1 nL, such as 0.1 pL-2 nL, for example 0.1 pL-3 nL, such as 0.1 pL-4 nL, for example 0.1 pL-5 nL, such as 0.1 pL-6 nL, for example 0.1 pL-7 nL, such as 0.1 pL-8 nL, for example 0.1 pL-9 nL, such as 0.1 pL-10 nL, for example 0.1 pL-15 nL, such as 0.1 pL-20 nL, for example 0.1 pL-25 nL, such as 0.1 pL-30 nL, for example 0.1 pL-35 nL, such as 0.1 pL-40 nL, for example 0.1 pL-45 nL, such as 0.1 pL-50 nL, for example 0.1 pL-60 nL, such as 0.1 pL-70 nL, for example 0.1 pL-80 nL, such as 0.1 pL-90 nL, for example 0.1 pL-100 nL.

The droplet size for each droplet is preferably essentially identical, wherein the droplet size of any two droplets expelled from a printer according to the present invention may vary less that 10%, such as less than 8%, for example less than 6%, such as less than 4%, for example less than 2%, such as less than 1%. The droplet size of any two droplets expelled from a printer according to the present invention may vary in the range of 0.1-10%, such as 0.1-1%, for example 1-2%, such as 2-3%, for example 3-4%, such as 4-5%, for example 5-6%, such as 6-7%, for example 7-8%, such as 8-9%, for example 9-10%.

The total volume of fluid or liquid composition to be deposited by printing in the form of droplets in a preferred embodiment essentially does not result in any swelling of the matrix material.

Distance Between Droplets Deposited onto a Surface by Printing

When printing a fluid or liquid composition onto a surface of a matrix material, the droplets expelled from the nozzles of the print head are preferably deposited onto said surface with a certain predetermined distance between every two droplets.

In one embodiment, the distance between every two droplets deposited by printing onto the matrix surface is less than 2 mm, such as less than 1.9 mm, for example less than 1.8 mm, such as less than 1.7 mm, for example less than 1.6 mm, such as less than 1.5 mm, for example less than 1.4 mm, such as less than 1.3 mm, for example less than 1.3 mm, such as less than 1.2 mm, for example less than 1.1 mm, such as less than 1.0 mm, for example less than 0.9 mm, such as less than 0.8 mm, for example less than 0.7 mm, such as less than 0.6 mm, for example less than 0.5 mm, such as less than 0.4 mm, for example less than 0.3 mm, such as less than 0.2 mm, for example less than 0.1 mm, such as less than 0.09 mm, for example less than 0.08 mm, such as less than 0.07 mm, for example less than 0.06 mm, such as less than 0.05 mm, for example less than 0.04 mm, such as less than 0.03 mm, for example less than 0.02 mm, such as less than 0.01 mm.

In another embodiment, the distance between every two droplets deposited by printing onto the matrix surface is in the range of 0.01 to 2 mm; for example 0.01-0.02 mm, such as 0.02-0.03 mm, for example 0.03-0.04 mm, such as 0.04-0.05 mm, for example 0.05-0.06 mm, such as 0.06-0.07 mm, for example 0.07-0.08 mm, such as 0.08-0.09 mm, for example 0.09-0.1 mm, such as 0.1-0.2 mm, for example 0.2-0.3 mm, such as 0.3-0.4 mm, for example 0.4-0.5 mm, such as 0.5-0.6 mm, for example 0.6-0.7 mm, such as 0.7-0.8 mm, for example 0.8-0.9 mm, such as 0.9-1.0 mm, for example 1.0-1.1 mm, such as 1.1-1.2 mm, for example 1.2-1.3 mm, such as 1.3-1.4 mm, for example 1.4-1.5 mm, such as 1.5-1.6 mm, for example 1.6-1.7 mm, such as 1.7-1.8 mm, for example 1.8-1.9 mm, such as 1.9-2.0 mm.

In another embodiment, the distance between every two droplets deposited by printing onto the matrix surface is in the range of 0.01-2.0 mm, such as 0.02-2.0 mm, for example 0.03-2.0 mm, such as 0.04-2.0 mm, for example 0.05-2.0 mm, such as 0.06-2.0 mm, for example 0.07-2.0 mm, such as 0.08-2.0 mm, for example 0.09-2.0 mm, such as 0.1-2.0 mm, for example 0.2-2.0 mm, such as 0.3-2.0 mm, for example 0.4-2.0 mm, such as 0.5-2.0 mm, for example 0.6-2.0 mm, such as 0.7-2.0 mm, for example 0.8-2.0 mm, such as 0.9-2.0 mm, for example 1.0-2.0 mm, such as 1.1-2.0 mm, for example 1.2-2.0 mm, such as 1.3-2.0 mm, for example 1.4-2.0 mm, such as 1.5-2.0 mm, for example 1.6-2.0 mm, such as 1.7-2.0 mm, for example 1.8-2.0 mm, such as 1.9-2.0 mm.

In yet another embodiment, the distance between every two droplets deposited by printing onto the matrix surface is in the range of 0.01-0.02 mm, such as 0.01-0.03 mm, for example 0.01-0.04 mm, such as 0.01-0.05 mm, for example 0.01-0.06 mm, such as 0.01-0.07 mm, for example 0.01-0.08 mm, such as 0.01-0.09 mm, for example 0.01-0.1 mm, such as 0.01-0.2 mm, for example 0.01-0.3 mm, such as 0.01-0.4 mm, for example 0.01-0.5 mm, such as 0.01-0.6 mm, for example 0.01-0.7 mm, such as 0.01-0.8 mm, for example 0.01-0.9 mm, such as 0.01-1.0 mm, for example 0.01-1.1 mm, such as 0.01-1.2 mm, for example 0.01-1.3 mm, such as 0.01-1.4 mm, for example 0.01-1.5 mm, such as 0.01-1.6 mm, for example 0.01-1.7 mm, such as 0.01-1.8 mm, for example 0.01-1.9 mm, such as 0.01-2.0 mm.

The distance between every two droplets deposited by printing onto the matrix surface is preferably essentially identical, wherein the distance may vary less that 10%, such as less than 8%, for example less than 6%, such as less than 4%, for example less than 2%, such as less than 1%. The droplet size of any two droplets expelled from a printer according to the present invention may vary in the range of 0.1-10%, such as 0.1-1%, for example 1-2%, such as 2-3%, for example 3-4%, such as 4-5%, for example 5-6%, such as 6-7%, for example 7-8%, such as 8-9%, for example 9-10%.

Droplet Evaporation

When tiny droplets of a fluid pharmaceutical composition comprising one or more bioactive agents is printed onto the surface of a matrix or a device, a subsequent drying step, including a lyophilisation step, of the matrix or device is not required; the reason being that the tiny droplets printed in discrete positions on the surface of the matrix or the device will readily evaporate. This has the further advantage of avoiding any undesirable swelling of the matrix material—a swelling which accompanies most if not all state-of-the-art spraying technologies.

Thus, in one embodiment, the fluid droplets comprising one or more bioactive agents which are printed onto the surface of a matrix or the surface of a device according to the present invention will not exceed a size that allows the droplets to evaporate within maximum 30 seconds, such as less than 25 seconds, for example less than 20 seconds, such as less than 15 seconds, for example less than 10 seconds, such as less than 5 seconds, for example less than 1 second after being printed onto the surface of the matrix or the surface of the device.

In one embodiment, the fluid droplets comprising one or more bioactive agents which are printed onto the surface of a matrix or the surface of a device according to the present invention will not exceed a size that allows the droplets to evaporate within 0.1-1 second, such as 1-2, for example 2-3, such as 3-4, for example 4-5, such as 5-6, for example 6-7, such as 7-8, for example 8-9, such as 9-10, for example 11-12, such as 12-13, for example 13-14, such as 14-15, for example 15-16, such as 16-17, for example 17-18, such as 18-19, for example 19-20, such as 20-25, for example 25-30 seconds after being printed onto the surface of the matrix or the surface of the device.

The above-cited time for evaporation can be achieved by controlling droplet size, temperature of the droplet and temperature of the surface of the matrix or the device onto which the droplet is printed. Further, modifying the surface properties of the underlying matrix material (hydrophobicity, chemical heterogeneity, roughness) may alter evaporation time.

The evaporation of the fluid droplets on the surface of a substrate can in principle be aided in various ways. In principle the droplets can evaporate on the surface without dissolution of the surface, or the fluid can be a solvent for the surface and thus be absorbed in the surface, thereby effectively aiding in the evaporation process.

It is preferred that the droplets evaporate without dissolving or interacting with the surface of the matrix material or the device comprising said matrix material. Thus, as a consequence of the rapid evaporation of the fluid part of the droplet printed onto the surface of the matrix, the matrix is printed with the pharmaceutical composition forming part of the droplet essentially without swelling and/or essentially without resulting in any other physical change of the surface structure of the matrix material or device.

When a droplet evaporates on the surface of a matrix material or device without dissolution of the surface material, different evaporation modes can be observed. A droplet can evaporate with the contact angle being essentially constant while the contact radius decreases (constant angle mode). Alternatively, the contact radius can remain essentially constant while the contact angle decreases, in which case the droplet becomes more flat over time (constant radius mode or pinning). Alternatively both of the above-mentioned modes can occur, in which case both the contact angle and the contact radius will change during evaporation (non-constant mode).

Usually, droplets evaporate in different modes. Thus, the use of tiny, uniformly sized droplets that evaporates rapidly upon contacting the surface of a matrix material or a device will add to the uniformity of printing of the compositions onto the surface of the matrix material or the device.

Operating Temperature

The temperature of the fluid or liquid composition, or the temperature of the environment wherein the fluid or liquid composition is to be printed, is in one embodiment the ambient temperature. In another embodiment, the temperature is in the range from sub-zero degrees celcius to 150 degrees celcius; such as −100° C. to −50° C., for example −50° C. to 0° C., such as 0-10° C., for example 10-20° C., such as 20-30° C., for example 30-40° C., such as 40-50° C., for example 50-60° C., such as 60-70° C., for example 70-80° C., such as 80-90° C., for example 90-100° C., such as 100-125° C., for example 125-150° C.

Deposition of One or More Pharmaceutical Compositions by Other Methods than Printing The present invention in one embodiment relates to a medical device comprising a composition, such as a pharmaceutical composition, which is deposited onto a matrix material e.g. onto the surface of the matrix material, wherein said matrix material comprising a pharmaceutical composition is comprised in a container according to the present invention. The deposition of the composition onto the matrix may in one embodiment be performed by any method know in the art such as by printing, spraying, soaking, dipping, coating, saturating, pressuring, sprinkling, pouring, spreading, greasing, smearing, dabbing, rubbing or painting the pharmaceutical composition onto a premade matrix or by dipping of a premade matrix into the pharmaceutical composition. Alternatively, the pharmaceutical composition can be deposited into or onto the matrix during preparation of said matrix e.g. by mixing it into one or more of the matrix material components.

Bioactive Agents of the Pharmaceutical Composition

In a preferred embodiment, the invention relates to a pharmaceutical composition initially in fluid or liquid form, comprising one or more bioactive agents, optionally in combination with further active agents or substances, thus comprising a pharmaceutical composition that includes a pharmaceutically acceptable carrier and one or more bioactive agents, such as thrombin or thrombin in combination with fibrinogen, or thrombin and fibrinogen in combination with Factor XIII, or thrombin and fibrinogen and Factor XIII in combination with tranexamic acid.

The pharmaceutical composition is in one embodiment printed onto a surface of the matrix of the device, thereby depositing the agents of the composition onto the surface of the matrix in a controlled manner. One or more of said compositions may be printed each at one or more discrete positions on the surface of the matrix material.

Non-limiting examples of useful biologically active agents which can be present alone or in combination with the above-cited bioactive agents selected from the group of thrombin or thrombin in combination with fibrinogen, or thrombin and fibrinogen in combination with Factor XIII, or thrombin and fibrinogen and Factor XIII in combination with tranexamic acid, include the following expanded therapeutic categories: hemostatic and anti-fibrinolytic agents, wound healing or promoting agents, adhesives and surfactants anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, anti-histamines, anti-tussives, appetite suppressants, biologicals, cerebral dilators, coronary dilators, decongestants, diuretics, diagnostic agents, erythropoietic agents, expectorants, gastrointestinal sedatives hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, analgetics and prodrugs.

Specific examples of useful biologically active substances from the above categories include: (a) anti-neoplastics such as androgen inhibitors, anti-metabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such aschlorpheniramine maleat, phenindamine tartrate, zyrilamine mafeate, doxylamine succinate, and phenyltcloxamine citrate; (d) decongestants such as phenylephrine hydrochloride, chenylpropanolamine hydrochloride, pseudoephedrine hydrochloride, and ephedrine; (e) various alkaloid such as codeine phosphate, codeine sulfate and morphine-(mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, RTI anti-virals, antiseptics and antibiotics; and (o) antigenic materials, particularly those useful in vaccine applications.

Pharmaceutically acceptable carriers may be prepared from a wide range of materials. Without being limited thereto, such materials include diluents, binders and adhesives, lubricants, disintegrants, colorants, bulking agents (an additive that increases the bulk of a substance), flavorings, sweeteners, and miscellaneous materials such as buffers and absorbents in order to prepare a particular medicated suppository.

Concentration of the Bioactive Agent of the Fluid or Liquid Composition

Bioactive agents of the fluid or liquid composition according to the present invention may be used in any suitable concentration, i.e. a pharmaceutical relevant concentration for achieving a biological effect.

In one embodiment, the bioactive agent is an enzyme, said enzyme being present in the fluid or liquid composition at a concentration of less than 1,000,000 IU/ml, such as less than 950,000 IU/ml, for example less than 900,000 IU/ml, such as less than 850,000 IU/ml, for example less than 800,000 IU/ml, such as less than 750,000 IU/ml, for example less than 700,000 IU/ml, such as less than 650,000 IU/ml, for example less than 600,000 IU/ml, such as less than 550,000 IU/ml, for example less than 500,000 IU/ml, such as less than 450,000 IU/ml, for example less than 400,000 IU/ml, such as less than 350,000 IU/ml, for example less than 300,000 IU/ml, such as less than 250,000 IU/ml, for example less than 200,000 IU/ml, such as less than 150,000 IU/ml, for example less than 100,000 IU/ml, such as less than 95,000 IU/ml, for example less than 90,000 IU/ml, such as less than 85,000 IU/ml, for example less than 80,000 IU/ml, such as less than 75,000 IU/ml, for example less than 70,000 IU/ml, such as less than 65,000 IU/ml, for example less than 60,000 IU/ml, such as less than 55,000 IU/ml, for example less than 50,000 IU/ml, such as less than 45,000 IU/ml, for example less than 40,000 IU/ml, such as less than 35,000 IU/ml, for example less than 30,000 IU/ml, such as less than 25,000 IU/ml, for example less than 20,000 IU/ml, such as less than 15,000 IU/ml, for example less than 10,000 IU/ml, such as less than 9,500 IU/ml, for example less than 9,000 IU/ml, such as less than 8,500 IU/ml, for example less than 8,000 IU/ml, such as less than 7,500 IU/ml, for example less than 7,000 IU/ml, such as less than 6,500 IU/ml, for example less than 6,000 IU/ml, such as less than 5,500 IU/ml, for example less than 5,000 IU/ml, such as less than 4,500 IU/ml, for example less than 4,000 IU/ml, such as less than 3,500 IU/ml, for example less than 3,000 IU/ml, such as less than 2,500 IU/ml, for example less than 2,000 IU/ml, such as less than 1,500 IU/ml, for example less than 1,000 IU/ml, such as less than 750 IU/ml, for example less than 500 IU/ml, such as less than 450 IU/ml, for example less than 400 IU/ml, such as less than 350 IU/ml, for example less than 300 IU/ml, such as less than 250 IU/ml, for example less than 200 IU/ml, such as less than 150 IU/ml, for example less than 100 IU/ml, such as less than 50 IU/ml, for example less than 10 IU/ml, such as less than 1 IU/ml.

In one embodiment, the bioactive agent is an enzyme, said enzyme being present in the fluid or liquid composition at a concentration in the range of 1 IU/ml to 1,000,000 IU/ml; such as 1-10 IU/ml, for example 10-50 IU/ml, such as 50-100 IU/ml, for example 100-150 IU/ml, such as 150-200 IU/ml, for example 200-250 IU/ml, such as 250-300 IU/ml, for example 300-350 IU/ml, such as 350-400 IU/ml, for example 400-450 IU/ml, such as 450-500 IU/ml, for example 500-750 IU/ml, such as 750-1000 IU/ml, for example 1000-1500 IU/ml, such as 1500-2000 IU/ml, for example 2000-2500 IU/ml, such as 2500-3000 IU/ml, for example 3000-3500 IU/ml, such as 3500-4000 IU/ml, for example 4000-4500 IU/ml, such as 4500-5000 IU/ml, for example 5000-5500 IU/ml, such as 5500-6000 IU/ml, for example 6000-6500 IU/ml, such as 6500-7000 IU/ml, for example 7000-7500 IU/ml, such as 7500-8000 IU/ml, for example 8000-8500 IU/ml, such as 8500-9000 IU/ml, for example 9000-9500 IU/ml, such as 9500-10,000 IU/ml, for example 10,000-11,000 IU/ml, such as 11,000-12,000 IU/ml, for example 12,000-13,000 IU/ml, such as 13,000-14,000 IU/ml, for example 14,000-15,000 IU/ml, such as 15,000-16,000 IU/ml, for example 16,000-17,000 IU/ml, such as 17,000-18,000 IU/ml, for example 18,000-19,000 IU/ml, such as 19,000-20,000 IU/ml, for example 20,000-25,000 IU/ml, such as 25,000-30,000 IU/ml, for example 30,000-35,000 IU/ml, such as 35,000-40,000 IU/ml, for example 40,000-45,000 IU/ml, such as 45,000-50,000 IU/ml, for example 50,000-55,000 IU/ml, such as 55,000-60,000 IU/ml, for example 60,000-65,000 IU/ml, such as 65,000-70,000 IU/ml, for example 70,000-75,000 IU/ml, such as 75,000-80,000 IU/ml, for example 80,000-85,000 IU/ml, such as 85,000-90,000 IU/ml, for example 90,000-95,000 IU/ml, such as 95,000-100,000 IU/ml, for example 100,000-150,000 IU/ml, such as 150,000-200,000 IU/ml, for example 200,000-250,000 IU/ml, such as 250,000-300,000 IU/ml, for example 300,000-350,000 IU/ml, such as 350,000-400,000 IU/ml, for example 400,000-450,000 IU/ml, such as 450,000-500,000 IU/ml, for example 500,000-550,000 IU/ml, such as 550,000-600,000 IU/ml, for example 600,000-650,000 IU/ml, such as 650,000-700,000 IU/ml, for example 700,000-750,000 IU/ml, such as 750,000-800,000 IU/ml, for example 800,000-850,000 IU/ml, such as 850,000-900,000 IU/ml, for example 900,000-950,000 IU/ml, such as 950,000-1,000,000 IU/ml.

In another embodiment, the bioactive agent is an enzyme, said enzyme being present in the fluid or liquid composition at a concentration in the range of 1-1,000,000 IU/ml, for example 10-1,000,000 IU/ml, such as 50-1,000,000 IU/ml, for example 100-1,000,000 IU/ml, such as 150-1,000,000 IU/ml, for example 200-1,000,000 IU/ml, such as 250-1,000,000 IU/ml, for example 300-1,000,000 IU/ml, such as 350-1,000,000 IU/ml, for example 400-1,000,000 IU/ml, such as 450-1,000,000 IU/ml, for example 500-1,000,000 IU/ml, such as 750-1,000,000 IU/ml, for example 1000-1,000,000 IU/ml, such as 1500-1,000,000 IU/ml, for example 2000-1,000,000 IU/ml, such as 2500-1,000,000 TU/ml, for example 3000-1,000,000 IU/ml, such as 3500-1,000,000 IU/ml, for example 4000-1,000,000 IU/ml, such as 4500-1,000,000 IU/ml, for example 5000-1,000,000 IU/ml, such as 5500-1,000,000 IU/ml, for example 6000-1,000,000 IU/ml, such as 6500-1,000,000 IU/ml, for example 7000-1,000,000 IU/ml, such as 7500-1,000,000 IU/ml, for example 8000-1,000,000 IU/ml, such as 8500-1,000,000 IU/ml, for example 9000-1,000,000 IU/ml, such as 9500-1,000,000 IU/ml, for example 10,000-1,000,000 IU/ml, such as 11,000-1,000,000 IU/ml, for example 12,000-1,000,000 IU/ml, such as 13,000-1,000,000 IU/ml, for example 14,000-1,000,000 IU/ml, such as 15,000-1,000,000 IU/ml, for example 16,000-1,000,000 IU/ml, such as 17,000-1,000,000 IU/ml, for example 18,000-1,000,000 IU/ml, such as 19,000-1,000,000 IU/ml, for example 20,000-1,000,000 IU/ml, such as 25,000-1,000,000 IU/ml, for example 30,000-1,000,000 IU/ml, such as 35,000-1,000,000 IU/ml, for example 40,000-1,000,000 IU/ml, such as 45,000-1,000,000 IU/ml, for example 50,000-1,000,000 IU/ml, such as 55,000-1,000,000 IU/ml, for example 60,000-1,000,000 IU/ml, such as 65,000-1,000,000 IU/ml, for example 70,000-1,000,000 IU/ml, such as 75,000-1,000,000 IU/ml, for example 80,000-1,000,000 IU/ml, such as 85,000-1,000,000 IU/ml, for example 90,000-1,000,000 IU/ml, such as 95,000-1,000,000 IU/ml, for example 100,000-1,000,000 IU/ml, such as 150,000-1,000,000 IU/ml, for example 200,000-1,000,000 IU/ml, such as 250,000-1,000,000 IU/ml, for example 300,000-1,000,000 IU/ml, such as 350,000-1,000,000 IU/ml, for example 400,000-1,000,000 IU/ml, such as 450,000-1,000,000 IU/ml, for example 500,000-1,000,000 IU/ml, such as 550,000-1,000,000 IU/ml, for example 600,000-1,000,000 IU/ml, such as 650,000-1,000,000 IU/ml, for example 700,000-1,000,000 IU/ml, such as 750,000-1,000,000 IU/ml, for example 800,000-1,000,000 IU/ml, such as 850,000-1,000,000 IU/ml, for example 900,000-1,000,000 IU/ml, such as 950,000-1,000,000 IU/ml.

In yet another embodiment, the bioactive agent is an enzyme, said enzyme being present in the fluid or liquid composition at a concentration in the range of such as 1-10 IU/ml, for example 1-50 IU/ml, such as 1-100 IU/ml, for example 1-150 IU/ml, such as 1-200 IU/ml, for example 1-250 IU/ml, such as 1-300 IU/ml, for example 1-350 IU/ml, such as 1-400 IU/ml, for example 1-450 IU/ml, such as 1-500 IU/ml, for example 1-750 IU/ml, such as 1-1000 IU/ml, for example 1-1500 IU/ml, such as 1-2000 IU/ml, for example 1-2500 IU/ml, such as 1-3000 IU/ml, for example 1-3500 IU/ml, such as 1-4000 IU/ml, for example 1-4500 IU/ml, such as 1-5000 IU/ml, for example 1-5500 IU/ml, such as 1-6000 IU/ml, for example 1-6500 IU/ml, such as 1-7000 IU/ml, for example 1-7500 IU/ml, such as 1-8000 IU/ml, for example 1-8500 IU/ml, such as 1-9000 IU/ml, for example 1-9500 IU/ml, such as 1-10,000 IU/ml, for example 1-11,000 IU/ml, such as 1-12,000 IU/ml, for example 1-13,000 IU/ml, such as 1-14,000 IU/ml, for example 1-15,000 IU/ml, such as 1-16,000 IU/ml, for example 1-17,000 IU/ml, such as 1-18,000 IU/ml, for example 1-19,000 IU/ml, such as 1-20,000 IU/ml, for example 1-25,000 IU/ml, such as 1-30,000 IU/ml, for example 1-35,000 IU/ml, such as 1-40,000 IU/ml, for example 1-45,000 IU/ml, such as 1-50,000 IU/ml, for example 1-55,000 IU/ml, such as 1-60,000 IU/ml, for example 1-65,000 IU/ml, such as 1-70,000 IU/ml, for example 1-75,000 IU/ml, such as 1-80,000 IU/ml, for example 1-85,000 IU/ml, such as 1-90,000 IU/ml, for example 1-95,000 IU/ml, such as 1-100,000 IU/ml, for example 1-150,000 IU/ml, such as 1-200,000 IU/ml, for example 1-250,000 IU/ml, such as 1-300,000 IU/ml, for example 1-350,000 IU/ml, such as 1-400,000 IU/ml, for example 1-450,000 IU/ml, such as 1-500,000 IU/ml, for example 1-550,000 IU/ml, such as 1-600,000 IU/ml, for example 1-650,000 IU/ml, such as 1-700,000 IU/ml, for example 1-750,000 IU/ml, such as 1-800,000 IU/ml, for example 1-850,000 IU/ml, such as 1-900,000 IU/ml, for example 1-950,000 IU/ml, such as 1-1,000,000 IU/ml.

In one embodiment, the bioactive agent is present in the fluid or liquid composition at a concentration of less than 1,000,000 mg/ml, such as less than 900,000 mg/ml, for example less than 800,000 mg/ml, such as less than 700,000 mg/ml, for example less than 600,000 mg/ml, such as less than 500,000 mg/ml, for example less than 400,000 mg/ml, such as less than 300,000 mg/ml, for example less than 200,000 mg/ml, such as less than 100,000 mg/ml, for example less than 90,000 mg/ml, such as less than 80,000 mg/ml, for example less than 70,000 mg/ml, such as less than 60,000 mg/ml, for example less than 50,000 mg/ml, such as less than 40,000 mg/ml, for example less than 30,000 mg/ml, such as less than 20,000 mg/ml, for example less than 10,000 mg/ml, such as less than 9000 mg/ml, for example less than 8000 mg/ml, such as less than 7000 mg/ml, for example less than 6000 mg/ml, such as less than 5000 mg/ml, for example less than 4000 mg/ml, such as less than 3000 mg/ml, for example less than 2000 mg/ml, such as less than 1000 mg/ml, for example less than 900 mg/ml, such as less than 800 mg/ml, for example less than 700 mg/ml, such as less than 600 mg/ml, for example less than 500 mg/ml, such as less than 400 mg/ml, for example less than 300 mg/ml, such as less than 200 mg/ml, for example less than 100 mg/ml, such as less than 10 mg/ml, for example less than 1 mg/ml, such as less than 1000 ug/ml, for example less than 900 ug/ml, such as less than 800 ug/ml, for example less than 700 ug/ml, such as less than 600 ug/ml, for example less than 500 ug/ml, such as less than 400 ug/ml, for example less than 300 ug/ml, such as less than 200 ug/ml, for example less than 100 ug/ml, such as less than 10 ug/ml, for example less than 1 ug/ml, such as less than 1000 ng/ml, for example less than 900 ng/ml, such as less than 800 ng/ml, for example less than 700 ng/ml, such as less than 600 ng/ml, for example less than 500 ng/ml, such as less than 400 ng/ml, for example less than 300 ng/ml, such as less than 200 ng/ml, for example less than 100 ng/ml, such as less than 10 ng/ml, for example less than 1 ng/ml.

In one embodiment, the bioactive agent is present in the fluid or liquid composition at a concentration in the range of 1 ng/ml to 1,000,000 mg/ml; such as 1-10 ng/ml, for example 10-100 ng/ml, such as 100-200 ng/ml, for example 300-400 ng/ml, such as 400-500 ng/ml, for example 500-600 ng/ml, such as 600-700 ng/ml, for example 700-800 ng/ml, such as 800-900 ng/ml, for example 900-1000 ng/ml, such as 1-10 ug/ml, for example 10-100 ug/ml, such as 100-200 ug/ml, for example 200-300 ug/ml, such as 300-400 ug/ml, for example 400-500 ug/ml, such as 500-600 ug/ml, for example 600-700 ug/ml, such as 700-800 ug/ml, for example 800-900 ug/ml, such as 900-1000 ug/ml, for example 1-10 mg/ml, such as 10-100 mg/ml, for example 100-200 mg/ml, such as 200-300 mg/ml, for example 300-400 mg/ml, such as 400-500 mg/ml, for example 500-600 mg/ml, such as 600-700 mg/ml, for example 700-800 mg/ml, such as 800-900 mg/ml, for example 900-1000 mg/ml, such as 1000-2000 mg/ml, for example 2000-3000 mg/ml, such as 3000-4000 mg/ml, for example 4000-5000 mg/ml, such as 5000-6000 mg/ml, for example 6000-7000 mg/ml, such as 7000-8000 mg/ml, for example 8000-9000 mg/ml, such as 9000-10,000 mg/ml, for example 10,000-20,000 mg/ml, such as 20,000-30,000 mg/ml, for example 30,000-40,000 mg/ml, such as 40,000-50,000 mg/ml, for example 50,000-60,000 mg/ml, such as 60,000-70,000 mg/ml, for example 70,000-80,000 mg/ml, such as 80,000-90,000 mg/ml, for example 90,000-100,000 mg/ml, such as 100,000-200,000 mg/ml, for example 200,000-300,000 mg/ml, such as 300,000-400,000 mg/ml, for example 400,000-500,000 mg/ml, such as 500,000-600,000 mg/ml, for example 600,000-700,000 mg/ml, such as 700,000-800,000 mg/ml, for example 800,000-900,000 mg/ml, such as 900,000-1,000,000 mg/ml.

In another embodiment, the bioactive agent is present in the fluid or liquid composition at a concentration in the range of 1 ng/ml-1,000,000 mg/ml, for example 10 ng/ml-1,000,000 mg/ml, such as 100 ng/ml-1,000,000 mg/ml, for example 300 ng/ml-1,000,000 mg/ml, such as 400 ng/ml-1,000,000 mg/ml, for example 500 ng/ml-1,000,000 mg/ml, such as 600 ng/ml-1,000,000 mg/ml, for example 700 ng/ml-1,000,000 mg/ml, such as 800 ng/ml-1,000,000 mg/ml, for example 900 ng/ml-1,000,000 mg/ml, such as 1 ug/ml-1,000,000 mg/ml, for example 10 ug/ml-1,000,000 mg/ml, such as 100 ug/ml-1,000,000 mg/ml, for example 200 ug/ml-1,000,000 mg/ml, such as 300 ug/ml-1,000,000 mg/ml, for example 400 ug/ml-1,000,000 mg/ml, such as 500 ug/ml-1,000,000 mg/ml, for example 600 ug/ml-1,000,000 mg/ml, such as 700 ug/ml-1,000,000 mg/ml, for example 800 ug/ml-1,000,000 mg/ml, such as 900 ug/ml-1,000,000 mg/ml, for example 1-1,000,000 mg/ml, such as 10-1,000,000 mg/ml, for example 100-1,000,000 mg/ml, such as 200-1,000,000 mg/ml, for example 300-1,000,000 mg/ml, such as 400-1,000,000 mg/ml, for example 500-1,000,000 mg/ml, such as 600-1,000,000 mg/ml, for example 700-1,000,000 mg/ml, such as 800-1,000,000 mg/ml, for example 900-1,000,000 mg/ml, such as 1000-1,000,000 mg/ml, for example 2000-1,000,000 mg/ml, such as 3000-1,000,000 mg/ml, for example 4000-1,000,000 mg/ml, such as 5000-1,000,000 mg/ml, for example 6000-1,000,000 mg/ml, such as 7000-1,000,000 mg/ml, for example 8000-1,000,000 mg/ml, such as 9000-1,000,000 mg/ml, for example 10,000-1,000,000 mg/ml, such as 20,000-1,000,000 mg/ml, for example 30,000-1,000,000 mg/ml, such as 40,000-1,000,000 mg/ml, for example 50,000-1,000,000 mg/ml, such as 60,000-1,000,000 mg/ml, for example 70,000-1,000,000 mg/ml, such as 80,000-1,000,000 mg/ml, for example 90,000-1,000,000 mg/ml, such as 100,000-1,000,000 mg/ml, for example 200,000-1,000,000 mg/ml, such as 300,000-1,000,000 mg/ml, for example 400,000-1,000,000 mg/ml, such as 500,000-1,000,000 mg/ml, for example 600,000-1,000,000 mg/ml, such as 700,000-1,000,000 mg/ml, for example 800,000-1,000,000 mg/ml, such as 900,000-1,000,000 mg/ml.

In yet another embodiment, the bioactive agent is present in the fluid or liquid composition at a concentration in the range of 1-10 ng/ml, for example 1-100 ng/ml, such as 1-200 ng/ml, for example 1-400 ng/ml, such as 1-500 ng/ml, for example 1-600 ng/ml, such as 1-700 ng/ml, for example 1-800 ng/ml, such as 1-900 ng/ml, for example 1-1000 ng/ml, such as 1 ng/ml-10 ug/ml, for example 1 ng/ml-100 ug/ml, such as 1 ng/ml-200 ug/ml, for example 1 ng/ml-300 ug/ml, such as 1 ng/ml-400 ug/ml, for example 1 ng/ml-500 ug/ml, such as 1 ng/ml-600 ug/ml, for example 1 ng/ml-700 ug/ml, such as 1 ng/ml-800 ug/ml, for example 1 ng/ml-900 ug/ml, such as 1 ng/ml-1000 ug/ml, for example 1 ng/ml-10 mg/ml, such as 1 ng/ml-100 mg/ml, for example 1 ng/ml-200 mg/ml, such as 1 ng/ml-300 mg/ml, for example 1 ng/ml-400 mg/ml, such as 1 ng/ml-500 mg/ml, for example 1 ng/ml-600 mg/ml, such as 1 ng/ml-700 mg/ml, for example 1 ng/ml-800 mg/ml, such as 1 ng/ml-900 mg/ml, for example 1 ng/ml-1000 mg/ml, such as 1 ng/ml-2000 mg/ml, for example 1 ng/ml-3000 mg/ml, such as 1 ng/ml-4000 mg/ml, for example 1 ng/ml-5000 mg/ml, such as 1 ng/ml-6000 mg/ml, for example 1 ng/ml-7000 mg/ml, such as 1 ng/ml-8000 mg/ml, for example 1 ng/ml-9000 mg/ml, such as 1 ng/ml-10,000 mg/ml, for example 1 ng/ml-20,000 mg/ml, such as 1 ng/ml-30,000 mg/ml, for example 1 ng/ml-40,000 mg/ml, such as 1 ng/ml-50,000 mg/ml, for example 1 ng/ml-60,000 mg/ml, such as 1 ng/ml-70,000 mg/ml, for example 1 ng/ml-80,000 mg/ml, such as 1 ng/ml-90,000 mg/ml, for example 1 ng/ml-100,000 mg/ml, such as 1 ng/ml-200,000 mg/ml, for example 1 ng/ml-300,000 mg/ml, such as 1 ng/ml-400,000 mg/ml, for example 1 ng/ml-500,000 mg/ml, such as 1 ng/ml-600,000 mg/ml, for example 1 ng/ml-700,000 mg/ml, such as 1 ng/ml-800,000 mg/ml, for example 1 ng/ml-900,000 mg/ml, such as 1 ng/ml-1,000,000 mg/ml.

The concentration of the bioactive agent in each droplet is preferably essentially identical, wherein the concentration of any two droplets expelled from a printer according to the present invention may vary less that 10%, such as less than 8%, for example less than 6%, such as less than 4%, for example less than 2%, such as less than 1%. The concentration of any two droplets may vary in the range of 0.1-10%, such as 0.1-1%, for example 1-2%, such as 2-3%, for example 3-4%, such as 4-5%, for example 5-6%, such as 6-7%, for example 7-8%, such as 8-9%, for example 9-10%.

Uniform Distribution

When printing a fluid or liquid composition onto a matrix material according to the present invention, the composition will be distributed in a uniform manner on the matrix material, i.e. there will be essentially no concentration gradient of the composition throughout the matrix material. This may be regarded as a uniform pattern arising from the uniform distribution. Further, deposition using the print technology is also very precise, allowing the specific deposition onto discrete locations of the matrix material.

The uniform distribution arises from the use of a predetermined and essentially fixed ratio between droplet volume, distance between every two droplets and the concentration of the bioactive material of the droplet. Achieving such a ratio is possible using the print technology, and permits the deposition of an essentially identical amount or volume of fluid or liquid composition and/or bioactive agent per area unit of the matrix material. Achieving such a uniform distribution is not possible to obtain from conventional techniques such as spraying.

Specific and numeric values for droplet volume or size, distance between every two droplets and the droplet concentration of the bioactive material of the composition are given herein above. The predetermined values for use in any embodiment to determine the ratio between droplet volume, distance between every two droplets and the concentration of the droplet may be chosen from any of the herein disclosed values.

A uniform distribution of a pharmaceutical composition initially in fluid or liquid form may be defined as a distribution wherein any two area units differ in volume of the printed composition or concentration of bioactive agent by the most 10%, such as by the most 8%, for example by the most 6%, such as by the most 4%, for example by the most 2%, such as by the most 1%. Any two area units has a uniform distribution that may vary in the range of 0.1-10%, such as 0.1-1%, for example 1-2%, such as 2-3%, for example 3-4%, such as 4-5%, for example 5-6%, such as 6-7%, for example 7-8%, such as 8-9%, for example 9-10%.

A uniform distribution also arises from essentially all the fluid or liquid composition leaving the nozzle of the print head contacts the matrix material, whereby essentially no fluid or liquid composition is wasted in the process. The amount of fluid or liquid composition not contacting the matrix material is less that 10%, such as less than 8%, for example less than 6%, such as less than 4%, for example less than 2%, such as less than 1%.

Hemostatic and Anti-Fibrinolytic Agents

Hemostatic agents, or pro-coagulants or thrombotic agents, are agents that induce hemostasis. Thus, they shift the balance in favor of blood coagulation or clotting. Anti-fibrinolytic agents are also hemostatic agents, in that they prevent the degradation of the formed blood clot.

In a preferred embodiment, the device according to the present invention is a hemostatic device. The hemostatic device may thus be imprinted with hemostatic agents.

The hemostatic device described herein may be used as a medicament. Accordingly, in a further aspect the present invention relates to a method of promoting hemostasis in a patient in need thereof, said method comprising printing a pharmaceutical composition as defined herein onto a device, and using the device to promote hemostasis.

Below are listed non-limiting examples of hemostatic agents that in one embodiment may be included in the composition that is printed onto the device of the present invention.

Specific examples of hemostatic agents include coagulation factors selected from the group consisting of prothrombin and/or thrombin, fibrinogen and/or fibrin, Factor V and/or Va, Factor VII and/or VIIa, Factor VIII and/or VIIIa, Factor IX and/or IXa, Factor X and/or Xa, Factor XI and/or XIa, Factor XII and/or XIIa, Factor XIII and/or XIIIa, and combinations thereof. Such compounds may be of any mammalian origin, such as of porcine or human origin, or may be obtained by recombinant means by methods well-known to the skilled person.

Coagulation factor concentrates are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII is are increasingly popular in the treatment of major bleeding.

Fibronectin is excreted by fibroblasts in the proliferative pase of wound healing. Fibrin and fibronectin cross-link together and form a plug that traps proteins and particles and prevents further blood loss. This fibrin-fibronectin plug is also the main structural support for the wound until collagen is deposited.

Additional agents that may be comprised in the composition to promote hemostasis include calcium ions to aid coagulation, and desmopressin which improve platelet function by activating arginine vasopressin receptor 1A.

Anti-fibrinolytic agents may be selected from the group consisting of tranexamic acid, aminocaproic acid, aprotinin, pepstatin, leupeptin, antipain, chymostatin, gabexate, and mixtures thereof. In a preferred embodiment of the present invention, tranexamic acid comprises part of the composition, if any anti-fibrinolytic agent is comprised in the composition.

Further, the use of adsorbent chemicals, such as zeolites, and other hemostatic agents is also being explored for use in sealing severe injuries quickly.

QuikClot® brand hemostatic agent is manufactured by Z-Medica Corporation. The original QuikClot® is a granular product that can be poured directly on wounds to stop bleeding. It stops bleeding by adsorbing water from the blood thereby concentrating the clotting factors, activating platelets and promoting steps in the coagulation cascade. It is composed of zeolite, a molecular sieve that traps molecules in a molecular "cage" and holding the trapped species by forming hydrogen bonds. The bond formation generates heat, which has been a drawback to the original QuikClot® brand hemostatic agent. Newer versions of the product have been developed by Z-Medica that have reduced and eliminated the exothermic reaction.

Other examples of suitable biologically absorbable materials with hemostatic or even wound healing effects include gelatin, collagen, chitin, chitosan, alginate, cellulose, polyglycolic acid, polyacetic acid and mixtures thereof. It will be understood that various forms thereof, such as linear or cross-linked forms, salts, esters and the like may also be used as the biologically absorbable material to be included in the haemostatic powder of the invention.

"Biologically absorbable" is a term which in the present context is used to describe that the materials of which the said powder are made can be degraded in the body to smaller molecules having a size which allows them to be transported into the blood stream. By said degradation and absorption the materials will gradually be removed from the site of application. For example, denatured gelatin can be degraded by proteolytic tissue enzymes to absorbable smaller molecules, whereby the denatured gelatin powder when applied in tissues typically is absorbed within about 3-6 weeks and when applied on bleeding surfaces and mucous membranes typically within 3-5 days.

TABLE 1

| Hemostatic and anti-fibrinolytic agents | | |
| --- | --- | --- |
| Pro-thrombin and/or thrombin | Cryoprecipitate | Chymostatin |
| Fibrinogen and/or fibrin | Fresh frozen plasma | Gabexate |
| Factor V and/or Va | Fibronectin | Zeolites |
| Factor VII and/or VIIa | Calcium ions | Gelatin |
| Factor VIII and/or VIIIa | Desmopressin | Collagen |
| Factor IX and/or IXa | Tranexamic acid | Chitin |
| Factor X and/or Xa | Aminocaproic acid | Chitosan |
| Factor XI and/or XIa | Aprotinin | Alginate |
| Factor XII and/or XIIa | Pepstatin | Cellulose |
| Factor XIII and/or XIIIa | Leupeptin | Polyglycolic acid |
| Prothrombin complex concentrate | Antipain | Polyacetic acid |

Wound Healing Promoting Agents

In one embodiment, the device according to the present invention is a wound healing device. The wound healing device may thus be imprinted with wound healing or wound healing promoting agents. A wound healing agent may be an agent that accelerates the wound healing process.

The wound healing device described herein may be used as a medicament. Accordingly, in a further aspect the present invention relates to a method of promoting wound healing in a patient in need thereof, said method comprising printing a pharmaceutical composition as defined herein onto a device, and using the device to promote wound healing.

Below are listed non-limiting examples of wound healing agents that in one embodiment may be included in the composition that is printed onto the device of the present invention.

Wound healing agents may be present on the device alone, may be combined or used together or in coordination with e.g. an antibiotic, antifungal, or antiviral substance or substances to accelerate the healing of sores or other infection-damaged tissue simultaneously or sequentially with the treatment of the underlying infection.

Further, growth factors to promote healing may also be employed in the composition for printing onto the device to promote wound healing.

Adrenaline or other substances capable of constricting blood vessels thereby reducing local blood flow may also be employed in the composition for printing onto the device to promote wound healing. Factors that trigger vasoconstriction can be of exogenous origin, such as medication and endogenous as well, as a response from the body itself. Examples of medications include: anti-histamines such as H1 receptor antagonists including Diphenhydramine, Loratadine, Meclizine and Quetiapine; inhibitors of histamine release such as mast cell stabilizers including Cromoglicate (cromolyn) and Nedocromil; caffeine; decongestants such as Ephedrine, Oxymetazoline, Phenylephrine, Pseudoephedrine, Tramazoline, phenylpropanolamine (PPA) and Xylometazoline that work on adrenoreceptor al.

Active wound healing compounds can be combined with or used simultaneously or sequentially with other tissue healing promoters, such as epidermal growth factor, fibroblast growth factor, platelet derived growth factor, transforming growth factor alpha, transforming growth factor beta, and insulin-like growth factor 1 (Brunt, J. V., and Tilansner, A., *Biotechnology* 6:25-30 (1988)) to promote a more rapid healing of damaged tissue.

It is also useful to imprint the device according to the invention with corticosteroid and anti-inflammatory agents to accelerate the healing of lesions in patients suffering from allergic or inflammatory processes, since steroids are known to slow the healing of wounds.

The following compounds can be printed onto the surface of the device according to the present invention in a method for the treatment of wounds. These include, but are not limited to: allantoin, retinoic acid, aloe vera, glycine, vitamin A, the B vitamins, especially nicotinamide, vitamins C and E, antibacterial agents (e.g., quaternary ammonium compounds, bacitracin, neomycin and polymyxin), comfrey root preparations, platelets and/or platelet extracts, ribonucleosides, proline, lysine, elastin, glycosaminoglycans, spermidine, spermine, putrescine, angiogenic factors, zinc, alpha-1 antitrypsin, SLPI (Secretory Leukocyte Protease Inhibitor), and various peptide growth factors such as the somatomedins, Iamin, EGF (epidermal growth factor), IGF1/2 (insulin-like growth factor 1 or 2), PDGF (platelet derived growth factor), FGF (fibroblast growth factor), TGF (transforming growth factor), MDGF (macrophage-derived growth factor), NGF (neuron growth factor), PDECGF (Platelet Derived Endothelial Cell Growth Factor), KGF (Keratinocyte Growth Factor), and TNF (Tumor Necrosis Factor). The pharmaceutically active device of the invention may also be used in conjunction with synthetic skin in treating burns and other wounds, and in supporting the healing of skin or corneal transplants.

Antimicrobial agents may be selected from bactericidal or bacteriostatic agents, such as antibiotics and sulphonamides, antiviral compounds, antimycotic agents and anti-infectives. Antibiotics may be selected from e.g. β-lactams, penicillins, cephalosporins, monobactams, macrolides, polymyxins, tetracyclines, chloramphenicol, thrimethoprim, aminoglycosides, clindamycin, and metronidazole; sulphonamides may as an example be selected from sulphadimidine or sulphadimethoxin; antimycotic agents may be selected from amphotericin B, ketoconazol and miconazol; and antiviral agent from idoxuridine and azidothymidin. Suitable antiinfectives may as an example be selected from halogens, chlorohexidine and quarternary ammonium compounds. Other examples of bactericidal or bacteriostatic compounds include silver ions, in particular in the form of silver ion complexes.

Medical or veterinary indications for the use of the invention include, but are not limited to the following situations. The pharmaceutical compositions can be used to accelerate the healing of mechanical wounds or abrasions of the skin or other tissues which are exposed by mechanical injury to the skin or gastrointestinal mucosa of the body. The invention can also be used to accelerate the healing of burns inflicted upon the skin, and any underlying tissues which may be exposed by such injury. The burns may be those caused by heat, ionizing radiation, ultraviolet radiation including sunlight, electricity, or chemical substances.

In one embodiment, the pharmaceutically active device according to the present invention is also useful in conditions in which normal wound healing is impaired. Examples of types of wounds that heal poorly or slowly include venous stasis ulcers, decubitus ulcers, and cutaneous and alimentary tract wounds, or ulcers in patients with diabetes, and in patients subjected to irradiation, cancer chemotherapy (e.g. with adriamycin or cyclophosphamide), and topical or systemic anti-inflammatory glucocorticosteriods.

Further, the compositions may be used to accelerate the healing of surgical incisions in any part of the body, external or internal, into which device according to the present invention may be introduced. The compositions can also be used to accelerate the healing of ischemic ulcers, pressure sores, bed sores, or ulcers caused by diabetes or other disease processes.

TABLE 2

| Wound healing agents | | |
|---|---|---|
| Adrenaline | Platelets and/or platelet extracts | β-lactams |
| Diphenhydramine | Ribonucleosides | Penicillins |
| Loratadine | Proline | Cephalosporins |
| Meclizine | Lysine | Monobactams |
| Quetiapine | Elastin | Macrolides |
| Cromoglicate (cromolyn) | Glycosaminoglycans | Polymyxins |
| Nedocromil | Spermidine | Tetracyclines |
| Caffeine | Spermine | Chloramphenicol |
| Ephedrine | Putrescine | Thrimethoprim |
| Oxymetazoline | Angiogenic factors | Aminoglycosides |
| Phenylephrine, | Zinc | Clindamycin |
| Pseudoephedrine | Somatomedins | Metronidazole |
| Tramazoline | Lamin | Sulphadimidine |
| Phenylpropanolamine (PPA) | FGF | Sulphadimethoxin |
| Xylometazoline | PDGF | Amphotericin B |
| Corticosteroid | TGF | Ketoconazol |
| Allantoin | IGF | Miconazol |
| Retinoic acid | EGF | Idoxuridine |
| *Aloe vera* | MDGF | Azidothymidin |
| Glycine | NGF | Halogens |
| Vitamin A | KGF | Chlorohexidine |
| The B vitamins, especially nicotinamide | TNF | Silver ions |
| Vitamin C | PDECGF | alpha-1 antitrypsin |
| Vitamin E | Bacitracin | SLPI |
| Comfrey root preparations | Neomycin | |
| Quaternary ammonium compounds | Polymyxin | |

Adhesive Agents

Suitable agents, which may improve the adhesive properties (or the tackiness) of the composition are well-known to the person skilled in the art. One class of suitable agents includes saccharides, such as monosaccharides, disaccharides, oligosaccharides, polysaccharides, and combinations thereof.

When used herein the term "saccharide", as well as the terms "monosaccharide", "disaccharide", "oligosaccharide" and "polysaccharide", also encompasses derivatives thereof, such as saccharides comprising one or more aminosugar units. In the present context, an aminosugar unit is a sugar unit wherein at least one of the hydroxy groups available in the sugar unit has been substituted by an amino group or an alkanoylated amino group such as an acetylated amino group. Accordingly, it will be understood that saccharides containing one or more glucosamine and/or N-acetylglucosamine unit(s) are also encompassed by the above-mentioned terms. Apart from the aminosugar units, the saccharide may contain unsubstituted sugar units or sugar units substituted with e.g. alkoxy (such as 2,3-dimethylglucose) or acyloxy.

Specific examples of monosaccharides include glucose, mannose, fructose, threose, gulose, arabinose, ribose, erythrose, lyxose, galactose, sorbose, altrose, tallose, idose, rhamnose, allose, and derivatives thereof, e.g. pentosamines, hexosamines, such as glucosamine or N-acetylglucosamine, and glucoronic acid. In particular glucose is preferred.

Specific examples of disaccharides include sucrose, maltose, lactose, cellubiose as well as derivatives thererof. In particular sucrose is preferred.

Specific examples of polysaccharides include glycogen, chitin, chitosan, starch such as potato starch, as well as combinations thereof. Specific examples of polysaccharide derivatives include glycosaminoglycans such as chondroitin, chondroitin sulfate, hyaluronic acid, dermatan sulfate and keratan sulfate; aminated dextrans including DEAE-dextran; aminated starch, aminated glycogen, aminated cellulose, aminated pectin, and salts, complexes, derivatives and mixtures thereof.

In an interesting embodiment of the invention, the composition further comprises an agent which improves the adhesive properties of said composition, where said agent is selected from the group consisting of glucose, sucrose, and a mixture thereof.

Other examples of agents which improve the adhesive properties of the composition include hydrocarbon resins, rosin resins and terpene resins. Hydrocarbon resins are commercially available under the tradenames Escorez® from ExxonMobil; Regalite®, Piccotac® and Picco® from Eastman; Indopol® from BP or Arkon®. Examples of rosin esters include esters of hydrogenated wood rosin e.g. pentaerythritol ester of hydrogenated wood rosin, esters of partially hydrogenated wood rosin e.g. pentaerythritol esters of partially hydrogenated wood rosin, esters of wood rosin, esters of modified wood rosin, esters of partially dimerized rosin, esters of tall oil rosin, esters of dimerized rosin, and similar rosins, and combinations and mixtures thereof. Such rosin esters are commercially available under the tradenames Foral®, Foralyn®, Pentalyn®, Permalyn® and Staybelite®.

Further examples of agents which improve the adhesive properties of the composition include Gum Karaya, sometimes known as Sterculia gum, Gum Arabicum, Gum Karrageenan, celluloseethers, such as sodium carboxymethylcellulose, Manuba Honey, casein, alginates or fatty acid esters, such as the fatty acid esters disclosed in WO 95/26715, and gecko-like or gecko-inspired medical adhesives.

Thus, in an interesting embodiment of the invention, the composition comprises at least one agent which improves the adhesive properties of the composition. Evidently, the exact amount of agent may vary depending on what specific agent is being used, but the composition typically comprises 0.1-50% (w/w) of the agent, based on the total weight of the composition. Preferably, and in particular when the agent which improves the adhesive properties of the composition is a saccharide, the composition comprises 1-25% (w/w), such as 5-20% (w/w), e.g. 5-15% (w/w), 5-10% (w/w), or 10-15% (w/w), based on the total weight of the composition.

In one embodiment, the pharmaceutical composition according to the present invention is printed onto an adhesive surface of a matrix material.

TABLE 3

| Adhesive agents | | |
|---|---|---|
| Glucose | hexosamines | aminated dextrans |
| mannose | glucosamine | aminated starch |
| fructose | N-acetylglucosamine | aminated glycogen |
| threose | glucoronic acid | aminated cellulose |
| gulose | Sucrose | aminated pectin |
| arabinose | maltose | Hydrocarbon resins |
| ribose | lactose | Rosin resins |
| erythrose | cellubiose | Terpene resins |
| lyxose | glycogen | Gum Karaya |
| galactose | chitin | Gum Arabicum |
| sorbose | chitosan | Gum Karrageenan |
| altrose | starch | Sodium carboxymethylcellulose |
| tallose | chondroitin | Manuba Honey |
| idose | chondroitin sulfate | Casein |
| rhamnose | hyaluronic acid | Alginates |

TABLE 3-continued

| Adhesive agents | | |
|---|---|---|
| allose | dermatan sulfate | Fatty acid esters |
| pentosamines | keratan sulfate | Gecko-like adhesive |

Surfactant Agents

In another interesting embodiment of the invention, the composition further comprises an agent which improves the surfactant properties of said composition, where said agent is selected from the group consisting of anionic surfactants, cationic surfactants, non-ionic surfactants and surface active biological modifiers.

Examples of anionic surfactants include surfactants selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose. In particular sodium lauryl sulfate is preferred.

Examples of cationic surfactants include surfactants selected from the group consisting of quaternary ammonium compounds, benzalkonium chloride, cetyltrimethylammonium bromide, chitosans and lauryldimethylbenzylammonium chloride.

Examples of non-ionic surfactants include surfactants selected from the group consisting of polyoxyethylene fatty alcohol ethers, polyoxyethylene sorbitan fatty acid esters, polyoxyethylene fatty acid esters, sorbitan esters, polyoxyethylene sorbitan esters (such as Tween 80 or Tween 20), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, Pluronic F68 and polyvinylpyrrolidone.

TABLE 4

| Surfactants | | |
|---|---|---|
| Potassium laurate | Glycodeoxycholic acid | Aryl alkyl polyether alcohols |
| Triethanolamine stearate | Calcium carboxymethylcellulose | Polyoxyethylene-polyoxypropylene copolymers |
| Sodium lauryl sulfate | Benzalkonium chloride | Polaxamines |
| Sodium dodecylsulfate | Cetyltrimethylammonium bromide | Methylcellulose |
| Alkyl polyoxyethylene sulfates | Chitosans | Hydroxycellulose |
| Sodium alginate | Lauryldimethylbenzylammonium chloride | Hydroxy propylcellulose |
| Dioctyl sodium sulfosuccinate | Polyoxyethylene fatty alcohol ethers | Hydroxy propylmethylcellulose |
| Phosphatidyl glycerol | Polyoxyethylene sorbitan fatty acid esters | Noncrystalline cellulose |
| Phosphatidyl inositol | Polyoxyethylene fatty acid esters | Polysaccharides |
| Phosphatidylserine | Sorbitan esters | Starch |
| Phosphatidic acid | Polyoxyethylene sorbitan esters | Starch derivatives |

TABLE 4-continued

| Surfactants | | |
|---|---|---|
| Glyceryl esters | Glycerol monostearate | Hydroxyethylstarch |
| Bile acids and their salts | Polyethylene glycols | Polyvinyl alcohol |
| Cholic acid | Polypropylene glycols | Polyvinyl-pyrrolidone |
| Deoxycholic acid | Cetyl alcohol | Albumin |
| Glycocholic acid | Cetostearyl alcohol | |
| Taurocholic acid | Stearyl alcohol | |

Other Bioactive Agents

Below are listed further non-limiting examples of bioactive agents that in one embodiment may be included in the composition that is printed onto the surface of the matrix of the present invention.

Analgetics are pharmaceutical that may be used to alleviate pain. In generalanalgetics may belong to one of 3 groups, i) opiodanalgetics, ii) weak non-opiod analgetics and iii) psychopharmacological drugs, lidocain analogues and antiepileptica. In a preferred embodiment of the present invention the analgetic is lidocain.

To further illustrate, antimetabolites which can be formulated in the subject polymers include, but are not limited to, methotrexate, 5-fluorouracil, cytosine arabinoside (ara-C), 5-azacytidine, 6-mercaptopurine, 6-thioguanine, and fludarabine phosphate.

Antitumor antibiotics may include but are not limited to doxorubicin, daunorubicin, dactinomycin, bleomycin, mitomycin C, plicamycin, idarubicin, and mitoxantrone.

Vinca alkaloid and epipodophyiotoxins may include, but are not limited to vincristine, vinblastine, vindesine, etoposide and teniposide.

Nitrosoureas can also be provided including carmustine, lomustine, semustine and streptozocin.

Hormonal therapeutics can also be included in the pharmaceutical composition, such as corticosteriods (cortisone acetate, hydrocortisone, prednisone, prednisolone, methylprednisolone and dexamethasone), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromatase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole).

Other compounds which in one embodiment may be included in the composition of the present invention include those classified as e.g. investigational drugs, and can include, but are not limited to alkylating agents such as Nimustine AZQ, BZQ, cyclodisone, DADAG, CB10-227, CY233, DABIS maleat, EDMN, Fotemustine, Hepsulfam, Hexamethylmelamine, Mafosamide, MDMS, PCNU, Spiromustine, TA077, TCNU and Temozolomide; antimetabolites, such as acivicin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iodo-doxorubicin, Marcellomycin, Menaril, Morpholinoanthracyclines, Pirarubicin, SM-5887; microtubule spindle inhibitors, such as Amphethinile, Navelbine, and Taxol; the alkyllysophospholipids, such as BM41-440, ET-18-OCH3, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; novel compounds such as, for example Aphidoicolin glycinate, Ambazone, BSO, Caracemide, DSG, Didemnin, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK, F104864, Suramin, Tallysomycin, Teniposide, THU, 2721, Toremifene, Trilosane, and zindoxifene.

Antitumor drugs that are radiation enhancers can also be formulated in the subject controlled release formulation. Examples of such drugs include, for example, the chemotherapeutic agents 5'-fluorouracil, mitomycin, cisplatin and its derivatives, taxol, bleomycins, daunomycins, and methamycins.

In one embodiment, the biologically active agent is selected from the group consisting of polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other antineoplastics, antibiotics, anti-virals, anti-fungals, anti-inflammatories, anticoagulants, an antigenic materials.

Further examples of medicaments according to the present invention are antimicrobial agents, analgesics, antiinflammatory agents, counterirritants, coagulation modifying agents, diuretics, sympathomimetics, anorexics, antacids and other gastrointestinal agents, antiparasitics, antidepressants, antihypertensives, anticholinergics, stimulants, antihormones, central and respiratory stimulants, drug antagonists, lipid-regulating agents, uricosurics, cardiacglycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, (3-blockers, purgatives, antiarrhythmics, contrast materials, radiopharmaceuticals, antiallergic agents, tranquilizers, vasodilators, antiviral agents, andantineoplastic or cytostatic agents or other agents with anticancer properties, or a combination thereof. Other suitable medicaments may be selected from contraceptives and vitamins as well as micro and macronutrients.

Further bioactive agents which may be comprised in the composition in accordance with the present invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrleals; antihistamines; anti inflammatory agents; antimigraine preparations; antinauseants; ahtineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Further specific examples of bioactive agents include acebutolol, acetaminophen, acetohydroxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, bethanechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colchicine, coloestipol, conjugated estrogen, contraceptives, cortisone, cromolyn, cyclacillM, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfuram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecamide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenyloin, mephobarbital, meprobamate, mercaptopurine; mesoridazine, metaproterenol, <RTI metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystatin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyltoloxamine, phenyloin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyrodoxine, pyrilamine, pyrvinium, quinestrol, quinethazone, uinidine, quinine, ranitidine, rauwolfia alkaloid, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocamide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B-12, vitamin C, vitamin D, vitamin E, vitamin K, xanthine, and the like.

Further examples of medicaments include, but are not limited to, antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastrointestinals, and antiemetics (e.g., metoclopramide), anti-epileptics (e.g., phenyloin, meprobamate and nitrazepam), vasodilators (e.g., nifedipine, papaverine, diltiazem and nicardipine), antitussive agents and expectorants (e.g., codeine phosphate), anti-asthmatics (e.g. theophylline), anti-spasmodics (e.g. atropine, scopolamine), hormones (e.g., insulin, heparin), diuretics (e.g., ethacrynic acid, bendroflumethiazide), antihypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including apetite suppressants such as phenylpropanolamine). The above list is not meant to be exclusive.

Other types of medicaments include flurazepam, nimetazepam, nitrazepam, perlapine, estazolam, haloxazolam, sodium valproate, sodium cromoglycate, primidone, alclofenac, perisoxal citrate, clidanac, indomethacin, sulpyrine, flufenamic acid, ketoprofen, sulindac, metiazinic acid, tolmetin sodium, fentiazac, naproxen, fenbufen, protizinic acid, pranoprofen, flurbiprofen, diclofenac sodium, mefenamic acid, ibuprofen, aspirin, dextran sulfate, carindacillin sodium, and the like.

The medicament may be in the form of a physiologically active polypeptide, which is selected from the group consisting of insulin, somatostatin, somatostatin derivatives, growth hormone, prolactin, adrenocorticotrophic hormone, melanocyte stimulating hormone, thyrotropin releasing hormone, its salts or its derivatives, thyroid stimulating hormone, luteinizing hormone, follicle stimulating hormone, vasopressin, vasopressin derivatives, oxytocin, carcitonin, parathyroid hormone, glucagon, gastrin, secretin, pancreozymin, cholecystokinin, angiotensin, human placentalactogen, human chorionic gonadotropin, enkephalin, enkephalin derivatives, endorphin, interferon (in one or more of the forms alpha, beta, and gamma), urokinase, kallikrein, thymopoietin, thymosin, motilin, dynorphin, bombesin, neurotensin, caerulein, bradykinin, substance P, kyotorophin, nerve growth factor, polymyxin B, colistin, gramicidin, bacitracin, bleomycin and neocarzinostatin.

Furthermore, the bioactive agent may be a polysaccharide, such as heparin, an antitumor agent such as lentinan, zymosan and PS-K (krestin), anaminoglycoside such as e.g. gentamycin, streptomycin, kanamycin, dibekacin, paromomycin, kanendomycin, lipidomycin, tobramycin, amikacin, fradiomycin and sisomicin, a beta-lactam antibiotic, such as e.g. a penicillin, such as e.g. sulbenicillin, mecillinam, carbenicillin, piperacillin and ticarcillin, thienamycin, and cephalosporins such ascefotiam, cefsulodine, cefmenoxime, cefmetazole, cefazolin, cefotaxime, cefoperazone, ceftizoxime andmoxalactam, or a nucleic acid drug such as e.g. citicoline and similar antitumor agents, for example cytarabine and 5-FU (5-fluorouracil).

Certain monomeric subunits of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

For the purposes of this application, unless expressly noted to the contrary, a named amino acid shall be construed to include both the D or L stereoisomers, preferably the L stereoisomer.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Antibiotic Agents

An antibiotic is a chemotherapeutic agent that inhibits or abolishes the growth of micro-organisms, such as bacteria, fungi, or protozoa. Below is a list of antibiotic agents that in one embodiment may be comprised in the pharmaceutical composition to be printed onto the surface of a matrix material.

Antibiotics are well known to those of skill in the art, and include, for example, penicillins, cephalosporins, tetracyclines, ampiciflin, aureothicin, bacitracin, chloramphenicol, cycloserine, erythromycin, gentamicin, gramacidins, kanamycins, neomycins, streptomycins, tobramycin, and vancomycin. Further antibiotic agents are listed in Table 5 below:

TABLE 5

Antibiotic agents

Amikacin, Anisomycin, Apramycin, Azithromycin, Blasticidine, Brefeldin A, Butirosin, Butirosin A, Chloramphenicol, Chlortetracycline hydrochloride, Clindamycin 2-phosphate, Clindamycin hydrochloride, Clotrimazole, Cycloheximide, Demeclocycline hydrochloride, Dibekacin sulfate salt, Dihydrostreptomycin sesquisulfate, Dihydrostreptomycin solution, Doxycycline hyclate, Duramycin, Emetine dihydrochloride hydrate, Erythromycin, Temephos PESTANAL ®, Erythromycin estolate, Erythromycin ethyl succinate, Erythromycin stearate, Fusidic acid sodium salt, Fusidic acid sodium salt, G 418 disulfate salt, Gentamicin solution, Gentamicin sulfate, Gentamicin-Glutamine solution, Helvolic acid, Hygromycin B, Hygromycin B solution, Josamycin, Josamycin solution, Kanamycin B sulfate salt, Kanamycin disulfate salt, Kanamycin monosulfate, Kanamycin solution, Kirromycin, Lincomycin hydrochloride, Lincomycin standard solution, Meclocycline sulfosalicylate salt, Mepartricin, Midecamycin, Minocycline hydrochloride, Neomycin solution, Neomycin trisulfate salt hydrate, Neomycin B, Netilmicin sulfate salt, Nitrofurantoin crystalline, Nourseothricin sulfate, Oleandomycin phosphate salt, Oleandomycin triacetate, Oxytetracycline dehydrate, Oxytetracycline hemicalcium salt, Oxytetracycline hydrochloride, Paromomycin sulfate salt, Puromycin dihydrochloride, Rapamycin, Ribostamycin sulfate salt, Rifampicin, Rifamycin SV sodium salt, Rosamicin, Sisomicin sulfate salt, Spectinomycin dihydrochloride hydrate, Spectinomycin dihydrochloride pentahydrate, Spectinomycin standard solution, Spiramycin, Spiramycin solution (mixture of spiramycin I, II and III), Streptomycin solution, Streptomycin sulfate salt, Tetracycline, Tetracycline hydrochloride, Thiamphenicol, Tobramycin, Tobramycin sulfate salt, Tunicamycin $A_1$, Tunicamycin $C_2$, Tunicamycin, Tylosin solution, Tylosin tartrate, Viomycin sulfate salt, Virginiamycin $M_1$, (S)-(+)-Camptothecin, 10-Deacetylbaccatin III, 5-Azacytidine, 7-Aminoactinomycin D, 8-Quinolinol crystalline, 8-Quinolinol hemisulfate salt crystalline, 9-Dihydro-13-acetylbaccatin III, Aclarubicin, Aclarubicin hydrochloride, Actinomycin D, Actinomycin D☐Mannitol, Actinomycin I, Actinomycin V, Aphidicolin, Bafilomycin A1, Bleomycin sulfate, Capreomycin sulfate, Chromomycin $A_3$, Cinoxacin, Ciprofloxacin, cis-Diammineplatinum(II)dichloride, Coumermycin A1, Cytochalasin B, Cytochalasin, Dacarbazine, Daunorubicin hydrochloride, Distamycin A hydrochloride, Doxorubicin hydrochloride, Echinomycin, Enrofloxacin, Etoposide, Flumequine, Formycin A, Fumagillin, Ganciclovir, Gliotoxin, Lomefloxacin hydrochloride, Metronidazole, Mithramycin A, Mitomycin C, Nalidixic acid, Nalidixic acid sodium salt, Netropsin dihydrochloride hydrate, Nitrofurantoin, Nogalamycin, Nonactin, Novobiocin sodium salt, Ofloxacin, Oxolinic acid, Paclitaxel, Phenazine methosulfate, Phleomycin, Pipemidic acid, Rebeccamycin, Sinefungin, Streptonigrin, Streptozocin, Succinylsulfathiazole, Sulfadiazine, Sulfadimethoxine, Sulfaguanidine, Sulfamethazine, Sulfamonomethoxine, Sulfanilamide, Sulfaquinoxaline sodium

TABLE 5-continued

Antibiotic agents salt, Sulfasalazine, Sulfathiazole sodium salt, Trimethoprim, Trimethoprim lactate salt,
Tubercidin, 5-Azacytidine, Cordycepin, Formycin A, Tubercidin, (+)-6-Aminopenicillanic acid, 7-
Aminodesacetoxycephalosporanic acid, Amoxicillin, Ampicillin, Ampicillin sodium salt,
Ampicillin trihydrate, Azlocillin sodium salt, Bacitracin, Bacitracin zinc salt, Carbenicillin
disodium salt, Cefaclor, Cefamandole lithium salt, Cefamandole nafate, Cefamandole sodium
salt, Cefmetazole sodium salt, Cefoperazone sodium salt, Cefotaxime sodium salt, Cefsulodin
sodium salt, Cefsulodin sodium salt hydrate, Ceftriaxone sodium salt, Cephalexin hydrate,
Cephalosporin C zinc salt, Cephalothin sodium salt, Cephapirin sodium salt, Cephradine,
Cloxacillin sodium salt, Cloxacillin sodium salt monohydrate, D-(☐)-Penicillamine hydrochloride,
D-Cycloserine, Dicloxacillin sodium salt monohydrate, D-Penicillamine, Econazole nitrate salt,
Ethambutol dihydrochloride, Lysostaphin, Moxalactam sodium salt, Nafcillin sodium salt
monohydrate, Nikkomycin, Nikkomycin Z, Nitrofurantoin, Oxacillin sodium salt, Penicillic acid,
Penicillin G potassium salt, Penicillin G sodium salt hydrate, Penicillin G sodium salt,
Phenethicillin potassium salt, Phenoxymethylpenicillinic acid potassium salt, Phosphomycin
disodium salt, Pipemidic acid, Piperacillin sodium salt, Piperacillin sodium salt, Ristomycin
monosulfate, ristocetin A, Ristocetin B, Ristomycin monosulfate, Vancomycin hydrochloride, 2-
Mercaptopyridine N-oxide sodium salt, 4-Bromocalcimycin A23187, Alamethicin,
Amphotericin B, Calcimycin A23187, Calcimycin A23187 hemi(calcium-magnesium) salt,
Calcimycin A23187 hemicalcium salt, Calcimycin A23187 hemimagnesium salt, Chlorhexidine
diacetate salt monohydrate, Chlorhexidine diacetate salt hydrate, Chlorhexidine digluconate,
Clotrimazole, Colistin sodium methanesulfonate, Colistin sulfate salt, Econazole nitrate salt,
Hydrocortisone 21-acetate VETRANAL ®, Filipin complex, Gliotoxin, Gramicidin A, Gramicidin,
Gramicidin, mixture of gramicidins A, B, C, and D, Ionomycin calcium salt, Lasalocid A sodium
salt, Lonomycin A sodium salt, Monensin sodium salt, N-(6-Aminohexyl)-5-chloro-1-
naphthalenesulfonamide hydrochloride, Narasin, Nigericin sodium salt, Nisin, Nonactin,
Nystatin, Phenazine methosulfate, Pimaricin, Polymyxin B, Polymyxin B sulfate salt, DL-
Penicillamine acetone adduct hydrochloride monohydrate, Praziquantel, Salinomycin,
Surfactin, Valinomycin, (+)-Usnic acid, (±)-Miconazole nitrate salt, (S)-(+)-Camptothecin, 1-
Deoxymannojirimycin hydrochloride, 1-Deoxymannojirimycin hydrochloride, 1-Deoxynojirimycin
hydrochloride, 2-Heptyl-4-hydroxyquinoline N-oxide, Cordycepin, 1,10-Phenanthroline
hydrochloride monohydrate, 6-Diazo-5-oxo-L-norleucine, 8-Quinolinol, 8-Quinolinol hemisulfate
salt, Antimycin A, Antimycin $A_1$, Antimycin $A_2$, Antimycin $A_3$, Antipain, Ascomycin, Azaserine,
Bafilomycin A1, Bafilomycin B1, Cerulenin, Chloroquine diphosphate salt, Cinoxacin,
Ciprofloxacin, Mevastatin, Concanamycin A, Concanamycin C, Coumermycin A1 , L(+)-Lactic
acid, Cyclosporin A, Econazole nitrate salt, Enrofloxacin, Etoposide, Flumequine, Formycin A,
Furazolidone, Fusaric acid, Geldanamycin, Gliotoxin, Gramicidin A, Gramicidin C, Gramicidin,
mixture of gramicidins A, B, C, and D, Herbimycin A, Indomethacin, Irgasan Lomefloxacin
hydrochloride, Mycophenolic acid, Myxothiazol, N-(6-Aminohexyl)-5-chloro-1-
naphthalenesulfonamide hydrochloride, Nalidixic acid, Nalidixic acid sodium salt, Netropsin
dihydrochloride hydrate, Niclosamide, Nikkomycin, N-Methyl-1-deoxynojirimycin, Nogalamycin,
Nonactin, Novobiocin sodium salt, Ofloxacin, Oleandomycin triacetate, Oligomycin, Oligomycin
A, Oligomycin B, Oligomycin C, Oxolinic acid, Piericidin A, Pipemidic acid, Radicicol,
Rapamycin, Rebeccamycin, Sinefungin, Staurosporine, Stigmatellin, Succinylsulfathiazole,
Sulfadiazine, Sulfadimethoxine, Sulfaguanidine, Sulfamethazine, Sulfamonomethoxine,
Sulfanilamide, Sulfaquinoxaline sodium salt, Sulfasalazine, Sulfathiazole sodium salt,
Sulfathiazole sodium salt, Triacsin C, Trimethoprim, Trimethoprim, Trimethoprim lactate salt,
Vineomycin $A_1$, Tectorigenin, Paracelsin.

Indicators Contained in the Pharmaceutical Composition

In one embodiment, the fluid or liquid composition to be printed onto a matrix material according to the present invention comprises one or more indicators. An indicator as used herein means a detector such as a chemical detector capable of detecting the presence of a condition or another chemical.

Detection of a condition by the indicator as printed onto the sponge may occur by e.g. a colour reaction, whereby one condition causes the composition comprising the indicator to acquire a certain colour change and another condition causes the composition comprising the indicator to acquire another certain colour change or alternatively no colour change. A colour change or the absence of a colour change is thus indicative of a certain condition. A colour reaction is a type of a visual indicator.

Thus, the indicator may in one embodiment be a visual indicator, such as a colour indicator.

In one embodiment, the indicator is a pH indicator, capable of revealing the pH condition in the skin or wound contacting area of the matrix material according to the present invention, selected from the non-limiting group of Bicarbonate indicator, Gentian violet (Methyl violet), Leucomalachite green, Thymol blue, Methyl yellow, Bromophenol blue, Congo red, Methyl orange, Bromocresol green, Methyl red, Methyl red/Bromocresol green, Azolitmin, Bromocresol purple, Bromothymol blue, Phenol red, Neutral red, Naphtholphthalein, Cresol Red, Phenolphthalein, Thymolphthalein, Alizarine Yellow R, and a universal indicator. A universal indicator is a pH indicator that transitions through numbers 3-12 on the pH chart. A universal indicator is typically composed of water, methanol, propan-1-ol, phenolphthalein sodium salt, methyl red sodium salt, bromothymol blue monosodium salt, and thymol blue monosodium salt.

It follows that any pH indicators may be used alone or in combination in the composition according to the present invention.

A blood type (also called a blood group) is a classification of blood based on the presence or absence of inherited antigenic substances on the surface of red blood cells (RBCs). These antigens may be proteins, carbohydrates, glycoproteins, or glycolipids, depending on the blood group system, and some of these antigens are also present on the surface of other types of cells of various tissues. Several of these red blood cell surface antigens, that stem from one allele (or very closely linked genes), collectively form a blood group system. Blood types are inherited and represent contributions from both parents. A total of 30 human blood group systems are now recognized by the International Society of Blood Transfusion (ISBT).

The indicator may an indicator of the blood type of an individual, capable of detecting the blood type of the ABO-system. According to this system, a person has the blood type of either type A (AO or AA), B (BO or BB), AB or O (O). Type A has the A antigen, and anti-B antibodies; Type B has the B antigen, and anti-A antibodies; Type AB has the A and B antigens, and no antibodies; Type O has no antigens, and both anti-A and anti-B antibodies.

The indicator may also be an indicator of the blood type of an individual, capable of detecting the blood type of the rhesus-system. According to this system, a person has the blood type of either rhesus negative or rhesus positive.

In one embodiment, the indicator is a blood type indicator, capable of revealing the blood type of an individual by contacting a wound area with the matrix material according to the present invention, such as an agglutination-type reaction. Agglutination-type reactions are known from e.g. the Coombs test.

An indicator may also one that is capable of detecting any type of disease or condition, such as the following non-limiting examples: Allergy, Autoimmune Diseases, Blood Diseases, Cancer, Blood Cholesterol, Diabetes, Genetic Testing, Drug Screening, Environmental Toxins, Nutrition, Gastrointestinal Diseases, Heart Diseases, Hormones, Metabolism (sodium, potassium, chloride, bicarbonate, blood urea nitrogen (BUN), magnesium, creatinine, glucose and/or calcium), Infectious Diseases, Kidney Diseases, Liver Diseases, Sexually Transmitted Diseases (STD's) and Thyroid Disease.

The one or more bioactive agents disclosed herein above may be comprised in the same fluid or liquid composition contained in the same reservoir and expelled from the same print head comprising one or more nozzles, or the one or more bioactive agents may be comprised in separate fluid or liquid compositions contained in separate reservoirs and expelled from separate print heads each comprising one or more nozzles or expelled from different channels of the same print head.

In one embodiment, two or more fluid or liquid compositions each comprising one or more bioactive agents may be imprinted at the same or different discrete positions on the surface of said matrix material.

Incompatible Agents or Bioactive Agents in Separate Compositions

In one embodiment, the present invention relates to a matrix material comprising a surface and a plurality of open and interconnected cells, wherein the surface of said matrix comprises two different pharmaceutical compositions, wherein the two pharmaceutical compositions comprises different agents or bioactive agents which are incompatible, and wherein said two pharmaceutical compositions are printed onto said surface in discrete and non-overlapping locations.

Two or more different fluid or liquid compositions each comprising at least one agent or bioactive agent may thus be imprinted at different and discrete positions on the surface of a matrix material. This is especially relevant when said agents or bioactive agents are not compatible when comprised in the same fluid or liquid composition for various reasons, and when said incompatible agents or bioactive agents may be printed separately but in close proximity to each other, for example in alternating positions on the surface of a matrix material. Printing of a fluid or liquid composition in individual and discrete locations with very high precision is possible only with the print technique; it is not possible using e.g. the spray-technique or any other conventional technique known at present.

Incompatibility may arise from the two agents or bioactive agents inappropriately interacting when in contact in the same position in either a fluid or liquid composition or on the surface of a matrix material. Thus, interaction between substances or bioactive agent may be controlled and postponed until desired with the printing technology.

In one embodiment, interaction of two agents or bioactive agents capable of interacting with each other, which are printed in close proximity to each other on the surface of a matrix material according to the present invention, is initiated by wetting of the matrix material, by compression of the matrix material, by contacting or rubbing the surface of the matrix material against another surface or any other means.

The two or more fluid or liquid compositions may each comprise one agent or bioactive agent which may be an enzyme and its substrate, respectively; an enzyme, its substrate and a catalyst, respectively; one component of a two-component glue and another component of said two-component glue; or thrombin and fibrinogen.

In a particular embodiment the two individual compositions each comprise one component of a two-component glue, such as a surgical glue, which constitute two different fluid or liquid compositions that are printed onto separate and discrete positions of the surface of a matrix material.

The Matrix Material of the Device

The device according to the present invention in a preferred embodiment comprises a matrix consisting of a matrix material, onto which a composition is printed on the surface of the matrix material.

In one embodiment, the matrix material comprises one or more polymers selected form the group consisting of collagen, gelatin, polyurethane, polysiloxanes (silicone), hydrogels, polyacrylamides, chitosan, sodium polyacrylate, agarose, alginates, xanthan gum, guar gum, arabic gum, agar gum, Locust Bean gum, Carrageenan gum, Xanthan gum, Karaya gum, tragacanth gum, Ghatti gum, Furcelleran gum, chitin, cellulose, methylcellulose, carboxymethyl cellulose, hydroxymethyl cellulose, hydroxypropyl methylcellulose, hydroxypropyl cellulose, hyaluronic acid, pectin, starch, glycogen, pentosans, polyoxyethylene, polyAMPS (poly(2-acrylamido-2-methyl-1-propanesulfonic acid), polyvinylpyrrolidone, polyvinyl alcohol, polyglycolic acid, polyacetic acid, acrylate polymers, polyhydroxyalkyl acrylates, methacrylates, polyvinyl lactams, polyvinyl alcohols, polyoxyalkylenes, polyacrylamides, polyacrylic acid, polystyrene sulfonates, synthetic hydrocolloids such as N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, hydroxyalkyl acrylates and methacrylates, (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid, tertiary amino-methacrylimide, (e.g. trimethyl-amino-methacrylimide), crotonic acid, pyridine, water soluble amides, (such as N-(hydroxymethyl)acrylamide and -methacrylamide, N-(3-hydroxpropyl)acrylamide, N-(2-hydroxyethyl)methacrylamide, N-(1,1-dimethyl-3-oxabutypacrylamide N-[2-(dimethylamine)ethyl]acrylamide and -methacrylamide, N-[3-(dimethylamino)-2-hydroxylpropyl]

methacrylamide, and N-[1,1-dimethyl-2-(hydroxymethyl)-3-oxabutyl]acrylamide); water-soluble hydrazine derivatives, (such as trialkylamine methacrylimide, and dimethyl-(2-hydroxypropyl)amine methacrylimide); mono-olefinic sulfonic acids and their salts, (such as sodium ethylene sulfonate, sodium styrene sulfonate, 2-acrylamideo-2-methylpropanesulfonic acid), 1-vinyl-imidazole, 1-vinyl-indole, 2-vinyl imidazole, 4(5)-vinyl-imidazole 2-vinyl-1-methyl-imidazole 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, 4-acrylyl-morpholine, Oxidized Regenerated Cellulose (ORC), poly(lactic-co-glycolic acid) (PLGA), Polylactic acid (PLA), Extracellular matrix (ECM), and mixtures thereof.

In a preferred embodiment of the present invention, the matrix of the device is a sponge. In yet another preferred embodiment, the sponge is a gelatin-sponge or a collagen-sponge or a gelatin- or collagen-comprising sponge.

The gelatin typically originates from a porcine source, but may originate from other animal sources, such as from bovine or fish sources. The gelatin may also be synthetically made, i.e. made by recombinant means.

The collagen typically originates from a bovine source, but may originate from other animal sources. The collagen may also be synthetically made, i.e. made by recombinant means.

The gelatin or collagen matrix may be commercially available. Non-limiting examples of commercially available gelatin or collagen matrixes include Spongostan, Surgifoam, Surgiflo (all Ferrosan A/S), Collastat (Kendall Co.), Avitene (Avicon Inc.), Surgicel (Johnson & Johnson) and Gelfoam (Pfizer).

In one embodiment of the present invention, the material comprising the matrix has some defined physical characteristics relating to the reconformation rate. The reconformation rate of the matrix material refers to the elasticity of the matrix material, and is typically determined by a method based on the rate at which the sponge regains its original size and shape, as described in Example 1. In one embodiment of the invention, the matrix material has a reconformation rate of no more than 10 seconds, such as no more than 9 seconds, for example no more than 8 seconds, such as no more than 7 seconds, for example no more than 6 seconds, such as no more than 5 seconds, for example no more than 4 seconds, such as no more than 3 seconds, for example no more than 3 seconds, such as no more than 1 second.

The physical characteristics defining the matrix material may also relate to the Compression modulus (or Young's modulus). The modulus is a measure of the hardness or softness of a material and is equal to stress divided by strain. Stress is equal to pressure. Strain or deflection is equal to the ratio of the change in thickness to the original thickness of the material. The lower the modulus, the softer the material. In short; the ratio of stress to strain in compression. To test this property, ASTM D695 is the standard test method in the USA, and the analogous test to measure compressive strength in the ISO system is ISO 604.

The modulus of the matrix material according to the present invention may be in the range of 0.1-50 GPa, such as 0.1-1, for example 1-2, such as 2-3, such as 3-4, for example 4-5, such as 5-6, for example, 6-7, such as 7-8, for example 8-9, such as 9-10, for example 10-20, such as 20-30, for example 30-40, such as 40-50 GPa.

In one embodiment of the present invention, the pore size of the matrix material has a normal distribution around 0.1-1.0 mm. The pore size may be less than 10 mm, such as less than 9 mm, for example less than 8 mm, such as less than 7 mm, for example less than 6 mm, such as less than 5 mm, for example less than 4 mm, such as less than 3 mm, for example less than 2.9 mm, such as less than 2.8 mm, for example less than 2.7 mm, such as less than 2.6 mm, for example less than 2.5 mm, such as less than 2.4 mm, for example less than 2.3 mm, such as less than 2.2 mm, for example less than 2.1 mm, such as less than 2 mm, for example less than 1.9 mm, such as less than 1.8 mm, for example less than 1.7 mm, such as less than 1.6 mm, for example less than 1.5 mm, such as less than 1.4 mm, for example less than 1.3 mm, such as less than 1.2 mm, for example less than 1.1 mm, such as less than 1.0 mm, for example less than 0.9 mm, such as less than 0.8 mm, for example less than 0.7 mm, such as less than 0.6 mm, for example less than 0.5 mm, such as less than 0.4 mm, for example less than 0.3 mm, such as less than 0.2 mm, for example less than 0.1 mm, such as less than 0.05, for example less than 0.01 mm.

In yet an embodiment, the pore size of the matrix material is in the range of 0.01-0.1 mm, such as 0.1-0.2 mm, for example 0.2-0.3 mm, such as 0.3-0.4 mm, for example 0.4-0.5 mm, such as 0.5-0.6 mm, for example 0.6-0.7 mm, such as 0.7-0.8 mm, for example 0.8-0.9 mm, such as 0.9-1 mm, for example 1-1.1 mm, such as 1.1-1.2 mm, for example 1.2-1.3 mm, such as 1.3-1.4 mm, for example 1.4-1.5 mm, such as 1.5-1.6 mm, for example 1.6-1.7 mm, such as 1.7-1.8 mm, for example 1.8-1.9 mm, such as 2-2.1 mm, for example 2.1-2.2 mm, such as 2.2-2.3 mm, for example 2.3-2.4 mm, such as 2.4-2.5 mm, for example 2.5-2.6 mm, such as 2.6-2.7 mm, for example 2.7-2.8 mm, such as 2.8-2.9 mm, for example 2.9-3 mm, such as 3-4 mm, for example 4-5 mm, such as 5-6 mm, for example 6-7 mm, such as 7-8 mm, for example 8-9 mm, such as 9-10 mm.

In another embodiment of the present invention, the surface of the matrix material has some defined properties relating to the porous or uneven surface of the matrix material. Porosity is a measure of the void spaces in a material, and is measured as a fraction, between 0-1, or as a percentage between 0-100%. The porosity of the surface may thus rely on the pore size of the material of the matrix.

By modifying the surface properties of the underlying matrix material (hydrophobicity, chemical heterogeneity, roughness), the evaporation process of the tiny droplets can be tuned in a definite way.

In one embodiment, the hydrophobicity of the surface of the matrix material may be modulated to increase evaporation. In chemistry, hydrophobicity refers to the physical property of a molecule (known as a hydrophobe) that is repelled from a mass of water. Hydrophobic molecules tend to be non-polar and thus prefer other neutral molecules and nonpolar solvents. Hydrophobic molecules in water often cluster together forming micelles. Water on hydrophobic surfaces will exhibit a high contact angle (meaning that the droplet will make the least possible contact area with the surface).

In another embodiment, the roughness of the surface of the matrix material can be modulated to increase evaporation. This may depend on pore size.

In one embodiment, the pharmaceutical composition of the present invention comprises the bioactive agent thrombin, as described in detail below. The composition is printed onto the surface of the matrix. In a preferred embodiment, the surface of the matrix contains less than 300 IU/cm$^2$ (international units per square centimeter), such as less than 290, for example less than 280, such as 270, for example less than 260, such as less than 250, for example less than 240, such as 230, for example less than 220, such as less than 210, for example less than 200, such as 190, for example less than 180, such as less than 170, for example less than 160, such as 150, for example less than 140, such as less than 130, for example less than 120, such as 110, for example less than 100 IU/cm$^2$, such as less than 95, for example less than 90, such as 85, for example less than 80, such as less than 75, for example less than 70, such as 65, for example less than 60, such as less than 55, for example less than 50, such as 45, for example less than 40, such as less than 35, for example less than 30, such as 25, for example less than 20, such as less than 15, for example less than 10, such as 5, for example less than 1 IU/cm$^2$.

In another preferred embodiment, the surface of the matrix contains between 1-5 IU/cm$^2$, such as 5-10, for example 10-15, such as 15-20, for example 20-25, such as 25-30, for example 30-35, such as 35-40, for example 40-45, such as 45-50, for example 50-55, such as 55-60, for example 60-65, such as 65-70, for example 70-75, such as 75-80, for example 80-85, such as 85-90, for example 90-95, such as 95-100, for example 100-110, such as 110-120, for example 120-130, such as 130-140, for example 140-150, such as 150-160, for example 160-170, such as 170-180, for example 180-190, such as 190-200, for example 200-210, such as 210-220, for example 220-230, such as 230-240, for example 240-250, such as 250-260, for example 260-270, such as 270-280, for example 280-290, such as 290-300 IU/cm$^2$.

In one embodiment of the present invention, different dimensions of the device comprising a matrix material may be engaged. Thus, the dimensions of the matrix material (length, width and height) may be less than 15 cm long, less than 10 cm wide and less than 2 cm high.

Furthermore, different shapes of the device comprising a matrix material may be engaged. Non-limiting examples include a square form, circular form, rectangular form, cubic form, spherical form and pyramid-shaped forms.

Different colors of the device comprising a matrix material may be engaged. Non-limiting examples include red, pink, yellow, blue, green, white, black, brown, purple, orange, grey and turquoise.

In one embodiment, these colours may aide in identifying the device according to the composition that has been printed onto the surface of the matrix material of the device. Thus, for example a purple device may signal that thrombin is printed onto the gelatin-based sponge of the matrix material of said device.

Different types of the device comprising a matrix material may be engaged. Thus, the device may comprise a sponge, a gel, a bandage, a swab, a dressing and a patch.

The temperature of the matrix material employed in the present invention may be adjusted to be within the range of 5-70° C., such as 5-10, for example 10-15, such as 15-20, for example 20-25, such as 25-30, for example 30-40, such as 40-50, for example 50-60, such as 60-70° C.

Sterilization of the Matrix or the Device

In one embodiment of the present invention, the device according to the present invention comprises a matrix and a pharmaceutical composition that has been printed onto the surface of a matrix or a device by printing, such as printing by any suitable state-of-the-art printing technology. The matrix or the device is preferably sterile and contained in a sterile, pre-packaged, ready-to-use container.

The sterilization preferably occurs after the packaging step. Sterilization refers to any process that effectively kills or eliminates transmissible agents (such as fungi, bacteria, viruses, prions and spore forms etc.) from e.g. a surface or equipment. Sterilization can be achieved through application of heat, chemicals, irradiation, high pressure or filtration. Heat sterilization include autoclaving (uses steam at high temperatures); radiation sterilization include X-rays, gamma rays, UV light and subatomic particles; chemical sterilization include using ethylene oxide gas, ozone, chlorine bleach, glutaraldehyde, formaldehyde, ortho phthalaldehyde, hydrogen peroxide and peracetic acid.

The Composition to be Printed onto the Matrix of Device

Besides comprising at least one agent or bioactive agent as discussed below, the composition subject to inkjet printing will in a preferred embodiment have certain characteristics, which makes it compatible for printing, such as inkjet printing.

The composition can also be referred to as the print medium. The composition may in one embodiment comprise a solvent and at least one agent or bioactive agent.

The solvent or fluid component of the composition may be an aqueous medium. The aqueous medium may contain salts, such as sodium chloride, dissolved therein, and thus the aqueous medium may be saline.

In another embodiment, the solvent or fluid component of the composition is a volatile fluid. A volatile liquid is a liquid with a high vapor pressure or low boiling point. In other words, a volatile liquid may evaporate at room temperature or vaporize easily.

In one embodiment, a water content stabilizer such as sorbitol, polysaccharides or polyols may be added to the composition.

Viscosity

The viscosity of a liquid may be increased by adding a substance that increases the viscosity of the liquid. Such substances may be long chain molecules (polymers) that are soluble in that liquid; and gelatin, starch, polyethlyleneoxide, polyvinylalcohol and polyethyleneglycols (macrogol) are examples hereof.

In another embodiment, a substance that increases the viscosity of the liquid may be added to the composition, selected from the non-limiting list of acacia, alginic acid, bentonite, carbomer, carboxymethylcellulose calcium, carboxymethylcellulose sodium, cetostearyl alcohol, colloidal silicon dioxide, guar gum, hydroxyethyl cellulose, hydroxypropyl cellulose, hydroxypropyl methylcellulose, hydroxypropyl methylcellulose phtalate, magnesium aluminium silicate, methylcellulose, microcrystalline cellulose, polyvinyl alcohol, povidone, sodium alginate, sucrose, tragacanth, gelatin, starch, albumin, casein, polyethlyleneoxide, polyvinylalcohol, polyethyleneglycols (macrogol), glycerine (1,2, 3-propanetriol) and glycol (1,2-propanediol).

The viscosity of the composition to be printed onto the surface of the matrix must be compatible with the print technology, and therefore must have its viscosity within a specific range.

Viscosity is a measure of the resistance of a fluid to being deformed by either shear stress or extensional stress. It is commonly perceived as "thickness", or resistance to flow. Viscosity describes a fluid's internal resistance to flow and may be thought of as a measure of fluid friction. Thus, water is "thin", having a lower viscosity, while vegetable oil is "thick" having a higher viscosity. All real fluids (except superfluids) have some resistance to stress, but a fluid which has no resistance to shear stress is known as an ideal fluid or inviscid fluid.

The SI physical unit of dynamic viscosity is the pascal-second (Pa·s), which is identical to 1 kg·m$^{-1}$·s$^{-1}$. If a fluid with a viscosity of one Pa·s is placed between two plates, and one plate is pushed sideways with a shear stress of one pascal, it moves a distance equal to the thickness of the layer between the plates in one second.

The cgs physical unit for dynamic viscosity is the poise (P), named after Jean Louis Marie Poiseuille. It is more commonly expressed, particularly in ASTM standards, as centipoise (cps). The centipoise is commonly used because water has a viscosity of 1.0020 cps (at 20° C.; the closeness to one is a convenient coincidence). The relation between poise and pascal-seconds is:

1 P=1 g·cm$^{-1}$·s$^{-1}$

10 P=1 kg·m$^{-1}$·s$^{-1}$=1 Pa·s 1 cps=0.001 Pa·s=1 mPa·s

In one embodiment of the invention, the viscosity of the composition to be deposited or printed onto the surface of the matrix is more than 1 cps, such as more than 5 cps, for example more than 10 cps, such as more than 20 cps, for example more than 30 cps, such as more than 40 cps, for example more than 50 cps, such as more than 60 cps, for example more than 70 cps, such as more than 80 cps, for example more than 90 cps, such as more than 100 cps, for example more than 150 cps, such as more than 200 cps, for example more than 250 cps, such as more than 300 cps, for example more than 350 cps, such as more than 400 cps, for example more than 500 cps, such as more than 550 cps, for example more than 600 cps, such as more than 650 cps, for example more than 700 cps, such as more than 750 cps, for example more than 800 cps, such as more than 850 cps, for example more than 900 cps, such as more than 950 cps, for example more than 1000 cps, such as more than 1100 cps, for example more than 1200 cps, such as more than 1300 cps, for example more than 1400 cps, such as more than 1500 cps, for example more than 1600 cps, such as more than 1700 cps, for example more than 1800 cps, such as more than 1900 cps, for example more than 2000 cps, such as more than 2250 cps, for example more than 2500 cps, such as more than 2750 cps, for example more than 3000 cps.

In another embodiment of the invention, the viscosity of the composition to be deposited or printed onto the surface of the matrix is in the range 1-5 cps, such as 5-10 cps, for example 10-15 cps, such as 15-20 cps, for example 20-30 cps, such as 30-40 cps, for example 40-50 cps, such as 50-60 cps, for example 60-70 cps, such as 70-80 cps, for example 80-90 cps, such as 90-100 cps, for example 100-150 cps, such as 150-200 cps, for example 200-250 cps, such as 250-300 cps, for example 300-350 cps, such as 350-400 cps, for example 400-450 cps, such as 450-500 cps, for example 500-550 cps, such as 550-600 cps, for example 600-650 cps, such as 700-750 cps, for example 750-800 cps, such as 800-850 cps, for example 850-900 cps, such as 900-950 cps, for example 950-1000 cps, such as 1000-1100 cps, for example 1100-1200 cps, such as 1200-1300 cps, for example 1300-1400 cps, such as 1400-1500 cps, for example 1500-1600 cps, such as 1600-1700 cps, for example 1700-1800 cps, such as 1800-1900 cps, for example 1900-2000 cps, such as 2000-2250 cps, for example 2250-2500 cps, such as 2500-2750 cps, for example 2750-3000 cps.

In a preferred embodiment of the invention, the viscosity of the composition is in the range of 0.1-20 cps; for example 0.1-1 cps, such as 1-2 cps, for example 2-3 cps, such as 3-4 cps, for example 4-5 cps, such as 5-6 cps, for example 6-7 cps, such as 7-8 cps, for example 8-9 cps, such as 9-10 cps, for example 10-11 cps, such as 11-12 cps, for example 12-13 cps, such as 13-14 cps, for example 14-15 cps, such as 15-16 cps, for example 16-17 cps, such as 17-18 cps, for example 18-19 cps, such as 19-20 cps.

Surface Tension

Surface tension is an attractive property of the surface of a liquid. It is what causes the surface portion of liquid to be attracted to another surface, such as that of another portion of liquid. Applying Newtonian physics to the forces that arise due to surface tension accurately predicts many liquid behaviors that are so commonplace that most people take them for granted. Applying thermodynamics to those same forces further predicts other more subtle liquid behaviors. Surface tension has the dimension of force per unit length (N/m or Newton per meter), or of energy per unit area (dyn/cm$^2$ or dyne per square centimeter).

In physics, dyne (meaning power, force) is a unit of force specified in the centimetre-gram-second (CGS) system of units, a predecessor of the modern SI. One dyne is equal to exactly 10 micronewtons. Equivalently, the dyne is defined as "the force required to accelerate a mass of one gram at a rate of one centimetre per second squared": 1 dyn=1 g·cm/s$^2$=10$^{-5}$ kg·m/s$^2$=10 μN In a preferred embodiment of the invention, the surface tension of the composition is in the range of 0.020 to 0.050 N/m; for example 0.020-0.022 N/m, such as 0.022-0.024 N/m, for example 0.024-0.026 N/m, such as 0.026-0.028 N/m, for example 0.028-0.030 N/m, such as 0.030-0.032 N/m, for example 0.032-0.034 N/m, such as 0.034-0.036 N/m, for example 0.036-0.038 N/m, such as 0.038-0.040 N/m, for example 0.040-0.042 N/m, such as 0.042-0.044 N/m, for example 0.044-0.046 N/m, such as 0.046-0.048 N/m, for example 0.048-0.050 N/m.

pH pH is a measure of the acidity or alkalinity of a solution. Aqueous solutions at 25° C. with a pH less than seven are considered acidic, while those with a pH greater than seven are considered basic (alkaline). When a pH level is 7.0, it is defined as 'neutral' at 25° C. because at this pH the concentration of H$_3$O$^+$ equals the concentration of OH$^-$ in pure water. The normal pH of blood is in the range of 7.35-7.45. pH is formally dependent upon the activity of hydronium ions (H$_3$O$^+$); pH=$-\log_{10}$ (aH$^+$).

The pH of the compositions employed in the invention may be adjusted by the addition of organic or inorganic acids or bases. Useful compositions may have a preferred pH of from about 2 to 10, depending upon the type of composition being used. Typical inorganic acids include hydrochloric, phosphoric, and sulfuric acids. Typical organic acids include methanesulfonic, acetic, and lactic acids. Typical inorganic bases include alkali metal hydroxides and carbonates. Typical organic bases include ammonia, triethanolamine and tetramethylethlenediamine.

Formulation of the Bioactive Agent of the Composition

The composition printed onto the surface of a matrix material may be further adapted to comprise controlled release formulation, incorporation into microspheres and/or aerogels or the like.

Controlled Release

Time release technology, also known as Sustained-release (SR), extended-release (ER, XR, or XL), time-release or timed-release, controlled-release (CR), or continuous-release (CR); refers to a composition formulated to dissolve slowly and release a drug or agent over time. The advantages of sustained-release compositions are that they can often be used less frequently than instant-release formulations of the same drug or agent, and that they keep steadier levels of the drug in the bloodstream. Sustained-release compositions are formulated so that the active ingredient is embedded in a matrix of insoluble substance so that the dissolving drug or agent has to find its way out through the holes in the matrix. In some CR formulations the matrix physically swells up to form a gel, so that the drug has first to dissolve in matrix, then exit through the outer surface.

In one embodiment, the composition according to the present invention is a controlled release composition, wherein the bioactive agent(s) of the composition is released from said composition in a prolonged manner. The bioactive agent may be released from the composition printed onto the surface of a matrix during a period of between 1 minute to 14 days; such as 1 to 5 minutes, for example 5 to 15 minutes, such as 15 to 30 minutes, for example 30 to 45 minutes, such as 45 to 60 minutes, for example 60 to 75 minutes, such as 75 to 90 minutes, for example 90 to 120 minutes, such as 120 to 150 minutes, for example 150 to 180 minutes, such as 180 to 210 minutes, for example 210 to 240 minutes, such as 4 hours to 5 hours, for example 5 to 6 hours, such as 6 to 7 hours, for example 7 to 8 hours, such as 8 to 9 hours, for example 9 to 10 hours, such as 10 to 11 hours, for example 11 to 12 hours, such as 12 to 13 hours, for example 13 to 14 hours, such as 14 to 15 hours, for example 15 to 16 hours, such as 16 to 17 hours, for example 17 to 18 hours, such as 18 to 19 hours, for example 19 to 20 hours, such as 20 to 21 hours, for example 21 to 22 hours, such as 22 to 23 hours, for example 23 to 24 hours, such as 24 to 30 hours, for example 30 to 36 hours, such as 36 to 42 hours, for example 42 to 48 hours, such as 48 to 54 hours, for example 54 to 60 hours, such as 60 to 66 hours, for example 66 to 72 hours, such as 3 days to 3.5 days, for example 3.5 to 4 days, such as 4 to 4.5 days, for example 4.5 to 5 days, such as 5 to 5.5 days, for example 5.5 to 6 days, such as 6 to 6.5 days, for example 6.5 to 7 days, such as 7 to 8 days, for example 8 to 9 days, such as 8 to 10 days, for example 10 to 11 days, such as 11 to 12 days, for example 12 to 13 days, such as 13 to 14 days.

The controlled release formulation may be any controlled release formulation known to the skilled person, such as those disclosed in WO 99/051208, WO 04/084869, WO 06/128471, WO 03/024429, WO 05/107713 and WO 03/024426 (Egalet as Applicant).

Aerogels

An aerogel is a low-density solid-state material derived from gel in which the liquid component of the gel has been replaced with gas. The result is an extremely low-density solid with several remarkable properties, most notably its effectiveness as a thermal insulator. Aerogels are produced by extracting the liquid component of a gel through supercritical drying. This allows the liquid to be slowly drawn off without causing the solid matrix in the gel to collapse from capillary action, as would happen with conventional evaporation. Aerogels may be produced from silica gels (Silaca aerosols), alumina (Alumina aerogels), chromia, tin oxide, agar (SEAgel), sulfur, chalcogens (Chalcogel), metals, cadmium selenide and carbon (Carbon aerogels).

In one embodiment, the composition according to the present invention is capable of forming an aerogel, wherein the bioactive agent(s) of the composition is retained or encapsulated in the aerogel composition on the surface of the matric material. The one or more encapsulated bioactive agents can in one preferred embodiment be released from the aerogel over time. In one embodiment the encapsulated bioactive agents comprises enzymes.

Microsperes

Microspheres are spherical particles composed of various natural and synthetic materials with diameters in the micrometer range In one embodiment, the composition comprising bioactive agent(s) according to the present invention is retained or encapsulated in microspheres on the surface of the matric material. The one or more encapsulated bioactive agents can in one preferred embodiment be released from the microsphere over time.

In one embodiment, the microspheres are biodegradable. Biodegradation is the process by which organic substances are broken down by the enzymes produced by living organisms.

Matrix Comprising Thrombin

In another embodiment the present invention relates to a kit-of-parts comprising a matrix comprising thrombin. The matrix comprising thrombin may also comprise further thrombin-stabilizing agents.

The matrix comprising thrombin comprises in one embodiment one or more of the compositions listed herein below:

- A matrix according to the present invention wherein thrombin and/or any other pharmaceutically active compound is printed onto said matrix
- Thrombi-Gel, Thrombi-Pad or ThrombiGel hemostatic foam (Vascular Solutions, Inc.)
- D-Stat Dry product (D-Stat Dry, D-Stat 2 Dry) (Vascular Solutions, Inc.)
- a gelatin foam pad and/or a gauze pad that provide a unique, premixed, sterile, gelatin/thrombin haemostat
- a premixed thrombin/gelatin pad
- thrombin freeze-dried into a gelatin foam
- any standard gelatin pad with thrombin
- A hemostatic paste composition comprising a hemostatic effective amount of thrombin in a polyethylene glycol base which is preferably prepared by admixing an aqueous solution of thrombin and polyethylene glycol and freeze-drying the mixture to remove substantially all of the water to yield a viscous water soluble paste of fine particles of thrombin uniformly dispersed throughout the polyethylene glycol base (as described in U.S. Pat. No. 5,595,735)
- collagen paste hemostats comprising thrombin e.g. as described in U.S. Pat. No. 4,891,359
- a stable collagen sponge having thrombin therein e.g. as described in U.S. Pat. No. 4,515,637.
- a collagen sponge having thrombin therein e.g. as described in U.S. Pat. No. 6,649,162
- FloSeal Matrix Hemostatic Sealant
- Gelfoam comprising thrombin
- Surgifoam comprising thrombin
- Surgiflo comprising thrombin
- Sponge comprising thrombin
- biologically absorbable material comprising thrombin
- Fibrinpaste based on e.g. a collagen sponge coated with fibrinogen and/or thrombin
- TachoSil (Nycomed)
- a collagen material (such as Avitene, Actifoam, Helistat, Inistat) comprising thrombin
- CoStasis hemostatic device
- a cellulose material (such as Surgicel Oxycel or Tabotamp) comprising thrombin The thrombin may be any thrombin, such as Thrombostat, Thrombin-JMI (King Pharmaceuticals), Recothrom (Bayer/Zymogenetics), Evithrom (OMRIX Biopharmaceuticals/Ethicon), Evicel or any other commercially available thrombin. Thrombin may also be produced from plasma using the Thrombin Activation Device (TAD) (Thermogenesis)

Hemostasis

The present invention is directed in one aspect to regulating or controlling or promoting hemostasis.

Coagulation is a complex process by which blood forms solid clots. It is an important part of hemostasis (the cessation of blood loss from a damaged vessel) whereby a damaged blood vessel wall is covered by a platelet- and fibrin-containing clot to stop bleeding and begin repair of the damaged vessel. Disorders of coagulation can lead to an increased risk of bleeding and/or clotting and embolism.

Coagulation is highly conserved throughout biology; in all mammals, coagulation involves both a cellular (platelet) and a protein (coagulation factor) component. Coagulation is initiated almost instantly after an injury to the blood vessel damages the endothelium (lining of the vessel). Platelets immediately form a hemostatic plug at the site of injury; this is called primary hemostasis. Secondary hemostasis occurs simultaneously—proteins in the blood plasma, called coagulation factors, respond in a complex cascade to form fibrin strands which strengthen the platelet plug. Later, as wound healing occurs, the platelet aggregate and fibrin clot are broken down.

Damage to blood vessel walls exposes collagen normally present under the endothelium. Circulating platelets bind to the collagen with the surface collagen-specific glycoprotein Ia/IIa receptor. This adhesion is strengthened further by the large multimeric circulating protein von Willebrand factor (vWF), which forms links between the platelet glycoprotein Ib/IX/V and collagen fibrils.

The platelets are then activated and release the contents of their granules into the plasma, in turn activating other platelets. The platelets undergo a change in their shape which exposes a phospholipid surface for those coagulation factors that require it. Fibrinogen links adjacent platelets by forming links via the glycoprotein IIb/IIIa. In addition, thrombin activates platelets.

The coagulation cascade of secondary hemostasis has two pathways, the contact activation pathway (formerly known as the intrinsic pathway) and the tissue factor pathway (formerly known as the extrinsic pathway) that lead to fibrin formation. It was previously thought that the coagulation cascade consisted of two pathways of equal importance joined to a common pathway. It is now known that the primary pathway for the initiation of blood coagulation is the tissue factor pathway. The pathways are a series of reactions, in which a zymogen (inactive enzyme precursor) of a serine protease and its glycoprotein co-factor are activated to become active components that then catalyze the next reaction in the cascade, ultimately resulting in cross-linked fibrin. Coagulation factors are generally indicated by Roman numerals, with a lowercase a appended to indicate an active form.

The coagulation factors are generally serine proteases (enzymes). There are some exceptions. For example, FVIII and FV are glycoproteins and Factor XIII is a transglutaminase. Serine proteases act by cleaving other proteins at specific sites. The coagulation factors circulate as inactive zymogens.

The coagulation cascade is classically divided into three pathways. The tissue factor and contact activation pathways both activate the "final common pathway" of factor X, thrombin and fibrin.

The main role of the tissue factor pathway is to generate a "thrombin burst", a process by which thrombin, the most important constituent of the coagulation cascade in terms of its feedback activation roles, is released instantaneously. FVIIa circulates in a higher amount than any other activated coagulation factor.

Following damage to the blood vessel, endothelium Tissue Factor (TF) is released, forming a complex with FVII and in so doing, activating it (TF-FVIIa). TF-FVIIa then activates FIX and FX. FVII is itself activated by thrombin, FXIa, plasmin, FXII and FXa. The activation of FXa by TF-FVIIa is almost immediately inhibited by tissue factor pathway inhibitor (TFPI). FXa and its co-factor FVa form the prothrombinase complex which activates prothrombin to thrombin. Thrombin then activates other components of the coagulation cascade, including FV and FVII (which activates FXI, which in turn activates FIX), and activates and releases FVIII from being bound to vWF. FVIIIa is the co-factor of FIXa and together they form the tenase complex which activates FX and so the cycle continues.

In one embodiment of the present invention, thrombin may be a bioactive agent comprised in the pharmaceutical composition of the present invention.

The contact activation pathway begins with formation of the primary complex on collagen by high-molecular weight kininogen (HMWK), prekallikrein, and FXII (Hageman factor). Prekallikrein is converted to kallikrein and FXII becomes FXIIa. FXIIa converts FXI into FXIa. Factor XIa activates FIX, which with its co-factor FVIIIa form the tenase complex, which activates FX to FXa. The minor role that the contact activation pathway has in initiating clot formation can be illustrated by the fact that patients with severe deficiencies of FXII, HMWK, and prekallikrein do not have a bleeding disorder.

The final common pathway. Thrombin has a large array of functions. Its primary role is the conversion of fibrinogen to fibrin, the building block of a hemostatic plug. In addition, it activates Factors VIII and V and their inhibitor protein C (in the presence of thrombomodulin), and it activates Factor XIII (denoted XIIIa in its activated form), which forms covalent bonds that crosslink the fibrin polymers that form from activated monomers. Following activation by the contact factor or tissue factor pathways the coagulation cascade is maintained in a prothrombotic state by the continued activation of FVIII and FIX to form the tenase complex, until it is down-regulated by the anticoagulant pathways.

In one embodiment of the present invention, thrombin may be a bioactive agent comprised in the pharmaceutical composition of the present invention. In a further embodiment, fibrinogen may be a bioactive agent comprised in the pharmaceutical composition of the present invention. In yet a further embodiment, Factor XIII and/or XIIIa may be a bioactive agent comprised in the pharmaceutical composition of the present invention.

Three mechanisms keep the coagulation cascade in check. Abnormalities can lead to an increased tendency toward thrombosis. 1) Protein C is a major physiological anticoagulant. It is a vitamin K-dependent serine protease enzyme that is activated by thrombin into activated protein C (APC). The activated form (with protein S and phospholipid as a cofactor) degrades Factor Va and Factor VIIIa. Quantitative or qualitative deficiency of either may lead to thrombophilia (a tendency to develop thrombosis). Impaired action of Protein C (activated Protein C resistance), for example by having the "Leiden" variant of Factor V or high levels of Factor VIII also may lead to a thrombotic tendency. 2) Antithrombin is a serine protease inhibitor (serpin) that degrades the serine proteases; thrombin and FXa, as well as Factor XIIa, and Factor IXa. It is constantly active, but its adhesion to these factors is increased by the presence of heparan sulfate (a glycosaminoglycan) or the administration of heparins (different heparinoids increase affinity to Factor Xa, thrombin, or both). Quantitative or qualitative deficiency of antithrombin (inborn or acquired, e.g. in proteinuria) leads to thrombophilia. 3) Tissue factor pathway inhibitor (TFPI) inhibits Factor VIIa-related activation of Factor IX and Factor X after its original initiation.

Various substances are required for the proper functioning of the coagulation cascade. Calcium and phospholipid (a platelet membrane constituent) are required for the tenase and prothrombinase complexes to function. Calcium mediates the binding of the complexes via the terminal gamma-carboxy residues on Factor Xa and Factor IXa to the phospholipid surfaces expressed by platelets as well as procoagulant microparticles or microvesicles shedded from them. Calcium is also required at other points in the coagulation cascade. Vitamin K is an essential factor to a hepatic gamma-glutamyl carboxylase that adds a carboxyl group to glutamic acid residues on Factors II, VII, IX and X, as well as Protein S, Protein C and Protein Z. Deficiency of vitamin K (e.g. in malabsorption), use of inhibiting anticoagulants (warfarin, acenocoumarol and phenprocoumon) or disease (hepatocellular carcinoma) impairs the function of the enzyme and leads to the formation of PIVKAs (proteins formed in vitamin K absence) this causes partial or non gamma carboxylation and affects the coagulation factors ability to bind to expressed phospholipid.

Wound Healing

The present invention is directed in one aspect to regulating or controlling or promoting wound healing.

The outer layer of skin surrounding the body performs an important protective function as a barrier against infection, and serves as a means of regulating the exchange of heat, fluid and gas between the body and external environment.

Wounds to the skin and the underlying tissues of animals may be caused by e.g. friction, abrasion, laceration, burning or chemical irritation. Tissue damage may also result from internal metabolic or physical dysfunction, including, but not limited to, bone protrudence, diabetes, circulatory insufficiencies, or inflammatory processes.

A wound to the skin and/or damage to the underlying tissues significantly reduce the protective function of the skin. Consequently, damaged skin results in an increased risk of infection of the underlying tissue by infectious agents such as bacteria and vira.

Areas of damaged skin are conventionally protected by the application of a wound or tissue dressing which facilitates wound healing. Wound or tissue dressings generally provide a suitable environment for wound healing, they absorb drainage, immobilize the wound, promote hemostasis and protect the wound and new tissue growth from bacterial contamination.

The healing of wounds or related forms of tissue damage generally depends on cellular proliferation and the formation of new connective, endothelial, and epithelial tissue as explained briefly herein below.

Several agents have been reported to favorably influence the cellular processes involved in wound healing, e.g., polypeptid growth factors, allantoin, Vitamin A (and derivatives), zinc, exogenous DNA, and aloe vera preparations. These compounds operate through various poorly defined mechanisms and display varying degrees of effectiveness in particular applications When an injury occurs, cell damage comes from the precipitating event, such as a cut, resulting in ruptured cells and severed or crushed capillaries and other blood vessels. The interruption of blood flow produces anoxia, causing the death of additional cells. Within 15 minutes of injury the wound is filled with dead and dying cells, extracellular substances collagen, elastic fibers, fat and ground substances, extravasated blood, and possibly bacteria and viruses introduced by the injurious agent. Tissue damage is not restricted to the initial area of injury; it may increase over the next several hours or days as a result of the release of lysomal enzymes from the injured cells or as a consequence of swelling and infection. (See Reese et al., Role of Fibronectin in Wound Healing, the subject matter of which is hereby incorporated by reference).

Coagulation, the first phase of the healing process, bridges the gap between the injury and the inflammatory response, the second phase of wound healing. It stops the loss of blood and restores some of the mechanical and physical integrity to the damaged tissue. The coagulation cascade is described in detail elsewhere herein.

The second phase of wound repair is the inflammatory response, which is necessary for subsequent phases of healing. It is initiated by the release of histamine and serotonin from platelets and mast cells and by kinins. Histamine and kinins act to increase capillary dilation, opening previously closed capillaries in the area of injury. The increased blood flow through the capillary beds produces two of the characteristics of the inflammatory response: redness and heat. Prostaglandin release within a few hours of injury results in the full development of the inflammatory response, which may last from 3 to 5 days depending on the extent of the injury. The extreme vasodilation produced by the factors just discussed causes a widening of the endothelial cell junctions lining the capillaries. Fluid and macromolecular components of blood escape into the tissues through the gaps, producing swelling, the third characteristic of the inflammatory response. If the swelling is extensive, it may interrupt blood flow, increasing the extent of injury as a result of anoxia. Pain, the final characteristic of inflammation, results from a combination of the kinins as well as the direct effect of lysosomal enzymes and pressure from the swelling on nerve endings.

Control of infection at the wound site is of critical importance in successful wound repair. Infections delay healing, enlarge the wound lesion, may lead to systemic infection, and greatly increase the likelihood of disfiguring and physically debilitating scars. Vasodilation of the capillary beds reduces the velocity of blood through the capillaries. This, along with the production of potent chemotactic factors from the complement fixation and the release of chemotactic agents from the damaged tissue, cause the accumulation of polymorphonuclear leukocytes ("PMN's") along the walls of the capillaries which are the host's major cellular defense against infection. The PMNs subsequently pass through the endothelial junctions of the capillary wall into the site of the injury. If bacteria are present in the wound, they may release soluble chemotactic factors and/or activate complement with the subsequent generation of chemotactic fragments. PMN's at the site of an infection or injury release substance that affect the PMNs' mobility, keeping them at the site. Fibronectin facilitates the attachment of the bacterium to the membrane of the phagocyte.

Dead cells, cellular debris, and extracellular proteins must then be removed or readsorbed to allow revascularization and repair to continue. Macrophages are primarily responsible for the clearance of wound debris. Wound macrophages, like wound PMN's, are actively phagocytic. They migrate into the wound using the fibers of the fibrin clot as a scaffold to move within the clot, attaching to the fibers through fibronectin. The macrophages encounter, engulf, and destroy the dead cells trapped in the clot matrix, as well as the damaged cells from the wound margin. The fibrin clot itself is resolved primarily by the activation of the plasminogen that was incorporated into the fibers during their formation. Some of the fibrin fragments are engulfed by macrophages in the area. Since most of the clot fragments are released away from the area of the most intense macrophage activity, many of the fragments are removed by lymphatic drainage and thus enter the circulation. These soluble complexes are removed by the sessile cells of the RES, primarily those of the spleen and liver. Also, PMN's trapped in the clot die as a result of anoxia, releasing their lysosomal contents. These enzymes attack the surrounding clot and dissolve it. Although the release of lysosomal enzymes by PMN's may be considered beneficial to the host in most cases, they may also increase tissue destruction and delay healing. If the PMN's accumulate rapidly within the wound and remain there (as in an infection), their lysosomal enzymes dissolve significant portions of the clot, removing the framework used by the macrophages and fibroblasts to move into the wound and re-colonize it. These areas of destruction must eventually be drained or slowly removed by the macrophages. The dissolved portion of the clot is then replaced as part of the chronic inflammatory response.

Repair, or fibroplasia, of the damaged tissue occurs during some of the above stages. Within 12 to 24 hours of injury, fibroblasts, including those at some distance from the wound margins, begin to move toward the area of injury and to proliferate. This response is apparently due to factors released by the injured tissue and platelets and possibly to factors released by the kinin, complement or coagulation cascades. The proliferating fibroblasts derive part of their nutrients from the components of tissue debris and cells released by macrophages. The fibroblast phase may last 2 to 4 weeks in a skin wound, whereas it may persist several months in an injury to the stomach or intestines. Fibroblasts, as the macrophages did, use the fibers of the fibrin clot as a scaffold to move into and within the damages area. The Fibroblasts synthesize and secrete sufficient quantities of fibronectin to promote their own attachment to fibronectin deficient substrates.

Angiogenesis, or revascularization, begins with the growth of capillary beds into the area directly behind the fibroblasts. In the early phases of wound repair, the capillaries are much more numerous than in normal tissue, which probably reflects the high oxygen and nutrient requirements of the rapidly regenerating tissue. The capillaries are very leaky, which facilitates the movement of cells and macromolecules into the wound site. Eventually, the capillaries originating from one side of the wound grow into contact with capillaries originating from the other sides and fuse, reestablishing complete circulation within the wound.

By the end of the fifth day after the injury, fibroblasts begin laying down large quantities of collagen. The collagen molecule is synthesized on the membrane of the endoplastic reticulum. It then undergoes extensive postranslational modification, hydroxylation, glycosylation, and further steps to form the procollagen molecule. The procollagen molecule is then secreted and is further modified to tropocollagen by specific serum peptidases. These activated tropocollagen molecules quickly polymerize to form increasingly large collagen fibers. Thereafter, crosslinking among the collagen fibers occurs. The collagen network in effect replaces the fibrin clot as the major structural element of the wound. This becomes particularly important during the remodeling phase of wound healing.

Reepithelialization begins to occur within a few hours of injury as the attachment of the epithelial cells to the dermis loosened near the margin of the wound, and the cells begin to migrate over the defect, always maintaining contact with the mesenchymal tissue. By 48 hours after the injury, the cells are also beginning to proliferate to replace the lost cells. The epithelial cells continue to divide after the bridge is complete to form a thicker epithelium. Wound contracture aids reepithelialization insofar as it reduces the size of the defect to be reepithelialized by as much as 50%. Contracture is believed to occur as a result of the cellular element of the granulation tissue in the wound—the fibroblasts and myofibroblasts.

Remodeling is the last step of wound healing. Scar tissue continues to gain tensile strength for several months after collagen content stabilizes. This gain in strength comes from the rearrangement of the collagen in the wound and perhaps from increased crosslinking of the collagen. Collagen accumulation is the sum of synthesis and destruction, and both occur simultaneously during the wound healing process. After about 14 days, a balance between collagen synthesis and degradation is reached. The collagenase involved in the remodeling comes from epithelial cells, from fibroblasts encountering new epithelium, and from macrophages that contain collagenase in their lysosomes.

Typical wound healing takes anywhere from 5 to 21 days. This time period is of course longer for the immune compromised patient because such patients are frequently unable to sufficiently stabilize the wound and ward off infection which prevents the proper adherence of fibrin, fibronectin or collagen at an acceptable rate at the locus of the wound. For example, those with vasculitis or other rheumatic or diabetic diseases frequently experience wound healing times far in excess of several weeks. Diabetics frequently develop lesions that take weeks to heal.

Others, such as those with artificial limbs, have continuous injuries at the point of contact between the limb and the point of attachment to the body. Burns also present healing problems insofar as the burned tissue is incapable of timely production of fibrin. Accordingly, there is a great need to shorten the duration of time necessary for wound or burn healing to occur.

Wound or Tissue Dressings

When referring to a wound or tissue dressing, it is understood that said wound or tissue dressings may be imprinted with the fluid or liquid composition according to the present invention primarily in the wound or tissue contacting area of said wound or tissue dressing.

Types of Wound and Tissue Dressings

"Wound" refers broadly to injuries to the skin and underlying (subcutaneous) tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The present invention relates to treatment of any type of wound mentioned above using one or more types of wound and/or tissue dressings as described below.

Several types of wound or tissue dressings exist. Most wound or tissue dressings are designed to maintain a moist wound bed. The most commonly used wound or tissue dressing are briefly introduced below. The present invention relates one or more types of wound and/or tissue dressings included the ones mentioned below printed with one or more pharmaceutical compositions.

Synthetic wound dressings originally consisted of two types; gauze-based dressings and paste bandages such as zinc paste bandages. In the mid-1980s the first modern wound dressings were introduced which delivered important characteristics of an ideal wound dressing: moisture keeping and absorbing (e.g. polyurethane foams, hydrocolloids) and moisture keeping and antibacterial (e.g. iodine-containing gels).

During the mid 1990s, synthetic wound dressings expanded into e.g. the following groups of products: 1) vapor-permeable adhesive films, 2) hydrogels, 3) hydrocolloids, 4) alginates, 5) synthetic foam dressings, 6) silicone meshes, 7) tissue adhesives, 8) barrier films and 9) silver- or collagen-containing dressings.

Synthetic wound dressings can be broadly categorized into the following types as indicated in the table below.

TABLE 6

| Type | Properties |
| --- | --- |
| Passive products | Traditional dressings that provide cover over the wound, e.g. gauze and tulle dressings |
| Interactive products | Polymeric films and forms which are mostly transparent, permeable to water vapour and oxygen, non-permeable to bacteria, e.g. hyaluronic acid, hydrogels, foam dressings |
| Bioactive products | Dressings which deliver substances active in wound healing, e.g. hydrocolloids, alginates, collagens, chitosan |

Alginate dressings are highly absorbent, biodegradable dressings derived from seaweed. They are used for wounds with moderate to large amounts of exudate, and for wounds requiring packing. These dressings work by combining with the wound exudate to form a hydrophilic gel that creates a moist healing environment.

Hydrocolloid dressings are among the oldest and most frequently used wound or tissue dressings. They are indicated for partial thickness wounds, Stage III, granulating Stage IV pressure ulcers, and can be used in the treatment of venous stasis ulcers. Hydrocolloid dressings are either occlusive (i.e. they do not allow air to escape through the dressing), or semi-occlusive (i.e. they do allow some air to escape through the dressing) and they are designed to seal the wound bed to retain and interact with exudate to promote healing. While absorbing exudate, the hydrocolloid dressing forms a gel.

Hydrogel dressings are either sheets of cross-linked polymers or hydrogel impregnated gauze, or non-wowen sponge, used to cover a wound. The hydrogel dressing can be in the form of a hydrogel sheet dressing or in the form of an amorphous hydrogel dressing. Hydrogel sheet dressings are indicated for partial and full thickness wounds, wounds with necrosis or slough, and burns. An amorphous hydrogel dressing is a soft, formless gel comprised of either polymers or copolymers and up to 95 percent water, whereas a hydrogel sheet dressing is a firm sheet. Amorphous hydrogels carry the same indications as hydrogel sheets and they can also be used to lightly pack full-thickness wounds.

Foam dressings are semipermeable sheets of a polymer, such as polyurethane, that provide a specific, controlled moisture and temperature environment for wound healing. They are indicated for full-thickness wounds with moderate to heavy exudate. Foam dressings are non-adherent and can repel contaminants.

Transparent film dressings are made of e.g. polyurethane, polyamide or gelatin. Although they are waterproof, transparent film dressings are somewhat porous allowing for oxygen and moisture to cross through their barriers. They are non-absorptive so they must be changed often for wounds with exudate. They are generally effective on dry wounds with necrotic tissue in need of autolytic debridement. Transparent film dressings are also used as a secondary material to secure e.g. non-adhesive gauzes and other types of dry dressings.

Composite dressings combine physically distinct components into a single dressing, and provide bacterial protection, absorption, and adhesion.

Gauze dressings are available in a number of forms including sponges, pads, ropes, strips, and rolls, gauze can also be impregnated with petroleum, antimicrobials, and saline. With removal of a dried dressing, there is a risk of wound damage to the healing skin surrounding the wound.

The following table describes some of the many different types of wound dressings and their main properties:

TABLE 7

| Type | Properties |
| --- | --- |
| Gauze | Dressings can stick to the wound surface and disrupt the wound bed when removed. Only use on minor wounds or as secondary dressings |
| Tulle | Dressing does not stick to wound surface. Suitable for flat, shallow wound. Useful in patient with sensitive skin. E.g. Jelonet ®, Paranet ® |
| Semipermeable film | Sterile sheet of polyurethane coated with acrylic adhesive. Transparent allowing wound checks. Suitable for shallow wound with low exudate. E.g. OpSite ®, Tegaderm ® |
| Hydrocolloids | Composed of carboxymethylcellulose, gelatin, pectin, elastomers and adhesives that turn into a gel when exudate is absorbed. This creates a warm, moist environment that promotes debridement and healing. Depending on the hydrocolloid dressing chosen can be used in wounds with light to heavy exudate, sloughing or granulating wounds. Available in many forms (adhesive or non-adhesive pad, paste, powder) |

TABLE 7-continued

| Type | Properties |
| --- | --- |
| | but most commonly as self-adhesive pads. E.g. DuoDERM ®, Tegasorb ® |
| Hydrogels | Composed mainly of water in a complex network or fibres that keep the polymer gel intact. Water is released to keep the wound moist. Used for necrotic or sloughy wound beds to rehydrate and remove dead tissue. Do not use for moderate to heavily exudating wounds. E.g. Tegagel ®, Intrasite ® |
| Alginates | Composed of calcium alginate (a seaweed component). When in contact with wound, calcium in the dressing is exchanged with sodium from wound fluid and this turns dressing into a gel that maintains a moist wound environment. Good for exudating wounds and helps in debridement of sloughing wounds. Do not use on low exudating wounds as this will cause dryness and scabbing. Dressing should be changed daily. E.g. Kaltostat ®, Sorbsan ® |
| Polyurethane or silicone foams | Designed to absorb large amounts of exudates. Maintain a moist wound environment but are not as useful as alginates or hydrocolloids for debridement. Do not use on low exudating wounds as this will cause dryness and scabbing. E.g. Allevyn ®, Lyofoam ® |
| Hydrofibre | Soft non-woven pad or ribbon dressing made from sodium carboxymethylcellulose fibres. Interact with wound drainage to form a soft gel. Absorb exudate and provide a moist environment in a deep wound that needs packing. |
| Collagens | Dressings come in pads, gels or particles. Promote the deposit of newly formed collagen in the wound bed. Absorb exudate and provide a moist environment |

No single dressing is suitable for all types of wounds. Often a number of different types of dressings will be used during the healing process of a single wound. The present invention relates in one embodiment to dressings with one or more of the following functions: 1) Maintain a moist environment at the wound/dressing interface; 2) Absorb excess exudate without leakage to the surface of the dressing; 3) Provide thermal insulation and mechanical protection; 4) Provide bacterial protection; 5) Allow gaseous and fluid exchange; 6) Absorb wound odor; 7) Be non-adherent to the wound and easily removed without trauma; 8) Provide some debridement action (remove dead tissue and/or foreign particles); 9) Be non-toxic, non-allergenic and non-sensitizing (to both patient and medical staff); 10) Sterile.

Wound or Tissue Dressings Comprising an Absorbent Compound

In another aspect there is provided a wound or tissue dressing comprising an absorbent compound for absorbing wound exudate, wherein said wound or tissue dressing has been printed with one or more pharmaceutical compositions. None limiting examples of absorbent compound is given below.

The absorbent compound in one embodiment comprises or consists of a hydrogel forming material. The hydrogel forming material can form an amorphous hydrogel, but the hydrogel forming material can also be in the form of e.g. a sheet—in which case the dressing will be a hydrogel sheet dressing.

In other embodiments, the absorbent compound of the wound or tissue dressing comprises or consists of a hydrocolloid forming material.

The absorbent compound can comprises or consist of a porous polymer suitable for entry of wound extrudate therein, i.e. the capillary force allows wound extrudate to enter into the porous polymer. The porous polymer is often hydrophilic or sufficiently hydrophilic to allow transport of wound extrudate.

In a still further embodiment the absorbent compound comprises or consists of a foam forming material.

It is important that the absorbent compound is in fluid contact with the wound e.g. through a gel or a matrix, such as a scaffold, or, alternatively, that the absorbent compound can contact the wound directly.

The bioabsorbable and/or porous material of the absorbent compound can be adapted for serving as scaffold for new cells to attach and proliferate. Such a "connective" absorbent compound can remain in place on the wound bed throughout the healing process, and later be absorbed and replaced by new tissue. During the wound healing process, the connective absorbent compound will transmit wound exudate from the wound bed to the bioabsorbable and/or porous material of the absorbent compound.

The absorbent compound can be a material that is absorbent to liquid while at the same time serves as a barrier for cell adhesion and penetration by growing cells and larger proteins in wound exudate. Such an absorbent compound can be referred to as an "absorbent barrier material". An absorbent barrier material can e.g. prevent bacteria present in the bioabsorbable and/or porous material of the absorbent compound from entering the wound itself. However, bioactive agents produced said bacteria and having wound healing promoting abilities are allowed to enter the wound area.

Besides absorbing wound exudate and inhibiting the loss of beneficial growth factors from the scaffold material, the absorbent compound can also act as a reservoir for liquids to hydrate the wound. The features of non-adhesion and resistance to penetration by cells provide the important advantage that the absorbent barrier material—and any subsequent connective compound—is easily removed and/or replaced as needed without causing trauma to growing cells or tissue.

If desirable, the absorbent compound can be in contact with a further compound, such as a breathable film that can serve as a barrier to the entry of contaminants into the wound bed. One example of such a barrier is a topfilm.

The absorbent compound can be any of the materials used in wound care. Materials that can be used as an absorbent compound include fabrics, foams or fibers of e.g. polyester, polypropylenes, polyethylenes and the which are optionally bonded to polyester film (such as Kendall's Novenette). Other suitable materials include, but are not limited to, natural and synthetic polymeric absorbents, hydrocolloids, superabsorbents, and cellulosic absorbents. Cellulosic materials include cotton, rayon, wood and cellulose.

The superabsorbent compound may be in any suitable form. Typical superabsorbents include starch grafted copolymers of acrylate salts, starch grafted copolymers of acrylamide salts, polyacrylate salts and the like, including mixtures thereof.

Superabsorbent compounds and composites are easily prepared or commercially available. Once such product is the composite air laid superabsorbent pad (dry forming process and the superabsorbent fiber flock SAFF) sold by Hanfspinnern Steen & Company. The superabsorbent may also be a delayed released web superabsorbent.

Superabsorbent webs that may be used in the present invention to serve as, or to be incorporated into, the absorbent compound can also include carded or random webs made from, for example, cotton, rayon, polyethylene, polyester, or wool. Another suitable web is a spun-laced web made from polyester, polypropylene, or polyethylene. The superabsorbent webs may also be in the form of tissues either single ply or multiple ply and either creped or uncreped. Delnet, a product of Applied Extrusion Technologies which consists of a range of materials manufactured from polyethylene or polypropylene using extrusion embossing and orientation processes may also be used as a web for preparing a superabsorbent web.

Superabsorbent webs can be formed by any convenient means, e.g., by slightly moistening or misting a web. After misting, a powdered superabsorbent may be applied followed by running the web through a dry oven or heating the roll. The powder adjacent to the moistened web will become tacky and adhere to the adjacent material (fibre, surface), and the loose powder would then be vacuumed off.

Alternatively, superabsorbent powder can be sandwiched between non-woven webs/paper and subjected to moist steam which would make the superabsorbent tacky so that it would then stick to adjacent surfaces. The sandwiched superabsorbent and web would then be dried, creating a two-ply web with superabsorbent between them. The superabsorbent connective compound can also be heat bonded to the other connective compounds.

The wound or tissue dressing according to the present invention can contain from about 5% to about 50% by weight of water, such as from about 5% to about 40% by weight of water, for example from about 5% to about 30% by weight of water, such as from about 5% to about 25% by weight of water, for example from about 5% to about 20% by weight of water, such as from about 5% to about 15% by weight of water, for example from about 5% to about 10% by weight of water, such as from about 10% to about 40% by weight of water, for example from about 10% to about 30% by weight of water, such as from about 10% to about 25% by weight of water, for example from about 10% to about 20% by weight of water, such as from about 10% to about 15% by weight of water, such as from about 15% to about 40% by weight of water, for example from about 15% to about 30% by weight of water, such as from about 15% to about 25% by weight of water, for example from about 15% to about 20% by weight of water.

Absorbent Compound Comprising an Adhesive Surface

In a further embodiment the present invention relates one or more wound or tissue dressings comprising one or more absorbent compound(s) for absorbing wound exudate, wherein said wound or tissue dressing has been printed with one or more pharmaceutical compositions and wherein said absorbent compound comprises an adhesive surface. Non-limiting examples of an adhesive surface are given below.

The absorbent compound can comprise at least one adhesive surface suitable for contacting a wound or the absorbent compound can be attached to at least one adhesive surface suitable for contacting a wound. When the absorbent compound is attached to at least one adhesive surface suitable for contacting a wound the absorbent compound and the adhesive surface are most often manufactured separately and only brought together during the manufacturing of the wound or tissue dressing according to the present invention. The adhesive surface can simply be positioned on or spread out over the corresponding surface of the absorbent compound, such as the absorbent compound surface which is going to be aligned with the surface of a wound.

The at least one adhesive surface can be separated from the absorbent compound by a permeable or semi-permeable barrier allowing wound extrudate to be diverted from the wound to the absorbent compound. Alternatively, the at least one adhesive surface can itself comprise a barrier acting as a permeable or semi-permeable barrier that allows wound extrudate to be diverted from the wound to the absorbent compound.

The absorbent compound can also be attached to a topfilm at least partly sealing the absorbent compound from the external environment. Alternatively, the absorbent compound itself comprises a functionality acting as a topfilm at least partly sealing the absorbent compound from the external environment.

The topfilm is often porous and the topfilm can comprise an oxygen- and vapor-permeable layer permitting transpiration of liquid from the absorbent compound.

Gelatin and Collagen Absorbent Compounds

In some embodiments the wound or tissue dressing according to the present invention comprises an absorbent compound comprising or consisting of gelatin and/or collagen, including a combination of gelatin and collagen.

When the absorbent compound comprises or consists of gelatin the gelatin can be cross-linked and form a matrix, such as a matrix in the form of a hydrogel.

Alternatively, the wound or tissue dressing can comprise or consist of gelatin which is not crosslinked. The gelatin can be in granulated or particulated form and most often such dressings employ hydrocolloids.

When the absorbent compound comprises or consists of collagen the collagen can be cross-linked and form a matrix, such as a matrix in the form of a hydrogel.

Alternatively, the wound or tissue dressing can comprise or consist of collagen which is not crosslinked. The collagen can be in granulated or particulated form and most often such dressings employ hydrocolloids.

Hyaluronic acid can be present in the dressing in a haemostasis promoting amount in combination with any or both of gelatin and collagen.

Alginate Absorbent Compounds

In one embodiment the absorbent compound comprises an optionally cross-linked alginate compound, such as an alginate ester, for example an alginate ester comprising propylene glycol alginate.

The degree of esterification of the alginate ester is typically from 35% to 95% and the absorbent compound can contain from 10% to 25% by weight of the alginate ester.

Wound or Tissue Dressings Comprising Hydrocolloids

The wound or tissue dressing can comprise a hydrocolloid, but in some embodiments the hydrocolloid can be omitted. In embodiments wherein a hydrocolloid is used, the hydrocolloid comprises about 20 to about 60 weight percent of the wound or tissue dressing, based on total weight.

The hydrocolloid can comprise e.g. from about 25 to about 55 weight percent of the composition, such as from about 30 to about 50 weight percent of the composition. In one embodiment, the hydrocolloid comprises about 40 weight percent of the composition.

The hydrocolloid used in the present invention can be synthetically prepared or naturally occurring. Varieties of hydrocolloids within the scope of the present invention include synthetic polymers prepared from single or multiple monomers, naturally occurring hydrophilic polymers, or chemically modified naturally occurring hydrophilic polymers. It is preferred that the hydrocolloid is dermatologically acceptable and non-reactive with the skin of the patient or other components of the composition. Preferred examples are hydrocolloids comprising gelatin and/or collagen.

Further specific examples include hydrocolloids comprising e.g. polyhydroxyalkyl acrylates and methacrylates, polyvinyl lactams, polyvinyl alcohols, polyoxyalkylenes, polyacrylamides, polyacrylic acid, polystyrene sulfonates, natural or synthetically modified polysaccharides, alginates, gums, and cellulosics and modified celluloses.

Representative polysaccharides include e.g. starch, glycogen, hemicelluloses, pentosans, celluloses, pectin, chitosan, and chitin.

Representative gums include e.g. Arabic, Locust Bean, Guar, Agar, Carrageenan, Xanthan, Karaya, tragacanth, Ghatti, and Furcelleran gums.

Representative modified celluloses include methyl cellulose, hydroxypropyl methyl cellulose, carboxymethylcellulose, and hydroxypropyl cellulose.

Hydrocolloids which are water soluble or swellable hydrocolloids can be selected e.g. from the group consisting of polyvinyl alcohols, powdered pectin, methyl cellulose, hydroxypropyl methyl cellulose, carboxymethylcellulose, hydroxypropyl cellulose and mixtures thereof.

Further examples of suitable hydrocolloids include synthetic polymers that may be either linear or crosslinked. Non-limiting examples of synthetic hydrocolloids include e.g. polymers prepared from N-vinyl lactams, e.g. N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, and N-vinyl-2-caprolactam.

Other monomers useful to prepare a synthetic hydrocolloid include hydroxyalkyl acrylates and methacrylates, (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid and a tertiary amino-methacrylimide, (e.g. trimethylamino-methacrylimide), crotonic acid, and pyridine. Additional monomers useful to prepare a synthetic hydrocolloid include water soluble amides, (such as N-(hydroxymethyl)acrylamide and -methacrylamide, N-(3-hydroxpropyl)acrylamide, N-(2-hydroxyethyl) methacrylamide, N-(1,1-dimethyl-3-oxabutyl)acrylamide N-[2-(dimethylamine)ethyl]acrylamide and -methacrylamide, N-[3-(dimethylamino)-2-hydroxylpropyl]methacrylamide, and N-[1,1-dimethyl-2-(hydroxymethyl)-3-oxabutyl] acrylamide); water-soluble hydrazine derivatives, (such as trialkylamine methacrylimide, and dimethyl-(2-hydroxypropyl)amine methacrylimide); mono-olefinic sulfonic acids and their salts, (such as sodium ethylene sulfonate, sodium styrene sulfonate and 2-acrylamideo-2-methylpropanesulfonic acid); and the following monomers containing nitrogen in the non-cyclic or cyclic backbone of the monomer: 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, and 4-acrylylmorpholine.

Hydrogels

Cross-linking of the linear polymer chains of the hydrocolloid may be desired to improve cohesive properties of the gel dispersed in the pressure sensitive adhesive matrix. When such crosslinking is desired for polymers made from vinyl monomers discussed above, a multi-ethylenically unsaturated compound with the ethylenic groups being vinyl, allyl, or methallyl groups bonded to nitrogen, oxygen or carbon atoms can be used.

Non-limiting examples of cross-linking agents for vinyl containing polymers include divinyl, diallyl, or dimethallyl esters (e.g. ethylene glycol dimethacrylate, divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate); divinyl, diallyl or dimethallyl ethers (e.g. diethyleneglycol divinyl ether, butane diol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether); divinyl, diallyl or dimethallyl amides including bis(N-vinyl lactams), (e.g., 3,3'-ethylene bis(N-vinyl-2-pyrrolidone) and methylene-bis-acrylamide); and divinyl, diallyl and dimethallyl ureas.

Preferred cross-linking agents include ethylene glycol dimethacrylate, methylene-bis-acrylamide, diallyl maleate, and 3,3'-ethylidene bis(N-vinyl-2-pyrrolidone). For n-vinyl lactams, the preferred crosslinking agents are diallyl maleate and 3,3'-ethylidene bis(N-vinyl-2-pyrrolidone). For acrylates and methacrylates, the preferred crosslinking agents are ethylene glycol dimethacrylate and methylene-bis-acrylamide.

Wound or Tissue Dressings Comprising Humectants

The dressing can also contain a humectant to reduce the partial vapor pressure of the water in the wound or tissue dressing or to reduce the rate at which the wound or tissue dressing dries out. Suitable humectants are miscible with water to a large extent and are generally suitable for application to the skin.

The humectant can be e.g. glycerol and propylene glycol and the absorbent compound typically contains from about 10% to about 90% by weight of the humectant.

Polyols are especially suitable for the purpose and suitable polyols may include monopropylene glycol or glycerin (glycerol). The polyol may be present in proportions of 20 to 50% (by weight) of the total formulation; alternatively the range is 30 to 40%. This relatively high proportion of polyol also ensures that if the paste should dry out to any degree, the resulting paste remains soft and flexible because the glycerin may act as a plasticiser for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly infected wounds.

Method for Manufacturing Wound or Tissue Dressings According to the Invention

The present method is also directed to a method for manufacturing the wound or tissue dressing according to the invention, said method comprising the steps of providing one or more pharmaceutical compositions, and printing said one or more pharmaceutical compositions onto the wound or tissue dressing and/or with the absorbent compound of the wound or tissue dressing, thereby obtaining the wound or tissue dressing according to the invention.

The method can comprise the further step of providing the absorbent compound with at least one adhesive surface suitable for contacting a wound, or the further step of attaching at least one adhesive surface suitable for contacting a wound to the absorbent compound.

In another further step there is provided a permeable or semi-permeable barrier for separating the at least one adhesive surface from the absorbent compound by introducing said permeable or semi-permeable barrier between the absorbent compound and the at least one adhesive surface, wherein said permeable or semi-permeable barrier allows wound extrudate to be diverted from the wound to the absorbent compound.

In a yet further step the method comprises providing a permeable or semi-permeable barrier capable of partly separating—during use—the at least one adhesive surface from the wound by introducing said permeable or semi-permeable barrier on the surface of the adhesive surface, wherein said permeable or semi-permeable barrier—during use—allows wound extrudate to be diverted from the wound to the absorbent compound through the adhesive surface.

In yet further step a topfilm can be provided and attached to the absorbent compound, wherein said topfilm seals at least partly the absorbent compound from the external environment. The absorbent compound can also comprise a topfilm as an integrated part, wherein said topfilm at least partly seals the absorbent compound from the external environment. The topfilm can be porous or non-porous. In one embodiment, the topfilm comprises an oxygen- and vapor-permeable layer permitting transpiration of liquid from the absorbent compound.

Wound Treatment Methods

Various uses of the wound or tissue dressings according to the present invention are envisaged. In one embodiment there is provided a method for treating a wound in an individual, said method comprising the steps of contacting said wound with the wound or tissue dressing according to the present invention, and treating the wound.

The treatment can in principle result in healing of the wound or in accelerated healing of the wound. The accelerated healing can be a result of e.g. administration of a wound-healing promoting substance. Alternatively, the wound healing can be promoted by preventing bacterial or viral infection, or by reducing the risk of such an infection which would otherwise have prolonged the wound treatment process.

In another embodiment there is provided a method for treating damaged tissue in an individual, said method comprising the steps of contacting said damaged tissue with the wound or tissue dressing according to the invention, and treating the damaged tissue.

Likewise, the treatment can in principle result in healing of the damaged tissue or in accelerated healing of the damaged tissue. The accelerated healing can be a result a e.g. administration of a tissue-healing promoting substance. Alternatively, the healing of damaged tissue can be promoted by preventing bacterial or viral infection, or by reducing the risk of such an infection which would otherwise have prolonged the treatment of the damaged tissue.

The tissue damage can e.g. be caused by bone protrudence, by diabetes, by circulatory insufficiencies or by undesirable inflammatory processes in an individual.

There is also provided a method for preventing or reducing the risk of wound or tissue infection in an individual having suffered a wound or damaged tissue, said method comprising the steps of contacting said wound or tissue with the wound or tissue dressing according to the invention, and treating the wound or tissue at risk of being infected. The infectious agent at risk of infecting the wound or tissue can be a bacteria or a virus.

As e.g. gelatin and hyaluronic acid independently and in combination have a haemostatic effect, there is also provided a method for promoting haemostasis in a wound in an individual, said method comprising the steps of contacting said wound with the wound dressing printed with one or more pharmaceutical compositions according to the invention, and promoting haemostasis in the wound.

In addition to contacting a wound or damaged tissue with the wound or tissue dressing according to the invention, there is also provided combination methods wherein one or more wound or tissue healing-promoting substance(s) are administered simultaneously or sequentially in any order one or more at the same time as the wound or tissue to be treated is contacted with the wound or tissue dressing according to the invention. This may be of particular importance when treating slow-healing wounds, partial thickness wound, deep wounds and chronic wounds.

Method for Manufacturing of Wound and/or Tissue Dressings

In a further aspect there is provided a method for manufacturing a wound or tissue dressing printed with one or more pharmaceutical compositions according to the present invention, said method comprising the steps of providing one or more pharmaceutical compositions, printing said one or more pharmaceutical compositions onto the wound or tissue dressing and/or onto the absorbent compound of the wound or tissue dressing, thereby obtaining a wound or tissue dressing according to the present invention.

There is also provided the use of printing of one or more pharmaceutical compositions for the manufacture of a wound or tissue dressing for treating or accelerating the healing of a wound in an individual.

In yet another aspect there is provided the use of printing of one or more pharmaceutical compositions for the manufacture of an absorbent compound for use in a wound or tissue dressing for treating or accelerating the healing of a wound in an individual.

The present invention also relates to the use of printing of one or more pharmaceutical compositions for the manufacture of an absorbent compound for use in a wound or tissue dressing for treating a wound or tissue or accelerating the healing of a wound or tissue in an individual.

In a further embodiment the present invention relates to the use of printing of one or more pharmaceutical compositions in the manufacture of a wound or tissue dressing for preventing or reducing the risk of wound or tissue infection in an individual having suffered a wound.

The present invention also relates to the use of printing of one or more pharmaceutical compositions in the manufacture of a wound or tissue dressing for promoting haemostasis in a wound in an individual.

A Container for Storage and/or Preparation of a Matrix Material

The present invention also relates to a container, box or packaging means e.g. for storage and/or preparation of a matrix material. In one embodiment this container, box or packaging provides a sterile environment for storage and/or preparation of the matrix material.

The container comprises an inner cavity (hollow space) for storage of a matrix material. In one embodiment the container comprises more than one inner cavity for storage of more than one matrix material such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 inner cavities, for storage of more than one matrix material such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 matrix materials.

In another embodiment, the container comprises one inner cavity for storage of more than one matrix material such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 matrix materials.

The inner cavity is made of a bottom with defined dimensions, and one or more sidewall(s) with a defined height. The one or more sidewalls of the cavity comprise in one embodiment a mark for the maximum volume that should be added to the cavity containing the matrix material. This mark can be any type of mark such as a line, dot or the one or more sides can comprise a bend e.g. the angle between the bottom and the side differ between the sidewall below and above the mark—i.e. one or more bevelled edges as a guiding tool for maximum amount of liquid/moisture to be added to the inner cavity containing the one or more matrix material(s). One advantage of the container is that the one or more mark(s) on the one or more sidewall(s) decreases the risk of addition of excess liquid to the container comprising one or more matrix materials.

The cavity should generally circumvent the matrix material. Accordingly, the shape of the cavity should be adjusted to fit or surround the shape of the matrix material.

The cavity defined by the size of the bottom of the inner cavity and the height of one or more sidewalls measured from the bottom of the inner cavity to the mark for maximum filling is referred to as the maximum volume of liquid to be added to the container comprising the matrix material.

In one embodiment the maximum volume of liquid to be added to the container comprising the matrix material is in the range of from 1 mL to 60 mL, such as from 1 mL to 2 mL, for example from 2 to 3 mL, such as from 3 mL to 4 mL, for example from 4 to 5 mL, such as from 5 mL to 6 mL, for example from 6 to 7 mL, such as from 7 mL to 8 mL, for example from 8 to 9 mL, such as from 9 mL to 10 mL, for example from 10 to 11 mL, such as from 11 mL to 12 mL, for example from 12 to 13 mL, such as from 13 mL to 14 mL, for example from 14 to 15 mL, such as from 15 mL to 16 mL, for example from 16 to 17 mL, such as from 17 mL to 18 mL, for example from 18 to 19 mL, such as from 19 mL to 20 mL, for example from 20 to 21 mL, such as from 21 mL to 22 mL, for example from 22 to 23 mL, such as from 23 mL to 24 mL, for example from 24 to 25 mL, such as from 25 mL to 26 mL, for example from 26 to 27 mL, such as from 27 mL to 28 mL, for example from 28 to 29 mL, such as from 29 mL to 30 mL, for example from 30 to 31 mL, such as from 31 mL to 32 mL, for example from 32 to 33 mL, such as from 33 mL to 34 mL, for example from 34 to 35 mL, such as from 35 mL to 36 mL, for example from 36 to 37 mL, such as from 37 mL to 38 mL, for example from 38 to 39 mL, such as from 39 mL to 40 mL, for example from 40 to 41 mL, such as from 41 mL to 42 mL, for example from 42 to 43 mL, such as from 43 mL to 44 mL, for example from 44 to 45 mL, such as from 45 mL to 46 mL, for example from 46 to 47 mL, such as from 47 mL to 48 mL, for example from 48 to 49 mL, such as from 49 mL to 50 mL, for example from 50 to 51 mL, such as from 51 mL to 52 mL, for example from 52 to 53 mL, such as from 53 mL to 54 mL, for example from 54 to 55 mL, such as from 55 mL to 56 mL, for example from 56 to 57 mL, such as from 57 mL to 58 mL, for example from 58 to 59 mL, such as from 59 mL to 60 mL. The maximum volume of liquid to be added to the container comprising the matrix material will depend on factors such as size of the cavity of the container and the liquid absorbability of the matrix material used.

In one embodiment the maximum volume of liquid to be added to the container should be in range of from 5% to 50% of the volume of the matrix material such as from 5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, such as from 15% to 16%, for example from 16% to 17%, such as from 17% to 18%, for example from 18% to 19%, such as from 19% to 20%, for example from 20% to 21%, such as from 21% to 22%, for example from 22% to 23%, such as from 23% to 24%, for example from 24% to 25%, such as from 25% to 26%, for example from 26% to 27%, such as from 27% to 28%, for example from 28% to 29%, such as from 29% to 30%, for example from 30% to 31%, such as from 31% to 32%, for example from 32% to 33%, such as from 33% to 34%, for example from 34% to 35%, such as from 35% to 36%, for example from 36% to 37%, such as from 37% to 38%, for example from 38% to 39%, such as from 39% to 40%, for example from 40% to 41%, such as from 41% to 42%, for example from 42% to 43%, such as from 43% to 44%, for example from 44% to 45%, such as from 45% to 46%, for example from 46% to 47%, such as from 47% to 48%, for example from 48% to 49%, or such as from 49% to 50%.

In one embodiment the preferred volume of liquid to be added to the container should be in range of from 5% to 50% of the volume of the inner cavity such as from 5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, such as from 15% to 16%, for example from 16% to 17%, such as from 17% to 18%, for example from 18% to 19%, such as from 19% to 20%, for example from 20% to 21%, such as from 21% to 22%, for example from 22% to 23%, such as from 23% to 24%, for example from 24% to 25%, such as from 25% to 26%, for example from 26% to 27%, such as from 27% to 28%, for example from 28% to 29%, such as from 29% to 30%, for example from 30% to 31%, such as from 31% to 32%, for example from 32% to 33%, such as from 33% to 34%, for example from 34% to 35%, such as from 35% to 36%, for example from 36% to 37%, such as from 37% to 38%, for example from 38% to 39%, such as from 39% to 40%, for example from 40% to 41%, such as from 41% to 42%, for example from 42% to 43%, such as from 43% to 44%, for example from 44% to 45%, such as from 45% to 46%, for example from 46% to 47%, such as from 47% to 48%, for example from 48% to 49%, or such as from 49% to 50%.

In one embodiment the preferred volume of liquid to be added to the container should be in range of from 1 mL to 60 mL, such as from 1 mL to 2 mL, for example from 2 to 3 mL, such as from 3 mL to 4 mL, for example from 4 to 5 mL, such as from 5 mL to 6 mL, for example from 6 to 7 mL, such as from 7 mL to 8 mL, for example from 8 to 9 mL, such as from 9 mL to 10 mL, for example from 10 to 11 mL, such as from 11 mL to 12 mL, for example from 12 to 13 mL, such as from 13 mL to 14 mL, for example from 14 to 15 mL, such as from 15 mL to 16 mL, for example from 16 to 17 mL, such as from 17 mL to 18 mL, for example from 18 to 19 mL, such as from 19 mL to 20 mL, for example from 20 to 21 mL, such as from 21 mL to 22 mL, for example from 22 to 23 mL, such as from 23 mL to 24 mL, for example from 24 to 25 mL, such as from 25 mL to 26 mL, for example from 26 to 27 mL, such as from 27 mL to 28 mL, for example from 28 to 29 mL, such as from 29 mL to 30 mL, for example from 30 to 31 mL, such as from 31 mL to 32 mL, for example from 32 to 33 mL, such as from 33 mL to 34 mL, for example from 34 to 35 mL, such as from 35 mL to 36 mL, for example from 36 to 37 mL, such as from 37 mL to 38 mL, for example from 38 to 39 mL, such as from 39 mL to 40 mL, for example from 40 to 41 mL, such as from 41 mL to 42 mL, for example from 42 to 43 mL, such as from 43 mL to 44 mL, for example from 44 to 45 mL, such as from 45 mL to 46 mL, for example from 46 to 47 mL, such as from 47 mL to 48 mL, for example from 48 to 49 mL, such as from 49 mL to 50 mL, for example from 50 to 51 mL, such as from 51 mL to 52 mL, for example from 52 to 53 mL, such as from 53 mL to 54 mL, for example from 54 to 55 mL, such as from 55 mL to 56 mL, for example from 56 to 57 mL, such as from 57 mL to 58 mL, for example from 58 to 59 mL, such as from 59 mL to 60 mL.

In one embodiment the container is made of plastic and has an exterior, an interior and a sealed outer periphery, the sealed outer periphery forming a sterile interior region which isolates the interior from a surrounding environment. A matrix material is located within the interior and is initially isolated from the surrounding environment by the sealed periphery.

In one embodiment the container comprises a bottom, one or more sidewalls, a mark for maximum filling of the container on one or more of the sidewalls, a sealing surface for a lid and a lid (e.g., as shown in FIGS. 2A and 2B, FIGS. 3A and 3B, FIG. 4, FIG. 5 and FIG. 6). The container can comprise one or more inner tray notches that make it easy to handle the matrix material without destroying the structure of the matrix material (e.g., as shown in FIGS. 2A and 2B, FIG. 4 and FIG. 5). In one embodiment the container has a base to provide stabile placement on all possible surfaces such as even or uneven surfaces including a sterile field, a mayo stand, a tray of instruments or on the chest of the patient (e.g., as shown in FIGS. 2A and 2B, FIGS. 3A and 3B, FIG. 4, FIG. 5 and FIG. 6). The base can provide stability during handling to minimize the risk of spilling. The container optionally also has a handle (e.g., as shown in FIGS. 2A and 2B, FIGS. 3A and 3B, FIG. 4, FIG. 5 and FIG. 6).

In one embodiment the bottom, base, sidewalls and optionally handle of the container is cast or moulded in one piece of e.g. plastic. The bottom, base, sidewalls and optionally handle of the container can also be cast or moulded in more than one piece of e.g. plastic such as 2, 3, 4, 5, 6, 7, 8, 9, 10, 11, 12 or more than 12 pieces of e.g. plastic. In one preferred embodiment, the container contains a handle and the bottom, base, sidewalls and handle are cast or moulded in one piece.

In one embodiment the bottom and lid and/or the bottom and the base and/or the base and the lid are parallel. In another embodiment the bottom and lid and/or the bottom and the base and/or the base and the lid are not parallel. In one embodiment the lid and/or the base and/or the bottom of the container is perpendicular to the one or more sidewalls of the container. In one embodiment the lid and/or the base and/or the bottom of the container is not perpendicular to the one or more sidewalls of the container. The angle between the lid and/or the base and/or the bottom of the container and the one or more sidewalls can be in the range of from 20 degrees to 160 degrees, such as from 20 degrees to 25 degrees, for example from 25 degrees to 30 degrees, such as from 30 degrees to 35 degrees, for example from 35 degrees to 40 degrees, such as from 40 degrees to 45 degrees, for example from 45 degrees to 50 degrees, such as from 50 degrees to 55 degrees, for example from 55 degrees to 60 degrees, such as from 60 degrees to 65 degrees, for example from 65 degrees to 70 degrees, such as from 70 degrees to 75 degrees, for example from 75 degrees to 80 degrees, such as from 80 degrees to 85 degrees, for example from 85 degrees to 90 degrees, such as from 90 degrees to 95 degrees, for example from 95 degrees to 100 degrees, such as from 100 degrees to 105 degrees, for example from 105 degrees to 110 degrees, such as from 110 degrees to 115 degrees, for example from 115 degrees to 120 degrees, such as from 120 degrees to 125 degrees, for example from 125 degrees to 130 degrees, such as from 130 degrees to 135 degrees, for example from 135 degrees to 140 degrees, such as from 140 degrees to 145 degrees, for example from 145 degrees to 150 degrees, such as from 150 degrees to 155 degrees, for example from 155 degrees to 160 degrees.

The bottom of the cavity of the container can be any shape such as a square, rectangle, triangle, circle, or oval:

In one embodiment the bottom is formed as a square e.g. with the dimensions of 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×9 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 11 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 13 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, 15 cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

The dimensions of the bottom of the container may also be any decimal number, for example 13.035 cm×9.74 cm (small), such as 13.035 cm×13.73 cm (medium) or for example 13.035 cm×20.04 cm (large).

In another embodiment the bottom is formed as a square e.g. with the dimensions of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 $cm^2$, for example 260 $cm^2$ to 270 $cm^2$, such as 270 $cm^2$ to 280 $cm^2$, for example 280 $cm^2$ to 290 $cm^2$, such as 290 $cm^2$ to 300 $cm^2$, for example 300 $cm^2$ to 320 $cm^2$, such as 320 $cm^2$ to 340 $cm^2$, for example 340 $cm^2$ to 360 $cm^2$, such as 360 $cm^2$ to 380 $cm^2$, for example 380 $cm^2$ to 400 $cm^2$, such as 400 $cm^2$ to 420 $cm^2$, for example 420 $cm^2$ to 440 $cm^2$, such as 440 $cm^2$ to 460 $cm^2$, for example 460 $cm^2$ to 480 $cm^2$, such as 480 $cm^2$ to 500 $cm^2$.

It follows that the dimension of the square bottom need not be a whole or counting number, but may also be any decimal number.

In one embodiment the bottom is formed to circumvent a matrix material shaped as a square with one of the dimensions selected from the group consisting of 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×9 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 11 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 13 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, 15 cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm ×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

In one embodiment the bottom is formed to circumvent a matrix material shaped as a square with a dimension of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 $cm^2$, for example 260 $cm^2$ to 270 $cm^2$, such as 270 $cm^2$ to 280 $cm^2$, for example 280 $cm^2$ to 290 $cm^2$, such as 290 $cm^2$ to 300 $cm^2$, for example 300 $cm^2$ to 320 $cm^2$, such as 320 $cm^2$ to 340 $cm^2$, for example 340 $cm^2$ to 360 $cm^2$, such as 360 $cm^2$ to 380 $cm^2$, for example 380 $cm^2$ to 400 $cm^2$, such as 400 $cm^2$ to 420 $cm^2$, for example 420 $cm^2$ to 440 $cm^2$, such as 440 $cm^2$ to 460 $cm^2$, for example 460 $cm^2$ to 480 $cm^2$, such as 480 $cm^2$ to 500 $cm^2$.

It follows that the dimension of the square matrix material need not be a whole or counting number, but may also be any decimal number.

In another embodiment the bottom is formed as a circle e.g. with a diameter in the range of from 1 cm to 40 cm, such as from 1 cm to 2 cm, for example from 2 cm to 4 cm, such as from 4 cm to 6 cm, for example from 6 cm to 8 cm, such as from 8 cm to 10 cm, for example from 10 cm to 12 cm, such as from 12 cm to 14 cm, for example from 14 cm to 16 cm, such as from 16 cm to 18 cm, for example from 18 cm to 20 cm, such as from 20 cm to 22 cm, for example from 22 cm to 24 cm, such as from 24 cm to 26 cm, for example from 26 cm to 28 cm, such as from 28 cm to 30 cm, for example from 30 cm to 32 cm, such as from 32 cm to 34 cm, for example from 34 cm to 36 cm, such as from 36 cm to 38 cm, for example from 38 cm to 40 cm.

In one embodiment the bottom is formed as a circle e.g. with a diameter of 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm or 40 cm.

In one embodiment the bottom is formed as a circle e.g. with the dimensions of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 $cm^2$, for example 260 $cm^2$ to 270 $cm^2$, such as 270 $cm^2$ to 280 $cm^2$, for example 280 $cm^2$ to 290 $cm^2$, such as 290 $cm^2$ to 300 $cm^2$, for example 300 $cm^2$ to 320 $cm^2$, such as 320 $cm^2$ to 340 $cm^2$, for example 340 $cm^2$ to 360 $cm^2$, such as 360 $cm^2$ to 380 $cm^2$, for example 380 $cm^2$ to 400 $cm^2$, such as 400 $cm^2$ to 420 $cm^2$, for example 420 $cm^2$ to 440 $cm^2$, such as 440 $cm^2$ to 460 $cm^2$, for example 460 $cm^2$ to 480 $cm^2$, such as 480 $cm^2$ to 500 $cm^2$.

It follows that the dimension of the circular bottom need not be a whole or counting number, but may also be any decimal number.

In one embodiment the bottom is formed as a circle e.g. with a diameter that can circumvent a matrix material such as a circular matrix material with a diameter in the range of from 1 cm to 40 cm, such as from 1 cm to 2 cm, for example from 2 cm to 4 cm, such as from 4 cm to 6 cm, for example from 6 cm to 8 cm, such as from 8 cm to 10 cm, for example from 10 cm to 12 cm, such as from 12 cm to 14 cm, for example from 14 cm to 16 cm, such as from 16 cm to 18 cm, for example from 18 cm to 20 cm, such as from 20 cm to 22 cm, for example from 22 cm to 24 cm, such as from 24 cm to 26 cm, for example from 26 cm to 28 cm, such as from 28 cm to 30 cm, for example from 30 cm to 32 cm, such as from 32 cm to 34 cm, for example from 34 cm to 36 cm, such as from 36 cm to 38 cm, for example from 38 cm to 40 cm.

In one embodiment the bottom is formed as a circle e.g. with a diameter that can circumvent a matrix material such as a circular matrix material with a diameter of from of 1 cm, 2, cm, 3, cm, 4, cm, 5, cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm or 40 cm.

In one embodiment the bottom is formed as a circle e.g. with a diameter that can circumvent a matrix material such as a circular matrix material with a dimension of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 cm², for example 260 cm² to 270 cm², such as 270 cm² to 280 cm², for example 280 cm² to 290 cm², such as 290 cm² to 300 cm², for example 300 cm² to 320 cm², such as 320 cm² to 340 cm², for example 340 cm² to 360 cm², such as 360 cm² to 380 cm², for example 380 cm² to 400 cm², such as 400 cm² to 420 cm², for example 420 cm² to 440 cm², such as 440 cm² to 460 cm², for example 460 cm² to 480 cm², such as 480 cm² to 500 cm².

It follows that the dimension of the circular matrix material need not be a whole or counting number, but may also be any decimal number.

In one embodiment the height of the sidewalls (from the bottom to the mark for maximum filling) is selected from the groups consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm, 20 mm to 22 mm, 22 mm to 24 mm, 24 mm to 26 mm, 26 mm to 28 mm, 28 mm to 30 mm, 30 mm to 32 mm, 32 mm to 34 mm, 34 mm to 36 mm, 36 mm to 38 mm, 38 mm to 40 mm, 40 mm to 42 mm, 42 mm to 44 mm, 44 mm to 46 mm, 46 mm to 48 mm or 48 mm to 50 mm.

In one embodiment the width of the sidewall(s) is in the range of 0 to 20 mm, preferably selected from the groups consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm.

In one embodiment the height from the mark for maximum filling to the lid can be selected from the group consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm, 20 mm to 22 mm, 22 mm to 24 mm, 24 mm to 26 mm, 26 mm to 28 mm, 28 mm to 30 mm, 30 mm to 32 mm, 32 mm to 34 mm, 34 mm to 36 mm, 36 mm to 38 mm, 38 mm to 40 mm, 40 mm to 42 mm, 42 mm to 44 mm, 44 mm to 46 mm, 46 mm to 48 mm or 48 mm to 50 mm.

In another embodiment the height from the bottom of the container to the lid of the container is selected from the groups consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm, 20 mm to 22 mm, 22 mm to 24 mm, 24 mm to 26 mm, 26 mm to 28 mm, 28 mm to 30 mm, 30 mm to 32 mm, 32 mm to 34 mm, 34 mm to 36 mm, 36 mm to 38 mm, 38 mm to 40 mm, 40 mm to 42 mm, 42 mm to 44 mm, 44 mm to 46 mm, 46 mm to 48 mm or 48 mm to 50 mm.

In one embodiment the cavity of the container also comprise space for contacting the matrix material e.g. with scissors, tweezers, forceps, another device or one or more fingers (inner tray notches). The container can comprise 1, 2, 3, 4, 5, 6, 7, 8, 9, 10 or more than 10 inner tray notches. These inner tray notches can have any size or form to provide easy contact with the matrix material. The one or more inner tray notches may be associated with the one or more sidewall(s) of the container.

The base of the container can have any shape such as a square, rectangle, triangle, circle, or oval.

In one embodiment the base is formed as a square e.g. with the dimensions 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 11 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 13 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, 15 cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

In one embodiment the bottom is formed as a square e.g. with the dimensions of between 1 cm² to 500 cm², such as 1 cm² to 5 cm², for example 5 cm² to 10 cm², such as 10 cm² to 20 cm², for example 20 cm² to 30 cm², such as 30 cm² to 40 cm², for example 40 cm² to 50 cm², such as 50 cm² to 60 cm², for example 60 cm² to 70 cm², such as 70 cm² to 80 cm², for example 80 cm² to 90 cm², such as 90 cm² to 100 cm², for example 100 cm² to 110 cm², such as 110 cm² to 120 cm², for example 120 cm² to 130 cm², such as 130 cm² to 140 cm², for example 140 cm² to 150 cm², such as 150 cm² to 160 cm², for example 160 cm² to 170 cm², such as 170 cm² to 180 cm², for example 180 cm² to 190 cm², such as 190 cm² to 200 cm², for example 200 cm² to 210 cm², such as 210 cm² to 220 cm², for example 220 cm² to 230 cm², such as 230 cm² to 240 cm², for example 240 cm² to 250 cm², such as 250 cm² to 260 cm², for example 260 cm² to 270 cm², such as 270 cm² to 280 cm², for example 280 cm² to 290 cm², such as 290 cm² to 300 cm², for example 300 cm² to 320 cm², such as 320 cm² to 340 cm², for example 340 cm² to 360 cm², such as 360 cm² to 380 cm², for example 380 cm² to 400 cm², such as 400 cm² to 420 cm², for example 420 cm² to 440 cm², such as 440 cm² to 460 cm², for example 460 cm² to 480 cm², such as 480 cm² to 500 cm².

It follows that the dimension of the square base need not be a whole or counting number, but may also be any decimal number.

In one embodiment the base of the container is formed as a circle e.g. with a diameter in the range of from 1 cm to 40 cm, such as from 1 cm to 2 cm, for example from 2 cm to 4 cm, such as from 4 cm to 6 cm, for example from 6 cm to 8 cm, such as from 8 cm to 10 cm, for example from 10 cm to 12 cm, such as from 12 cm to 14 cm, for example from 14 cm to 16 cm, such as from 16 cm to 18 cm, for example from 18 cm to 20 cm, such as from 20 cm to 22 cm, for example from 22 cm to 24 cm, such as from 24 cm to 26 cm, for example from 26 cm to 28 cm, such as from 28 cm to 30 cm, for example from 30 cm to 32 cm, such as from 32 cm to 34 cm, for example from 34 cm to 36 cm, such as from 36 cm to 38 cm, for example from 38 cm to 40 cm.

In one embodiment the base of the container is formed as a circle e.g. with a diameter of 1 cm, 2, cm, 3, cm, 4, cm, 5, cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm or 40 cm.

In one embodiment the bottom is formed as a circle e.g. with the dimensions of between 1 cm² to 500 cm², such as 1 cm² to 5 cm², for example 5 cm² to 10 cm², such as 10 cm² to 20 cm², for example 20 cm² to 30 cm², such as 30 cm² to 40 cm², for example 40 cm² to 50 cm², such as 50 cm² to 60 cm², for example 60 cm² to 70 cm², such as 70 cm² to 80 cm², for example 80 cm² to 90 cm², such as 90 cm² to 100 cm², for example 100 cm² to 110 cm², such as 110 cm² to 120 cm², for example 120 cm² to 130 cm², such as 130 cm² to 140 cm², for example 140 cm² to 150 cm², such as 150 cm² to 160 cm², for example 160 cm² to 170 cm², such as 170 cm² to 180 cm², for example 180 cm² to 190 cm², such as 190 cm² to 200 cm², for example 200 cm² to 210 cm², such as 210 cm² to 220 cm², for example 220 cm² to 230 cm², such as 230 cm² to 240 cm², for example 240 cm² to 250 cm², such as 250 cm² to 260 cm², for example 260 cm² to 270 cm², such as 270 cm² to 280 cm², for example 280 cm² to 290 cm², such as 290 cm² to 300 cm², for example 300 cm² to 320 cm², such as 320 cm² to 340 cm², for example 340 cm² to 360 cm², such as 360 cm² to 380 cm², for example 380 cm² to 400 cm², such as 400 cm² to 420 cm², for example 420 cm² to 440 cm², such as 440 cm² to 460 cm², for example 460 cm² to 480 cm², such as 480 cm² to 500 cm².

It follows that the dimension of the circular base need not be a whole or counting number, but may also be any decimal number.

The base of the container can comprise an extended base portion at on or more sides. In one embodiment the extended base portion is placed at the same side as the handle of the container. The handle and extended base portion can be casted or moulded in one or more pieces.

The lid of the container can have any shape such as a square, rectangle, triangle, circle, or oval.

In one embodiment the lid of the container is formed as a square e.g. with the dimensions 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×9 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 1 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 3 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

In one embodiment the lid is formed as a square e.g. with the dimensions of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 $cm^2$, for example 260 $cm^2$ to 270 $cm^2$, such as 270 $cm^2$ to 280 $cm^2$, for example 280 $cm^2$ to 290 $cm^2$, such as 290 $cm^2$ to 300 $cm^2$, for example 300 $cm^2$ to 320 $cm^2$, such as 320 $cm^2$ to 340 $cm^2$, for example 340 $cm^2$ to 360 $cm^2$, such as 360 $cm^2$ to 380 $cm^2$, for example 380 $cm^2$ to 400 $cm^2$, such as 400 $cm^2$ to 420 $cm^2$, for example 420 $cm^2$ to 440 $cm^2$, such as 440 $cm^2$ to 460 $cm^2$, for example 460 $cm^2$ to 480 $cm^2$, such as 480 $cm^2$ to 500 $cm^2$.

It follows that the dimension of the square lid need not be a whole or counting number, but may also be any decimal number.

In one embodiment the lid of the container is formed as a circle e.g. with a diameter in the range of from 1 cm to 40 cm, such as from 1 cm to 2 cm, for example from 2 cm to 4 cm, such as from 4 cm to 6 cm, for example from 6 cm to 8 cm, such as from 8 cm to 10 cm, for example from 10 cm to 12 cm, such as from 12 cm to 14 cm, for example from 14 cm to 16 cm, such as from 16 cm to 18 cm, for example from 18 cm to 20 cm, such as from 20 cm to 22 cm, for example from 22 cm to 24 cm, such as from 24 cm to 26 cm, for example from 26 cm to 28 cm, such as from 28 cm to 30 cm, for example from 30 cm to 32 cm, such as from 32 cm to 34 cm, for example from 34 cm to 36 cm, such as from 36 cm to 38 cm, for example from 38 cm to 40 cm.

In one embodiment the lid of the container is formed as a circle e.g. with a diameter of 1 cm, 2, cm, 3, cm, 4, cm, 5, cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm or 40 cm.

In one embodiment the lid is formed as a circle e.g. with the dimensions of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 $cm^2$, for example 260 $cm^2$ to 270 $cm^2$, such as 270 $cm^2$ to 280 $cm^2$, for example 280 $cm^2$ to 290 $cm^2$, such as 290 $cm^2$ to 300 $cm^2$, for example 300 $cm^2$ to 320 $cm^2$, such as 320 $cm^2$ to 340 $cm^2$, for example 340 $cm^2$ to 360 $cm^2$, such as 360 $cm^2$ to 380 $cm^2$, for example 380 $cm^2$ to 400 $cm^2$, such as 400 $cm^2$ to 420 $cm^2$, for example 420 $cm^2$ to 440 $cm^2$, such as 440 $cm^2$ to 460 $cm^2$, for example 460 $cm^2$ to 480 $cm^2$, such as 480 $cm^2$ to 500 $cm^2$.

It follows that the dimension of the circular lid need not be a whole or counting number, but may also be any decimal number.

The lid of the container can comprise one or more flaps to facilitate opening of the lid of the container, i.e. for easier handling of the lid when opening the container. The flap(s) can have any shape and size that would facilitate opening of the lid.

The container can further comprise one or more handles such as 1, 2, 3, 4, 5, 6, 7, 8, 9, 10 or more than 10 handles. The one or more handle(s) of the container can have any size and shape that provide easy handling of the container.

The one or more handles may be associated with the bottom of the container, the one or more sidewall(s) of the container or the base of the container.

The one or more handles, the one or more sidewall(s) or the base of the container according to the present invention may comprise one or more recesses or indentations for improved grip.

In one embodiment the container and/or the lid and/or the base and/or the bottom and/or the sidewall(s) is made of plastic such as any suitable plastic known in the art such as medical grade plastic and/or a transparent plastic and/or a non-transparent plastic. The plastic can be a flexible or rigid plastic material with a thickness and strength properties which allow the container to be opened by simply tearing the lid from the sealing surface for the lid. Alternatively, a thicker or stronger material may be utilized and the container may be opened by cutting with scissors or otherwise puncturing the container.

In one embodiment the container and/or the lid and/or the base and/or the bottom and/or the sidewall(s) is made of or comprises plastic such as one or more types of flexible plastic and/or one or more types of transparent plastic and/or non-transparent plastic and/or biodegradable plastic.

In one embodiment the container and/or the lid and/or the base and/or the bottom and/or the sidewall(s) is made of or comprises one or more materials selected from the group consisting of TECAFORM™ AH MT, CELCON® (Acetal Copolymer), RADEL®, TECASON™ P XRO (Polyphenylsulfone, also Radio Opacifer), UDEL® Polysulfone, ULTEM® (Polyetherimide), UHMW Lot Controlled, LENNITE® UHME-PE, TECANAT™ PC (USP Class VI Polycarbonate Rod), ZELUX® GS (Gamma Stabilized Polycarbonate), ACRYLIC (Medical grade Cast Acrylic), TECAMAX™ SRP (Ultra High Performance Thermoplastic), TECAPRO™ MT (Polypropylene Heat Stabilized), TECAPEEK™ MT (USP Class VI compliant), TECAFORM™ AH SAN, ANTIMICROBIAL filled plastics, TECASON™ P XRO (Biocompatible Radio Opacifer PPSU), TECAPEEK™ CLASSIX, POLYSULFONE® (Medical grade), TECANYL™ (Medical grade Noryl®), TYGON® (Medical grade Tubing), TEXOLON™ Medical Grade PTFE (USP CLASS VI), PROPYLUX HS and HS2, ABS (FDA Approved Medical Grades), TOPAS® (Medical grade), and other Medical Grade/FDA approved plastic products.

In one embodiment the container and/or the lid and/or the base and/or the bottom and/or the sidewall(s) is made of or comprises one or more types of medical grade polymer such as plastic.

Plastic is the general common term for a wide range of synthetic or semisynthetic organic solid materials suitable for the manufacture of industrial products. Plastics are typically polymers of high molecular weight, and may contain other substances to improve performance and/or reduce costs. Types of plastic includes Rubber, Cellulose-based plastics, Bakelite, Polystyrene, PVC, Nylon, Synthetic rubber. Plastics can be classified by their chemical structure. Some important groups in these classifications are the acrylics, polyesters, silicones, polyurethanes, and halogenated plastics. Plastics can also be classified by the chemical process used in their synthesis, e.g. as condensation, poly-addition, cross-linking. Other classifications are based on qualities that are relevant for manufacturing or product design. Examples of such classes are the thermoplastic and thermoset, elastomer, structural, biodegradable, electrically conductive. Plastics can also be ranked by various physical properties, such as density, tensile strength, glass transition temperature, resistance to various chemical products, etc. In one embodiment the container and/or the lid and/or the base is made of or comprises one or more types of plastic mention herein above or below.

Common thermoplastics range from 20,000 to 500,000 in molecular mass, while thermosets are assumed to have infinite molecular weight. In one embodiment the container and/or the lid and/or the base is made of or comprises one or more types of polymers and/or plastics with a molecular weight in the range from 10,000 to 1,000,000 Da, such as from 10,000 to 50,000 Da, for example 50,000 to 100,000 Da, such as from 100,000 to 150,000 Da, for example 150,000 to 200,000 Da, such as from 200,000 to 250,000 Da, for example 250,000 to 300,000 Da, such as from 300,000 to 350,000 Da, for example 350,000 to 400,000 Da, such as from 400,000 to 450,000 Da, for example 450,000 to 500,000 Da, such as from 500,000 to 550,000 Da, for example 550,000 to 600,000 Da, such as from 600,000 to 650,000 Da, for example 650,000 to 700,000 Da, such as from 700,000 to 750,000 Da, for example 750,000 to 800,000 Da, such as from 800,000 to 850,000 Da, for example 850,000 to 900,000 Da, such as from 900,000 to 950,000 Da, for example 950,000 to 1,000,000 Da.

These chains are made up of many repeating molecular units, known as "repeat units", derived from "monomers"; each polymer chain will have several thousand repeat units. The vast majority of plastics are composed of polymers of carbon and hydrogen alone or with oxygen, nitrogen, chlorine, or sulfur in the backbone.

In one embodiment the container and/or the lid and/or the base and/or the bottom and/or the sidewall(s) is made of or comprises one or more materials selected from the group consisting of Biodegradable plastic, Bioplastics obtained from biomass e.g. from pea starch or from biopetroleum, Polypropylene (PP), Polystyrene (PS), High impact polystyrene (HIPS), Acrylonitrile butadiene styrene (ABS), Polyethylene terephthalate (PET), Amorphous PET (APET), Polyester (PES), Fibers, textiles, Polyamides (PA), (Nylons), Poly(vinyl chloride) (PVC), Polyurethanes (PU), Polycarbonate (PC), Polyvinylidene chloride (PVDC) (Saran), Polyvinylidene Fluoride (PVDF), Polyethylene (PE), Polymethyl methacrylate (PMMA), Polytetrafluoroethylene (PTFE) (trade name Teflon), Fluorinated ethylene propylene (FEP), Polyetheretherketone (PEEK) (Polyetherketone), Polyetherimide (PEI) (Ultem), Phenolics (PF), (phenol formaldehydes), Perfluoroalkoxy (PFA), Poly(methyl methacrylate) (PMMA), Urea-formaldehyde (UF), Melamine formaldehyde (MF), Polylactic acid and Plastarch material or any mixture thereof.

The container and/or the lid and/or the base and/or the bottom and/or the sidewall(s) can be made of any suitable material such as plastic, rubber or glass.

The lid and/or the base and/or the bottom and/or the sidewall(s) can be plane, curved, arched upwards or downwards or any other shape.

The sealing surface for the lid can have any size or shape that facilitates sealing of the lid to and/or removal of the lid from the container.

In one embodiment the container comprises a reclosable lid such as a lid that can be resealed by e.g. the glue on the sealing surface for the lid or by a screw, click or snap mechanism. In another embodiment the container comprises a lid that can not be reclosed after opening of the lid.

The container can comprise any type of lid such as a sealing foil, a screw top, a screw cap, a snap cap, a lid glued to or by any other means fastened to the sealing surface of the container.

The sealing surface for the lid may be comprised in the upper portion of the one or more sidewall(s) or the base.

In one particular embodiment, the lid of the container is peelable (a peel-off lid). It follows that the lid may be made of or comprise a peelable material, such as a polyethylene (PE)-based material, a thermoplastic elastomer, a thermoset elastomer, Tyvek, Teslin, paper, foil (plastic foil or metal foil such as alufoil) or any other peelable material.

The lid may be reinforced with a coating, such as a synthetic coating selected from the group consisting of Perfluorooctanoic acid (PFOA), hydrocarbon based petrochemicals, zein or others.

For the purpose of the present invention, peelability will be defined as the ability to separate two materials in the course of opening a package without compromising the integrity of either of the two. In medical packaging, a peelable system provides a controlled, reliable, aseptic means of opening a package and presenting a device. The sealant layer of one or both webs is responsible for bonding the two materials together, which is accomplished via the application of heat, pressure or glue.

The force required to pull a seal apart is called its seal strength. Seal strength in a peelable system is controlled by the composition of either the heat seal coating or the sealant layer. Typical medical packages have a seal strength of 1-3 lb per in. of seal width, as measured via a standard test such as ASTM F88-94.

Peelable films are generally based on polybutylene-polyolefin technology first pioneered by Shell in the mid-1970s. The incompatibility of the two polymers inhibits the sealant layer from forming a complete bond by reducing the number of available bonding sites. These peelable systems provide seal transfer by internal cohesive splitting between the polyethylene and polybutylene layers because of poor interfacial adhesion, which reduces internal bond strength. This is in contrast to heat-sealed coated (HSC) materials, which undergo the cohesive failure that occurs when the internal strength of the adhesive is less than the strength of the bonds between the adhesive and sealed materials.

Peelable films are generally limited to similar-type materials that are primarily polyethylene (PE) based, and tend to have a narrower sealing window and/or a steeper peel-strength slope compared with HSC materials. However, new peelable technologies are being introduced that can provide increased sealing windows with smaller variations in peel strength over their useful range. These new peelable resin systems are being developed to seal to a wide variety of materials, including but not limited to PETG, HIPS, and PVC.

Thermoplastic elastomers (TPE), sometimes referred to as thermoplastic rubbers, are a class of copolymers or a physical mix of polymers (usually a plastic and a rubber) which consist of materials with both thermoplastic and elastomeric properties. The principal difference between thermoset elastomers and thermoplastic elastomers is the type of cross-linking bond in their structures. There are six generic classes of TPEs generally considered to exist commercially. They are styrenic block copolymers, polyolefin blends, elastomeric alloys, thermoplastic polyurethanes, thermoplastic copolyester and thermoplastic polyamides.

Paper is thin material mainly used for writing upon, printing upon or packaging. It is produced by pressing together moist fibers, typically cellulose pulp derived from wood, rags or grasses, and drying them into flexible sheets. Synthetic coatings (such as PFOA), hydrocarbon based petrochemicals, and zein (corn protein) may be used as a coating for paper. Also, synthetics such as Tyvek (a brand of flashspun high-density polyethylene/olefin fibers) and Teslin have been introduced for medical packaging as a more durable material than paper.

The container described in the present invention has the following advantages:
  It is very stable—even on uneven surfaces (allows stabile placement on all possible positions: on sterile field, on mayo stand, on tray of instruments or on the chest of the patient) minimizing the risk of spilling
  It eliminates any need for other mixing bowls/specimen cups
  It has superior ergonomic handling making handling and presentation easier and faster from all directions
  The inner tray notches make it easy to grasp the sponge and thus not destroying the structure of the matrix material
  Embossed brand name in tray reduces need to spend additional time on writing labels for sterile field documentation
  Dwelling for easier handling of the sponge
  Bevelled edges to ensure that e.g. the saline volume stays inside the tray thus not dripping onto the sterile field
  Bevelled edges or other indication as a guiding tool for maximum amount of moisture to add In one embodiment addition of liquid to the container results in that the liquid/moisture is evenly distributed throughout the matrix material. The even distribution of liquid/moisture can be obtained by manual massage of the matrix material (e.g. with the fingers).

In one embodiment the liquid added to the container does not cover the matrix material before and/or after the absorption of liquid into the matrix material. In one embodiment the liquid added to the matrix material in the container reaches from ½-⅔ of the height from the bottom of the inner tray to the mark for maximum filling of the tray before absorption of liquid into the matrix material.

In another embodiment the liquid added to the matrix material in the container reaches from 10% to 100% of the height from the bottom of the inner tray to the mark for maximum filling of the tray before absorption of liquid into the matrix material, such as from 10% to 12%, for example from 12% to 14%, such as from 14% to 16%, for example from 16% to 18%, such as from 18% to 20%, for example from 20% to 22%, such as from 22% to 24%, for example from 24% to 26%, such as from 26% to 28%, for example from 28% to 30%, such as from 30% to 32%, for example from 32% to 34%, such as from 34% to 36%, for example from 36% to 38%, such as from 38% to 40%, for example from 40% to 42%, such as from 42% to 44%, for example from 44% to 46%, such as from 46% to 48%, for example from 48% to 50%, such as from 50% to 52%, for example from 52% to 54%, such as from 54% to 56%, for example from 56% to 58%, such as from 58% to 60%, for example from 60% to 62%, such as from 62% to 64%, for example from 64% to 66%, such as from 66% to 68%, for example from 68% to 70%, such as from 70% to 72%, for example from 72% to 74%, such as from 74% to 76%, for example from 76% to 78%, such as from 78% to 80%, for example from 80% to 82%, such as from 82% to 84%, for example from 84% to 86%, such as from 86% to 88%, for example from 88% to 90%, such as from 90% to 92%, for example from 92% to 94%, such as from 94% to 96%, for example from 96% to 98%, such as from 98% to 100% of the height from the bottom of the inner tray to the mark for maximum filling.

In another embodiment the liquid added to the matrix material in the container reaches from 10% to 100% of the height from the bottom of the inner tray to the mark for maximum filling of the tray after absorption of liquid into the matrix material, such as from 10% to 12%, for example from 12% to 14%, such as from 14% to 16%, for example from 16% to 18%, such as from 18% to 20%, for example from 20% to 22%, such as from 22% to 24%, for example from 24% to 26%, such as from 26% to 28%, for example from 28% to 30%, such as from 30% to 32%, for example from 32% to 34%, such as from 34% to 36%, for example from 36% to 38%, such as from 38% to 40%, for example from 40% to 42%, such as from 42% to 44%, for example from 44% to 46%, such as from 46% to 48%, for example from 48% to 50%, such as from 50% to 52%, for example from 52% to 54%, such as from 54% to 56%, for example from 56% to 58%, such as from 58% to 60%, for example from 60% to 62%, such as from 62% to 64%, for example from 64% to 66%, such as from 66% to 68%, for example from 68% to 70%, such as from 70% to 72%, for example from 72% to 74%, such as from 74% to 76%, for example from 76% to 78%, such as from 78% to 80%, for example from 80% to 82%, such as from 82% to 84%, for example from 84% to 86%, such as from 86% to 88%, for example from 88% to 90%, such as from 90% to 92%, for example from 92% to 94%, such as from 94% to 96%, for example from 96% to 98%, such as from 98% to 100% of the height from the bottom of the inner tray to the mark for maximum filling.

The mark for maximum filling of the inner tray helps to ensure that too much liquid can not be added to the matrix material in the container. If too much liquid has been added to the matrix material in the container, the liquid that remains in the tray after absorption of liquid into the matrix material will comprise the pharmaceutical composition from the matrix material (e.g. Thrombin).

One advantage of using a matrix material with added liquid is that the matrix material becomes more mouldable and softer than a dry matrix material.

In one embodiment the pharmaceutical composition such as Thrombin is only applied e.g. by printing on one or more of the surfaces of the matrix material. In another embodiment the pharmaceutical composition such as Thrombin is applied throughout the matrix materiel. However, after liquid has been added to the matrix material and after absorption of liquid into the matrix material has occurred the pharmaceutical composition such as Thrombin will often be distributed throughout the matrix material.

Figure 4:
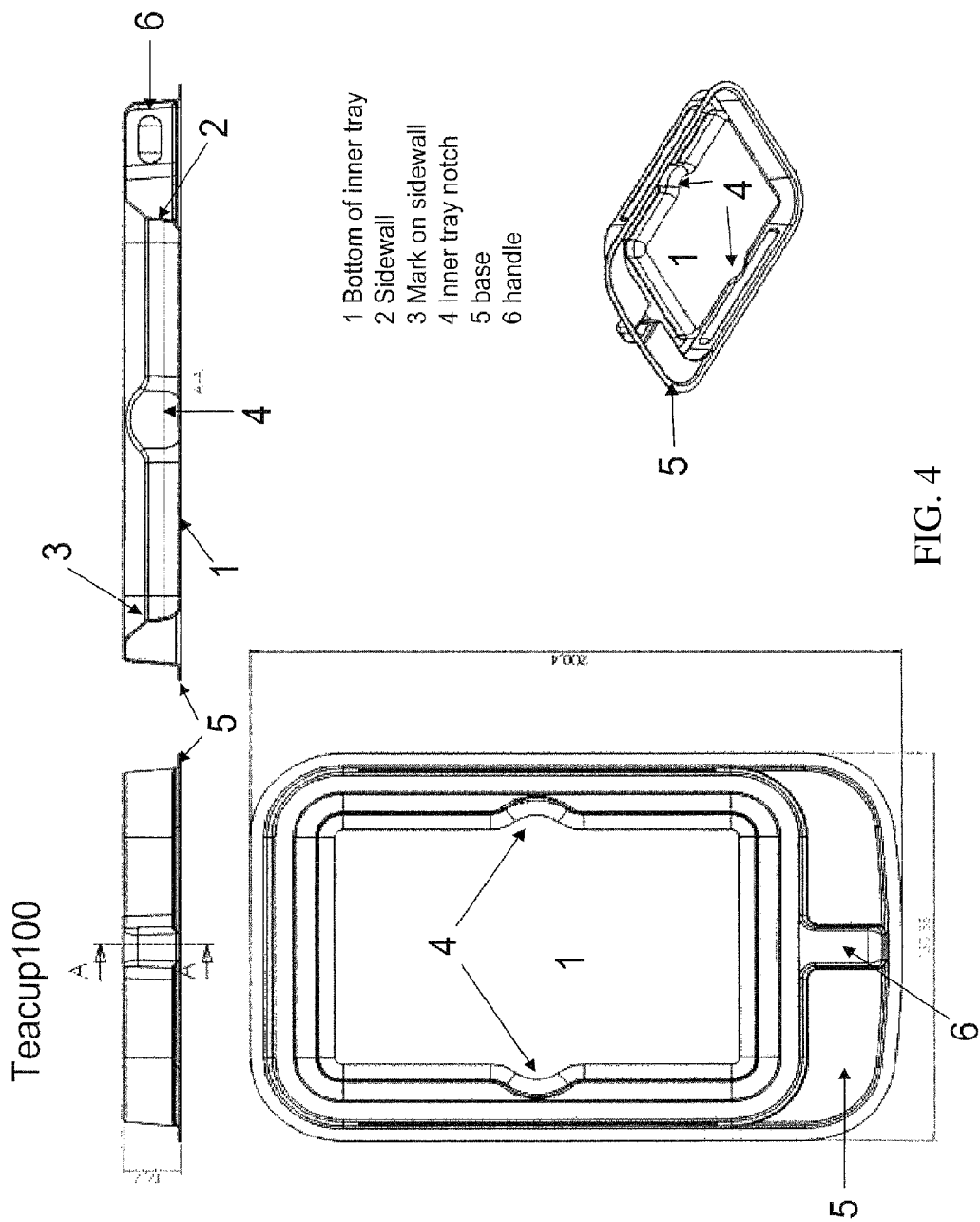
FIG. 4 illustrates a preferred container for a matrix material termed Teacup100. The bottom of the inner tray is marked (1), the sidewall is marked (2), the mark on the sidewall is marked (3), the inner tray notch is marked (4), the base is marked (5), and the handle is marked (6). The length (200.4 mm) and width (130.35 mm) of the base is indicated.

In one preferred embodiment the container with the matrix material according to the present invention has the shape and size shown in FIG. 4—termed Teacup100. Teacup100 is made for addition of a volume of liquid of maximum 20 mL.

Figure 5:
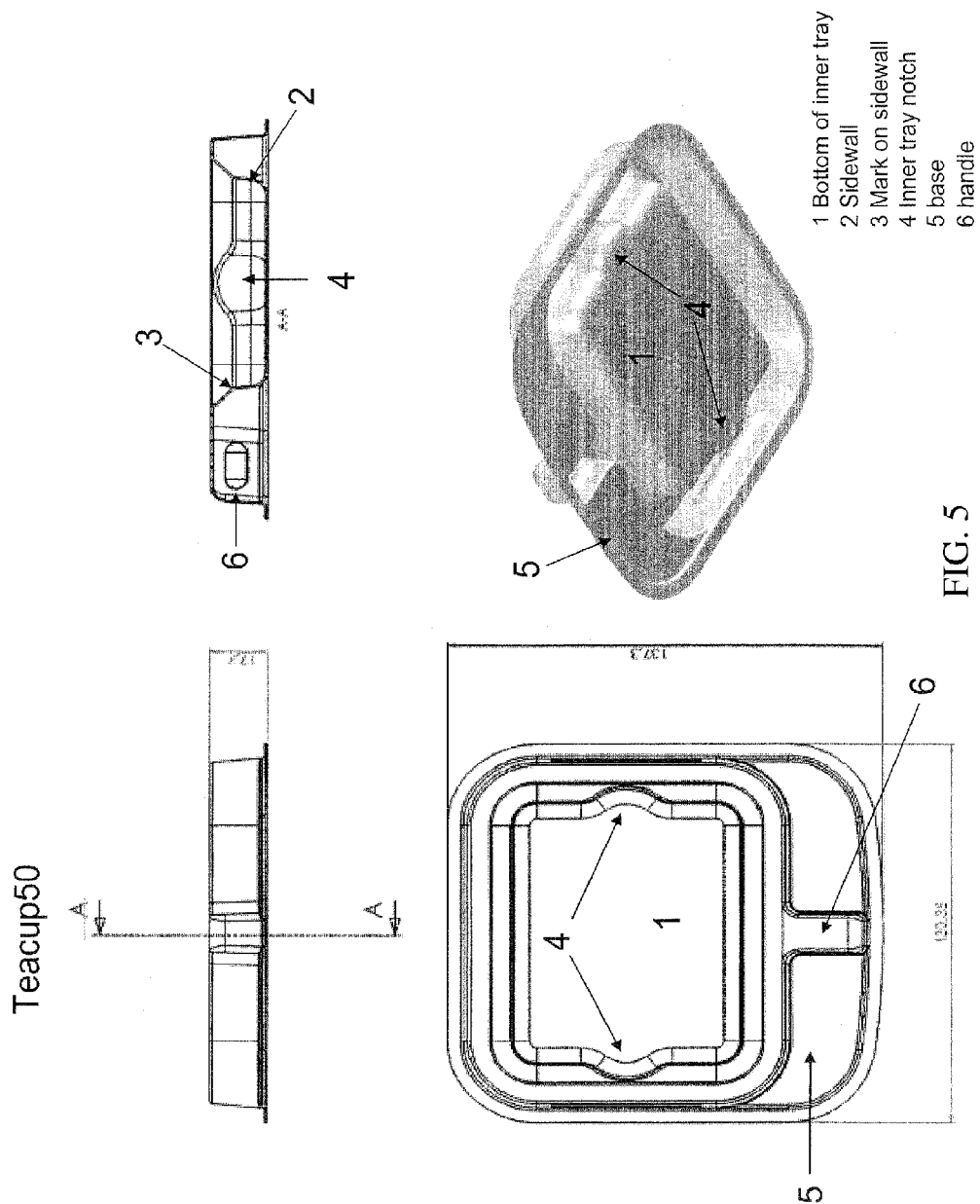
FIG. 5 illustrates a preferred container for a matrix material termed Teacup50. The bottom of the inner tray is marked (1), the sidewall is marked (2), the mark on the sidewall is marked (3), the inner tray notch is marked (4), the base is marked (5), and the handle is marked (6). The length (137.3 mm) and width (130.35 mm) of the base is indicated.

In one preferred embodiment the container with the matrix material according to the present invention has the shape and size shown in FIG. 5—termed Teacup50. Teacup50 is made for addition of a volume of liquid of maximum 10 mL.

Figure 6:
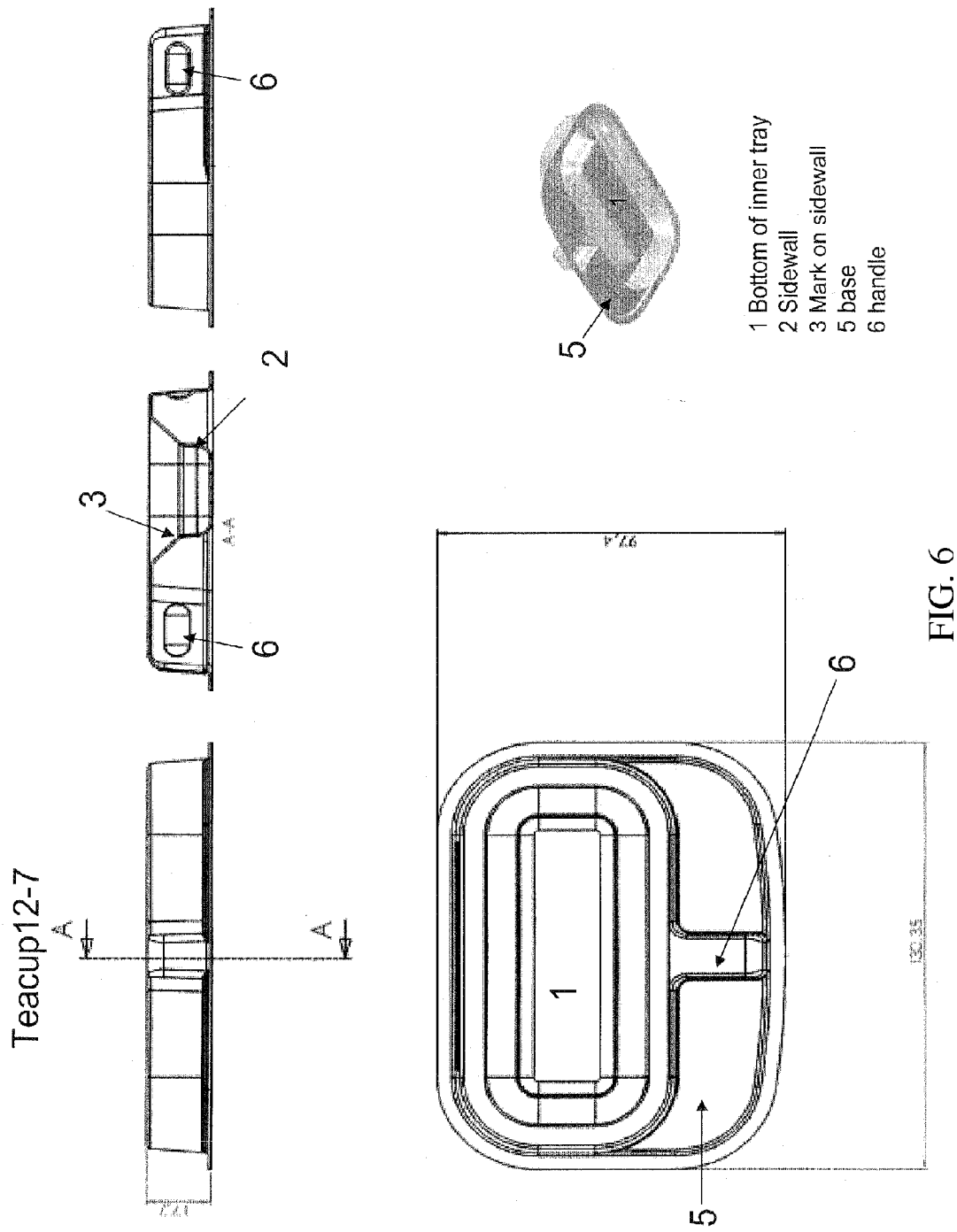
FIG. 6 illustrates a preferred container for a matrix material termed Teacup12-7. The bottom of the inner tray is marked (1), the sidewall is marked (2), the mark on the sidewall is marked (3), the inner tray notch is marked (4), the base is marked (5), and the handle is marked (6). The length (97.4 mm) and width (130.35 mm) of the base is indicated.

In one preferred embodiment the container with the matrix material according to the present invention has the shape and size shown in FIG. 6—termed Teacup12-7. Teacup12-7 is made for addition of a volume of liquid of maximum 2 mL.

The liquid to be added to the container used for wetting the matrix material may be selected from the group consisting of an aqueous solution; a saline solution such as NaCl 0.9% (normal saline); medical-grade water; water for injection; water for irrigation; saline for injection; saline for irrigation; an antibiotic solution comprising an antiobiotic selected from those listed in Table 5 above including penicillins, cephalosporins, tetracyclines, ampiciflin, aureothicin, bacitracin, chloramphenicol, cycloserine, erythromycin, gentamicin, gramacidins, kanamycins, neomycins, streptomycins, tobramycin, and vancomycin; an anaesthetic solution comprising a local anaesthetic selected from Lidocaine/prilocalne (EMLA), Articaine, Bupivacaine, Carticaine, Cinchocaine/Dibucaine, Etidocaine, Levobupivacaine, Lidocaine/Lignocaine, Mepivacaine, Piperocaine, Prilocalne, Ropivacaine, Trimecaine, Benzocaine, Chloroprocaine, Cocaine, Cyclomethycaine, Dimethocaine/Larocaine, Propoxycaine, Procaine/Novocaine, Proparacaine, Tetracaine/Amethocaine; a solution comprising adrenaline (epinephrine), and others.

A Kit of Parts

The present invention also relates to a kit of parts and use of said kit of parts. In one embodiment the kit of parts comprises a matrix material as described elsewhere herein such as a matrix material printed with one or more pharmaceutical compositions or a matrix material comprising thrombin. In another embodiment the kit of parts comprises the container for storage of a matrix material as described herein above.

The kit of parts can be used to apply a matrix material e.g. a matrix material comprising thrombin such as a matrix material with thrombin printed onto one or more surfaces of the matrix material onto an injured portion of a mammalian body such a wound on a human being.

The kit of parts can be used to treat a wound, to accelerate or promote hemostasis or accelerate or promote wound healing in an individual in need thereof. The kit of parts comprising the container and a matrix material comprising a pharmaceutical composition such as thrombin provides a sterile storage of said matrix material. The appropriate medical personnel decide which pharmaceutical composition is appropriate for the wound in question.

The container is opened either completely or partly by removement of the lid e.g. by cutting, peeling or tearing of the lid from the lid sealing surface. The matrix material can then optionally be removed and cut into pieces of relevant size(s) and be placed in the container again. A predetermined volume of liquid/moisture such as water or saline is added to the container e.g. up to the mark on the one or more sidewalls. After absorption of liquid into the matrix material, the matrix material is placed on the wound. Alternatively, the matrix material can be cut into pieces of relevant sizes after liquid has been added to the matrix material.

Combination Therapy

The fluid or liquid composition according to the present invention may contain substances selected form the group consisting of hemostatic or anti-fibrinolytic agents, wound healing agents, adhesive agents and surfactants, as disclosed above.

In a preferred embodiment of the invention, the pharmaceutical composition according to the present invention may comprise more than one agent, selected from tables 1 to 4.

Thus, the composition may comprise more than 1, such as 2, for example 3, such as 4, for example 5, such as 6, for example 7, such as 8 different agents selected from tables 1 to 4. Table 1 comprises examples of hemostatic or anti-fibrinolytic agents; table 2 comprises examples of wound healing agents; table 3 comprises examples of adhesive agents and table 4 comprises examples of surfactants.

In one embodiment, the composition comprises at least 1, such as 2, for example 3, such as 4, for example 5, such as 6, for example 7, such as 8 different agents selected from table 1, further comprising at least 1, such as 2, for example 3, such as 4, for example 5, such as 6, for example 7, such as 8 different agents selected from table 2.

In another embodiment, the composition comprises at least 1, such as 2, for example 3, such as 4, for example 5, such as 6, for example 7, such as 8 different agents selected from table 1, further comprising at least 1, such as 2, for example 3, such as 4, for example 5, such as 6, for example 7, such as 8 different agents selected from table 3.

In yet another embodiment, the composition comprises at least 1, such as 2, for example 3, such as 4, for example 5, such as 6, for example 7, such as 8 different agents selected from table 1, further comprising at least 1, such as 2, for example 3, such as 4, for example 5, such as 6, for example 7, such as 8 different agents selected from table 4.

In one embodiment, the composition comprises at least 1, such as 2, for example 3, such as 4, for example 5, such as 6, for example 7, such as 8 different agents selected from table 2, further comprising at least 1, such as 2, for example 3, such as 4, for example 5, such as 6, for example 7, such as 8 different agents selected from table 3.

In another embodiment, the composition comprises at least 1, such as 2, for example 3, such as 4, for example 5, such as 6, for example 7, such as 8 different agents selected from table 2, further comprising at least 1, such as 2, for example 3, such as 4, for example 5, such as 6, for example 7, such as 8 different agents selected from table 4.

In one embodiment, the composition comprises at least 1, such as 2, for example 3, such as 4, for example 5, such as 6, for example 7, such as 8 different agents selected from table 1, further comprising at least 1, such as 2, for example 3, such as 4, for example 5, such as 6, for example 7, such as 8 different agents selected from table 2, still further comprising at least 1, such as 2, for example 3, such as 4, for example 5, such as 6, for example 7, such as 8 different agents selected from table 3.

In another embodiment, the composition comprises at least 1, such as 2, for example 3, such as 4, for example 5, such as 6, for example 7, such as 8 different agents selected from table 1, further comprising at least 1, such as 2, for example 3, such as 4, for example 5, such as 6, for example 7, such as 8 different agents selected from table 2, still further comprising at least 1, such as 2, for example 3, such as 4, for example 5, such as 6, for example 7, such as 8 different agents selected from table 4.

In yet another embodiment, the composition comprises at least 1, such as 2, for example 3, such as 4, for example 5, such as 6, for example 7, such as 8 different agents selected from table 1, further comprising at least 1, such as 2, for example 3, such as 4, for example 5, such as 6, for example 7, such as 8 different agents selected from table 2, further comprising at least 1, such as 2, for example 3, such as 4, for example 5, such as 6, for example 7, such as 8 different agents selected from table 3, and also further comprising at least 1, such as 2, for example 3, such as 4, for example 5, such as 6, for example 7, such as 8 different agents selected from table 4.

According to the preferred embodiments cited here above, agents may be administered onto the matrix of the device of the invention via inkjet printing, by printing a pharmaceutical composition containing agents from either 1, 2, 3 or 4 classes of agents, as cited in tables 1 to 4.

EXAMPLES

The invention will be further described in the following examples, which do not limit the scope of the invention described in the claims.

Example 1

Determination of the Reconformation Rate of Gelatin-Based Sponges

The purpose of this method is to determine the reconformation rate of a gelatin-based sponge. The method comprises soaking the sponge, and subsequently squeezing it. The appearance of the native shape of the sponge is monitored as a function of time, and the time that lapses until the sponge has reached its native shape is termed the reconformation time.

The method comprises the following steps:
1. Cut a suitable piece of absorbable gelatin-based sponge, approximately 1×1 cm, and thoroughly soak it in water at room temperature.
2. Remove the sample from the water, and squeeze it until it is flat and no more air bubbles or drops of water can be pressed out.
3. Place the sample in a beaker filled with water at room temperature and measure the time (in seconds) until the sample has gained its former size and shape.
4. Repeat the test twice and report the result as the average of three determinations.

Example 2

This gives an example of a possible print medium or composition for printing onto a surface of a matrix. In this example, the bioactive agent comprised in the pharmaceutical composition is thrombin, and the matrix is a collagen-based sponge.

Print media: sterile MQ-water, sterile saline or another appropriate sterile aqueous solvent is adjusted with a suitable biocompatible viscosity enhancer, such as gelatin, to 10 cps. Thrombin is reconstituted to a suitable concentration in the media. This concentration should be adjusted so that the final concentration of thrombin yields 30 IU/cm$^2$ on the surface of the matrix to be imprinted. The pH is kept within physiological ranges, and the temperature is held at ambient temperature (around 25° C.). If desired, a suitable surfactant may be added to the medium.

The matrix chosen is in one embodiment a gelatin-based sponge, such as the commercially available Spongostan®, Surgifoam® or Surgiflo® (Ferrosan A/S). The sponge may be cut into a suitable form and shape.

The accuracy of the printing head and the control of the printing head must be very high, since this controls the amount that is printed and thus the dosage of thrombin on the fabricated sponge. This is important even at high rates of production (such as 60 sponges per minute).

Example 3

Hemostatic Effect for a Matrix Printed with Thrombin

A pig model has been used to test the effect on hemostasis of different amounts of thrombin printed onto a matrix (Surgifoam™; Johnson and Jonhson). Wet and dry application of the thrombin matrix is compared. For dry applications thrombin was when indicated in the diagram printed onto the matrix for low concentrations of thrombin (20, 10 or 5 IU/cm$^2$). A matrix printed with thrombin used for dry applications has a surprisingly effective hemostatic effect (measured in time for hemostasis) at low concentrations of thrombin (see FIG. 8).

Figure 8:
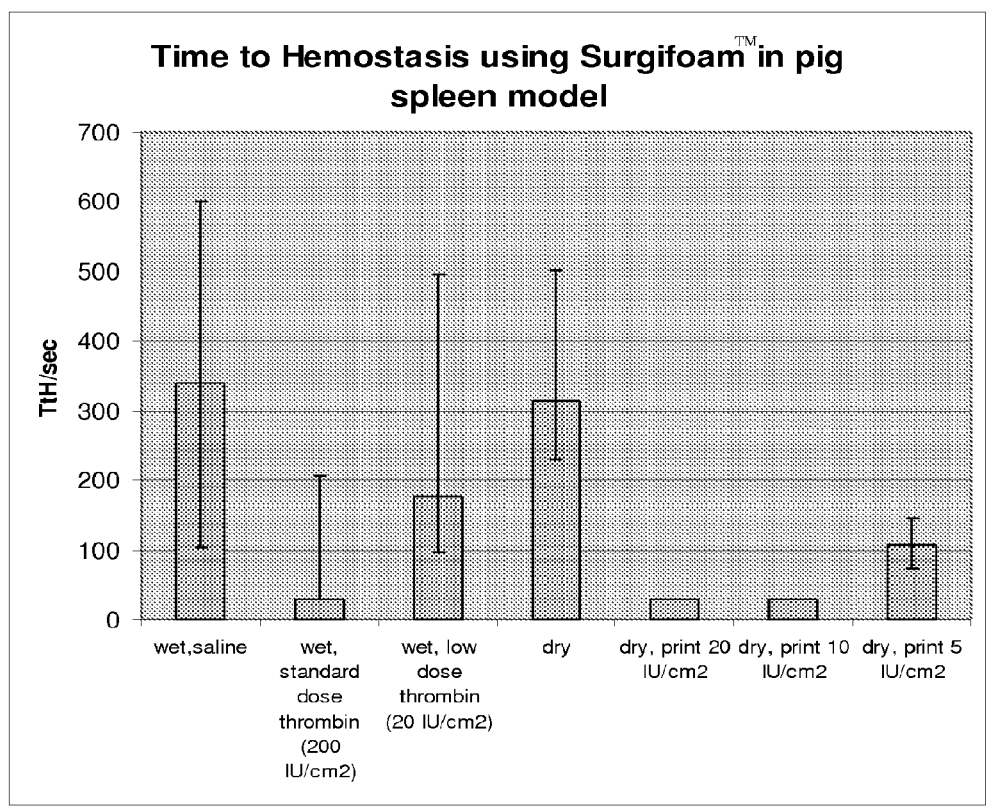
FIG. 8 shows the time to hemostasis using Surgiform™ in pig spleen model. The efficacy of Surgifoam™ with thrombin applied by ink-jet printing was examined in a pig spleen model and compared to the standard wet use of Surgifoam™+thrombin. Results are medians+/−max/min. The Surgifoam™ was either applied wet or dry. For the wet application 4 cm² Surgifoam™ was moistened in either 800 ul Saline, 800 ul standard thrombin solution at 1000 IU/ml (~200 IU/cm$^2$) or 800 ul low thrombin solution at 100 IU/ml (~20 IU/cm$^2$). Standard use of thrombin with gelatin sponge today is 1000 IU/ml. For the dry application Surgifoam™ alone or printed with 20, 10 or 5 IU/cm$^2$ was applied on the spleen wound. Each product was tested 3 or 4 times.

FIG. 8 shows that dry application of 20 IU/cm$^2$ printed thrombin results in faster hemostasis than wet application of the same amount of thrombin. Furthermore, dry application of 10 IU/cm$^2$ printed thrombin results in similar or even faster hemostatis than wet application of 200 IU/cm$^2$ thrombin.

The present invention relates in one embodiment to a matrix such as Surgifoam™ printed with an amount of thrombin resulting in a time of hemostasis after dry application (measured by the assay described above) below 200 seconds, such as below 190 seconds, for example below 180 seconds, such as below 170 seconds, for example below 160 seconds, such as below 150 seconds, for example below 140 seconds, such as below 130 seconds, for example below 120 seconds, such as below 110 seconds, for example below 100 seconds, such as below 90 seconds, for example below 80 seconds, such as below 70 seconds, for example below 60 seconds, such as below 50 seconds, for example below 48 seconds, such as below 46 seconds, for example below 44 seconds, such as below 42 seconds, for example below 40 seconds, such as below 38 seconds, for example below 36 seconds, such as below 34 seconds, for example below 32 seconds, such as below 30 seconds, for example below 28 seconds, such as below 26 seconds, for example below 24 seconds, such as below 22 seconds, for example below 20 seconds, such as below 18 seconds, for example below 16 seconds, such as below 14 seconds, for example below 12 seconds, such as below 10 seconds, for example below 8 seconds, such as below 6 seconds, for example below 4 seconds, such as below 2 seconds, for example below 1 second.

Example 4

Use of a Container with a Matrix Material in an Operating Room

This example describes one example of use of a container with a matrix material in an operating room.

A person such as a scrub tech/RN places the container/tray on a sterile field, uses the handle to hold the container/tray while removing the lid e.g. a tyvek lid. In one embodiment everything on the sterile field is labelled to minimize any mistakes. The person such as the scrub tech/RN checks that the product name has been embossed on the container/tray thus giving confidence that no additional labeling needs to be done. The mixing preparation on the lid serves as a guiding to remind the person how to mix the product correctly. The scrub tech/RN uses the notches (inside dwellings) to take up the matrix material such as a sponge from the container/tray with the fingers, tweezers, forceps or an alternative device. The scrub tech/RN cuts the matrix material such as a sponge into the container/tray omitting the need for a bowl. When matrix material pieces have been cut, the scrub tech/RN applies the appropriate amount of liquid, such as sodium chloride, such as sodium chloride 0.9%, on top of the matrix material/sponge pieces. The Scrub tech may use for example fingers or a pair of forceps to poke the liquid/sodium chloride/sodium chloride 0.9% into the matrix materials/sponge pieces. When this is done, the scrub tech/RN optionally uses the handle on the tray to place the tray until needed by e.g. the surgeon: the tray may e.g. be placed on the sterile field, back table (sterile), on the mayo stand, on the chest of the patient (e.g. on sterile cover). The scrub tech/RN may hold the handle when presenting the product to the surgeon and while the surgeon picks up the sponges that he wants from the tray. Alternatively, the tray may be placed on e.g. the mayo stand and the scrub tech/RN gives the surgeon individual matrix materials/sponge pieces on a pair forceps. If surgeon desires to use soaked e.g. saline soaked patties or cottonoids on top of the matrix material/sponge pieces for compression, these can be placed on the flat part of the tray.

Example 5

This example describes one example of printing a fluid, pharmaceutical composition with thrombin onto a matrix material; wherein the ratio of droplet volume, the distance between droplets deposited on the surface of the matrix material and the concentration of thrombin is fixed to achieve a uniform distribution pattern.

In this example, the bioactive agent comprised in the fluid or liquid composition is thrombin, and the matrix is a gelatin-based sponge.

Print media: sterile MQ-water, sterile saline or another appropriate sterile aqueous solvent is adjusted with a suitable biocompatible viscosity enhancer, such as gelatin, to 10 cps. Thrombin is reconstituted to a concentration of 8-10,000 IU/ml in the media. The pH is kept within physiological ranges, and the temperature is held at ambient temperature (around 25° C.). If desired, a suitable surfactant may be added to the medium.

A fluid or liquid composition comprising thrombin at a concentration of 8-10,000 IU/ml is filled in a reservoir connected to a print head, such as a Spectra® Galaxy Printhead 256/80 HM piezoelectric inkjet printhead. The distance between the printhead and the gelatin-sponge is adjusted to 2 mm.

Printing is initiated and droplets of essentially 80 µL in size are expelled from the 256 nozzles of the print head at a velocity of 8 m/sec, such that the distance between any two droplets is 254 microns. The jet straightness is 5 mrad (0.29°).

Items

1. A matrix material comprising a surface and a plurality of open and interconnected cells, wherein the surface of said matrix comprises at least one pharmaceutical composition printed onto said surface in individual and discrete locations.
2. The matrix material according to item 1, wherein the matrix comprises one or more polymers.
3. The matrix material according to item 2, wherein said polymers are cross-linked.
4. The matrix material according to item 2, wherein said polymers are not cross-linked.
5. The matrix material according to item 2, wherein said polymers are selected from the group consisting of collagen, gelatin, polyurethane, polysiloxanes (silicone), hydrogels, polyacrylamides, chitosan, sodium polyacrylate, agarose, alginates, xanthan gum, guar gum, arabic gum, agar gum, Locust Bean gum, Carrageenan gum, Xanthan gum, Karaya gum, tragacanth gum, Ghatti gum, Furcelleran gum, chitin, cellulose, methylcellulose, carboxymethyl cellulose, hydroxymethyl cellulose, hydroxypropyl methylcellulose, hydroxypropyl cellulose, hyaluronic acid, pectin, starch, glycogen, pentosans, polyoxyethylene, polyAMPS (poly(2-acrylamido-2-methyl-1-propanesulfonic acid), polyvinylpyrrolidone, polyvinyl alcohol, polyglycolic acid, polyacetic acid, acrylate polymers, polyhydroxyalkyl acrylates, methacrylates, polyvinyl lactams, polyvinyl alcohols, polyoxyalkylenes, polyacrylamides, polyacrylic acid, polystyrene sulfonates, synthetic hydrocolloids such as N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, hydroxyalkyl acrylates and methacrylates, (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid, tertiary amino-methacrylimide, (e.g. trimethylamino-methacrylimide), crotonic acid, pyridine, water soluble amides, (such as N-(hydroxymethyl)acrylamide and -methacrylamide, N-(3-hydroxpropyl)acrylamide, N-(2-hydroxyethyl)methacrylamide, N-(1,1-dimethyl-3-oxabutypacrylamide N-[2-(dimethylamine)ethyl]acrylamide and -methacrylamide, N-[3-(dimethylamino)-2-hydroxylpropyl]methacrylamide, and N-[1,1-dimethyl-2-(hydroxymethyl)-3-oxabutyl]acrylamide); water-soluble hydrazine derivatives, (such as trialkylamine methacrylimide, and dimethyl-(2-hydroxypropyl)amine methacrylimide); mono-olefinic sulfonic acids and their salts, (such as sodium ethylene sulfonate, sodium styrene sulfonate, 2-acrylamideo-2-methylpropanesulfonic acid), 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, 4-acrylyl-morpholine, Oxidized Regenerated Cellulose (ORC), polylactic-co-glycolic acid) (PLGA), Polylactic acid (PLA), Extracellular matrix (ECM), and mixtures thereof.

6. The matrix material according to item 2, wherein the polymers originates from an animal source such as porcine, bovine or fish sources.
7. The matrix material according to item 2, wherein the polymers are synthetically made i.e. by recombinant means.
8. The matrix material according to item 2, wherein the polymers are selected from collagen and gelatin.
9. The matrix material according to item 2, wherein the polymers comprise gelatin.
10. The matrix material according to item 2, wherein the polymers comprise collagen.
11. The matrix material according to item 1, wherein the interconnected open cells form pores having a diameter of from about 0.1 mm to about 5.0 mm.
12. The matrix material according to item 1, wherein the matrix has the dimensions (length, width and height) of less than 15 cm long, less than 10 cm wide and less than 2 cm high.
13. The matrix material according to item 1, wherein the matrix is a shape selected from the group consisting of square form, circular form, rectangular form, cubic form, cylinder form, spherical or pyramid-shaped.
14. The matrix material according to item 1, wherein the matrix has a colour selected from the group consisting of red, pink, yellow, blue, green, white, black, brown, purple, orange, grey and turquoise.
15. The matrix material according to item 1, wherein the matrix material has a reconformation rate of no more than 10 seconds, such as no more than 9 seconds, for example no more than 8 seconds, such as no more than 7 seconds, for example no more than 6 seconds, such as no more than 5 seconds, for example no more than 4 seconds, such as no more than 3 seconds, for example no more than 3 seconds, such as no more than 1 second.
16. The matrix material according to item 1, wherein the matrix material has a pore size with a normal distribution around 0.1-1.0 mm.
17. The matrix material according to item 1, wherein the matrix material has a pore size of less than 10 mm, such as less than 9 mm, for example less than 8 mm, such as less than 7 mm, for example less than 6 mm, such as less than 5 mm, for example less than 4 mm, such as less than 3 mm, for example less than 2.9 mm, such as less than 2.8 mm, for example less than 2.7 mm, such as less than 2.6 mm, for example less than 2.5 mm, such as less than 2.4 mm, for example less than 2.3 mm, such as less than 2.2 mm, for example less than 2.1 mm, such as less than 2 mm, for example less than 1.9 mm, such as less than 1.8 mm, for example less than 1.7 mm, such as less than 1.6 mm, for example less than 1.5 mm, such as less than 1.4 mm, for example less than 1.3 mm, such as less than 1.2 mm, for example less than 1.1 mm, such as less than 1.0 mm, for example less than 0.9 mm, such as less than 0.8 mm, for example less than 0.7 mm, such as less than 0.6 mm, for example less than 0.5 mm, such as less than 0.4 mm, for example less than 0.3 mm, such as less than 0.2 mm, for example less than 0.1 mm, such as less than 0.05, for example less than 0.01 mm.
18. The matrix material according to item 1, wherein the matrix material has a pore size in the range of 0.01-0.1 mm, such as 0.1-0.2 mm, for example 0.2-0.3 mm, such as 0.3-0.4 mm, for example 0.4-0.5 mm, such as 0.5-0.6 mm, for example 0.6-0.7 mm, such as 0.7-0.8 mm, for example 0.8-0.9 mm, such as 0.9-1 mm, for example 1-1.1 mm, such as 1.1-1.2 mm, for example 1.2-1.3 mm, such as 1.3-1.4 mm, for example 1.4-1.5 mm, such as 1.5-1.6 mm, for example 1.6-1.7 mm, such as 1.7-1.8 mm, for example 1.8-1.9 mm, such as 2-2.1 mm, for example 2.1-2.2 mm, such as 2.2-2.3 mm, for example 2.3-2.4 mm, such as 2.4-2.5 mm, for example 2.5-2.6 mm, such as 2.6-2.7 mm, for example 2.7-2.8 mm, such as 2.8-2.9 mm, for example 2.9-3 mm, such as 3-4 mm, for example 4-5 mm, such as 5-6 mm, for example 6-7 mm, such as 7-8 mm, for example 8-9 mm, such as 9-10 mm.
19. The matrix material according to item 1, wherein the matrix material has a modulus in the range of 0.1-50 GPa, such as 0.1-1, for example 1-2, such as 2-3, such as 3-4, for example 4-5, such as 5-6, for example, 6-7, such as 7-8, for example 8-9, such as 9-10, for example 10-20, such as 20-30, for example 30-40, such as 40-50 GPa.
20. The matrix material according to item 1, wherein the surface of the matrix contains less than 100 IU/cm$^2$, such as less than 95, for example less than 90, such as 85, for example less than 80, such as less than 75, for example less than 70, such as 65, for example less than 60, such as less than 55, for example less than 50, such as 45, for example less than 40, such as less than 35, for example less than 30, such as 25, for example less than 20, such as less than 15, for example less than 10, such as 5, for example less than 1 IU/cm$^2$ of the pharmaceutical composition.
21. The matrix material according to item 1, wherein the surface of the matrix contains between 1-5 IU/cm$^2$, such as 5-10, for example 10-15, such as 15-20, for example 20-25, such as 25-30, for example 30-35, such as 35-40, for example 40-45, such as 45-50, for example 50-55, such as 55-60, for example 60-65, such as 65-70, for example 70-75, such as 75-80, for example 80-85, such as 85-90, for example 90-95, such as 95-100 IU/cm$^2$ of the pharmaceutical composition.
22. The matrix material according to item 1, wherein the matrix material is a sponge.
23. The matrix material according to item 22, wherein the sponge is a gelatin or collagen sponge.
24. The matrix material according to item 23, wherein the gelatin or collagen sponge is selected from the group consisting of Spongostan, Surgifoam, Surgiflo (all Ferrosan A/S), Collastat (Kendall Co.), Avitene (Avicon Inc.), Surgicel, Surgifoam (both Johnson & Johnson) and Gelfoam (Phizer).
25. The matrix material according to item 1, wherein the matrix material is a patch.
26. The matrix material according to item 1, wherein the matrix material is a swab.
27. The matrix material according to item 1, wherein the matrix material is a bandage.
28. The matrix material according to item 1, wherein the matrix material is a wound dressing.
29. The matrix material according to item 1, wherein the matrix material is a tissue dressing.
30. The matrix material according to item 1, wherein the matrix material is sterile.
31. The matrix material according to item 1, wherein the matrix material is sterile and contained in a sterile, pre-packaged, ready-to-use container.
32. The matrix material according to item 1, wherein the matrix material is sterilized.
33. The matrix material according to item 1, wherein the matrix material is sterilized by application of heat.
34. The matrix material according to item 1, wherein the matrix material is sterilized by application of one or more chemicals.

35. The matrix material according to item 1, wherein the matrix material is sterilized by application of high pressure.
36. The matrix material according to item 1, wherein the matrix material is sterilized by application of filtration.
37. The matrix material according to item 1, wherein the matrix material is sterilized by application of autoclaving.
38. The matrix material according to item 1, wherein the matrix material is sterilized by application of radiation sterilization such as sterilization using X-rays, gamma rays, UV light and/or subatomic particles.
39. The matrix material according to item 1, wherein the matrix material is sterilized by application of chemical sterilization include use of one or more of the chemicals selected from the group consisting of ethylene oxide gas, ozone, chlorine bleach, glutaraldehyde, formaldehyde, ortho phthalaldehyde, hydrogen peroxide and peracetic acid.
40. The matrix material according to item 30, wherein the matrix material is contained in a sterile container and separated from an external, non-sterile environment.
41. The matrix material according to item 1, wherein the pharmaceutical composition comprises one or more bioactive agent(s).
42. The pharmaceutical composition according to item 41, wherein said bioactive agent is of a concentration in the range of 1 IU/ml to 1,000,000 IU/ml; such as 1-10 IU/ml, for example 10-50 IU/ml, such as 50-100 IU/ml, for example 100-150 IU/ml, such as 150-200 IU/ml, for example 200-250 IU/ml, such as 250-300 IU/ml, for example 300-350 IU/ml, such as 350-400 IU/ml, for example 400-450 IU/ml, such as 450-500 IU/ml, for example 500-750 IU/ml, such as 750-1000 IU/ml, for example 1000-1500 IU/ml, such as 1500-2000 IU/ml, for example 2000-2500 IU/ml, such as 2500-3000 IU/ml, for example 3000-3500 IU/ml, such as 3500-4000 IU/ml, for example 4000-4500 IU/ml, such as 4500-5000 IU/ml, for example 5000-5500 IU/ml, such as 5500-6000 IU/ml, for example 6000-6500 IU/ml, such as 6500-7000 IU/ml, for example 7000-7500 IU/ml, such as 7500-8000 IU/ml, for example 8000-8500 IU/ml, such as 8500-9000 IU/ml, for example 9000-9500 IU/ml, such as 9500-10,000 IU/ml, for example 10,000-11,000 IU/ml, such as 11,000-12,000 IU/ml, for example 12,000-13,000 IU/ml, such as 13,000-14,000 IU/ml, for example 14,000-15,000 IU/ml, such as 15,000-16,000 IU/ml, for example 16,000-17,000 IU/ml, such as 17,000-18,000 IU/ml, for example 18,000-19,000 IU/ml, such as 19,000-20,000 IU/ml, for example 20,000-25,000 IU/ml, such as 25,000-30,000 IU/ml, for example 30,000-35,000 IU/ml, such as 35,000-40,000 IU/ml, for example 40,000-45,000 IU/ml, such as 45,000-50,000 IU/ml, for example 50,000-55,000 IU/ml, such as 55,000-60,000 IU/ml, for example 60,000-65,000 IU/ml, such as 65,000-70,000 IU/ml, for example 70,000-75,000 IU/ml, such as 75,000-80,000 IU/ml, for example 80,000-85,000 IU/ml, such as 85,000-90,000 IU/ml, for example 90,000-95,000 IU/ml, such as 95,000-100,000 IU/ml, for example 100,000-150,000 IU/ml, such as 150,000-200,000 IU/ml, for example 200,000-250,000 IU/ml, such as 250,000-300,000 IU/ml, for example 300,000-350,000 IU/ml, such as 350,000-400,000 IU/ml, for example 400,000-450,000 IU/ml, such as 450,000-500,000 IU/ml, for example 500,000-550,000 IU/ml, such as 550,000-600,000 IU/ml, for example 600,000-650,000 IU/ml, such as 650,000-700,000 IU/ml, for example 700,000-750,000 IU/ml, such as 750,000-800,000 IU/ml, for example 800,000-850,000 IU/ml, such as 850,000-900,000 IU/ml, for example 900,000-950,000 IU/ml, such as 950,000-1,000,000 IU/ml.
43. The pharmaceutical composition according to item 41, wherein said bioactive agent is of a concentration in the range of 1 ng/ml to 1,000,000 mg/ml; such as 1-10 ng/ml, for example 10-100 ng/ml, such as 100-200 ng/ml, for example 300-400 ng/ml, such as 400-500 ng/ml, for example 500-600 ng/ml, such as 600-700 ng/ml, for example 700-800 ng/ml, such as 800-900 ng/ml, for example 900-1000 ng/ml, such as 1-10 ug/ml, for example 10-100 ug/ml, such as 100-200 ug/ml, for example 200-300 ug/ml, such as 300-400 ug/ml, for example 400-500 ug/ml, such as 500-600 ug/ml, for example 600-700 ug/ml, such as 700-800 ug/ml, for example 800-900 ug/ml, such as 900-1000 ug/ml, for example 1-10 mg/ml, such as 10-100 mg/ml, for example 100-200 mg/ml, such as 200-300 mg/ml, for example 300-400 mg/ml, such as 400-500 mg/ml, for example 500-600 mg/ml, such as 600-700 mg/ml, for example 700-800 mg/ml, such as 800-900 mg/ml, for example 900-1000 mg/ml, such as 1000-2000 mg/ml, for example 2000-3000 mg/ml, such as 3000-4000 mg/ml, for example 4000-5000 mg/ml, such as 5000-6000 mg/ml, for example 6000-7000 mg/ml, such as 7000-8000 mg/ml, for example 8000-9000 mg/ml, such as 9000-10,000 mg/ml, for example 10,000-20,000 mg/ml, such as 20,000-30,000 mg/ml, for example 30,000-40,000 mg/ml, such as 40,000-50,000 mg/ml, for example 50,000-60,000 mg/ml, such as 60,000-70,000 mg/ml, for example 70,000-80,000 mg/ml, such as 80,000-90,000 mg/ml, for example 90,000-100,000 mg/ml, such as 100,000-200,000 mg/ml, for example 200,000-300,000 mg/ml, such as 300,000-400,000 mg/ml, for example 400,000-500,000 mg/ml, such as 500,000-600,000 mg/ml, for example 600,000-700,000 mg/ml, such as 700,000-800,000 mg/ml, for example 800,000-900,000 mg/ml, such as 900,000-1,000,000 mg/ml.
44. The matrix material according to item 41, wherein the concentration of the bioactive agent of any two droplets expelled from a print head vary less that 10%, such as less than 8%, for example less than 6%, such as less than 4%, for example less than 2%, such as less than 1%.
45. The matrix material according to item 44, wherein the concentration of the bioactive agent of any two droplets is essentially identical.
46. The matrix material according to item 1, wherein the pharmaceutical composition comprises one or more bioactive agent(s) that stimulates hemostasis.
47. The matrix material according to item 1, wherein the pharmaceutical composition comprises one or more bioactive agent(s) that stimulates wound healing.
48. The matrix material according to item 1, wherein the pharmaceutical composition comprises one or more bioactive agent(s) that stimulates wound healing by inhibition of one or more infections of the wound.
49. The matrix material according to item 1, wherein the pharmaceutical composition comprises one or more bioactive agent(s) which comprises one or more anti-fibrinolytic agents.
50. The matrix material according to item 1, wherein the pharmaceutical composition comprises one or more bioactive agent(s) which comprises one or more pro-coagulants.
51. The matrix material according to item 1, wherein the pharmaceutical composition comprises one or more bioactive agent(s) that stimulates platelets.

52. The matrix material according to item 1, wherein the pharmaceutical composition comprises one or more bioactive agent(s) that stimulate formation of a hemostatic plug.
53. The matrix material according to item 1, wherein the pharmaceutical composition comprises one or more bioactive agent(s) that stimulates one or more coagulation factors.
54. The matrix material according to item 1, wherein the pharmaceutical composition comprises one or more bioactive agent(s) selected from the group consisting of endothelium Tissue Factor (TF), Factor VII, TF-Factor VIIa, Factor IX, Factor X, thrombin, Factor XIa, plasmin, Factor XII, Factor Xa, TFPI, Factor Va, prothrombinase complex, prothrombin, Factor V, Factor XI, Factor VIII, vWF, Factor VIIIa, Factor IXa and the tenase complex.
55. The matrix material according to item 1, wherein the pharmaceutical composition comprises one or more bioactive agent(s) that stimulates the formation of fibrin strands.
56. The matrix material according to item 1, wherein the pharmaceutical composition comprises one or more bioactive agent(s) that stimulates platelate aggregation.
57. The matrix material according to item 1, wherein the pharmaceutical composition comprises one or more bioactive agent(s) which comprises thrombin.
58. The matrix material according to items 1 and 57, wherein the pharmaceutical composition comprises one or more bioactive agent(s) which comprises fibrinogen.
59. The matrix material according to items 1 and 57, wherein the pharmaceutical composition comprises one or more bioactive agent(s) which comprises Factor XIII and/or XIIIa.
60. The matrix material according to items 1 and 57, wherein the pharmaceutical composition comprises one or more bioactive agent(s) which comprises tranexamic acid.
61. The matrix material according to items 1 and 57, wherein the pharmaceutical composition comprises one or more bioactive agent(s) which comprises Willebrand factor (vWF).
62. The matrix material according to item 1, wherein the pharmaceutical composition comprises one or more bioactive agent(s) that stimulates the contact activation pathway.
63. The matrix material according to item 1, wherein the pharmaceutical composition comprises one or more bioactive agent(s) that stimulates the tissue factor pathway.
64. The matrix material according to item 1, wherein the pharmaceutical composition comprises one or more bioactive agent(s) that stimulates fibrin formation.
65. The matrix material according to item 1, wherein the pharmaceutical composition comprises one or more bioactive agent(s) that stimulates fibrin cross-linking.
66. The matrix material according to item 1, wherein the pharmaceutical composition comprises one or more bioactive agent(s) which comprises Factor VIII.
67. The matrix material according to item 1, wherein the pharmaceutical composition comprises one or more bioactive agent(s) which comprises Factor V.
68. The matrix material according to item 1, wherein the pharmaceutical composition comprises one or more bioactive agent(s) which comprises Factor XIII.
69. The matrix material according to item 1, wherein the pharmaceutical composition comprises one or more bioactive agent(s) which comprises Factor VII.
70. The matrix material according to item 1, wherein the pharmaceutical composition comprises one or more bioactive agent(s) which stimulates the coagulation cascade.
71. The matrix material according to item 1, wherein the pharmaceutical composition comprises thrombin.
72. The matrix material according to item 71, wherein the matrix contains less than 300 IU thrombin per square cm ($cm^2$) surface area, such as less than 290, for example less than 280, such as 270, for example less than 260, such as less than 250, for example less than 240, such as 230, for example less than 220, such as less than 210, for example less than 200, such as 190, for example less than 180, such as less than 170, for example less than 160, such as 150, for example less than 140, such as less than 130, for example less than 120, such as 110, for example less than 100 $IU/cm^2$, such as less than 95, for example less than 90, such as 85, for example less than 80, such as less than 75, for example less than 70, such as 65, for example less than 60, such as less than 55, for example less than 50, such as 45, for example less than 40, such as less than 35, for example less than 30, such as 25, for example less than 20, such as less than 15, for example less than 10, such as 5, for example less than 1 $IU/cm^2$.
73. The matrix material according to item 71, wherein the surface of the matrix contains between 1-5 $IU/cm^2$ thrombin, such as 5-10, for example 10-15, such as 15-20, for example 20-25, such as 25-30, for example 30-35, such as 35-40, for example 40-45, such as 45-50, for example 50-55, such as 55-60, for example 60-65, such as 65-70, for example 70-75, such as 75-80, for example 80-85, such as 85-90, for example 90-95, such as 95-100, for example 100-110, such as 110-120, for example 120-130, such as 130-140, for example 140-150, such as 150-160, for example 160-170, such as 170-180, for example 180-190, such as 190-200, for example 200-210, such as 210-220, for example 220-230, such as 230-240, for example 240-250, such as 250-260, for example 260-270, such as 270-280, for example 280-290, such as 290-300 $IU/cm^2$.
74. The matrix material according to item 1, wherein the pharmaceutical composition is printed onto the surface of the matrix material by deposition of an amount of liquid per position of less than 100 nL, such as less than 90 nL, for example less than 80 nL, such as less than 70 nL, for example less than 60 nL, such as less than 50 nL, for example less than 40 nL, such as less than 30 nL, for example less than 20 nL, such as less than 10 nL, for example less than 1 nL or 1000 pL, such as less than 900 pL, for example less than 800 pL, such as less than 700 pL, for example less than 600 pL, such as less than 500 pL, for example less than 400 pL, such as less than 300 pL, for example less than 250 pL, such as less than 200 pL, for example less than 150 pL, such as less than 100 pL, for example less than 90 pL, such as less than 80 pL, for example less than 70 pL, such as less than 60 pL, for example less than 50 pL, such as less than 40 pL, for example less than 30 pL, such as less than 20 pL, for example less than 10 pL, such as less than 9 pL, for example less than 8 pL, such as less than 7 pL, for example less than 6 pL, such as less than 5 pL, for example less than 4 pL, such as less than 3 pL, for example less than 2 pL, such as less than 1 pL per position.
75. The matrix material according to item 1, wherein the pharmaceutical composition is printed onto the surface of the matrix material by deposition of an amount of liquid per position in pico litre (pL) to nano litre (nL) range, such as 1-10 pL, for example 10-20 pL, such as 20-30 pL, for example 30-40 pL, such as 40-50 pL, for example 50-60 pL, such as 60-70 pL, for example 70-80 pL, such as 80-90 pL, for example 100-150 pL, such as 150-200 pL, for example 200-250 pL, such as 250-300 pL, for example 300-400 pL, such as 400-500 pL, for example 500-600 pL, such as 600-700 pL, for example 700-800 pL, such as 800-900 pL, for example 900-1000 pL or 1 nL, such as 1-10 nL, for example 10-20 nL, such as 20-30 nL, for example 30-40 nL, such as 40-50 nL, for example 50-60 nL, such as 60-70 nL, for example 70-80 nL, such as 80-90 nL, for example 90-100 nL.

76. The matrix material according to item 1, wherein the pharmaceutical composition comprises one or more adhesive agents.

77. The matrix material according to item 76, wherein the one or more adhesive agents can be selected from the group consisting of saccharides, monosaccharides, disaccharides, oligosaccharides, polysaccharides, glucose, mannose, fructose, threose, gulose, arabinose, ribose, erythrose, lyxose, galactose, sorbose, altrose, tallose, idose, rhamnose, allose, pentosamines, hexosamines, glucosamine, N-acetylglucosamine, glucoronic acid, sucrose, maltose, lactose, cellubiose, glycogen, chitin, chitosan, starch, potato starch, glycosaminoglycans, chondroitin, chondroitin sulfate, hyaluronic acid, dermatan sulphate, keratan sulphate, aminated dextrans, DEAE-dextran, aminated starch, aminated glycogen, aminated cellulose, aminated pectin, and salts, complexes, derivatives and mixtures thereof.

78. The matrix material according to item 76, wherein the one or more adhesive agents can be selected from the group consisting of hydrocarbon resins, rosin resins, terpene resins, Escorez® from ExxonMobil; Regalite®, Piccotac® and Picco® from Eastman; Indopol® from BP or Arkon®, esters of hydrogenated wood rosin, pentaerythritol ester of hydrogenated wood rosin, esters of partially hydrogenated wood rosin, pentaerythritol esters of partially hydrogenated wood rosin, esters of wood rosin, esters of modified wood rosin, esters of partially dimerized rosin, esters of tall oil rosin, esters of dimerized rosin, Foral®, Foralyn®, Pentalyn®, Permalyn® and Staybelite®.

79. The matrix material according to item 76, wherein the one or more adhesive agents can be selected from the group consisting of Gum Karaya, Sterculia gum, Gum Arabicum, Gum Karrageenan, celluloseethers, sodium carboxymethylcellulose, Manuba Honey, casein, alginates and fatty acid esters.

80. The matrix material according to item 76, wherein the one or more adhesive agents comprises between 0.1-50% (w/w) of the pharmaceutical composition, based on the total weight of the composition such as 1-25% (w/w), such as 5-20% (w/w), e.g. 5-15% (w/w), 5-10% (w/w), or 10-15% (w/w), based on the total weight of the composition.

81. The matrix material according to item 1, wherein the pharmaceutical composition comprises one or more surfactant agents.

82. The matrix material according to item 81, wherein the one or more surfactant agents can be selected from the group consisting of anionic surfactants, cationic surfactants, non-ionic surfactants and surface active biological modifiers.

83. The matrix material according to item 81, wherein the one or more surfactant agents can be selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

84. The matrix material according to item 81, wherein the one or more surfactant agents can be selected from the group consisting of samples of cationic surfactants include surfactants selected from the group consisting of quaternary ammonium compounds, benzalkonium chloride, cetyltrimethylammonium bromide, chitosans and lauryldimethylbenzylammonium chloride.

85. The matrix material according to item 81, wherein the one or more surfactant agents can be selected from the group consisting of polyoxyethylene fatty alcohol ethers, polyoxyethylene sorbitan fatty acid esters, polyoxyethylene fatty acid esters, sorbitan esters, polyoxyethylene sorbitan esters (such as Tween 80 or Tween 20), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, Pluronic F68, and polyvinylpyrrolidone.

86. The matrix material according to item 1, wherein the pharmaceutical composition comprises a solvent component and/or a fluid component.

87. The matrix material according to item 86, wherein the solvent component and/or fluid component is an aqueous medium.

88. The matrix material according to item 87, wherein the aqueous medium contains one or more salts such as sodium chloride.

89. The matrix material according to item 87, wherein the solvent component and/or fluid component is a volatile fluid.

90. The matrix material according to item 1, wherein the pharmaceutical composition comprises one or more water content stabilizer such as sorbitol, polysaccaharides or polyols.

91. The matrix material according to item 1, wherein the pharmaceutical composition comprises one or more long chain molecules (polymers) such as gelatin, starch, polyethyleneoxide, polyvinylalcohol and polyethyleneglycols (macrogol).

92. The matrix material according to item 1, wherein the pharmaceutical composition comprises one or more substances that increases the viscosity of the composition, selected from acacia, alginic acid, bentonite, carbomer, carboxymethylcellulose calcium, carboxymethylcellulose sodium, cetostearyl alcohol, colloidal silicon dioxide, guar gum, hydroxyethyl cellulose, hydroxypropyl cellulose, hydroxypropyl methylcellulose, hydroxypropyl methylcellulose phtalate, magnesium aluminium silicate, methylcellulose, microcrystalline cellulose, polyvinyl alcohol, povidone, sodium alginate, sucrose, tragacanth, gelatin, starch, albumin, casein, polyethyleneoxide, polyvinylalcohol, polyethyleneglycols (macrogol), glycerine (1,2,3-propanetriol) and glycol (1,2-propanediol).

93. The matrix material according to item 1, wherein the pharmaceutical composition has a viscosity in the range of 0.1-20 cps; for example 0.1-1 cps, such as 1-2 cps, for example 2-3 cps, such as 3-4 cps, for example 4-5 cps, such as 5-6 cps, for example 6-7 cps, such as 7-8 cps, for example 8-9 cps, such as 9-10 cps, for example 10-11 cps, such as 11-12 cps, for example 12-13 cps, such as 13-14 cps, for example 14-15 cps, such as 15-16 cps, for example 16-17 cps, such as 17-18 cps, for example 18-19 cps, such as 19-20 cps.

94. The matrix material according to item 1, wherein the pharmaceutical composition has a surface tension in the range of 0.020 to 0.050 N/m; for example 0.020-0.022 N/m, such as 0.022-0.024 N/m, for example 0.024-0.026 N/m, such as 0.026-0.028 N/m, for example 0.028-0.030 N/m, such as 0.030-0.032 N/m, for example 0.032-0.034 N/m, such as 0.034-0.036 N/m, for example 0.036-0.038 N/m, such as 0.038-0.040 N/m, for example 0.040-0.042 N/m, such as 0.042-0.044 N/m, for example 0.044-0.046 N/m, such as 0.046-0.048 N/m, for example 0.048-0.050 N/m.

95. The matrix material according to item 1, wherein the pharmaceutical composition has a temperature in the range from sub-zero degrees celcius to 150 degrees celcius; such as −100° C. to −50° C., for example −50° C. to 0° C., such as 0-10° C., for example 10-20° C., such as 20-30° C., for example 30-40° C., such as 40-50° C., for example 50-60° C., such as 60-70° C., for example 70-80° C., such as 80-90° C., for example 90-100° C., such as 100-125° C., for example 125-150° C.

96. The matrix material according to item 1, wherein the pharmaceutical composition comprises one bioactive agent.

97. The matrix material according to item 1, wherein the pharmaceutical composition comprises two or more agents or bioactive agents.

98. The matrix material according to item 1, wherein the surface of the matrix material comprises one pharmaceutical composition comprising one or more bioactive agents.

99. The matrix material according to item 1, wherein the surface of the matrix material comprises two or more different pharmaceutical compositions each comprising one or more agents or bioactive agents.

100. The matrix material according to item 99, wherein the two or more different pharmaceutical compositions are each printed onto the surface of the matrix material in discrete and non-overlapping positions of said surface.

101. The matrix material according to item 100, wherein the two or more different pharmaceutical compositions are incompatible if contained in the same pharmaceutical composition.

102. The matrix material according to item 101, wherein the two or more different pharmaceutical compositions are separate components of a two-component glue.

103. The matrix material according to item 102, wherein said two-component glue is a surgical glue.

104. The matrix material according to item 100, wherein the two or more pharmaceutical compositions comprise thrombin and fibrinogen, respectively 105. The matrix according to item 1, wherein said pharmaceutical composition is uniformly distributed.

106. The matrix according to item 105, wherein a predetermined ratio of droplet volume of the pharmaceutical composition, distance between any two droplets deposited on the surface of said matrix material and the concentration of a bioactive agent in said pharmaceutical composition is used.

107. The matrix material according to item 105, wherein any two area units of said matrix material differ in volume of the pharmaceutical composition or concentration of bioactive agent of the pharmaceutical composition by the most 10%, such as by the most 8%, for example by the most 6%, such as by the most 4%, for example by the most 2%, such as by the most 1%.

108. A matrix according to any of items 1 to 107, said matrix being obtained by a method comprising the steps of providing a matrix material and printing said at least one pharmaceutical composition onto the surface of said matrix material at individual and discrete locations.

109. The matrix according to item 108, wherein said method does not employ a drying step.

110. The matrix according to item 108, wherein said method essentially does not alter the physical characteristics and appearance of the matrix.

111. The matrix according to item 108, wherein said method essentially does not alter the physical characteristics of the surface of said matrix.

112. The matrix according to item 108, wherein said method essentially does not cause any swelling of the matrix.

113. The matrix according to item 108, wherein said method essentially does not cause any swelling of the surface of said matrix.

114. The matrix according to item 108, wherein said method essentially does not alter the initial absorption rate of the matrix.

115. The matrix according to item 108, wherein said method essentially does not lower the initial absorption rate of the surface of said matrix.

116. The matrix according to item 108, wherein said method essentially does not generate aerosols.

117. The matrix according to item 108, wherein the amount of fluid or liquid composition not contacting the matrix material is less that 10%, such as less than 8%, for example less than 6%, such as less than 4%, for example less than 2%, such as less than 1%.

118. The matrix according to item 108, wherein printing of the pharmaceutical composition occurs essentially perpendicular to the surface of said matrix material.

119. The matrix according to item 108, wherein said printing of said pharmaceutical composition onto the surface of said matrix material results in the generation of droplets that evaporate within maximum 30 seconds, such as less than 25 seconds, for example less than 20 seconds, such as less than 15 seconds, for example less than 10 seconds, such as less than 5 seconds, for example less than 1 second after being printed onto the surface of the matrix.

120. The matrix according to item 108, wherein said printing of said pharmaceutical composition onto the surface of said matrix material results in the generation of droplets each with a volume of less than 100 nL, such as less than 90 nL, for example less than 80 nL, such as less than 70 nL, for example less than 60 nL, such as less than 50 nL, for example less than 40 nL, such as less than 30 nL, for example less than 20 nL, such as less than 10 nL, for example less than 1 nL or 1000 pL, such as less than 900 pL, for example less than 800 pL, such as less than 700 pL, for example less than 600 pL, such as less than 500 pL, for example less than 400 pL, such as less than 300 pL, for example less than 250 pL, such as less than 200 pL, for example less than 150 pL, such as less than 100 pL, for example less than 90 pL, such as less than 80 pL, for example less than 70 pL, such as less than 60 pL, for example less than 50 pL, such as less than 40 pL, for example less than 30 pL, such as less than 20 pL, for example less than 10 pL, such as less than 9 pL, for example less than 8 pL, such as less than 7 pL, for example less than 6 pL, such as less than 5 pL, for example less than 4 pL, such as less than 3 pL, for example less than 2 pL, such as less than 1 pL per droplet.

121. The matrix according to item 120, wherein the droplet size of any two droplets vary less that 10%, such as less than 8%, for example less than 6%, such as less than 4%, for example less than 2%, such as less than 1%.

122. The matrix according to item 121, wherein the droplet size of any two droplets is essentially identical.

123. The matrix according to item 99, wherein the distance between every two droplets deposited by printing onto the matrix surface is less than 2 mm, such as less than 1.9 mm, for example less than 1.8 mm, such as less than 1.7 mm, for example less than 1.6 mm, such as less than 1.5 mm, for example less than 1.4 mm, such as less than 1.3 mm, for example less than 1.3 mm, such as less than 1.2 mm, for example less than 1.1 mm, such as less than 1.0 mm, for example less than 0.9 mm, such as less than 0.8 mm, for example less than 0.7 mm, such as less than 0.6 mm, for example less than 0.5 mm, such as less than 0.4 mm, for example less than 0.3 mm, such as less than 0.2 mm, for example less than 0.1 mm, such as less than 0.09 mm, for example less than 0.08 mm, such as less than 0.07 mm, for example less than 0.06 mm, such as less than 0.05 mm, for example less than 0.04 mm, such as less than 0.03 mm, for example less than 0.02 mm, such as less than 0.01 mm.

124. The matrix according to item 123, wherein the distance between every two droplets deposited by printing onto the matrix surface vary less that 10%, such as less than 8%, for example less than 6%, such as less than 4%, for example less than 2%, such as less than 1%.

125. The matrix according to item 124, wherein the distance between every two droplets deposited by printing onto the matrix surface is essentially identical.

126. The matrix according to item 108, wherein said printing of said pharmaceutical composition onto the surface of said matrix material results in the generation of droplets, wherein the distance traversed by any droplet from the print head to the surface of the matrix material is less than 0.01 mm, such as less than 0.02 mm, for example less than 0.03 mm, such as less than 0.04 mm, for example less than 0.05 mm, such as less than 0.06 mm, for example less than 0.07 mm, such as less than 0.08 mm, for example less than 0.09 mm, such as less than 0.1 mm, for example less than 0.2 mm, such as less than 0.3 mm, for example less than 0.4 mm, such as less than 0.5 mm, for example less than 0.6 mm, such as less than 0.7 mm, for example less than 0.8 mm, such as less than 0.9 mm, for example less than 1.0 mm, such as less than 1.1 mm, for example less than 1.2 mm, such as less than 1.3 mm, for example less than 1.4 mm, such as less than 1.5 mm, for example less than 1.6 mm, such as less than 1.7 mm, for example less than 1.8 mm, such as less than 1.9 mm, for example less than 2.0 mm, such as less than 2.1 mm, for example less than 2.2 mm, such as less than 2.3 mm, for example less than 2.4 mm, such as less than 2.5 mm, for example less than 2.6 mm, such as less than 2.7 mm, for example less than 2.8 mm, such as less than 2.8 mm, for example less than 3.0 mm, such as less than 3.5 mm, for example less than 4.0 mm, such as less than 4.5 mm, for example less than 5.0 mm, such as less than 6.0 mm, for example less than 7.0 mm, such as less than 8.0 mm, for example less than 9.0 mm, such as less than 10.0 mm.

127. The matrix according to item 126, wherein each droplet traverses a distance from print head to the surface of a matrix material that varies between each droplet within a range of 0.01% to a maximum of 10%; such as 0.01 to 0.1%, for example 0.1 to 1%, such as 1 to 2%, for example 2 to 3%, such as 3 to 4%, for example 4 to 5%, such as 5 to 6%, for example 6 to 7%, such as 7 to 8%, for example 8 to 9%, such as 9 to 10%.

128. The matrix according to item 127, wherein the distance each droplet traverses from print head to the surface of a matrix material is essentially identical.

129. The matrix according to item 108, wherein a print head ejects droplets at a velocity in the range of 0.1-100 m/sec; such as 0.1-1 m/sec, for example 1-2 m/sec, such as 2-3 m/sec, for example 3-4 m/sec, such as 4-5 m/sec, for example 5-6 m/sec, such as 6-7 m/sec, for example 7-8 m/sec, such as 8-9 m/sec, for example 9-10 m/sec, such as 10-15 m/sec, for example 15-20 m/sec, such as 20-30 m/sec, for example 30-40 m/sec, such as 40-50 m/sec, for example 50-60 m/sec, such as 60-70 m/sec, for example 70-80 m/sec, such as 80-90 m/sec, for example 90-100 m/sec.

130. The matrix according to item 129, wherein the velocity between each droplet varies within a range of 0.01% to a maximum of 10%; such as 0.01 to 0.1%, for example 0.1 to 1%, such as 1 to 2%, for example 2 to 3%, such as 3 to 4%, for example 4 to 5%, such as 5 to 6%, for example 6 to 7%, such as 7 to 8%, for example 8 to 9%, such as 9 to 10%.

131. The matrix according to item 130, wherein the velocity of each droplet from print head to the surface of a matrix material is essentially identical.

132. The matrix material according to item 108, wherein said pharmaceutical composition is printed onto said surface of said matrix by jet or inkjet printing.

133. The matrix material according to item 132, wherein the inkjet printing comprises piezoelectric jet printing.

134. The matrix material according to item 132, wherein the jet printing comprises thermal jet printing.

135. The matrix material according to item 132, wherein the inkjet printing comprises continuous inkjet printing.

136. The matrix material according to item 132, wherein said inkjet printing comprises at least one print head comprising at least one nozzle.

137. The matrix material according to item 136, wherein the nozzle diameter is in the range of 1-1000 microns; such as 1-5 microns, for example 5-10 microns, such as 10-20 microns, for example 20-30 microns, such as 30-40 microns, for example 40-50 microns, such as 50-60 microns, for example 60-70 microns, such as 70-80 microns, for example 80-90 microns, such as 90-100 microns, for example 100-200 microns, such as 200-300 microns, for example 300-400 microns, such as 400-500 microns, for example 500-600 microns, such as 600-700 microns, for example 700-800 microns, such as 800-900 microns, for example 900-1000 microns.

138. The matrix material according to item 136, wherein the at least one print head comprises between 1-50, 50-100, 100-150, 150-200, 200-250, 250-300, 300-350, 350-400, 400-450, 450-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2500, 2500-3000, 3000-4000, 4000-5000, 5000-10,000 nozzles per print head.

139. A device comprising the matrix material printed with a pharmaceutical composition according to items 1-138.

140. A kit of parts comprising the device according to item 139 and at least one additional component.

141. A method for making the device according to item 139 comprising the steps of a. providing a matrix material, and
b. printing a pharmaceutical composition onto the surface of said matrix material at individual and discrete locations.

142. Use of the device according to item 139 to promote wound healing in an individual in need thereof 143. Use of the device according to item 139 to promote hemostasis in an individual in need thereof 144. A matrix material comprising a surface and a plurality of open and interconnected cells, wherein one or more pharmaceutical compositions have been applied onto said matrix material.

145. The matrix material according to item 144, wherein the matrix comprises one or more polymers.

146. The matrix material according to item 144, wherein said polymers are cross-linked.

147. The matrix material according to item 144, wherein said polymers are not cross-linked.

148. The matrix material according to item 145, wherein said polymers are selected from the group consisting of collagen, gelatin, polyurethane, polysiloxanes (silicone), hydrogels, polyacrylamides, chitosan, sodium polyacrylate, agarose, alginates, xanthan gum, guar gum, arabic gum, agar gum, Locust Bean gum, Carrageenan gum, Xanthan gum, Karaya gum, tragacanth gum, Ghatti gum, Furcelleran gum, chitin, cellulose, methylcellulose, carboxymethyl cellulose, hydroxymethyl cellulose, hydroxypropyl methylcellulose, hydroxypropyl cellulose, hyaluronic acid, pectin, starch, glycogen, pentosans, polyoxyethylene, polyAMPS (poly(2-acrylamido-2-methyl-1-propanesulfonic acid), polyvinylpyrrolidone, polyvinyl alcohol, polyglycolic acid, polyacetic acid, acrylate polymers, polyhydroxyalkyl acrylates, methacrylates, polyvinyl lactams, polyvinyl alcohols, polyoxyalkylenes, polyacrylamides, polyacrylic acid, polystyrene sulfonates, synthetic hydrocolloids such as N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, hydroxyalkyl acrylates and methacrylates, (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid, tertiary amino-methacrylimide, (e.g. trimethylamino-methacrylimide), crotonic acid, pyridine, water soluble amides, (such as N-(hydroxymethyl)acrylamide and -methacrylamide, N-(3-hydroxpropyl)acrylamide, N-(2-hydroxyethyl)methacrylamide, N-(1,1-dimethyl-3-oxabutyl)acrylamide N-[2-(dimethylamine)ethyl]acrylamide and -methacrylamide, N-[3-(dimethylamino)-2-hydroxylpropyl]methacrylamide, and N-[1,1-dimethyl-2-(hydroxymethyl)-3-oxabutyl]acrylamide); water-soluble hydrazine derivatives, (such as trialkylamine methacrylimide, and dimethyl-(2-hydroxypropyl)amine methacrylimide); mono-olefinic sulfonic acids and their salts, (such as sodium ethylene sulfonate, sodium styrene sulfonate, 2-acrylamideo-2-methylpropanesulfonic acid), 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, 4-acrylyl-morpholine, Oxidized Regenerated Cellulose (ORC), poly(lactic-co-glycolic acid) (PLGA), Polylactic acid (PLA), Extracellular matrix (ECM) and mixtures thereof 149. The matrix material according to item 145, wherein the polymers originates from an animal source such as porcine, bovine or fish sources.

150. The matrix material according to item 145, wherein the polymers are synthetically made i.e. by recombinant means.

151. The matrix material according to item 145, wherein the polymers are selected from collagen and gelatin.

152. The matrix material according to item 145, wherein the polymers comprise gelatin.

153. The matrix material according to item 145, wherein the polymers comprise collagen.

154. The matrix material according to item 144, wherein the interconnected open cells form pores having a diameter of from about 0.1 mm to about 5.0 mm.

155. The matrix material according to item 144, wherein the matrix has the dimensions (length, width and height) of less than 15 cm long, less than 10 cm wide and less than 2 cm high.

156. The matrix material according to item 144, wherein the matrix is a shape selected from the group consisting of square form, circular form, rectangular form, cubic form, cylinder form, spherical or pyramid-shaped.

157. The matrix material according to item 144, wherein the matrix has a colour selected from the group consisting of red, pink, yellow, blue, green, white, black, brown, purple, orange, grey and turquoise.

158. The matrix material according to item 144, wherein the matrix material has a reconformation rate of no more than 10 seconds, such as no more than 9 seconds, for example no more than 8 seconds, such as no more than 7 seconds, for example no more than 6 seconds, such as no more than 5 seconds, for example no more than 4 seconds, such as no more than 3 seconds, for example no more than 3 seconds, such as no more than 1 second.

159. The matrix material according to item 144, wherein the matrix material has a pore size with a normal distribution around 0.1-1.0 mm.

160. The matrix material according to item 144, wherein the matrix material has a pore size of less than 10 mm, such as less than 9 mm, for example less than 8 mm, such as less than 7 mm, for example less than 6 mm, such as less than 5 mm, for example less than 4 mm, such as less than 3 mm, for example less than 2.9 mm, such as less than 2.8 mm, for example less than 2.7 mm, such as less than 2.6 mm, for example less than 2.5 mm, such as less than 2.4 mm, for example less than 2.3 mm, such as less than 2.2 mm, for example less than 2.1 mm, such as less than 2 mm, for example less than 1.9 mm, such as less than 1.8 mm, for example less than 1.7 mm, such as less than 1.6 mm, for example less than 1.5 mm, such as less than 1.4 mm, for example less than 1.3 mm, such as less than 1.2 mm, for example less than 1.1 mm, such as less than 1.0 mm, for example less than 0.9 mm, such as less than 0.8 mm, for example less than 0.7 mm, such as less than 0.6 mm, for example less than 0.5 mm, such as less than 0.4 mm, for example less than 0.3 mm, such as less than 0.2 mm, for example less than 0.1 mm, such as less than 0.05, for example less than 0.01 mm.

161. The matrix material according to item 144, wherein the matrix material has a pore size in the range of 0.01-0.1 mm, such as 0.1-0.2 mm, for example 0.2-0.3 mm, such as 0.3-0.4 mm, for example 0.4-0.5 mm, such as 0.5-0.6 mm, for example 0.6-0.7 mm, such as 0.7-0.8 mm, for example 0.8-0.9 mm, such as 0.9-1 mm, for example 1-1.1 mm, such as 1.1-1.2 mm, for example 1.2-1.3 mm, such as 1.3-1.4 mm, for example 1.4-1.5 mm, such as 1.5-1.6 mm, for example 1.6-1.7 mm, such as 1.7-1.8 mm, for example 1.8-1.9 mm, such as 2-2.1 mm, for example 2.1-2.2 mm, such as 2.2-2.3 mm, for example 2.3-2.4 mm, such as 2.4-2.5 mm, for example 2.5-2.6 mm, such as 2.6-2.7 mm, for example 2.7-2.8 mm, such as 2.8-2.9 mm, for example 2.9-3 mm, such as 3-4 mm, for example 4-5 mm, such as 5-6 mm, for example 6-7 mm, such as 7-8 mm, for example 8-9 mm, such as 9-10 mm.

162. The matrix material according to item 144, wherein the matrix material has a modulus in the range of 0.1-50 GPa, such as 0.1-1, for example 1-2, such as 2-3, such as 3-4, for example 4-5, such as 5-6, for example, 6-7, such as 7-8, for example 8-9, such as 9-10, for example 10-20, such as 20-30, for example 30-40, such as 40-50 GPa.

163. The matrix material according to item 144, wherein the matrix contains less than 100 IU/cm$^2$ (units per square centimeter), such as less than 95, for example less than 90, such as 85, for example less than 80, such as less than 75, for example less than 70, such as 65, for example less than 60, such as less than 55, for example less than 50, such as 45, for example less than 40, such as less than 35, for example less than 30, such as 25, for example less than 20, such as less than 15, for example less than 10, such as 5, for example less than 1 IU/cm$^2$ of the pharmaceutical composition.

164. The matrix material according to item 144, wherein the surface of the matrix contains between 1-5 IU/cm$^2$, such as 5-10, for example 10-15, such as 15-20, for example 20-25, such as 25-30, for example 30-35, such as 35-40, for example 40-45, such as 45-50, for example 50-55, such as 55-60, for example 60-65, such as 65-70, for example 70-75, such as 75-80, for example 80-85, such as 85-90, for example 90-95, such as 95-100 IU/cm$^2$ of the pharmaceutical composition.

165. The matrix material according to item 144, wherein the matrix material is a sponge.

166. The matrix material according to item 144, wherein the sponge is a gelatin or collagen sponge.

167. The matrix material according to item 166, wherein the gelatin or collagen sponge is selected from the group consisting of Spongostan, Surgifoam, Surgiflo (all Ferrosan A/S), Collastat (Kendall Co.), Avitene (Avicon Inc.), Surgicel, Surgifoam (both Johnson & Johnson) and Gelfoam (Phizer).

168. The matrix material according to item 144, wherein the matrix material is a patch.

169. The matrix material according to item 144, wherein the matrix material is a swab.

170. The matrix material according to item 144, wherein the matrix material is a bandage.

171. The matrix material according to item 144, wherein the matrix material is a wound dressing.

172. The matrix material according to item 144, wherein the matrix material is a tissue dressing.

173. The matrix material according to item 144, wherein the matrix material is sterile.

174. The matrix material according to item 144, wherein the matrix material is sterile and contained in a sterile, pre-packaged, ready-to-use container.

175. The matrix material according to item 144, wherein the matrix material is sterilized.

176. The matrix material according to item 144, wherein the matrix material is sterilized by application of heat.

177. The matrix material according to item 144, wherein the matrix material is sterilized by application of one or more chemicals.

178. The matrix material according to item 144, wherein the matrix material is sterilized by application of high pressure.

179. The matrix material according to item 144, wherein the matrix material is sterilized by application of filtration.

180. The matrix material according to item 144, wherein the matrix material is sterilized by application of autoclaving.

181. The matrix material according to item 144, wherein the matrix material is sterilized by application of radiation sterilization such as sterilization using X-rays, gamma rays, UV light and/or subatomic particles.

182. The matrix material according to item 144, wherein the matrix material is sterilized by application of chemical sterilization include use of one or more of the chemicals selected from the group consisting of ethylene oxide gas, ozone, chlorine bleach, glutaraldehyde, formaldehyde, ortho phthalaldehyde, hydrogen peroxide and peracetic acid.

183. The matrix material according to item 175, wherein the sterile matrix material is contained in a sterile container and separated from an external, non-sterile environment.

184. The matrix material according to item 144, wherein the pharmaceutical composition comprises one or more bioactive agent(s) that stimulates hemostasis.

185. The matrix material according to item 144, wherein the pharmaceutical composition comprises one or more bioactive agent(s) that stimulates wound healing.

186. The matrix material according to item 144, wherein the pharmaceutical composition comprises one or more bioactive agent(s) that stimulates wound healing by inhibition of one or more infections of the wound.

187. The matrix material according to item 144, wherein the pharmaceutical composition comprises one or more bioactive agent(s) which comprises one or more anti-fibrinolytic agents.

188. The matrix material according to item 144, wherein the pharmaceutical composition comprises one or more bioactive agent(s) which comprises one or more pro-coagulants.

189. The matrix material according to item 144, wherein the pharmaceutical composition comprises one or more bioactive agent(s) that stimulates platelets.

190. The matrix material according to item 144, wherein the pharmaceutical composition comprises one or more bioactive agent(s) that stimulate formation of a hemostatic plug.

191. The matrix material according to item 144, wherein the pharmaceutical composition comprises one or more bioactive agent(s) that stimulates one or more coagulation factors.

192. The matrix material according to item 144, wherein the pharmaceutical composition comprises one or more bioactive agent(s) selected from the group consisting of endothelium Tissue Factor (TF), Factor VII, TF-Factor VIIa, Factor IX, Factor X, thrombin, Factor XIa, plasmin, Factor XII, Factor Xa, TFPI, Factor Va, prothrombinase complex, prothrombin, Factor V, Factor XI, Factor VIII, vWF, Factor VIIIa, Factor IXa and the tenase complex.

193. The matrix material according to item 144, wherein the pharmaceutical composition comprises one or more bioactive agent(s) that stimulates the formation of fibrin strands.

194. The matrix material according to item 144, wherein the pharmaceutical composition comprises one or more bioactive agent(s) that stimulates platelate aggregation.
195. The matrix material according to item 144, wherein the pharmaceutical composition comprises one or more bioactive agent(s) which comprises thrombin.
196. The matrix material according to items 144 and 195, wherein the pharmaceutical composition comprises one or more bioactive agent(s) which comprises fibrinogen.
197. The matrix material according to items 144 and 195, wherein the pharmaceutical composition comprises one or more bioactive agent(s) which comprises Factor XIII and/or XIIIa.
198. The matrix material according to items 144 and 195, wherein the pharmaceutical composition comprises one or more bioactive agent(s) which comprises tranexamic acid.
199. The matrix material according to items 144 and 195, wherein the pharmaceutical composition comprises one or more bioactive agent(s) which comprises Willebrand factor (vWF).
200. The matrix material according to item 144, wherein the pharmaceutical composition comprises one or more bioactive agent(s) that stimulates the contact activation pathway.
201. The matrix material according to item 144, wherein the pharmaceutical composition comprises one or more bioactive agent(s) that stimulates the tissue factor pathway.
202. The matrix material according to item 144, wherein the pharmaceutical composition comprises one or more bioactive agent(s) that stimulates fibrin formation.
203. The matrix material according to item 144, wherein the pharmaceutical composition comprises one or more bioactive agent(s) that stimulates fibrin cross-linking.
204. The matrix material according to item 144, wherein the pharmaceutical composition comprises one or more bioactive agent(s) which comprises Factor VIII.
205. The matrix material according to item 144, wherein the pharmaceutical composition comprises one or more bioactive agent(s) which comprises Factor V.
206. The matrix material according to item 144, wherein the pharmaceutical composition comprises one or more bioactive agent(s) which comprises Factor XIII.
207. The matrix material according to item 144, wherein the pharmaceutical composition comprises one or more bioactive agent(s) which comprises Factor VII.
208. The matrix material according to item 144, wherein the pharmaceutical composition comprises one or more bioactive agent(s) which stimulates the coagulation cascade.
209. The matrix material according to item 144, wherein the pharmaceutical composition comprises thrombin.
210. The matrix material according to item 209, wherein the matrix contains less than 300 IU thrombin per square cm ($cm^2$) surface area, such as less than 290, for example less than 280, such as 270, for example less than 260, such as less than 250, for example less than 240, such as 230, for example less than 220, such as less than 210, for example less than 200, such as 190, for example less than 180, such as less than 170, for example less than 160, such as 150, for example less than 140, such as less than 130, for example less than 120, such as 110, for example less than 100 IU/$cm^2$, such as less than 95, for example less than 90, such as 85, for example less than 80, such as less than 75, for example less than 70, such as 65, for example less than 60, such as less than 55, for example less than 50, such as 45, for example less than 40, such as less than 35, for example less than 30, such as 25, for example less than 20, such as less than 15, for example less than 10, such as 5, for example less than 1 IU/$cm^2$.
211. The matrix material according to item 209, wherein the surface of the matrix contains between 1-5 IU/$cm^2$, such as 5-10, for example 10-15, such as 15-20, for example 20-25, such as 25-30, for example 30-35, such as 35-40, for example 40-45, such as 45-50, for example 50-55, such as 55-60, for example 60-65, such as 65-70, for example 70-75, such as 75-80, for example 80-85, such as 85-90, for example 90-95, such as 95-100, for example 100-110, such as 110-120, for example 120-130, such as 130-140, for example 140-150, such as 150-160, for example 160-170, such as 170-180, for example 180-190, such as 190-200, for example 200-210, such as 210-220, for example 220-230, such as 230-240, for example 240-250, such as 250-260, for example 260-270, such as 270-280, for example 280-290, such as 290-300 IU/$cm^2$.
212. The matrix material according to item 144, wherein the pharmaceutical composition comprises one or more adhesive agents.
213. The matrix material according to item 212, wherein the one or more adhesive agents can be selected from the group consisting of saccharides, monosaccharides, disaccharides, oligosaccharides, polysaccharides, glucose, mannose, fructose, threose, gulose, arabinose, ribose, erythrose, lyxose, galactose, sorbose, altrose, tallose, idose, rhamnose, allose, pentosamines, hexosamines, glucosamine, N-acetylglucosamine, glucoronic acid, sucrose, maltose, lactose, cellubiose, glycogen, chitin, chitosan, starch, potato starch, glycosaminoglycans, chondroitin, chondroitin sulfate, hyaluronic acid, dermatan sulphate, keratan sulphate, aminated dextrans, DEAE-dextran, aminated starch, aminated glycogen, aminated cellulose, aminated pectin, and salts, complexes, derivatives and mixtures thereof.
214. The matrix material according to item 212, wherein the one or more adhesive agents can be selected from the group consisting of hydrocarbon resins, rosin resins, terpene resins, Escorez® from ExxonMobil; Regalite®, Piccotac® and Picco® from Eastman; Indopol® from BP or Arkon®, esters of hydrogenated wood rosin, pentaerythritol ester of hydrogenated wood rosin, esters of partially hydrogenated wood rosin, pentaerythritol esters of partially hydrogenated wood rosin, esters of wood rosin, esters of modified wood rosin, esters of partially dimerized rosin, esters of tall oil rosin, esters of dimerized rosin, Foral®, Foralyn®, Pentalyn®, Permalyn® and Staybelite®.
215. The matrix material according to item 212, wherein the one or more adhesive agents can be selected from the group consisting of Gum Karaya, Sterculia gum, Gum Arabicum, Gum Karrageenan, celluloseethers, sodium carboxymethylcellulose, Manuba Honey, casein, alginates and fatty acid esters.
216. The matrix material according to item 212, wherein the one or more adhesive agents comprises between 0.1-50% (w/w) of the pharmaceutical composition, based on the total weight of the composition such as 1-25% (w/w), such as 5-20% (w/w), e.g. 5-15% (w/w), 5-10% (w/w), or 10-15% (w/w), based on the total weight of the composition.
217. The matrix material according to item 144, wherein the pharmaceutical composition comprises one or more surfactant agents.
218. The matrix material according to item 217, wherein the one or more surfactant agents can be selected from the group consisting of anionic surfactants, cationic surfactants, non-ionic surfactants and surface active biological modifiers.

219. The matrix material according to item 217, wherein the one or more surfactant agents can be selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose.

220. The matrix material according to item 217, wherein the one or more surfactant agents is a cationic surfactant selected from the group consisting of quaternary ammonium compounds, benzalkonium chloride, cetyltrimethylammonium bromide, chitosans and lauryldimethylbenzylammonium chloride.

221. The matrix material according to item 217, wherein the one or more surfactant agents can be selected from the group consisting of polyoxyethylene fatty alcohol ethers, polyoxyethylene sorbitan fatty acid esters, polyoxyethylene fatty acid esters, sorbitan esters, polyoxyethylene sorbitan esters (such as Tween 80 or Tween 20), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, Pluronic F68 and polyvinylpyrrolidone.

222. The matrix material according to item 144, wherein the pharmaceutical composition comprises a solvent component and/or a fluid component.

223. The matrix material according to item 222, wherein the solvent component and/or fluid component is an aqueous medium.

224. The matrix material according to item 223, wherein the aqueous medium contains one or more salts such as sodium chloride.

225. The matrix material according to item 222, wherein the solvent component and/or fluid component is a volatile fluid.

226. The matrix material according to item 144, wherein the pharmaceutical composition comprises one or more water content stabilizer such as sorbitol, polysaccaharides or polyols.

227. The matrix material according to item 144, wherein the pharmaceutical composition comprises one or more substances that increases the viscosity of the composition, selected from acacia, alginic acid, bentonite, carbomer, carboxymethylcellulose calcium, carboxymethylcellulose sodium, cetostearyl alcohol, colloidal silicon dioxide, guar gum, hydroxyethyl cellulose, hydroxypropyl cellulose, hydroxypropyl methylcellulose, hydroxypropyl methylcellulose phtalate, magnesium aluminium silicate, methylcellulose, microcrystalline cellulose, polyvinyl alcohol, povidone, sodium alginate, sucrose, tragacanth, gelatin, starch, albumin, casein, polyethlyleneoxide, polyvinylalcohol, polyethyleneglycols (macrogol), glycerine (1,2,3-propanetriol) and glycol (1,2-propanediol).

228. The matrix material according to item 144, wherein the pharmaceutical composition has a viscosity in the range of 0.1-20 cps; for example 0.1-1 cps, such as 1-2 cps, for example 2-3 cps, such as 3-4 cps, for example 4-5 cps, such as 5-6 cps, for example 6-7 cps, such as 7-8 cps, for example 8-9 cps, such as 9-10 cps, for example 10-11 cps, such as 11-12 cps, for example 12-13 cps, such as 13-14 cps, for example 14-15 cps, such as 15-16 cps, for example 16-17 cps, such as 17-18 cps, for example 18-19 cps, such as 19-20 cps.

229. The matrix material according to item 144, wherein the pharmaceutical composition has a surface tension in the range of 0.020 to 0.050 N/m; for example 0.020-0.022 N/m, such as 0.022-0.024 N/m, for example 0.024-0.026 N/m, such as 0.026-0.028 N/m, for example 0.028-0.030 N/m, such as 0.030-0.032 N/m, for example 0.032-0.034 N/m, such as 0.034-0.036 N/m, for example 0.036-0.038 N/m, such as 0.038-0.040 N/m, for example 0.040-0.042 N/m, such as 0.042-0.044 N/m, for example 0.044-0.046 N/m, such as 0.046-0.048 N/m, for example 0.048-0.050 N/m.

230. The matrix material according to item 144, wherein the pharmaceutical composition has a temperature is in the range from sub-zero degrees celcius to 150 degrees celcius; such as −100° C. to −50° C., for example −50° C. to 0° C., such as 0-10° C., for example 10-20° C., such as 20-30° C., for example 30-40° C., such as 40-50° C., for example 50-60° C., such as 60-70° C., for example 70-80° C., such as 80-90° C., for example 90-100° C., such as 100-125° C., for example 125-150° C.

231. The matrix material according to item 144, wherein the one or more pharmaceutical compositions are deposited into and/or onto said matrix material by spraying of the one or more pharmaceutical compositions into and/or onto said matrix.

232. The matrix material according to item 144, wherein the one or more pharmaceutical compositions are deposited into and/or onto said matrix material by sprinkling of the one or more pharmaceutical compositions into and/or onto said matrix.

233. The matrix material according to item 144, wherein the one or more pharmaceutical compositions are deposited into and/or onto said matrix material by pouring of the one or more pharmaceutical compositions into and/or onto said matrix.

234. The matrix material according to item 144, wherein the one or more pharmaceutical compositions are deposited into and/or onto said matrix material by dipping of said matrix into the one or more pharmaceutical compositions.

235. The matrix material according to item 144, wherein the one or more pharmaceutical compositions are deposited into or onto the matrix during preparation of said matrix.

236. A device comprising the matrix material and a pharmaceutical composition according to items 144-235.

237. A kit of parts comprising the device according to item 236 and at least one additional component.

238. A method for making the device according to item 236 comprising the steps of
  a. providing a matrix material, and
  b. applying a pharmaceutical composition onto the surface of said matrix material at individual and discrete locations.

239. Use of the device according to item 236 to promote wound healing in an individual in need thereof 240. Use of the device according to item 236 to promote hemostasis in an individual in need thereof.

241. A matrix material comprising a surface and a plurality of open and interconnected cells, wherein said matrix material comprises a haemostatically effective amount of thrombin or a precursor thereof.

242. The matrix material according to item 241, wherein said matrix further comprises one or more thrombin-stabilizing agents.
243. The matrix material according to item 241, wherein said thrombin is applied to the matrix material by e.g. printing, spraying, soaking, dipping, coating, saturating, pressuring, sprinkling, pouring, spreading, greasing, smearing, dabbing, rubbing or painting.
244. The matrix material according to item 241, wherein the matrix material comprises a biologically absorbable material comprising thrombin.
245. The matrix material according to item 241, wherein the matrix material comprises a sponge comprising thrombin.
246. The matrix material according to item 241, wherein the matrix material comprises a gelatin foam pad and/or a gauze pad that provide a unique, premixed, sterile, gelatin/thrombin haemostat.
247. The matrix material according to item 241, wherein the matrix material comprises a premixed thrombin/gelatin pad.
248. The matrix material according to item 241, wherein the matrix material comprises thrombin freeze-dried into a gelatin foam.
249. The matrix material according to item 241, wherein the matrix material comprises any standard gelatin pad with thrombin.
250. The matrix material according to item 241, wherein the matrix material comprises a fibrin paste based on e.g. a collagen sponge coated with fibrinogen and/or thrombin.
251. The matrix material according to item 241, wherein the matrix material comprises Thrombi-Gel® (Vascular Solutions, Inc.).
252. The matrix material according to item 241, wherein the matrix material comprises Thrombi-Pad™ (Vascular Solutions, Inc.).
253. The matrix material according to item 241, wherein the matrix material comprises D-Stat Dry product (such as D-Stat Dry, D-Stat 2 Dry) (Vascular Solutions, Inc.).
254. The matrix material according to item 241, wherein the matrix material comprises ThrombiGel hemostatic foam (Vascular Solutions, Inc.).
255. The matrix material according to item 241, wherein the matrix material comprises Gelfoam (Pfizer).
256. The matrix material according to item 241, wherein the matrix material comprises Surgifoam (Johnson & Johnson).
257. The matrix material according to item 241, wherein the matrix material comprises Surgiflo (Johnson & Johnson).
258. The matrix material according to item 241, wherein the matrix material comprises FloSeal Matrix Hemostatic Sealant (Baxter International Inc.).
259. The matrix material according to item 241, wherein the matrix material comprises TachoSil (Nycomed).
260. The matrix material according to item 241, wherein the matrix material comprises a collagen material such as Avitene, Actifoam, Helistat, Inistat, or CoStasis hemostatic device.
261. The matrix material according to item 241, wherein the matrix material comprises a cellulose material such as Surgicel (Ethicon/Johnson & Johnson), Oxycel or Tabotamp.
262. The matrix material according to item 241, wherein the thrombin is Thrombostat, Thrombin-JMI (King Pharmaceuticals), Recothrom (Bayer/Zymogenetics), Evithrom (OMRIX Biopharmaceuticals/Ethicon), or any other commercially available thrombin.
263. The matrix material according to item 241, wherein the thrombin is produced from plasma using the Thrombin Activation Device (TAD) (Thermogenesis).
264. The matrix material according to item 241, wherein the matrix material comprises a hemostatic paste composition comprising a hemostatic effective amount of thrombin in a polyethylene glycol base which is preferably prepared by admixing an aqueous solution of thrombin and polyethylene glycol and freeze-drying the mixture to remove substantially all of the water to yield a viscous water soluble paste of fine particles of thrombin uniformly dispersed throughout the polyethylene glycol base (as described in U.S. Pat. No. 5,595,735).
265. The matrix material according to item 241, wherein the matrix material comprises a collagen paste hemostat comprising thrombin e.g. as described in U.S. Pat. No. 4,891,359.
266. The matrix material according to item 241, wherein the matrix material comprises a stable collagen sponge having thrombin therein e.g. as described in U.S. Pat. No. 4,515,637.
267. The matrix material according to item 241, wherein the matrix material comprises a collagen sponge having thrombin therein e.g. as described in U.S. Pat. No. 6,649,162.
268. A device comprising the matrix material and thrombin according to items 241-267.
269. A kit of parts comprising the device according to item 268 and at least one additional component.
270. A method for making the device according to item 268 comprising the steps of
   a. providing a matrix material, and
   b. printing thrombin onto the surface of said matrix material at individual and discrete locations.
271. Use of the device according to item 268 to promote wound healing in an individual in need thereof
272. Use of the device according to item 268 to promote hemostasis in an individual in need thereof.
273. A container for storage and/or preparation of a matrix material comprising
   i) a bottom,
   ii) one or more sidewall(s) continuously surrounding said bottom,
   iii) a sealing surface for a lid, and
   iv) a lid,
   wherein the one or more sidewall(s) and the bottom defines an inner cavity suitable for storage and/or preparation of a matrix material.
274. The container according to item 273, wherein the one or more sidewalls comprises one or more marks for maximum filling of the container with a liquid.
275. The container according to item 274, wherein the mark for maximum filling is a bevelled edge on the one or more sidewalls.
276. The container according to item 274, wherein the mark for maximum filling is a line.
277. The container according to item 274, wherein the mark for maximum filling is a dot.
278. The container according to item 274, wherein the mark for maximum filling is a dent in the one or more sidewalls.
279. The container according to item 274, wherein said liquid is selected from the group consisting of an aqueous solution, a saline solution, medical-grade water or others.
280. The container according to item 273, wherein the inner cavity comprises one or more matrix materials.
281. The container according to item 273, wherein the inner cavity can circumvent a matrix material.

282. The container according to item 273, wherein the inner cavity comprises one or more matrix materials according to items 1 to 103 (matrix material printed with a pharmaceutical composition).
283. The container according to item 273, wherein the inner cavity comprises one or more matrix materials according to items 109 to 201 (matrix material with a pharmaceutical composition).
284. The container according to item 273, wherein the inner cavity comprises one or more matrix materials according to items 207 to 233 (matrix material with thrombin).
285. The container according to item 273, wherein the container comprises one or more handles.
286. The container according to item 285, wherein the container comprises one handle.
287. The container according to item 285, wherein the container comprises two handles.
288. The container according to item 285, wherein the one or more handles are associated with the bottom of the container.
289. The container according to item 285, wherein the one or more handles are associated with the one or more sidewall(s) of the container.
290. The container according to item 285, wherein the one or more handles comprises one or more recesses or indentations for improved grip.
291. The container according to item 273, wherein the one or more sidewall(s) comprises one or more recesses or indentations for improved grip.
292. The container according to item 273, wherein the container comprises one or more inner tray notches for easy handling of product.
293. The container according to item 292, wherein the container comprises one inner tray notches.
294. The container according to item 292, wherein the container comprises two inner tray notches.
295. The container according to item 292, wherein the container comprises three inner tray notches.
296. The container according to item 292, wherein the container comprises four inner tray notches.
297. The container according to item 292, wherein the one or more inner tray notches are associated with the one or more sidewall(s) of the container.
298. The container according to item 273, wherein the lid is peelable (a peel-off lid).
299. The container according to item 273, wherein the lid is reclosable.
300. The container according to item 273, wherein the inner cavity is a sterile environment.
301. The container according to item 273, wherein the container is sterilized by application of dry heat.
302. The container according to item 273, wherein the container is sterilized by application of one or more chemicals.
303. The container according to item 302, wherein the container is sterilized by application of chemical sterilization including use of one or more of the chemicals selected from the group consisting of ethylene oxide gas, ozone, chlorine bleach, glutaraldehyde, formaldehyde, ortho phthalaldehyde, hydrogen peroxide and peracetic acid.
304. The container according to item 273, wherein the container is sterilized by application of high pressure.
305. The container according to item 273, wherein the container is sterilized by application of radiation sterilization such as sterilization using X-rays, gamma rays, UV light, microwaves, electron beam and/or subatomic particles.
306. The container according to item 273, wherein the bottom of the inner cavity is formed as a square.
307. The container according to item 273, wherein the bottom of the inner cavity is formed as a rectangle.
308. The container according to item 273, wherein the bottom of the inner cavity is formed as a triangle.
309. The container according to item 273, wherein the bottom of the inner cavity is formed as a circle.
310. The container according to item 273, wherein the bottom of the inner cavity is formed as an oval.
311. The container according to item 273, wherein the bottom of the inner cavity is formed as a square with dimensions selected from the group consisting of 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×9 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 11 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 13 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, 15 cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

312. The container according to item 273, wherein the bottom of the inner cavity is formed as a square with dimensions of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 $cm^2$, for example 260 $cm^2$ to 270 $cm^2$, such as 270 $cm^2$ to 280 $cm^2$, for example 280 $cm^2$ to 290 $cm^2$, such as 290 $cm^2$ to 300 $cm^2$, for example 300 $cm^2$ to 320 $cm^2$, such as 320 $cm^2$ to 340 $cm^2$, for example 340 $cm^2$ to 360 $cm^2$, such as 360 $cm^2$ to 380 $cm^2$, for example 380 $cm^2$ to 400 $cm^2$, such as 400 $cm^2$ to 420 $cm^2$, for example 420 $cm^2$ to 440 $cm^2$, such as 440 $cm^2$ to 460 $cm^2$, for example 460 $cm^2$ to 480 $cm^2$, such as 480 $cm^2$ to 500 $cm^2$.

313. The container according to item 273, wherein the bottom is formed to circumvent a matrix material shaped as a square with one of the dimensions selected from the group consisting of 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×9 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 11 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 13 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, 15 cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

314. The container according to item 273, wherein the bottom is formed to circumvent a matrix material shaped as a square with dimensions of between 1 $cm^2$ to 500 $cm^2$, such as 1 $cm^2$ to 5 $cm^2$, for example 5 $cm^2$ to 10 $cm^2$, such as 10 $cm^2$ to 20 $cm^2$, for example 20 $cm^2$ to 30 $cm^2$, such as 30 $cm^2$ to 40 $cm^2$, for example 40 $cm^2$ to 50 $cm^2$, such as 50 $cm^2$ to 60 $cm^2$, for example 60 $cm^2$ to 70 $cm^2$, such as 70 $cm^2$ to 80 $cm^2$, for example 80 $cm^2$ to 90 $cm^2$, such as 90 $cm^2$ to 100 $cm^2$, for example 100 $cm^2$ to 110 $cm^2$, such as 110 $cm^2$ to 120 $cm^2$, for example 120 $cm^2$ to 130 $cm^2$, such as 130 $cm^2$ to 140 $cm^2$, for example 140 $cm^2$ to 150 $cm^2$, such as 150 $cm^2$ to 160 $cm^2$, for example 160 $cm^2$ to 170 $cm^2$, such as 170 $cm^2$ to 180 $cm^2$, for example 180 $cm^2$ to 190 $cm^2$, such as 190 $cm^2$ to 200 $cm^2$, for example 200 $cm^2$ to 210 $cm^2$, such as 210 $cm^2$ to 220 $cm^2$, for example 220 $cm^2$ to 230 $cm^2$, such as 230 $cm^2$ to 240 $cm^2$, for example 240 $cm^2$ to 250 $cm^2$, such as 250 $cm^2$ to 260 cm², for example 260 cm² to 270 cm², such as 270 cm² to 280 cm², for example 280 cm² to 290 cm², such as 290 cm² to 300 cm², for example 300 cm² to 320 cm², such as 320 cm² to 340 cm², for example 340 cm² to 360 cm², such as 360 cm² to 380 cm², for example 380 cm² to 400 cm², such as 400 cm² to 420 cm², for example 420 cm² to 440 cm², such as 440 cm² to 460 cm², for example 460 cm² to 480 cm², such as 480 cm² to 500 cm².

315. The container according to item 273, wherein the bottom is flat.
316. The container according to item 273, wherein the bottom is plane.
317. The container according to item 273, wherein the bottom is curved.
318. The container according to item 273, wherein the bottom is concave.
319. The container according to item 273, wherein the bottom is convex.
320. The container according to item 273, wherein the bottom is not plane.
321. The container according to item 273, wherein the bottom is irregular and/or non-uniform.
322. The container according to item 273, wherein the bottom is rough.
323. The container according to item 273, wherein the height of the sidewall(s) (from the bottom to the mark for maximum filling) is selected from the groups consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm, 20 mm to 22 mm, 22 mm to 24 mm, 24 mm to 26 mm, 26 mm to 28 mm, 28 mm to 30 mm, 30 mm to 32 mm, 32 mm to 34 mm, 34 mm to 36 mm, 36 mm to 38 mm, 38 mm to 40 mm, 40 mm to 42 mm, 42 mm to 44 mm, 44 mm to 46 mm, 46 mm to 48 mm or 48 mm to 50 mm.
324. The container according to item 273, wherein the width of the sidewall(s) is selected from the groups consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm.
325. The container according to item 273, wherein the height from the bottom to the lid is selected from the groups consisting of 0 mm to 2 mm, 2 mm to 4 mm, 4 mm to 6 mm, 6 mm to 8 mm, 8 mm to 10 mm, 10 mm to 12 mm, 12 mm to 14 mm, 14 mm to 16 mm, 16 mm to 18 mm, 18 mm to 20 mm, 20 mm to 22 mm, 22 mm to 24 mm, 24 mm to 26 mm, 26 mm to 28 mm, 28 mm to 30 mm, 30 mm to 32 mm, 32 mm to 34 mm, 34 mm to 36 mm, 36 mm to 38 mm, 38 mm to 40 mm, 40 mm to 42 mm, 42 mm to 44 mm, 44 mm to 46 mm, 46 mm to 48 mm or 48 mm to 50 mm.
326. The container according to item 273, wherein the sealing surface for a lid is comprised in the upper portion of the one or more sidewall(s).
327. The container according to item 273, wherein the container comprises a base.
328. The container according to item 327, wherein the base of the container is formed as a square.
329. The container according to item 327, wherein the base of the container is formed as a rectangle.
330. The container according to item 327, wherein the base of the container is formed as a triangle.
331. The container according to item 327, wherein the base of the container is formed as a circle.
332. The container according to item 327, wherein the base of the container is formed as an oval.
333. The container according to item 327, wherein the base of the container is formed as a square with dimensions selected from the group consisting of 1 cm×1 cm, 1 cm×2 cm, 1 cm×3 cm, 1 cm×4 cm, 1 cm×5 cm, 1 cm×6 cm, 1 cm×7 cm, 1 cm×8 cm, 1 cm×9 cm, 1 cm×10 cm, 1 cm×15 cm, 1 cm×20 cm, 2 cm×1 cm, 2 cm×2 cm, 2 cm×3 cm, 2 cm×4 cm, 2 cm×5 cm, 2 cm×6 cm, 2 cm×7 cm, 2 cm×8 cm, 2 cm×9 cm, 2 cm×10 cm, 2 cm×15 cm, 2 cm×20 cm, 3 cm×1 cm, 3 cm×2 cm, 3 cm×3 cm, 3 cm×4 cm, 3 cm×5 cm, 3 cm×6 cm, 3 cm×7 cm, 3 cm×8 cm, 3 cm×9 cm, 3 cm×10 cm, 3 cm×15 cm, 3 cm×20 cm, 4 cm×1 cm, 4 cm×2 cm, 4 cm×3 cm, 4 cm×4 cm, 4 cm×5 cm, 4 cm×6 cm, 4 cm×7 cm, 4 cm×8 cm, 4 cm×9 cm, 4 cm×10 cm, 4 cm×15 cm, 4 cm×20 cm, 5 cm×1 cm, 5 cm×2 cm, 5 cm×3 cm, 5 cm×4 cm, 5 cm×5 cm, 5 cm×6 cm, 5 cm×7 cm, 5 cm×8 cm, 5 cm×9 cm, 5 cm×10 cm, 5 cm×15 cm, 5 cm×20 cm, 6 cm×1 cm, 6 cm×2 cm, 6 cm×3 cm, 6 cm×4 cm, 6 cm×5 cm, 6 cm×6 cm, 6 cm×7 cm, 6 cm×8 cm, 6 cm×9 cm, 6 cm×10 cm, 6 cm×15 cm, 6 cm×20 cm, 7 cm×1 cm, 7 cm×2 cm, 7 cm×3 cm, 7 cm×4 cm, 7 cm×5 cm, 7 cm×6 cm, 7 cm×7 cm, 7 cm×8 cm, 7 cm×9 cm, 7 cm×10 cm, 7 cm×15 cm, 7 cm×20 cm, 8 cm×1 cm, 8 cm×2 cm, 8 cm×3 cm, 8 cm×4 cm, 8 cm×5 cm, 8 cm×6 cm, 8 cm×7 cm, 8 cm×8 cm, 8 cm×9 cm, 8 cm×10 cm, 8 cm×15 cm, 8 cm×20 cm, 9 cm×1 cm, 9 cm×2 cm, 9 cm×3 cm, 9 cm×4 cm, 9 cm×5 cm, 9 cm×6 cm, 9 cm×7 cm, 9 cm×8 cm, 9 cm×9 cm, 9 cm×10 cm, 9 cm×15 cm, 9 cm×20 cm, 10 cm×1 cm, 10 cm×2 cm, 10 cm×3 cm, 10 cm×4 cm, 10 cm×5 cm, 10 cm×6 cm, 10 cm×7 cm, 10 cm×8 cm, 10 cm×9 cm, 10 cm×10 cm, 10 cm×15 cm, 10 cm×20 cm, 11 cm×1 cm, 11 cm×2 cm, 11 cm×3 cm, 11 cm×4 cm, 11 cm×5 cm, 11 cm×6 cm, 11 cm×7 cm, 11 cm×8 cm, 11 cm×9 cm, 11 cm×10 cm, 11 cm×15 cm, 11 cm×20 cm, 12 cm×1 cm, 12 cm×2 cm, 12 cm×3 cm, 12 cm×4 cm, 12 cm×5 cm, 12 cm×6 cm, 12 cm×7 cm, 12 cm×8 cm, 12 cm×9 cm, 12 cm×10 cm, 12 cm×15 cm, 12 cm×20 cm, 13 cm×1 cm, 13 cm×2 cm, 13 cm×3 cm, 13 cm×4 cm, 13 cm×5 cm, 13 cm×6 cm, 13 cm×7 cm, 13 cm×8 cm, 13 cm×9 cm, 13 cm×10 cm, 13 cm×15 cm, 13 cm×20 cm, 14 cm×1 cm, 14 cm×2 cm, 14 cm×3 cm, 14 cm×4 cm, 14 cm×5 cm, 14 cm×6 cm, 14 cm×7 cm, 14 cm×8 cm, 14 cm×9 cm, 14 cm×10 cm, 14 cm×15 cm, 14 cm×20 cm, 15 cm×1 cm, 15 cm×2 cm, 15 cm×3 cm, 15 cm×4 cm, 15 cm×5 cm, 15 cm×6 cm, 15 cm×7 cm, 15 cm×8 cm, 15 cm×9 cm, 15 cm×10 cm, 15 cm×15 cm, 15 cm×20 cm, 16 cm×1 cm, 16 cm×2 cm, 16 cm×3 cm, 16 cm×4 cm, 16 cm×5 cm, 16 cm×6 cm, 16 cm×7 cm, 16 cm×8 cm, 16 cm×9 cm, 16 cm×10 cm, 16 cm×15 cm, 16 cm×20 cm, 17 cm×1 cm, 17 cm×2 cm, 17 cm×3 cm, 17 cm×4 cm, 17 cm×5 cm, 17 cm×6 cm, 17 cm×7 cm, 17 cm×8 cm, 17 cm×9 cm, 17 cm×10 cm, 17 cm×15 cm, 17 cm×20 cm, 18 cm×1 cm, 18 cm×2 cm, 18 cm×3 cm, 18 cm×4 cm, 18 cm×5 cm, 18 cm×6 cm, 18 cm×7 cm, 18 cm×8 cm, 18 cm×9 cm, 18 cm×10 cm, 18 cm×15 cm, 18 cm×20 cm, 19 cm×1 cm, 19 cm×2 cm, 19 cm×3 cm, 19 cm×4 cm, 19 cm×5 cm, 19 cm×6 cm, 19 cm×7 cm, 19 cm×8 cm, 19 cm×9 cm, 19 cm×10 cm, 19 cm×15 cm, 19 cm×20 cm, 20 cm×1 cm, 20 cm×2 cm, 20 cm×3 cm, 20 cm×4 cm, 20 cm×5 cm, 20 cm×6 cm, 20 cm×7 cm, 20 cm×8 cm, 20 cm×9 cm, 20 cm×10 cm, 20 cm×15 cm, 20 cm×20 cm, 25 cm×1 cm, 25 cm×2 cm, 25 cm×3 cm, 25 cm×4 cm, 25 cm×5 cm, 25 cm×6 cm, 25 cm×7 cm, 25 cm×8 cm, 25 cm×9 cm, 25 cm×10 cm, 25 cm×15 cm, 25 cm×20 cm, 30 cm×1 cm, 30 cm×2 cm, 30 cm×3 cm, 30 cm×4 cm, 30 cm×5 cm, 30 cm×6 cm, 30 cm×7 cm, 30 cm×8 cm, 30 cm×9 cm, 30 cm×10 cm, 30 cm×15 cm, 30 cm×20 cm, 40 cm×1 cm, 40 cm×2 cm, 40 cm×3 cm, 40 cm×4 cm, 40 cm×5 cm, 40 cm×6 cm, 40 cm×7 cm, 40 cm×8 cm, 40 cm×9 cm, 40 cm×10 cm, 40 cm×15 cm, 40 cm×20 cm, 50 cm×1 cm, 50 cm×2 cm, 50 cm×3 cm, 50 cm×4 cm, 50 cm×5 cm, 50 cm×6 cm, 50 cm×7 cm, 50 cm×8 cm, 50 cm×9 cm, 50 cm×10 cm, 50 cm×15 cm, or 50 cm×20 cm.

334. The container according to item 327, wherein the base of the container is formed as a square with dimensions of between 1 cm$^2$ to 500 cm$^2$, such as 1 cm$^2$ to 5 cm$^2$, for example 5 cm$^2$ to 10 cm$^2$, such as 10 cm$^2$ to 20 cm$^2$, for example 20 cm$^2$ to 30 cm$^2$, such as 30 cm$^2$ to 40 cm$^2$, for example 40 cm$^2$ to 50 cm$^2$, such as 50 cm$^2$ to 60 cm$^2$, for example 60 cm$^2$ to 70 cm$^2$, such as 70 cm$^2$ to 80 cm$^2$, for example 80 cm$^2$ to 90 cm$^2$, such as 90 cm$^2$ to 100 cm$^2$, for example 100 cm$^2$ to 110 cm$^2$, such as 110 cm$^2$ to 120 cm$^2$, for example 120 cm$^2$ to 130 cm$^2$, such as 130 cm$^2$ to 140 cm$^2$, for example 140 cm$^2$ to 150 cm$^2$, such as 150 cm$^2$ to 160 cm$^2$, for example 160 cm$^2$ to 170 cm$^2$, such as 170 cm$^2$ to 180 cm$^2$, for example 180 cm$^2$ to 190 cm$^2$, such as 190 cm$^2$ to 200 cm$^2$, for example 200 cm$^2$ to 210 cm$^2$, such as 210 cm$^2$ to 220 cm$^2$, for example 220 cm$^2$ to 230 cm$^2$, such as 230 cm$^2$ to 240 cm$^2$, for example 240 cm$^2$ to 250 cm$^2$, such as 250 cm$^2$ to 260 cm$^2$, for example 260 cm$^2$ to 270 cm$^2$, such as 270 cm$^2$ to 280 cm$^2$, for example 280 cm$^2$ to 290 cm$^2$, such as 290 cm$^2$ to 300 cm$^2$, for example 300 cm$^2$ to 320 cm$^2$, such as 320 cm$^2$ to 340 cm$^2$, for example 340 cm$^2$ to 360 cm$^2$, such as 360 cm$^2$ to 380 cm$^2$, for example 380 cm$^2$ to 400 cm$^2$, such as 400 cm$^2$ to 420 cm$^2$, for example 420 cm$^2$ to 440 cm$^2$, such as 440 cm$^2$ to 460 cm$^2$, for example 460 cm$^2$ to 480 cm$^2$, such as 480 cm$^2$ to 500 cm$^2$.

335. The container according to item 327, wherein the base is contacting the one or more sidewall(s) at one or more points, such as 1, 2, 3, 4, 5, 6, 7, 8, 9 or 10 points.

336. The container according to item 327, wherein the base is contacting the bottom at one or more points, such as 1, 2, 3, 4, 5, 6, 7, 8, 9 or 10 points.

337. The container according to item 327, wherein the base comprises a flat bottom.

338. The container according to item 327, wherein the base comprises one or more handles.

339. The container according to item 327, wherein the base comprises one or more recesses or indentations.

340. The container according to item 327, wherein the base comprises the sealing surface for a lid.

341. The container according to item 327, wherein the base comprises a flat portion.

342. The container according to item 327, wherein the base comprises a plane portion.

343. The container according to item 327, wherein the base comprises a curved portion.

344. The container according to item 327, wherein the base comprises a concave portion.

345. The container according to item 327, wherein the base comprises a convex portion.

346. The container according to item 327, wherein the base is not plane.

347. The container according to item 327, wherein the base is irregular and/or non-uniform.

348. The container according to item 327, wherein the base is rough.

349. The container according to item 327, wherein the base comprises one or more extended base plate(s).

350. The container according to item 327, wherein the base comprises a vertical portion.

351. The container according to item 327, wherein the base comprises a horizontal portion.

352. The container according to item 273, wherein the container is made of or comprises plastic.

353. The container according to item 273, wherein the container is made of or comprises flexible plastic.

354. The container according to item 273, wherein the container is made of or comprises rigid plastic.

355. The container according to item 273, wherein the container is made of or comprises transparent plastic.

356. The container according to item 273, wherein the container is made of or comprises a medical grade polymer such as plastic.

357. The container according to item 273, wherein the container is made of or comprises one or more of the materials selected from the group consisting of Biodegradable plastic, Bioplastics obtained from biomass e.g. from pea starch or from biopetroleum, Polypropylene (PP), Polystyrene (PS), High impact polystyrene (HIPS), Acrylonitrile butadiene styrene (ABS), Polyethylene terephthalate (PET), Amorphous PET (APET), Polyester (PES), Fibers, textiles, Polyamides (PA), (Nylons), Poly (vinyl chloride) (PVC), Polyurethanes (PU), Polycarbonate (PC), Polyvinylidene chloride (PVDC) (Saran), Polyvinylidene Fluoride (PVDF), Polyethylene (PE), Polymethyl methacrylate (PMMA), Polytetrafluoroethylene (PTFE) (trade name Teflon), Fluorinated ethylene propylene (FEP), Polyetheretherketone (PEEK) (Polyetherketone), Polyetherimide (PEI) (Ultem), Phenolics (PF), (phenol formaldehydes), Perfluoroalkoxy (PFA), Poly(methyl methacrylate) (PMMA), Urea-formaldehyde (UF), Melamine formaldehyde (MF), Polylactic acid and Plastarch material or any mixture thereof 358. The container according to item 273, wherein the container is made of or comprises one or more materials selected from the group consisting of TECAFORM™ AH MT, CELCON® (Acetal Copolymer), RADEL®, TECASON™ P XRO (Polyphenylsulfone, also Radio Opacifer), UDEL® Polysulfone, ULTEM® (Polyetherimide), UHMW Lot Controlled, LENNITE® UHME-PE, TECANAT™ PC (USP Class VI Polycarbonate Rod), ZELUX® GS (Gamma Stabilized Polycarbonate), ACRYLIC (Medical grade Cast Acrylic), TECAMAX™ SRP (Ultra High Performance Thermoplastic), TECAPRO™ MT (Polypropylene Heat Stabilized), TECAPEEK™ MT (USP Class VI compliant), TECAFORM™ AH SAN, ANTIMICROBIAL filled plastics, TECASON™ P XRO (Biocompatible Radio Opacifer PPSU), TECAPEEK™ CLASSIX, POLYSULFONE® (Medical grade), TECANYL™ (Medical grade Noryl®), TYGON® (Medical grade Tubing), TEXOLON™ Medical Grade PTFE (USP CLASS VI), PROPYLUX HS and HS2, ABS (FDA Approved Medical Grades), TOPAS® (Medical grade), and other Medical Grade/FDA approved plastic products.

359. The container according to item 273, wherein the container is made of or comprises one or more polymers of high molecular weight.

360. The container according to item 359, wherein the container is made of or comprises one or more polymers and/or plastics with a molecular weight in the range from 10,000 to 1,000,000 Da, such as from 10,000 to 50,000 Da, for example 50,000 to 100,000 Da, such as from 100,000 to 150,000 Da, for example 150,000 to 200,000 Da, such as from 200,000 to 250,000 Da, for example 250,000 to 238,000 Da, such as from 238,000 to 350,000 Da, for example 350,000 to 400,000 Da, such as from 400,000 to 450,000 Da, for example 450,000 to 500,000 Da, such as from 500,000 to 550,000 Da, for example 550,000 to 600,000 Da, such as from 600,000 to 650,000 Da, for example 650,000 to 700,000 Da, such as from 700,000 to 750,000 Da, for example 750,000 to 800,000 Da, such as from 800,000 to 850,000 Da, for example 850,000 to 900,000 Da, such as from 900,000 to 950,000 Da, for example 950,000 to 1,000,000 Da.

361. The container according to item 273, wherein the container is made of or comprises one or more types of Rubber.
362. The container according to item 273, wherein the container is made of or comprises one or more types of Cellulose-based plastics.
363. The container according to item 273, wherein the container is made of or comprises one or more types of Bakelite.
364. The container according to item 273, wherein the container is made of or comprises one or more types of Polystyrene.
365. The container according to item 273, wherein the container is made of or comprises one or more types of PVC.
366. The container according to item 273, wherein the container is made of or comprises one or more types of Nylon.
367. The container according to item 273, wherein the container is made of or comprises one or more types of Synthetic rubber.
368. The container according to item 273, wherein the container is made of or comprises one or more acrylics.
369. The container according to item 273, wherein the container is made of or comprises one or more polyesters.
370. The container according to item 273, wherein the container is made of or comprises one or more silicones.
371. The container according to item 273, wherein the container is made of or comprises one or more polyurethanes.
372. The container according to item 273, wherein the container is made of or comprises one or more halogenated plastics.
373. The container according to item 273, wherein the one or more sidewalls and/or bottom is made of or comprises plastic.
374. The container according to item 273, wherein the one or more sidewalls and/or bottom is made of or comprises flexible plastic.
375. The container according to item 273, wherein the one or more sidewalls and/or bottom is made of or comprises rigid plastic.
376. The container according to item 273, wherein the one or more sidewalls and/or bottom is made of or comprises transparent plastic.
377. The container according to item 273, wherein the one or more sidewalls and/or bottom is made of or comprises medical grade polymer such as plastic.
378. The container according to item 273, wherein the one or more sidewalls and/or bottom is made of or comprises one or more materials selected from the group consisting of Biodegradable plastic, Bioplastics obtained from biomass e.g. from pea starch or from biopetroleum, Polypropylene (PP), Polystyrene (PS), High impact polystyrene (HIPS), Acrylonitrile butadiene styrene (ABS), Polyethylene terephthalate (PET), Amorphous PET (APET), Polyester (PES), Fibers, textiles, Polyamides (PA), (Nylons), Poly(vinyl chloride) (PVC), Polyurethanes (PU), Polycarbonate (PC), Polyvinylidene chloride (PVDC) (Saran), Polyvinylidene Fluoride (PVDF), Polyethylene (PE), Polymethyl methacrylate (PMMA), Polytetrafluoroethylene (PTFE) (trade name Teflon), Fluorinated ethylene propylene (FEP), Polyetheretherketone (PEEK) (Polyetherketone), Polyetherimide (PEI) (Ultem), Phenolics (PF), (phenol formaldehydes), Perfluoroalkoxy (PFA), Poly(methyl methacrylate) (PMMA), Urea-formaldehyde (UF), Melamine formaldehyde (MF), Polylactic acid and Plastarch material or any mixture thereof.
379. The container according to item 273, wherein the one or more sidewalls and/or bottom is made of or comprises one or more of the materials selected from the group consisting of TECAFORM™ AH MT, CELCON® (Acetal Copolymer), RADEL®, TECASON™ P XRO (Polyphenylsulfone, also Radio Opacifer), UDEL® Polysulfone, ULTEM® (Polyetherimide), UHMW Lot Controlled, LENNITE® UHME-PE, TECANAT™ PC (USP Class VI Polycarbonate Rod), ZELUX® GS (Gamma Stabilized Polycarbonate), ACRYLIC (Medical grade Cast Acrylic), TECAMAX™ SRP (Ultra High Performance Thermoplastic), TECAPRO™ MT (Polypropylene Heat Stabilized), TECAPEEK™ MT (USP Class VI compliant), TECAFORM™ AFI SAN, ANTIMICROBIAL filled plastics, TECASON™ P XRO (Biocompatible Radio Opacifer PPSU), TECAPEEK™ CLASSIX, POLYSULFONE® (Medical grade), TECANYL™ (Medical grade Noryl®), TYGON® (Medical grade Tubing), TEXOION™ Medical Grade PTFE (USP CLASS VI), PROPYLUX HS and HS2, ABS (FDA Approved Medical Grades), TOPAS® (Medical grade), and other Medical Grade/FDA approved plastic products.
380. The container according to item 273, wherein the one or more sidewalls and/or bottom is made of or comprises one or more polymers of high molecular weight.
381. The container according to item 380, wherein the one or more sidewalls and/or bottom is made of or comprises one or more polymers and/or plastics with a molecular weight in the range from 10,000 to 1,000,000 Da, such as from 10,000 to 50,000 Da, for example 50,000 to 100,000 Da, such as from 100,000 to 150,000 Da, for example 150,000 to 200,000 Da, such as from 200,000 to 250,000 Da, for example 250,000 to 238,000 Da, such as from 238,000 to 350,000 Da, for example 350,000 to 400,000 Da, such as from 400,000 to 450,000 Da, for example 450,000 to 500,000 Da, such as from 500,000 to 550,000 Da, for example 550,000 to 600,000 Da, such as from 600,000 to 650,000 Da, for example 650,000 to 700,000 Da, such as from 700,000 to 750,000 Da, for example 750,000 to 800,000 Da, such as from 800,000 to 850,000 Da, for example 850,000 to 900,000 Da, such as from 900,000 to 950,000 Da, for example 950,000 to 1,000,000 Da.
382. The container according to item 273, wherein the one or more sidewalls and/or bottom is made of or comprises one or more types of Rubber.
383. The container according to item 273, wherein the one or more sidewalls and/or bottom is made of or comprises one or more types of Cellulose-based plastics.
384. The container according to item 273, wherein the one or more sidewalls and/or bottom is made of or comprises one or more types of Bakelite.
385. The container according to item 273, wherein the one or more sidewalls and/or bottom is made of or comprises one or more types of Polystyrene.

386. The container according to item 273, wherein the one or more sidewalls and/or bottom is made of or comprises one or more types of PVC.

387. The container according to item 273, wherein the one or more sidewalls and/or bottom is made of or comprises one or more types of Nylon.

388. The container according to item 273, wherein the one or more sidewalls and/or bottom is made of or comprises one or more types of Synthetic rubber.

389. The container according to item 273, wherein the one or more sidewalls and/or bottom is made of or comprises one or more acrylics.

390. The container according to item 273, wherein the one or more sidewalls and/or bottom is made of or comprises one or more polyesters.

391. The container according to item 273, wherein the one or more sidewalls and/or bottom is made of or comprises one or more silicones.

392. The container according to item 273, wherein the one or more sidewalls and/or bottom is made of or comprises one or more polyurethanes.

393. The container according to item 273, wherein the one or more sidewalls and/or bottom is made of or comprises one or more halogenated plastics.

394. The container according to item 273, wherein the lid is made of or comprises a peelable material.

395. The container according to item 394, wherein the peelable material is selected from the group consisting of polyethylene (PE), thermoplastic elastomer, thermoset elastomer, Tyvek, Teslin, paper, plastic foil or metal foil.

396. The container according to item 394, wherein the lid is reinforced with a coating, such as a synthetic coating.

397. The container according to item 396, wherein the synthetic coating is selected from the group consisting of Perfluorooctanoic acid (PFOA), hydrocarbon based petrochemicals, zein or others.

398. The container according to item 273, wherein the lid is made of or comprises plastic.

399. The container according to item 273, wherein the lid is made of or comprises flexible plastic.

400. The container according to item 273, wherein the lid is made of or comprises rigid plastic.

401. The container according to item 273, wherein the lid is made of or comprises transparent plastic.

402. The container according to item 273, wherein the lid is made of or comprises medical grade polymer such as plastic.

403. The container according to item 273, wherein the lid is made of or comprises one or more materials selected from the group consisting of Biodegradable plastic, Bioplastics obtained from biomass e.g. from pea starch or from biopetroleum, Polypropylene (PP), Polystyrene (PS), High impact polystyrene (HIPS), Acrylonitrile butadiene styrene (ABS), Polyethylene terephthalate (PET), Amorphous PET (APET), Polyester (PES), Fibers, textiles, Polyamides (PA), (Nylons), Poly(vinyl chloride) (PVC), Polyurethanes (PU), Polycarbonate (PC), Polyvinylidene chloride (PVDC) (Saran), Polyvinylidene Fluoride (PVDF), Polyethylene (PE), Polymethyl methacrylate (PMMA), Polytetrafluoroethylene (PTFE) (trade name Teflon), Fluorinated ethylene propylene (FEP), Polyetheretherketone (PEEK) (Polyetherketone), Polyetherimide (PEI) (Ultem), Phenolics (PF), (phenol formaldehydes), Perfluoroalkoxy (PFA), Poly(methyl methacrylate) (PMMA), Urea-formaldehyde (UF), Melamine formaldehyde (MF), Polylactic acid and Plastarch material or any mixture thereof.

404. The container according to item 273, wherein the lid is made of or comprises one or more of the materials selected from the group consisting of TECAFORM™ AH MT, CELCON® (Acetal Copolymer), RADEL®, TECASON™ P XRO (Polyphenylsulfone, also Radio Opacifier), UDEL® Polysulfone, ULTEM® (Polyetherimide), UHMW Lot Controlled, LENNITE® UHME-PE, TECANAT™ PC (USP Class VI Polycarbonate Rod), ZELUX® GS (Gamma Stabilized Polycarbonate), ACRYLIC (Medical grade Cast Acrylic), TECAMAX™ SRP (Ultra High Performance Thermoplastic), TECAPRO™ MT (Polypropylene Heat Stabilized), TECAPEEK™ MT (USP Class VI compliant), TECAFORM™ AH SAN, ANTIMICROBIAL filled plastics, TECASON™ P XRO (Biocompatible Radio Opacifier PPSU), TECAPEEK™ CLASSIX, POLYSULFONE® (Medical grade), TECANYL™ (Medical grade Noryl®), TYGON® (Medical grade Tubing), TEXOLON™ Medical Grade PTFE (USP CLASS VI), PROPYLUX HS and HS2, ABS (FDA Approved Medical Grades), TOPAS® (Medical grade), and other Medical Grade/FDA approved plastic products.

405. The container according to item 273, wherein the lid is made of or comprises one or more polymers of high molecular weight.

406. The container according to item 405, wherein the lid is made of or comprises one or more polymers and/or plastics with a molecular weight in the range from 10,000 to 1,000,000 Da, such as from 10,000 to 50,000 Da, for example 50,000 to 100,000 Da, such as from 100,000 to 150,000 Da, for example 150,000 to 200,000 Da, such as from 200,000 to 250,000 Da, for example 250,000 to 238,000 Da, such as from 238,000 to 350,000 Da, for example 350,000 to 400,000 Da, such as from 400,000 to 450,000 Da, for example 450,000 to 500,000 Da, such as from 500,000 to 550,000 Da, for example 550,000 to 600,000 Da, such as from 600,000 to 650,000 Da, for example 650,000 to 700,000 Da, such as from 700,000 to 750,000 Da, for example 750,000 to 800,000 Da, such as from 800,000 to 850,000 Da, for example 850,000 to 900,000 Da, such as from 900,000 to 950,000 Da, for example 950,000 to 1,000,000 Da.

407. The container according to item 273, wherein the lid is made of or comprises one or more types of Rubber.

408. The container according to item 273, wherein the lid is made of or comprises one or more types of Cellulose-based plastics.

409. The container according to item 273, wherein the lid is made of or comprises one or more types of Bakelite.

410. The container according to item 273, wherein the lid is made of or comprises one or more types of Polystyrene.

411. The container according to item 273, wherein the lid is made of or comprises one or more types of PVC.

412. The container according to item 273, wherein the lid is made of or comprises one or more types of Nylon.

413. The container according to item 273, wherein the lid is made of or comprises one or more types of Synthetic rubber.

414. The container according to item 273, wherein the lid is made of or comprises one or more acrylics.

415. The container according to item 273, wherein the lid is made of or comprises one or more polyesters.

416. The container according to item 273, wherein the lid is made of or comprises one or more silicones.

417. The container according to item 273, wherein the lid is made of or comprises one or more polyurethanes.

418. The container according to item 273, wherein the lid is made of or comprises one or more halogenated plastics.
419. The container according to item 327, wherein the base is made of or comprises plastic.
420. The container according to item 327, wherein the base is made of or comprises flexible plastic.
421. The container according to item 327, wherein the base is made of or comprises transparent plastic.
422. The container according to item 327, wherein the base is made of or comprises medical grade polymer such as plastic.
423. The container according to item 327, wherein the base is made of or comprises one or more materials selected from the group consisting of TECAFORM™ AH MT, CELCON® (Acetal Copolymer), RADEL®, TECASON™ P XRO (Polyphenylsulfone, also Radio Opacifer), UDEL® Polysulfone, ULTEM® (Polyetherimide), UHMW Lot Controlled, LENNITE® UI TECANAT™ PC (USP Class VI Polycarbonate Rod), ZELUX® GS (Gamma Stabilized Polycarbonate), ACRYLIC (Medical grade Cast Acrylic), TECAMAX™ SRP (Ultra High Performance Thermoplastic), TECAPRO™ MT (Polypropylene Heat Stabilized), TECAPEEK™ MT (USP Class VI compliant), TECAFORM™ AH SAN, ANTI-MICROBIAL filled plastics, TECASON™ P XRO (Biocompatible Radio Opacifer PPSU), TECAPEEK™ CLASSIX, POLYSULFONE® (Medical grade), TECA-NYL™ (Medical grade Noryl®), TYGON® (Medical grade Tubing), TEXOLON™ Medical Grade PTFE (USP CLASS VI), PROPYLUX HS and HS2, ABS (FDA Approved Medical Grades), TOPAS® (Medical grade), and other Medical Grade/FDA approved plastic products.
424. The container according to item 327, wherein the base is made of or comprises one or more of the materials selected from the group consisting of Biodegradable plastic, Bioplastics obtained from biomass e.g. from pea starch or from biopetroleum, Polypropylene (PP), Polystyrene (PS), High impact polystyrene (HIPS), Acrylonitrile butadiene styrene (ABS), Polyethylene terephthalate (PET), Amorphous PET (APET), Polyester (PES), Fibers, textiles, Polyamides (PA), (Nylons), Poly(vinyl chloride) (PVC), Polyurethanes (PU), Polycarbonate (PC), Polyvinylidene chloride (PVDC) (Saran), Polyvinylidene Fluoride (PVDF), Polyethylene (PE), Polymethyl methacrylate (PMMA), Polytetrafluoroethylene (PTFE) (trade name Teflon), Fluorinated ethylene propylene (FEP), Polyetheretherketone (PEEK) (Polyetherketone), Polyetherimide (PEI) (Ultem), Phenolics (PF), (phenol formaldehydes), Perfluoroalkoxy (PFA), Poly(methyl methacrylate) (PMMA), Urea-formaldehyde (UF), Melamine formaldehyde (MF), Polylactic acid and Plastarch material or any mixture thereof.
425. The container according to item 327, wherein the base is made of or comprises one or more polymers of high molecular weight.
426. The container according to item 425, wherein the base is made of or comprises one or more polymers and/or plastics with a molecular weight in the range from 10,000 to 1,000,000 Da, such as from 10,000 to 50,000 Da, for example 50,000 to 100,000 Da, such as from 100,000 to 150,000 Da, for example 150,000 to 200,000 Da, such as from 200,000 to 250,000 Da, for example 250,000 to 238,000 Da, such as from 238,000 to 350,000 Da, for example 350,000 to 400,000 Da, such as from 400,000 to 450,000 Da, for example 450,000 to 500,000 Da, such as from 500,000 to 550,000 Da, for example 550,000 to 600,000 Da, such as from 600,000 to 650,000 Da, for example 650,000 to 700,000 Da, such as from 700,000 to 750,000 Da, for example 750,000 to 800,000 Da, such as from 800,000 to 850,000 Da, for example 850,000 to 900,000 Da, such as from 900,000 to 950,000 Da, for example 950,000 to 1,000,000 Da.
427. The container according to item 327, wherein the base is made of or comprises one or more types of Rubber.
428. The container according to item 327, wherein the base is made of or comprises one or more types of Cellulose-based plastics.
429. The container according to item 327, wherein the base is made of or comprises one or more types of Bakelite.
430. The container according to item 327, wherein the base is made of or comprises one or more types of Polystyrene.
431. The container according to item 327, wherein the base is made of or comprises one or more types of PVC.
432. The container according to item 327, wherein the base is made of or comprises one or more types of Nylon.
433. The container according to item 327, wherein the base is made of or comprises one or more types of Synthetic rubber.
434. The container according to item 327, wherein the base is made of or comprises one or more acrylics.
435. The container according to item 327, wherein the base is made of or comprises one or more polyesters.
436. The container according to item 327, wherein the base is made of or comprises one or more silicones.
437. The container according to item 327, wherein the base is made of or comprises one or more polyurethanes.
438. The container according to item 327, wherein the base is made of or comprises one or more halogenated plastics.
439. The container according to item 273, wherein the container comprises an inner cavity where the maximum volume of liquid that can be added to the inner cavity comprising a matrix material is in range of from 5% to 50% of the volume of the matrix material such as from 5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, such as from 15% to 16%, for example from 16% to 17%, such as from 17% to 18%, for example from 18% to 19%, such as from 19% to 20%, for example from 20% to 21%, such as from 21% to 22%, for example from 22% to 23%, such as from 23% to 24%, for example from 24% to 25%, such as from 25% to 26%, for example from 26% to 27%, such as from 27% to 28%, for example from 28% to 29%, such as from 29% to 30%, for example from 30% to 31%, such as from 31% to 32%, for example from 32% to 33%, such as from 33% to 34%, for example from 34% to 35%, such as from 35% to 36%, for example from 36% to 37%, such as from 37% to 38%, for example from 38% to 39%, such as from 39% to 40%, for example from 40% to 41%, such as from 41% to 42%, for example from 42% to 43%, such as from 43% to 44%, for example from 44% to 45%, such as from 45% to 46%, for example from 46% to 47%, such as from 47% to 48%, for example from 48% to 49%, or such as from 49% to 50%.
440. A kit of parts comprising a matrix material according to any of the items 1 to 138, 144 to 235 and 241 to 267 and at least one additional component.
441. The kit of part according to item 440, wherein the one additional component is the container according to items 273 to 439.

442. A kit of parts comprising the matrix material according to any of the items 1 to 138 and the container according to items 273 to 439.

443. A method for making the kit of parts according to any of items 440 to 442.

444. Use of the kit of parts according to any of items 440 to 442 in a method for promoting wound healing in an individual in need thereof.

445. Use of the kit of parts according to any of items 440 to 442 in a method for promoting hemostasis in an individual in need thereof.

446. A method for use of the kit of parts according to any of items 440 to 442 comprising the steps of
   i) storing of the matrix material in the container
   ii) opening of said container
   iii) optional addition of liquid/moisture to container comprising the matrix material
   iv) transfer of said matrix material to an individual in need thereof
   to promote wound healing in the individual in need thereof.

447. A method for use of the kit of parts according to any of items 440 to 442 comprising the steps of
   i) storing of the matrix material in the container
   ii) opening of said container
   iii) optional addition of liquid/moisture to container comprising the matrix material
   iv) transfer of said matrix material to an individual in need thereof
   to promote hemostasis in the individual in need thereof.

448. The method according to any of items 446 or 447, wherein the addition of liquid/moisture comprises addition of a volume of liquid/moisture in range of from 5% to 50% of the volume of the matrix material such as from 5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, such as from 15% to 16%, for example from 16% to 17%, such as from 17% to 18%, for example from 18% to 19%, such as from 19% to 20%, for example from 20% to 21%, such as from 21% to 22%, for example from 22% to 23%, such as from 23% to 24%, for example from 24% to 25%, such as from 25% to 26%, for example from 26% to 27%, such as from 27% to 28%, for example from 28% to 29%, such as from 29% to 30%, for example from 30% to 31%, such as from 31% to 32%, for example from 32% to 33%, such as from 33% to 34%, for example from 34% to 35%, such as from 35% to 36%, for example from 36% to 37%, such as from 37% to 38%, for example from 38% to 39%, such as from 39% to 40%, for example from 40% to 41%, such as from 41% to 42%, for example from 42% to 43%, such as from 43% to 44%, for example from 44% to 45%, such as from 45% to 46%, for example from 46% to 47%, such as from 47% to 48%, for example from 48% to 49%, or such as from 49% to 50%.

449. The method according to any of items 446 or 447, wherein the liquid/moisture added to the container comprising the matrix material is a sterile saline solution.

450. The method according to item 449, wherein the sterile saline solution is a sterile sodium chloride solution.

451. The method according to item 450, wherein the sterile sodium chloride solution is a sterile sodium chloride 0.9% solution.

452. The method according to any of items 446 or 447, wherein the liquid/moisture added to the container comprising the matrix material is sterile water.

The invention claimed is:

1. A hemostatic matrix material comprising a surface and a plurality of open and interconnected cells, said matrix material comprising gelatin or collagen, wherein the surface of said matrix material has a single hemostatic composition consisting of thrombin distributed in a uniform manner, wherein the surface of the matrix material contains between 8 and 50 IU/cm$^2$ of thrombin.

2. The matrix material according to claim 1, wherein the hemostatic composition consisting of thrombin is distributed such that any two area units differ in the concentration of thrombin by 10% at the most.

3. The matrix material according to claim 1, wherein the matrix material is a sponge.

4. The matrix material according to claim 3, wherein the sponge is a gelatin sponge.

5. The matrix material according to claim 1, wherein the matrix material is sterile and contained in a sterile, pre-packaged, ready-to-use container.

6. The matrix material according to claim 1, wherein the hemostatic composition comprises a fluid component.

7. The matrix material according to claim 6, wherein the fluid component is an aqueous medium.

8. The matrix material according to claim 1, wherein the hemostatic composition has a viscosity in the range of 0.1-20 cps.

9. The matrix material according to claim 1, wherein the hemostatic composition has a surface tension in the range of 0.020 N/m to 0.050 N/m.

10. The matrix material according to claim 1, wherein said matrix material is dry.

11. The matrix material according to claim 1, wherein the surface of the matrix material containing less than 40 IU/cm$^2$ of thrombin.

12. The matrix material according to claim 1, wherein the surface of the matrix material containing less than 30 IU/cm$^2$ of thrombin.

13. A method for making a hemostatic matrix material according to claim 1 comprising:
   a) providing a hemostatic matrix material comprising a surface and a plurality of open and interconnected cells, said matrix material comprising gelatin or collagen; and
   b) applying a single hemostatic composition consisting of thrombin onto the surface of said matrix material such that the surface of the matrix material contains between 8 and 50 IU/cm$^2$ of thrombin.

14. The method according to claim 13, wherein said method essentially does not alter the physical characteristics of the surface of said matrix material.

15. The method according to claim 13, wherein said method essentially does not cause any swelling of the matrix material.

16. The method according to claim 13, wherein said method essentially does not cause any swelling of the surface of said matrix material.

17. The method according to claim 13, wherein said method essentially does not alter the initial absorption rate of the matrix material.

18. A method for promoting wound healing in an individual in need thereof, comprising applying to a wound, a hemostatic matrix material comprising a surface and a plurality of open and interconnected cells, said matrix material comprising gelatin or collagen, wherein the surface of said matrix material has a single hemostatic composition consisting of thrombin distributed in a uniform manner, wherein the surface of the matrix material contains between 8 and 50 IU/cm$^2$ of thrombin.

19. A method for promoting hemostasis in an individual in need thereof, comprising applying to a wound, a hemostatic matrix material comprising a surface and a plurality of open and interconnected cells, said matrix material comprising gelatin or collagen, wherein the surface of said matrix material has a single hemostatic composition consisting of thrombin distributed in a uniform manner, wherein the surface of the matrix material contains between 8 and 50 IU/cm$^2$ of thrombin.

* * * * *